US012263178B2

(12) United States Patent
Altshul et al.

(10) Patent No.: US 12,263,178 B2
(45) Date of Patent: *Apr. 1, 2025

(54) PHARMACEUTICAL COMPOSITIONS AND METHODS

(71) Applicant: Pop Test Oncology LLC, Cliffside Park, NJ (US)

(72) Inventors: Randice Lisa Altshul, Cliffside Park, NJ (US); Neil David Thiese, New York, NY (US); Andreas J. Kesel, Munich (DE); Myron Rapkin, Indianapolis, IN (US); Rebecca O'Brien, Shell Knob, MO (US); Anthony Arment, Fairborn, OH (US)

(73) Assignee: Pop Test Oncology LLC, Cliffside Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,371

(22) Filed: Oct. 31, 2022

(65) Prior Publication Data

US 2023/0142627 A1 May 11, 2023

Related U.S. Application Data

(60) Continuation of application No. 16/690,282, filed on Nov. 21, 2019, now Pat. No. 11,576,921, which is a continuation of application No. 16/242,273, filed on Jan. 8, 2019, now Pat. No. 10,517,881, which is a division of application No. 15/825,982, filed on Nov. 29, 2017, now Pat. No. 10,238,666, which is a division of application No. 15/370,680, filed on Dec. 6, 2016, now Pat. No. 9,855,284, which is a division of application No. 15/222,062, filed on Jul. 28, 2016, now Pat. No. 9,598,459.

(60) Provisional application No. 62/361,125, filed on Jul. 12, 2016, provisional application No. 62/358,211, filed on Jul. 5, 2016, provisional application No. 62/352,572, filed on Jun. 21, 2016, provisional application No. 62/352,611, filed on Jun. 21, 2016, provisional application No. 62/352,576, filed on Jun. 21, 2016, provisional application No. 62/352,624, filed on Jun. 21, 2016, provisional application No. 62/349,235, filed on Jun. 13, 2016, provisional application No. 62/345,095, filed on Jun. 3, 2016, provisional application No. 62/345,319, filed on Jun. 3, 2016, provisional application No. 62/342,967, filed on May 29, 2016, provisional application No. 62/342,965, filed on May 29, 2016, provisional application No. 62/342,966, filed on May 29, 2016, provisional application No. 62/342,103, filed on May 26, 2016, provisional application No. 62/339,906, filed on May 22, 2016, provisional application No. 62/339,909, filed on May 22, 2016, provisional application No. 62/314,046, filed on Mar. 28, 2016, provisional application No. 62/299,120, filed on Feb. 24, 2016, provisional application No. 62/296,673, filed on Feb. 18, 2016, provisional application No. 62/280,073, filed on Jan. 18, 2016, provisional application No. 62/271,038, filed on Dec. 22, 2015, provisional application No. 62/241,875, filed on Oct. 15, 2015, provisional application No. 62/220,583, filed on Sep. 18, 2015, provisional application No. 62/282,525, filed on Aug. 3, 2015.

(51) Int. Cl.
| | |
|---|---|
| C07D 407/14 | (2006.01) |
| A61K 31/485 | (2006.01) |
| A61K 31/513 | (2006.01) |
| A61K 31/57 | (2006.01) |
| A61K 31/58 | (2006.01) |
| A61K 31/7068 | (2006.01) |
| A61K 45/06 | (2006.01) |
| C07H 19/06 | (2006.01) |
| C07H 19/067 | (2006.01) |
| C07J 17/00 | (2006.01) |
| C07J 41/00 | (2006.01) |

(52) U.S. Cl.
CPC ............ *A61K 31/58* (2013.01); *A61K 31/485* (2013.01); *A61K 31/513* (2013.01); *A61K 31/57* (2013.01); *A61K 31/7068* (2013.01); *A61K 45/06* (2013.01); *C07H 19/06* (2013.01); *C07H 19/067* (2013.01); *C07J 17/00* (2013.01); *C07J 41/0005* (2013.01)

(58) Field of Classification Search
CPC ......... C07D 407/14; C07J 9/005; C07J 17/00; C07J 41/0005; A61K 31/513; A61K 31/57; A61K 31/58; A61K 31/7068; A61K 31/485; A61K 45/06; C07H 19/06
See application file for complete search history.

(56) References Cited

U.S. PATENT DOCUMENTS

| | | | | |
|---|---|---|---|---|
| 8,986,677 B2 * | 3/2015 | Altschul | ................ | A61K 31/58 |
| | | | | 424/78.08 |
| 9,598,459 B2 * | 3/2017 | Altschul | ................ | A61K 31/58 |
| 9,855,284 B2 * | 1/2018 | Altschul | ................ | A61K 45/06 |
| 9,878,139 B2 * | 1/2018 | Altschul | ............ | A61B 5/14542 |
| 10,010,703 B2 * | 7/2018 | Altschul | ............ | A61B 5/14546 |
| 10,245,323 B2 * | 4/2019 | Altschul | ................ | A61B 5/073 |
| 11,040,037 B2 * | 6/2021 | Altschul | ................ | A61P 31/12 |

(Continued)

*Primary Examiner* — Brenda L Coleman

(57) ABSTRACT

This invention relates the use of cortisol blockers (e.g., glucocorticoid receptor [GR] antagonists) for the treating or preventing viral infections, treating or preventing treatment resistant prostate cancer, treating or preventing neoplasia, and treating or preventing infection related to acute or chronic injury or disease.

14 Claims, 16 Drawing Sheets

(56) References Cited

U.S. PATENT DOCUMENTS 11,527,315 B2 * 12/2022 Altschul ................ A61K 31/58
11,702,443 B2 *  7/2023 Altschul .............. A61K 31/655
                                                              514/49

* cited by examiner unnatural ent-(-)-PT150 | natural steroid enantiomer (+)-PT150 mirror plane

PHARMACEUTICAL COMPOSITIONS AND METHODS

This is a Continuation application which claims the benefit under 35 U.S.C. § 120 of application Ser. No. 16/690,282 filed Nov. 21, 2019 which is a Continuation application of U.S. Ser. No. 16/242,273 filed Jan. 8, 2019 which is a Divisional application of U.S. Ser. No. 15/825,982, filed Nov. 29, 2017, now U.S. Pat. No. 10,238,666 issued Mar. 26, 2019, which is a Divisional application of U.S. Ser. No. 15/370,680 filed Dec. 6, 2016 now U.S. Pat. No. 9,855,284 issued Jan. 2, 2018, which is a Divisional application of U.S. Ser. No. 15/222,062, filed Jul. 28, 2016, now U.S. Pat. No. 9,598,459, issued Mar. 21, 2017, which claims benefit under 35 U.S.C. § 119(e) of U.S. Provisional Patent Application No. 62/282,525, filed Aug. 3, 2015; U.S. Provisional Patent Application No. 62/220,583, filed Sep. 18, 2015; U.S. Provisional Patent Application No. 62/241,875, filed Oct. 15, 2015; U.S. Provisional Patent Application No. 62/271,038, filed Dec. 22, 2015; U.S. Provisional Patent Application No. 62/280,073, filed Jan. 18, 2016; U.S. Provisional Patent Application No. 62/296,673, filed Feb. 18, 2016; U.S. Provisional Patent Application No. 62/299,120, filed Feb. 24, 2016; U.S. Provisional Patent Application No. 62/314,046, filed Mar. 28, 2016; U.S. Provisional Patent Application No. 62/339,909, filed May 22, 2016; U.S. Provisional Patent Application No. 62/339,906, filed May 22, 2016; U.S. Provisional Patent Application No. 62/342,103, filed May 26, 2016; U.S. Provisional Patent Application No. 62/342,965, filed May 29, 2016; U.S. Provisional Patent Application No. 62/342,966, filed May 29, 2016; U.S. Provisional Patent Application No. 62/342,967, filed May 29, 2016; U.S. Provisional Patent Application No. 62/345,319, filed Jun. 3, 2016; U.S. Provisional Patent Application No. 62/345,095, filed Jun. 3, 2016; U.S. Provisional Patent Application No. 62/349,235, filed Jun. 13, 2016; U.S. Provisional Patent Application No. 62/352,624, filed Jun. 21, 2016; U.S. Provisional Patent Application No. 62/352,611, filed Jun. 21, 2016; U.S. Provisional Patent Application No. 62/352,572, filed Jun. 21, 2016; U.S. Provisional Patent Application No. 62/352,576, filed Jun. 21, 2016; U.S. Provisional Patent Application No. 62/358,211, filed Jul. 5, 2016; U.S. Provisional Patent Application No. 62/361,125, filed Jul. 12, 2016, the disclosures of which are incorporated herein in their entirety.

SPECIFICATION

Background of the Invention

This invention relates the use of cortisol blockers (e.g., glucocorticoid receptor [GR] antagonists) for the treating or preventing viral infections, treatment resistant prostate cancer, treating or preventing neoplasia, and treating or preventing infection related to acute or chronic injury or disease.

Rapid advances in technology of all kinds and advances in travel and globalization have had substantial impacts on improving the human condition within the United States and internationally. However, both all of these advances have proven to be a double-edged sword, allowing for the easy spread of invasive species and disease, whether it be accidental or intentional. The United States government has been proactive in its work to legislate and fund medical countermeasures work in response to the potential for public health emergencies initiated by the introduction of pathogens. Key among these responses have been the 2004 Project Bioshield Act and the 2006 Pandemic and All Hazards Preparedness Act, the latter of which provides opportunities through the Biomedical Advanced Research and Development Authority (BARDA).

The National Institute of Allergy and Infectious Diseases Institutes of Health (NIAID), a component of the National Institute of Health (NIH), maintains a list of emerging infectious diseases and pathogens for purposes of prioritization and research guidance. Pathogens are prioritized from A-C based on the traits of transmissibility, morbidity, mortality and diagnostics. Additionally, a list of emerging pathogens and diseases is included, which are unclassified with a priority level. These lists were used as a springboard for study of a series of compounds developed by Palisades Therapeutics (PT), a division of Pop Test Oncology LLC, that have been demonstrated to have antiviral activity against a wide range of human pathogens.

The following sections will provide detailed information on the compounds PT150 and PT155, and viral pathogens from the NIAID lists against which they show, or are hypothesized to show, activity. We confirmed this activity both in vitro and in animal models. This activity includes Zika virus. We believe their activity levels as antivirals against Flavivirus, and possibly other RNA virus, prioritizes their movement into clinical testing.

PT-150 is a re-purposed drug acquired from a major pharmaceutical company that has a transferable IND that would allow it to be rapidly placed into a human clinical trial population if it is determined that this is justified. The compound previously completed all of its IND enabling preclinical studies, a significant Phase 1 study in humans and two large Phase 2 human trials for psychotic depression. PT-150 has unique properties as an antiviral drug in that it has the ability to penetrate to sanctuary sites like the brain, thymus, and testicles. It, thus, may have the potential to clear virus from these sites through direct antiviral activity whereby infected cells are inhibited from replicating virus and are cleared by apoptosis.

PT-155 is a derivative of PT-150 that has demonstrated even higher activity related to the putative mechanism of action that could result in even greater efficacy. PT150 would require a Phase III Clinical Trial. PT155 would require IND enabling safety pharmacology and toxicology studies and IND enabling CMC programs.

PT-150 (formerly Org34517) and its derivative molecules PT-155 and PT-156 have at least two general mechanisms of anti-viral action effect against a broad array of viruses infecting animals and humans. The first anti-viral effects are mediated through binding of these molecules to glucocorticoid response elements (GREs) present in some viral genomes. The second is through binding of these molecules to phosphatidylserine (PS) present in the envelope of all enveloped viruses.

The mechanism of action through binding to GRE's is as follows:

Viruses that infect animals and humans infect cells by placing their genetic material within the cytoplasm and/or nucleoplasm of the infected cell. "Response elements" within the genome, which may comprise coding regions or non-coding regions, respond to molecular signaling of the host cell and/or other elements of the virus' own molecular network. Viruses often have GREs, namely response elements that are under the influence of glucocorticoid signaling mediated by the binding of cortisol (or other glucocorticoids) to the glucocorticoid receptor (GCR).

The viruses that have been identified as having GRE's include: Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus Binding of PT-155, as a GCR antagonist, as well as of its derivatives, including but not limited to PT-155 and PT-156, also modulates the viral GRE to directly or indirectly inhibit fundamental viral functions (including, but not limited to genetic replication, production of virus-associated proteins, assembly of genetic material and viral proteins into complete viruses, increasing genetic diversity, promotion of viral active or passive virus release from the cell, and viral infectivity).

Moreover, these viruses contain viral DNA transcripts that are pro-viruses that enable viruses to remain latent in sequestered cellular compartments in the body; these DNA pro-viral genomes are responsible for latent infection which may erupt into full viral replication in situations when an individual becomes immunocompromised or when suppressive anti-viral regimens are interrupted. Binding of these molecules inactivates such pro-viral activities by either inactiving the pro-virus directly or by causing pro-viral genomic mutations that trigger p53 mediated host cell apoptosis. Either way, the pro-viral genome is destroyed. In these susceptible viruses, PT-150, PT-155, and PT-156, as well as other possible derivatives of these molecules, will lead to cure of chronic viral infection.

The mechanisms of anti-viral action related to PS binding are as follows:

PS is normally sequestered to the inner leaflet of the plasma membrane bilayer, but during apoptosis the mechanism that normally maintains PS in the inner leaflet is down-regulated, allowing the appearance of PS on the cell surface. PS exposure is recognition signal for phagocytic cells that clear dying cells. Several macrophage receptors have been implicated in recognizing PS on apoptotic cells, including various scavenger receptors, CD36, CD14, and PS receptor (PSR). Thus, PS has a demonstrated ability to mediate cell-cell interactions and to function as a ligand for a variety of PS-binding receptors.

Enveloped viruses expose PS on their host-captured lipid bilayer membranes constantly. Enveloped viruses utilize this PS-exposure to evade attacks by the human immune system and to enter phagocytic cells like monocytes/macrophages making its appearance in the viral membrane highly suspect as a factor in virus-target cell fusion.

Viruses that infect animals and humans infect cells by placing their genetic material within the cytoplasm and/or nucleoplasm of the infected cell. "Response elements" within the genome, which may comprise coding regions or non-coding regions, respond to molecular signaling of the host cell and/or other elements of the virus' own molecular network. Viruses often have "glucocorticoid response elements" (GRE), namely response elements that are under the influence of glucocorticoid signaling mediated by the binding of cortisol (or other glucocorticoids) to the glucocorticoid receptor (GCR).

This binding, which is activating, leads to signaling cascades modulating endogenous GRE of the host cell as well as viral GRE. Modulation of the viral GRE may directly or indirectly promote viral physiology that will promote fundamental viral functions (including, but not limited to genetic replication, production of virus-associated proteins, assembly of genetic material and viral proteins into complete viruses, increasing genetic diversity, promotion of viral active or passive virus release from the cell, and viral infectivity.

ORG 34517, PT150, PT155, PT156, PT157, PT158, and TCY1 are members of a class of therapeutic agents designed to block the glucorticoid receptor (GR), acting as an antagonist for endogenous cortisol. Its primary developmental pathway has been as a treatment for neuropsychiatric diseases that are characterized by dysregulated signaling in the hypothalamic-pituitary-adrenal axis, often with higher than normal circulating levels of endogenous cortisol. Of particular note are the phase 2 clinical trials that have been completed for the treatment of psychotic depression. Other possible uses in this disease category which are under investigation include: post-traumatic stress disorder, weight gain in patients requiring long term anti-psychotic medication, hospital delirium of the elderly, etc.

The endogenous glucocorticoids are steroids predominantly produced in the adrenal cortex. Glucocorticoids are important steroids for intermediary metabolism, immune, musculoskeletal, connective tissue and brain function. The main glucocorticoid in the body is cortisol. The production and secretion of cortisol is governed by a complex and highly efficient system that includes the hypothalamus, pituitary and the adrenal glands i.e., hypothalamic-pituitary-adrenal axis (HPA). Cortisol secretion has a circadian release rhythm with peak values in early morning and trough values at midnight.

The production and secretion of the most important glucocorticoid, cortisol, is governed by a complex and highly efficient system that includes the hypothalamus, pituitary and the adrenal glands i.e., hypothalamic-pituitary-adrenal axis. Cortisol secretion is regulated by the suprachiasmatic nucleus of the hypothalamus into a circadian release rhythm. The timing is synchronized with the solar day by dark-light shifts, which normally reflect the habitual sleep-wake pattern. Therefore in healthy persons, the cortisol secretion has a 24-hour circadian pattern with peak serum levels in the early morning, 3-6 hours after onset of sleep, and nadir levels around midnight. Physical and psychological stressors also activate cortisol secretion. Changed patterns of serum cortisol levels have been observed in connection with abnormal adrenocorticotropic hormone (ACTH), levels, clinical depression, psychological stress, and physiological stressors such as hypoglycemia, illness, fever, trauma, surgery, fear, pain, physical exertion, or temperature extremes. Cortisol levels and responsiveness may also differ from normal for elderly individuals and in individuals with autism or Asperger's syndrome.

Glucocorticoids (GCs) such as, in humans, cortisol, perform several important functions. These include participating in the regulation of carbohydrate, protein and fat metabolism by signaling the liver to make glucose and glycogen, the adipose tissues to release lipids and fatty acids into the bloodstream, and the skeletal muscles to release proteins or amino acids into the bloodstream. GCs also decrease bone formation.

GCs also regulate the body's inflammatory response as well. GCs are part of the feedback mechanism in the immune system that inhibits immune activity (i.e., inflammation). GCs cause their effects by binding to the GCR. The activated GCR complex in turn up-regulates the expression of anti-inflammatory proteins in the nucleus (a process known as transactivation) and represses the expression of pro-inflammatory proteins in the cytosol by preventing the translocation of other transcription factors from the cytosol into the nucleus (transrepression) (Rhen T and Cidlowski J A. NEJM 2005; 353: 1711-23).

GCR antagonist or active agent therapy is helpful in patients with abnormally high levels of cortisol (but maintained circadian rhythm), over responsiveness to normal levels, or high night time cortisol levels as a feature of disrupted circadian rhythm. Such altered cortisol physiology may relate to acute or chronic stress (e.g. related to physical or psychological trauma) or as an age related change in elderly individuals. Successful therapeutic use of such agents is thus often dependent on determining circadian cortisol levels (either peak levels during the day, e.g., at noon, or measurements taken every 4 hours or 6 hours over a 24 hour period). This combined system of salivary cortisol quantification as an enabling device for its paired GCR antagonist will identify individuals for whom GCR antagonist or active agent therapy has a benefit.

The glucocorticoid receptor (GR) is expressed at high levels in some normal tissues, but not in others. Likewise, malignant tumors of diverse types and sites have variable GR expression. When present in normal or tumor (benign or malignant) tissues, this GR expression may be variously located in some or all of their cellular sub-compartments: 1. stem cells; 2. progenitor (so called "transit amplifying") cell descendants of activated stem cells; and 3. differentiated progeny of activated stem or progenitor cells.

The present invention therefore relates to the use of GR antagonists or active agents (e.g., ORG34517, PT150—a relatively specific GR antagonist, RU486—a non-specific GR antagonist, and others), optionally in combination with at least one other agent, for treating or preventing treatment resistant prostate cancer, treating or preventing neoplasia, and/or treating or preventing infection related to acute or chronic injury or disease.

ORG 34517, PT150, PT155, PT156, PT157, PT158, TCY1 are members of a class of therapeutic agents designed to block the glucocorticoid receptor (GR), acting as an antagonist for endogenous cortisol. Its primary developmental pathway has been as a treatment for neuropsychiatric diseases that are characterized by dysregulated signaling in the hypothalamic-pituitary-adrenal axis, often with higher than normal circulating levels of endogenous cortisol. Of particular note are the phase 2 clinical trials that have been completed for the treatment of psychotic depression. Other possible uses in this disease category which are under investigation include: post-traumatic stress disorder, weight gain in patients requiring long term anti-psychotic medication, hospital delirium of the elderly, etc. In addition, the diverse data indicate a possible role for GR-blockade as a means of promoting chemo-sensitization of target tumors. Pre-clinical trials demonstrate significant outcomes—breast cancer growth slowed and reversed. These are preclinical trials in which the company has successfully demonstrated the efficacy of a chemotherapy sensitizer for "triple negative" breast cancer, ovarian cancer and prostate cancer.

The "triple negative" breast cancer is the most difficult to treat type of breast cancer, and is indicated by the patient testing negative for estrogen-receptor, progesterone-receptor and her-2/neu. The triple negative breast cancer is resistant to chemotherapy. Primary drug resistance and early onset of resistance are seen in other tumor types, as well for example in liver and ovarian cancers, where there is a significant unmet medical need for effective therapy. Chemotherapy is still a key approach to cancer treatment. Chemosensitizers would contribute to improve the efficacy of current therapeutic drugs and potentially improve their side effect profile. The world cancer market was estimated at $23 billion in 2004 and is expected to grow to at least $61 billion by 2013 with a CAGR of 14.7%.

The present invention provides a low cost rapid response diagnostic system to determine salivary cortisol levels in patients selected as potential candidates for GCR (glucocorticoid receptor) antagonist therapy utilizing a GCR antagonist or active agent such as ORG 34517, PT150, PT155, PT156, PT157, PT158, TCY1, combinations thereof, and pharmaceutically acceptable salts thereof. The inventors have developed a saliva based diagnostic device for cortisol detection to accompany the development of ORG 34517, PT150, PT155, PT156, PT157, PT158, TCY1, combinations thereof, and pharmaceutically acceptable salts thereof as a therapeutic agent for multiple indications. Clinical testing of cortisol levels in patients is a high cost, laborious test that can be salivary or serum, with samples taken from a patient and sent to a lab to await results. The cost and time factor for such tests has, to date, been prohibitive, preventing the rapid quantitative determination necessary to assign treatment with a glucocorticoid receptor (GCR) antagonist due to the inability to make the determinations of cortisol levels at point of need or to monitor changes in cortisol as a measure of treatment response. By allowing the physician to determine the elevated cortisol level of a patient and in turn provide a therapeutic for such elevation at point of measurement, the physician can qualify the best candidates suited for this type of therapeutic. The system also enables continual monitoring of the patient during treatment for assessment of responsiveness to treatment.

The present invention provides a system in which an apparatus uses a high void volume carrier to absorb sufficient amounts of saliva to then be placed into a reaction vessel with a reagent. The reagent is mixed with the sample and then is combined with, for example, a fluorescent ligand or pigment-labeled ligand and placed into a device to determine salivary cortisol levels of the patient in less than 5 minutes, in either a portable, miniaturized fluorescence polarization reader (in the former case) or into a lateral flow device (in the latter) for measuring amounts of substrate in a small amount of fluid by direct or indirect methods.

The reader apparatus, for example, provides temperature control and on-board mixing as an aid in viscosity control of the reaction to ensure better accuracy and precision. The invention and method for non-invasive sampling and detecting the presence of a biological substance of interest in a test sample of, for example, saliva, or a bodily fluid, combining said test sample with a buffering system (Reagent 1) containing viscosity controllers and stabilizers in a reaction vessel, mix solution well, combining said test sample and buffering system mixture with a fluorescence-labeled ligand (Reagent 2) to said biological substance (assay solution) in a reaction vessel, mix solution well, and detecting a change of the assay solution in the fluorescence polarization reader, or a pigment labeled ligand.

The ongoing development of the present invention has yielded new findings; the thiosemicarbazone of ORG34517 could not be dimerized by treatment with sodium hydroxide NaOH. However, in-depth considerations indicated that this is in fact better for the goal to eliminate human hepatitis B and immunodeficiency proviruses, since the crucial point is the binding mode on human glucocorticoid receptor (hGR). It could be shown that the anticipated dimer would not bind to hGR. The thiosemicarbazone of ORG34517 could bind to hGR and force nuclear translocation of the ligand-receptor complex. This is important, since nuclear translocation is the prerequisite for our mode of action, and the ORG34517- hGR complex itself does not translocate into the nucleus. In addition, the thiosemicarbazone of ORG34517 will be activated to reactive sulfenic acid and carbodiimide metabolites by human flavin-containing monooxygenases (hFMO1, hFMO2.1, hFMO3). The activation is achieved not by an activated bond in a putative dimer, but by metabolic activation with human enzymes. In addition, oxidative stress is enhanced in human hepatitis B and human immunodeficiency virus-infected cells, this might lead to enhanced activation in virus-infected cells. The material PT155 is the complex of choice to be used in antiviral studies in vitro. The present invention relates to the use of glucocorticoid receptor (GCR) antagonists or active agents (e.g. ORG 34517, PT150, PT155, PT156, PT157, PT158, TCY1, combinations thereof, and pharmaceutically acceptable salts thereof) enabled by a device for rapidly, sensitively, specifically quantifying salivary cortisol levels as a surrogate for serum cortisol levels in a low cost manner. One purpose of this combination of inventions is to determine patients who have non-normal cortisol produced by the adrenal cortex or disordered circadian rhythms as a method for selecting subjects for GCR antagonist or active agent therapy for whom it is likely to have beneficial and/or therapeutic effects, i.e., those with abnormal high levels (but maintained circadian rhythm), over responsiveness to normal levels, high night-time cortisol levels as a feature of disrupted circadian rhythm. The rapid, sensitive, and inexpensive test can also be used to monitor changes in cortisol levels in response to treatment, in patients who have nonnormal cortisol produced by the adrenal cortex or disordered circadian rhythms as a method for selecting subjects for GCR antagonist or active agent therapy for whom it is likely to have beneficial and/or therapeutic effects, but also in patients having normal baseline cortisol at the start of treatment, but for whom changing cortisol levels during treatment will indicate responsiveness to the GCR antagonist.

The endogenous glucocorticoids are steroids predominantly produced in the adrenal cortex. Glucocorticoids are important steroids for intermediary metabolism, immune, musculoskeletal, connective tissue and brain function. The main glucocorticoid in the body is cortisol. The production and secretion of cortisol is governed by a complex and highly efficient system that includes the hypothalamus, pituitary and the adrenal glands i.e., hypothalamic-pituitary-adrenal axis (HPA). Cortisol secretion has a circadian release rhythm with peak values in early morning and trough values at midnight.

The production and secretion of the most important glucocorticoid, cortisol, is governed by a complex and highly efficient system that includes the hypothalamus, pituitary and the adrenal glands i.e., hypothalamic-pituitary-adrenal axis. Cortisol secretion is regulated by the suprachiasmatic nucleus of the hypothalamus into a circadian release rhythm. The timing is synchronized with the solar day by dark-light shifts, which normally reflect the habitual sleep-wake pattern. Therefore in healthy persons, the cortisol secretion has a 24-hour circadian pattern with peak serum levels in the early morning, 3-6 hours after onset of sleep, and nadir levels around midnight. Physical and psychological stressors also activate cortisol secretion. Changed patterns of serum cortisol levels have been observed in connection with abnormal adrenocorticotropic hormone (ACTH), levels, clinical depression, psychological stress, and physiological stressors such as hypoglycemia, illness, fever, trauma, surgery, fear, pain, physical exertion, or temperature extremes. Cortisol levels and responsiveness may also differ from normal for elderly individuals and in individuals with autism or Asperger's syndrome.

Glucocorticoids (GCs) such as, in humans, cortisol, perform several important functions. These include participating in the regulation of carbohydrate, protein and fat metabolism by signaling the liver to make glucose and glycogen, the adipose tissues to release lipids and fatty acids into the bloodstream, and the skeletal muscles to release proteins or amino acids into the bloodstream. GCs also decrease bone formation.

GCs also regulate the body's inflammatory response as well. GCs are part of the feedback mechanism in the immune system that inhibits immune activity (i.e., inflammation). GCs cause their effects by binding to the GCR. The activated GCR complex in turn up-regulates the expression of anti-inflammatory proteins in the nucleus (a process known as transactivation) and represses the expression of pro-inflammatory proteins in the cytosol by preventing the translocation of other transcription factors from the cytosol into the nucleus (transrepression) (Rhen T and Cidlowski J A. NEJM 2005; 353: 1711-23).

GCR antagonist or active agent therapy is helpful in patients with abnormally high levels of cortisol (but maintained circadian rhythm), over responsiveness to normal levels, or high night time cortisol levels as a feature of disrupted circadian rhythm. Successful therapeutic use of such agents is thus dependent on determining circadian cortisol levels (either peak levels during the day, e.g., at noon, or measurements taken every 4 hours or 6 hours over a 24 hour period). This combined system of salivary cortisol quantification as an enabling device for its paired GCR antagonist will identify individuals for whom GCR antagonist or active agent therapy has a benefit.

The glucocorticoid receptor (GR) is expressed at high levels in some normal tissues, but not in others. Likewise, malignant tumors of diverse types and sites have variable GR expression. When present in normal or tumor (benign or malignant) tissues, this GR expression may be variously located in some or all of their cellular subcompartments: 1. stem cells; 2. progenitor (so called "transit amplifying") cell descendants of activated stem cells; and 3. differentiated progeny of activated stem or progenitor cells.

As an example, in the gastrointestinal tract, GR are highly expressed in esophageal squamous epithelia, hepatocytes, and pancreatic islet cells, but are not highly expressed in other gastrointestinal epithelia (stomach, small and large intestines, pancreatic and biliary ducts). In corresponding malignancies arising in these epithelia, hepatocellular carcinoma (HCC) and squamous cell carcinomas (SCC) of the esophagus have consistently highGR expression. Gastric and colorectal adenocarcinomas have little to no GR expression.

Dexamethasone (DEX), a binding activator of GR, has been found to confer chemoresistance in oesophageal SCC and HCC cells, suggesting that GR expression may be biologically important in some GR-expressing carcinomas. This not only suggests why DEX or other glucocorticoids are not useful in treatment of these malignancies, but it implies that endogenous, circulating cortisol itself may actually promote chemoresistance, even in the absence of iatrogenic glucocorticoid administration. Therefore, these findings suggest that blockade of GR within such malignant tumors, by preventing activation by endogenous, circulating cortisol, can play a role in maintaining or promoting chemosensitivity and/or treating neoplasia.

The present invention therefore relates to the use of GR antagonists or active agents (e.g., ORG 34517, PT150, PT155, PT156, PT157, PT158, TCY1, combinations thereof, and pharmaceutically acceptable salts thereof) for the treatment of, for example, esophageal SCC and HCC or other tumors with high GR expression as a means of inhibiting promotion of chemoresi stance by endogenous cortisol. These effects may be present in all tumor cells or, when tumors have stem or progenitor cell compartments, these, specifically, as well. Thus, the present invention relates to the inhibition of chemoprevention in the bulk of cells making up a given tumor and/or in the rare stem/progenitor cells within the tumor that are often responsible for tumor resistance to therapy and reoccurrence, i.e., as a novel, targeted "cancer stem cell" treatment.

To avoid possible negative side effects of systemic blockade of GR, the present invention further relates to localized tumor treatment with GR antagonists through direct vascular infusion of tumor feeding vessels or by direct, intratumoral injection.

The present invention relates to the use of GR antagonists for the treatment of, for example, breast and other cancers. The invention is based on the observation that GR inhibition will increase tumor cell susceptibility. GR antagonists will block anti-apoptotic GR signaling in GR-overexpressing breast cancer cells and subsequently render breast cancer cells more susceptible to conventional and novel cytotoxic therapies (via blocking GR's pro-cell survival signaling pathway).

All references cited herein are incorporated herein by reference in their entireties.

BRIEF SUMMARY OF THE INVENTION

The invention provides a compound selected from the group consisting of:

PT155:

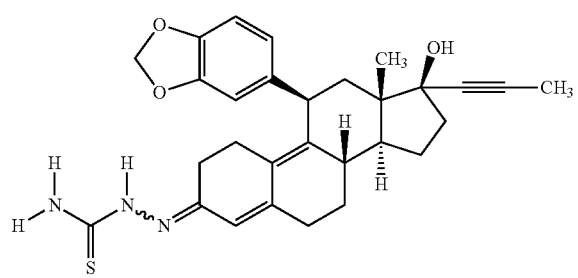

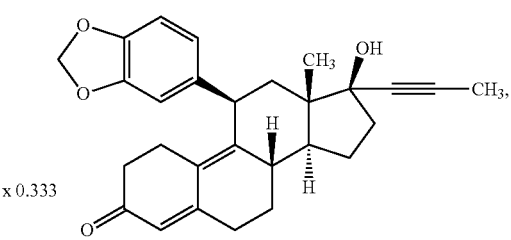

or pharmaceutically acceptable salts thereof;

PT156:

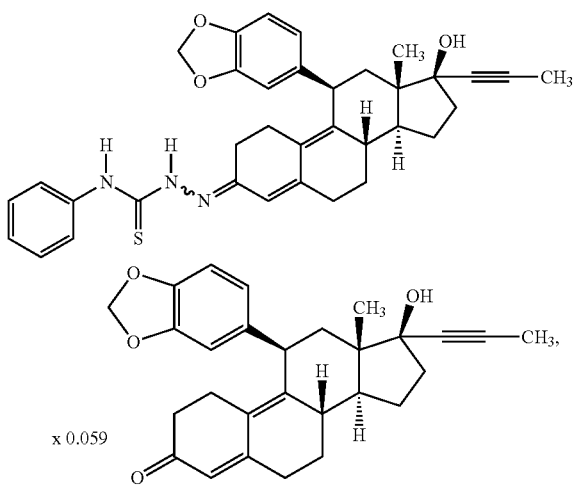

or pharmaceutically acceptable salts thereof;

PT157:

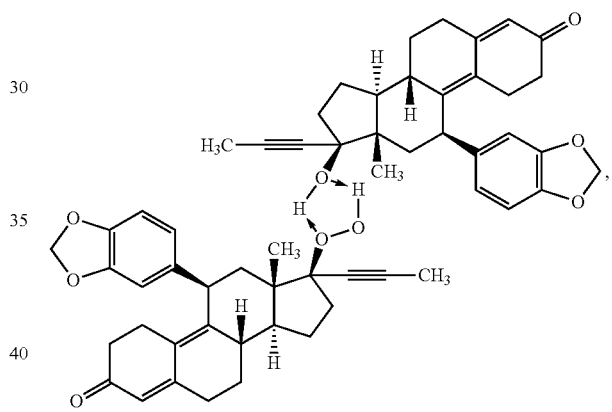

or pharmaceutically acceptable salts thereof;

PT158:

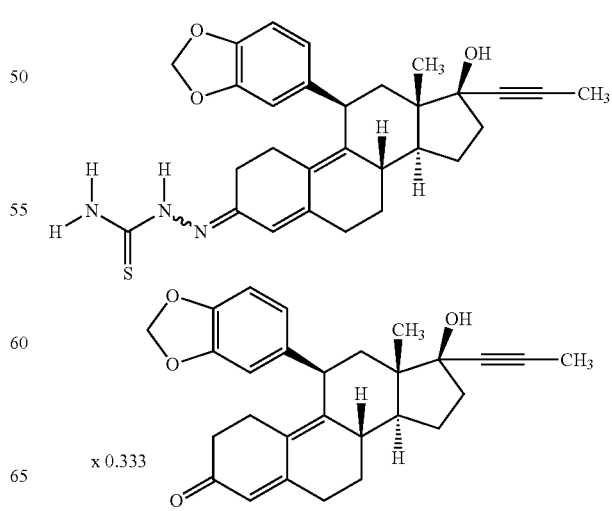

-continued

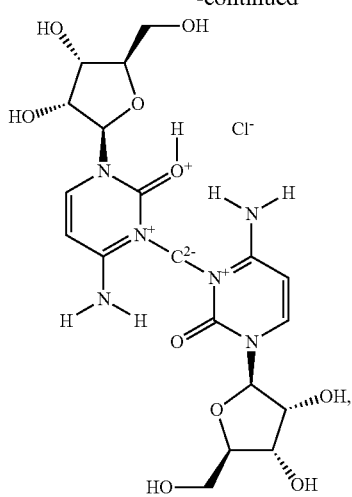

or pharmaceutically acceptable salts thereof;
TCY1:

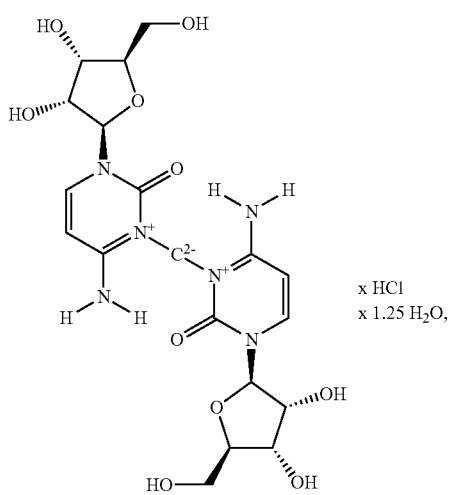

x HCl
x 1.25 H$_2$O, or pharmaceutically acceptable salts thereof; and, combinations thereof.

The invention provides a pharmaceutical composition comprising a therapeutically effective amount of at least one active agent, wherein the active agent is selected from the group consisting of:

PT155:

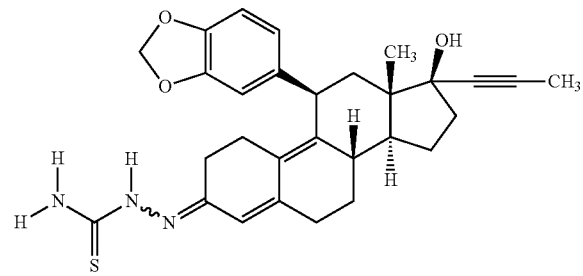

-continued

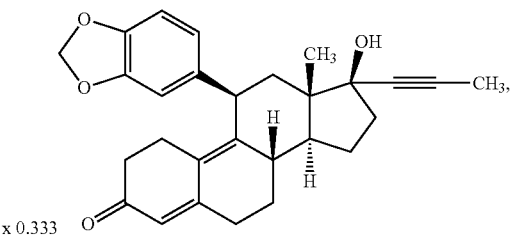

x 0.333 or pharmaceutically acceptable salts thereof;
PT156:

or pharmaceutically acceptable salts thereof;
PT157:

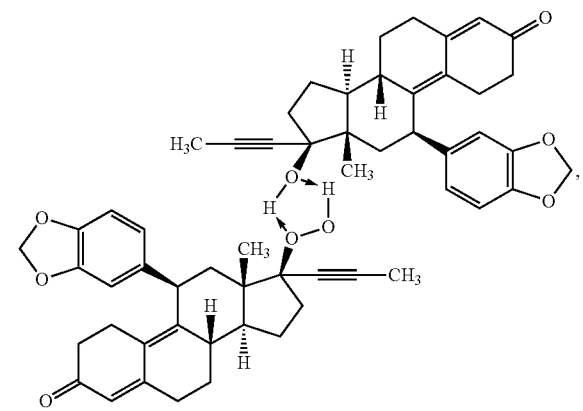

or pharmaceutically acceptable salts thereof;

PT158:

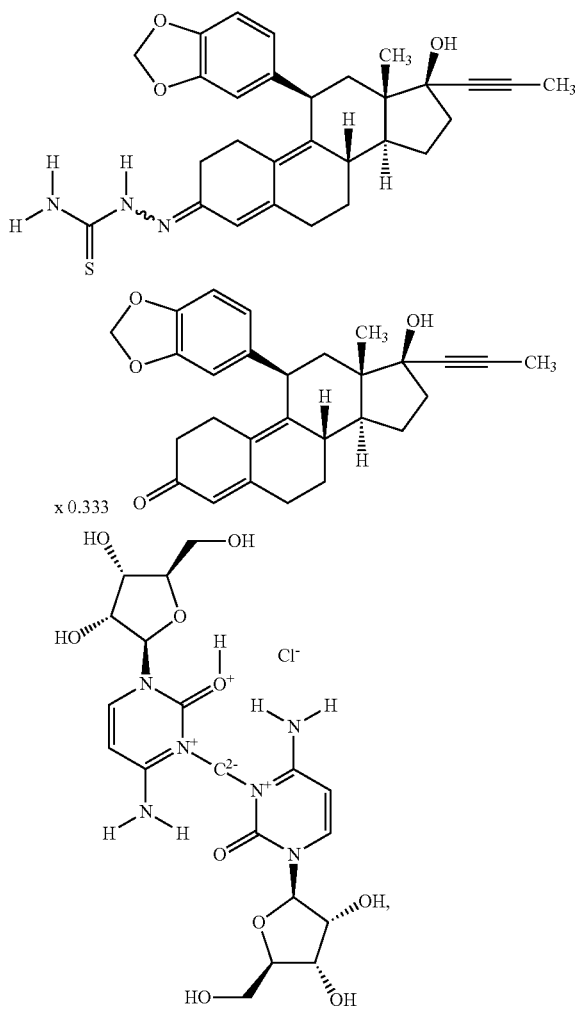

or pharmaceutically acceptable salts thereof;

TCY1:

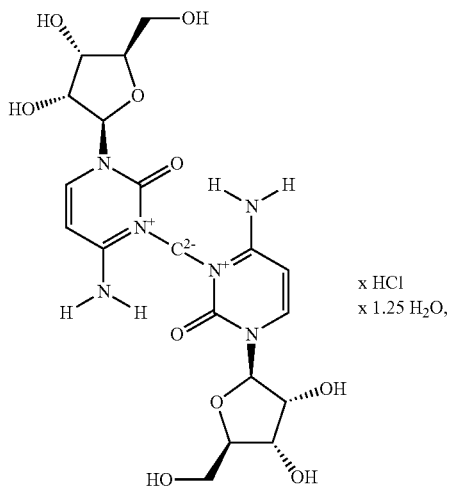 [SMILES: Nc1ccn([C@@H]2O[C@H](CO)[C@@H](O)[C@H]2O)c(=O)[n+]1[C-2][n+]1c(N)ccn([C@@H]2O[C@H](CO)[C@@H](O)[C@H]2O)c1=O]

or pharmaceutically acceptable salts thereof; combinations thereof; optionally, at least one additional pharmaceutically active agent; and at least one pharmaceutically acceptable excipient.

The invention provides a pharmaceutical composition in a dosage form selected from the group consisting of a minicapsule, a capsule, a tablet, an implant, a troche, a lozenge, a minitablet, a temporary or permanent suspension, an injectable, an ovule, a suppository, a wafer, a chewable tablet, a quick or fast dissolving tablet, an effervescent tablet, a buccal or sublingual solid, a granule, a film, a sprinkle, a pellet, a topical formulation, a patch, a bead, a pill, a powder, a triturate, a smart pill, a smart capsule, a platelet, a strip, and a sachet.

The invention provides a pharmaceutical composition in a dosage form for topical application, and at least one pharmaceutically acceptable excipient. The invention provides a pharmaceutical composition in a dosage form for topical application wherein said formulation is in a form selected from the group consisting of: cream, lotion, gel, oil, ointment, suppository, spray, foam, liniment, aerosol, buccal and sublingual tablet or a transdermal device or patch for absorption through the skin or mucous membranes.

The invention provides a kit for treating or preventing a condition in a patient, the kit comprising: (a) the pharmaceutical composition in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for using the pharmaceutical composition.

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof, wherein the viral condition is to prevent or eliminate acute viral infection, to diminish intensity of viral infection, to diminish length of viral infection, to speed time to resolution and healing of viral infection, to speed time to suppression of viral infection, to increase likelihood of viral eradication, and/or to diminish infectivity of viral infection, with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting the patient in need of treating and/or preventing a viral condition; administering at least one active agent selected from the group consisting of PT150, PT155, PT156, PT157, PT158, TCY1, combinations thereof, and pharmaceutically acceptable salts thereof, wherein the viral condition is to prevent acute viral infection from becoming chronic active or latent infection with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting a patient in need of treating and/or preventing a viral condition; administering at least one active agent selected from the group consisting of PT150, PT155, PT156, PT157, PT158, TCY1, combinations thereof, and pharmaceutically acceptable salts thereof, wherein the viral condition is to prevent chronic latent viral infection from becoming active (reactivation), to diminish intensity of viral reactivation, to diminish length of viral reactivation, to speed time to resolution and healing of viral reactivation, to speed time to suppression of viral reactivation, to increase likelihood of viral eradication, and/or to diminish infectivity of viral reactivation with: Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting a patient in need of treating and/or preventing a viral condition; administering at least one active agent selected from the group consisting of PT150, PT155, PT156, PT157, PT158, TCY1, combinations thereof, and pharmaceutically acceptable salts thereof, wherein the viral condition is to inactivate latent pro-viral genome eliminating ("curing") chronic viral infections with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting a patient in need of treating and/or preventing a viral condition; administering an active agent selected from the group consisting of PT150, PT155, PT156, PT157, PT158, TCY1, combinations thereof, and pharmaceutically acceptable salts thereof, wherein the viral condition is to prevent or eliminate acute viral infection, to diminish intensity of viral infection, to diminish length of viral infection, to speed time to resolution and healing of viral infection, to speed time to suppression of viral infection, to increase likelihood of viral eradication, and/or to diminish infectivity of viral infection. The invention provides a method wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amaparí virus, Pichindé virus, Tacaribe virus, Junín virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); *Autographa californica* nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amaparí virus, Pichindé virus, Tacaribe virus, Junín virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus).

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof, wherein the viral condition is to prevent acute viral infection from becoming chronic active or latent infection. The invention provides a method wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amaparí virus, Pichindé virus, Tacaribe virus, Junín virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); *Autographa californica* nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amaparí virus, Pichindé virus, Tacaribe virus, Junín virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus).

The invention provides a pharmaceutical composition comprising a therapeutically effective amount of any one or more of a compound selected from the group consisting of PT150, PT155, PT156, PT157, PT158, TCY1, combinations thereof, and pharmaceutically acceptable salts thereof; at least one additional active agent selected from the group consisting of molecules with potential to bind viral PS, annexin-5, anti-PS monoclonal or polyclonal antibodies, bavituximab, and/or bind to viral glucocorticoid response elements (GREs), retinazone, RU486, or their derivatives; and at least one pharmaceutically acceptable carrier; optionally, at least one blister package; a lidded blister; a blister card or packet; a clamshell; an intravenous (IV) package, IV packette or IV container; a tray or a shrink wrap comprising the pharmaceutical composition and instructions for use of the pharmaceutical composition.

The invention provides a pharmaceutical composition comprising: a therapeutically effective amount of one or more of PT150, PT155, PT156, PT157, PT158, TCY1, combinations thereof, and pharmaceutically acceptable salts thereof; at least one additional active agent selected from the group consisting of molecules with potential to bind viral PS, annexin-5, anti-PS monoclonal or polyclonal antibodies, bavituximab, and/or bind to viral glucocorticoid response elements (GREs), retinazone and RU486 or derivatives, cell entry inhibitors, uncoating inhibitors, reverse transcriptase inhibitors, integrase inhibitors, transcription inhibitors, antisense translation inhibitors, ribozyme translation inhibitors, prein processing and targeting inhibitors, protease inhibitors, assembly inhibitors, release phase inhibitors, immunosystem modulators and vaccines, including, but not limited to Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof; at least one pharmaceutically acceptable carrier; and optionally, and at least one blister package; a lidded blister; a blister card or packet; a clamshell; an intravenous (IV) package, IV packette or IV container; a tray or a shrink wrap comprising the pharmaceutical composition and instructions for use of the pharmaceutical composition.

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of other molecules with potential to bind viral glucocorticoid response elements (GREs), retinazone, RU486, derivatives thereof, wherein the viral condition is to prevent or eliminate acute viral infection, to diminish intensity of viral infection, to diminish length of viral infection, to speed time to resolution and healing of viral infection, to speed time to suppression of viral infection, to increase likelihood of viral eradication, and/or to diminish infectivity of viral infection, with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting the patient in need of treating and/or preventing a viral condition; administering at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral glucocorticoid response elements (GREs), retinazone, RU486, and derivatives thereof, wherein the viral condition is to prevent acute viral infection from becoming chronic active or latent infection with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting a patient in need of treating and/or preventing a viral condition; administering at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral glucocorticoid response elements (GREs), retinazone, RU486, or their derivatives, wherein the viral condition is to prevent chronic latent viral infection from becoming active (reactivation), to diminish intensity of viral reactivation, to diminish length of viral reactivation, to speed time to resolution and healing of viral reactivation, to speed time to suppression of viral reactivation, to increase likelihood of viral eradication, and/or to diminish infectivity of viral reactivation with: Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting a patient in need of treating and/or preventing a viral condition; administering at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral glucocorticoid response elements (GREs), retinazone, RU486 or their derivatives wherein the viral condition is to inactivate latent pro-viral genome eliminating ("curing") chronic viral infections with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), *Cytomegalovirus* (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, *Vaccinia* virus, Cowpox virus, Monkeypox virus.

The invention provides a method of treating and/or preventing a viral condition in a patient comprising: selecting a patient in need of treating and/or preventing a viral condition; administering an active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral PS, annexin-5, anti-PS monoclonal or polyclonal antibodies, bavituximab, wherein the viral condition is to prevent or eliminate acute viral infection, to diminish intensity of viral infection, to diminish length of viral infection, to speed time to resolution and healing of viral infection, to speed time to suppression of viral infection, to increase likelihood of viral eradication, and/or to diminish infectivity of viral infection. The invention provides a method wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amaparí virus, Pichindé virus, Tacaribe virus, Junín virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); *Autographa californica* nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amaparí virus, Pichindé virus, Tacaribe virus, Junín virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus)

The invention provide s a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral PS, annexin-5, anti-PS monoclonal or polyclonal antibodies, bavituximab, wherein the viral condition is to prevent acute viral infection from becoming chronic active or latent infection. The invention provides a method wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amaparí virus, Pichindé virus, Tacaribe virus, Junín virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); *Autographa californica* nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amaparí virus, Pichindé virus, Tacaribe virus, Junín virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus)

The invention provides a pharmaceutical composition comprising: at least one active agent selected from the group consisting of PT150, PT155, PT156, PT157, PT158, TCY1, combinations thereof, and pharmaceutically acceptable salts thereof; optionally, at least one auxiliary agent selected from the group consisting of opiates. The invention provides a pharmaceutical composition wherein the composition is in a dosage form selected from the group consisting of a capsule, a tablet, a smart pill delivery device, and a smart capsule delivery device.

The invention provides a pharmaceutical composition comprising a therapeutically effective amount of one or more of PT150, PT155, PT156, PT157, PT158, TCY1, combinations thereof, and pharmaceutically acceptable salts thereof; at least one additional therapeutically active agent selected from the group consisting of molecules with potential to bind viral PS, annexin-5, anti-PS monoclonal or polyclonal antibodies, bavituximab, and/or bind to viral glucocorticoid response elements (GREs), (including, but not limited to retinazone and RU486, derivatives thereof; and optionally at least one further active agent selected from the group consisting of anti-viral medications, cell entry inhibitors, uncoating inhibitors, reverse transcriptase inhibitors, integrase inhibitors, transcription inhibitors, translation (anti sense) inhibitors, translation (ribozyme) inhibitors, prein processing and targeting inhibitors, protease inhibitors, assembly inhibitors, release phase inhibitos, immunosystem modulators and vaccines, including, but not limited to Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine, and combinations thereof; and at least one pharmaceutically acceptable carrier.

The invention provides a pharmaceutical composition comprising: i) a first therapeutic agent which is at least one an antiviral agent or pharmaceutically acceptable salt thereof; ii) a second therapeutic agent which at least one GCR antagonist selected from the group consisting of PT150, PT155, PT156, PT157, PT158, TCY1, combinations thereof, and pharmaceutically acceptable salts thereof; and iii) at least one pharmaceutically acceptable carrier; wherein the antiviral agent and the GCR antagonist are each present in an amount which, in combination, is a therapeutically effective amount for treating or preventing viral infection in a patient. The invention provides a pharmaceutical composition wherein the antiviral agent is selected from the group consisting of: Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine, and combinations thereof.

The invention provides a pharmaceutical composition comprising: i) a first therapeutic agent which is selected from the group consisting of PT150, PT155, PT156, PT157, PT158, TCY1, combinations thereof, and pharmaceutically acceptable salts thereof; ii) a second therapeutic agent which is selected from the group consisting of: cholinesterase inhibitors, Aricept, Exelon, Razadyne, memantine, and combinations thereof; and iii) at least one pharmaceutically acceptable carrier. The invention provides a pharmaceutical composition comprising: i) a first therapeutic agent which is at least one antiviral agent or pharmaceutically acceptable salt thereof; ii) a second therapeutic agent which is a GCR antagonist selected from the group consisting of PT150, PT155, PT156, PT157, PT158, TCY1, combinations thereof, and pharmaceutically acceptable salts thereof; and iii) at least one pharmaceutically acceptable carrier, wherein the pharmaceutical composition is formulated or manufactured as a liquid, an elixir, an aerosol, a spray, a powder, a tablet, a pill, a capsule, a gel, a geltab, a nano-suspension, a nano-particle, an extended release dosage form, or a topical formulation, further wherein the antiviral agent and the GCR antagonist are each present in an amount which, in combination, is a therapeutically effective amount for treating or preventing a viral infection in a patient. The invention provides a pharmaceutical composition wherein the antiviral agent is selected from the group consisting of: Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine, and combinations thereof.

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral PS, annexin-5, anti-PS monoclonal or polyclonal antibodies, bavituximab, wherein the viral condition is to prevent chronic latent viral infection from becoming active (reactivation), to diminish intensity of viral reactivation, to diminish length of viral reactivation, to speed time to resolution and healing of viral reactivation, to speed time to suppression of viral reactivation, to increase likelihood of viral eradication, and/or to diminish infectivity of viral reactivation.

The invention provides a method wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amaparí virus, Pichindé virus, Tacaribe virus, Junín virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); Autographa californica nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amaparí virus, Pichindé virus, Tacaribe virus, Junín virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus)

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral PS, annexin-5, anti-PS monoclonal or polyclonal antibodies, bavituximab, and/or bind to viral glucocorticoid response elements (GREs), retinazone, RU486 or their derivatives, wherein the at least one active agent and the at least one additional active agent may be used together or in sequence, to act in an additive or synergistic fashion to prevent or treat acute viral infection, to prevent acute viral infection from becoming latent or active chronic infection, to prevent chronic latent infection from becoming active infection, or to eliminate chronic latent viral infection.

The invention provides a method wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amaparí virus, Pichindé virus, Tacaribe virus, Junín virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); Autographa californica nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amaparí virus, Pichindé virus, Tacaribe virus, Junín virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus).

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of molecule with potential to bind to viral glucocorticoid response elements (GREs), retinazone, RU486 or their derivatives may be used together or in sequence, to act in an additive or synergistic fashion to prevent or treat acute viral infection, to prevent acute viral infection from becoming latent or active chronic infection, to prevent chronic latent infection from becoming active infection, or to eliminate chronic latent viral infection and thereby.

The invention provides a method wherein the viral condition is selected from the group consisting of treat diseases caused by viral induced or associated injuries and diseases (necrosis, inflammation, sclerosis) in tissues including, but not limited to: eye (retina, sclera, lens, iris, pupil, cornea, macula, retinal blood vessels, optic nerve), ear (ear canal, bones of middle ear, tympanic membrane, Eustachian, cochlear nerve, vestibular nerve, semicircular canals, cochlea), nose (naris, vestibule, turbinates, sinuses), oral cavity and oropharynx (lips, gingiva, hard and soft palates, salivary glands, uvula, tonsils, adenoids, teeth), central nervous system and associated structures (brain, cerebrum, cerebellum, olfactory bulb, hypothalamus, reticular formation, medulla oblongata, meninges, ventricles, thalamus, pineal gland), peripheral and enteric nervous systems (autonomic nerves, sympathetic nerves, parasympathetic nerves, sensory nerves, ganglion cells, ganglia), skin (epidermis, dermis, adnexal structures, sebaceous glands, hair follicles, stratum corneum, granular cells, spinous cells, sweat glands), respiratory tract (larynx, trachea, bronchi, bronchioles, lung, alveoli, pleura), digestive tract (pharynx, esophagus, stomach, small intestine, duodenum, jejunum, ileum, colon, rectum, appendix, anus), liver (intra- and extra-hepatic bile ducts, gallbladder, liver, hepatocytes, ductules, canals of Hering), pancreas (endocrine pancreas, exocrine pancreas, pancreatic ducts, pancreatic acini), urinary tract (renal cortex, renal tubules, renal pelvis, glomeruli, ureters, urinary bladder, urethra), male genital tract (prostate, testes, scrotum, epididymis, vas deferens, glans, foreskin, corpus spongiosum, corpus cavernosum, Cowper's gland), female genital tract (ovary, fimbria, fallopian tubes, uterus, endometrium, endocervix, endocervical glands, cervix, ectocervix, vagina, labia, placenta), endocrine system (pineal glands, pituitary gland, thyroid gland, parathyroid glands, adrenal glands, adrenal cortex, adrenal medulla), cardiovascular system (heart, pericardium, myocardium, endocardium, atria, ventricles, coronary arteries, tricuspid valve, aortic valve, mitral valve, pulmonic valve, aorta, arteries, arterioles, capillaries, venules, veins, inferior vena cava, superior vena cava, pulmonary artery, pulmonic vein), musculoskeletal system (bones, tendons, ligaments, skeletal muscle, smooth muscle, fascia) and blood (platelets, red blood cells, white blood cells, and all their precursors, and bone marrow).

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral PS, annexin-5, anti-PS monoclonal or polyclonal antibodies, bavituximab may be used together or in sequence, to act in an additive or synergistic fashion to prevent or treat acute viral infection, to prevent acute viral infection from becoming latent or active chronic infection, to prevent chronic latent infection from becoming active infection, or to eliminate chronic latent viral infection and thereby treat diseases caused by viral induced or associated injuries and diseases (necrosis, inflammation, sclerosis) in tissues including, but not limited to: eye (retina, sclera, lens, iris, pupil, cornea, macula, retinal blood vessels, optic nerve), ear (ear canal, bones of middle ear, tympanic membrane, Eustachian, cochlear nerve, vestibular nerve, semicircular canals, cochlea), nose (naris, vestibule, turbinates, sinuses), oral cavity and oropharynx (lips, gingiva, hard and soft palates, salivary glands, uvula, tonsils, adenoids, teeth), central nervous system and associated structures (brain, cerebrum, cerebellum, olvactory bulb, hypothalamus, reticular formation, medulla oblongata, meninges, ventricles, thalamus, pineal gland), peripheral and enteric nervous systems (autonomic nerves, sympathetic nerves, parasympathetic nerves, sensory nerves, ganglion cells, ganglia), skin (epidermis, dermis, adnexal structures, sebaceous glands, hair follicles, stratum corneum, granular cells, spinous cells, sweat glands), respiratory tract (larynx, trachea, bronchi, bronchioles, lung, alveoli, pleura), digestive tract (pharynx, esophagus, stomach, small intestine, duodenum, jejunum, ileum, colon, rectum, appendix, anus), liver (intra- and extra-hepatic bile ducts, gallbladder, liver, hepatocytes, ductules, canals of Hering), pancreas (endocrine pancreas, exocrine pancreas, pancreatic ducts, pancreatic acini), urinary tract (renal cortex, renal tubules, renal pelvis, glomeruli, ureters, urinary bladder, urethra), male genital tract (prostate, testes, scrotum, epididymis, vas deferens, glans, foreskin, corpus spongiosum, corpus cavernosum, Cowper's gland), female genital tract (ovary, fimbria, fallopian tubes, uterus, endometrium, endocervix, endocervical glands, cervix, ectocervix, vagina, labia, placenta), endocrine system (pineal glands, pituitary gland, thyroid gland, parathyroid glands, adrenal glands, adrenal cortex, adrenal medulla), cardiovascular system (heart, pericardium, myocardium, endocardium, atria, ventricles, coronary arteries, tricuspid valve, aortic valve, mitral valve, pulmonic valve, aorta, arteries, arterioles, capillaries, venules, veins, inferior vena cava, superior vena cava, pulmonary artery, pulmonic vein), musculoskeletal system (bones, tendons, ligaments, skeletal muscle, smooth muscle, fascia) and blood (platelets, red blood cells, white blood cells, and all their precursors, and bone marrow).

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral PS, annexin-5, anti-PS monoclonal or polyclonal antibodies, bavituximab, and/or bind to viral glucocorticoid response elements (GREs), retinazone, RU486 or their derivatives, wherein the active agents may be used together or in sequence, to act in an additive or synergistic fashion to prevent or treat acute viral infection, to prevent acute viral infection from becoming latent or active chronic infection, to prevent chronic latent infection from becoming active infection, or to eliminate chronic latent viral infection and thereby treat diseases caused by viral induced or associated injuries and diseases (necrosis, inflammation, sclerosis) in tissues including, but not limited to: eye (retina, sclera, lens, iris, pupil, cornea, macula, retinal blood vessels, optic nerve), ear (ear canal, bones of middle ear, tympanic membrane, Eustachian, cochlear nerve, vestibular nerve, semicircular canals, cochlea), nose (naris, vestibule, turbinates, sinuses), oral cavity and oropharynx (lips, gingiva, hard and soft palates, salivary glands, uvula, tonsils, adenoids, teeth), central nervous system and associated structures (brain, cerebrum, cerebellum, olvactory bulb, hypothalamus, reticular formation, medulla oblongata, meninges, ventricles, thalamus, pineal gland), peripheral and enteric nervous systems (autonomic nerves, sympathetic nerves, parasympathetic nerves, sensory nerves, ganglion cells, ganglia), skin (epidermis, dermis, adnexal structures, sebaceous glands, hair follicles, stratum corneum, granular cells, spinous cells, sweat glands), respiratory tract (larynx, trachea, bronchi, bronchioles, lung, alveoli, pleura), digestive tract (pharynx, esophagus, stomach, small intestine, duodenum, jejunum, ileum, colon, rectum, appendix, anus), liver (intra- and extra-hepatic bile ducts, gallbladder, liver, hepatocytes, ductules, canals of Hering), pancreas (endocrine pancreas, exocrine pancreas, pancreatic ducts, pancreatic acini), urinary tract (renal cortex, renal tubules, renal pelvis, glomeruli, ureters, urinary bladder, urethra), male genital tract (prostate, testes, scrotum, epididymis, vas deferens, glans, foreskin, corpus spongiosum, corpus cavernosum, Cowper's gland), female genital tract (ovary, fimbria, fallopian tubes, uterus, endometrium, endocervix, endocervical glands, cervix, ectocervix, vagina, labia, placenta), endocrine system (pineal glands, pituitary gland, thyroid gland, parathyroid glands, adrenal glands, adrenal cortex, adrenal medulla), cardiovascular system (heart, pericardium, myocardium, endocardium, atria, ventricles, coronary arteries, tricuspid valve, aortic valve, mitral valve, pulmonic valve, aorta, arteries, arterioles, capillaries, venules, veins, inferior vena cava, superior vena cava, pulmonary artery, pulmonic vein), musculoskeletal system (bones, tendons, ligaments, skeletal muscle, smooth muscle, fascia) and blood (platelets, red blood cells, white blood cells, and all their precursors, and bone marrow).

The invention provides a method of treating and/or preventing a viral condition in a patient comprising: selecting a patient in need of treating and/or preventing a viral condition; administering to the patient at least one active agent selected from the group consisting of PT150, PT155, PT156, PT157, PT158, TCY1, combinations thereof, and pharmaceutically acceptable salts thereof; administering at least one additional active agent selected from the group consisting of molecules with potential to bind viral PS annexin-5, anti-PS monoclonal or polyclonal antibodies, bavituximab and/or bind to viral glucocorticoid response elements (GREs), retinazone, RU486 or their derivatives) and one or more anti-viral medications including, but not limited to cell entry inhibitors, uncoating inhibitors, reverse transcriptase inhibitors, integrase inhibitors, transcription inhibitors, translation (antisense) inhibitors, translation (ribozyme) inhibitors, prein processing and targeting inhibitors, protease inhibitors, assembly inhibitors, release phase inhibitos, immuno-system modulators and vaccines may be used together or in sequence, to act in an additive or synergistic fashion to prevent or treat acute viral infection, to prevent acute viral infection from becoming latent or active chronic infection, to prevent chronic latent infection from becoming active infection, or to eliminate chronic latent viral infection and thereby treat diseases caused by viral induced or associated injuries and diseases (necrosis, inflammation, sclerosis) in tissues including, but not limited to: eye (retina, sclera, lens, iris, pupil, cornea, macula, retinal blood vessels, optic nerve), ear (ear canal, bones of middle ear, tympanic membrane, Eustachian, cochlear nerve, vestibular nerve, semicircular canals, cochlea), nose (naris, vestibule, turbinates, sinuses), oral cavity and oropharynx (lips, gingiva, hard and soft palates, salivary glands, uvula, tonsils, adenoids, teeth), central nervous system and associated structures (brain, cerebrum, cerebellum, olvactory bulb, hypothalamus, reticular formation, medulla oblongata, meninges, ventricles, thalamus, pineal gland), peripheral and enteric nervous systems (autonomic nerves, sympathetic nerves, parasympathetic nerves, sensory nerves, ganglion cells, ganglia), skin (epidermis, dermis, adnexal structures, sebaceous glands, hair follicles, stratum corneum, granular cells, spinous cells, sweat glands), respiratory tract (larynx, trachea, bronchi, bronchioles, lung, alveoli, pleura), digestive tract (pharynx, esophagus, stomach, small intestine, duodenum, jejunum, ileum, colon, rectum, appendix, anus), liver (intra- and extra-hepatic bile ducts, gallbladder, liver, hepatocytes, ductules, canals of Hering), pancreas (endocrine pancreas, exocrine pancreas, pancreatic ducts, pancreatic acini), urinary tract (renal cortex, renal tubules, renal pelvis, glomeruli, ureters, urinary bladder, urethra), male genital tract (prostate, testes, scrotum, epididymis, vas deferens, glans, foreskin, corpus spongiosum, corpus cavernosum, Cowper's gland), female genital tract (ovary, fimbria, fallopian tubes, uterus, endometrium, endocervix, endocervical glands, cervix, ectocervix, vagina, labia, placenta), endocrine system (pineal glands, pituitary gland, thyroid gland, parathyroid glands, adrenal glands, adrenal cortex, adrenal medulla), cardiovascular system (heart, pericardium, myocardium, endocardium, atria, ventricles, coronary arteries, tricuspid valve, aortic valve, mitral valve, pulmonic valve, aorta, arteries, arterioles, capillaries, venules, veins, inferior vena cava, superior vena cava, pulmonary artery, pulmonic vein), musculoskeletal system (bones, tendons, ligaments, skeletal muscle, smooth muscle, fascia) and blood (platelets, red blood cells, white blood cells, and all their precursors, and bone marrow).

The invention provides a method of treating immunocompetent patients who have mycobacterial infection comprising: selecting a patient in need of treating and/or preventing the condition; administering to the patient at least one active agent selected from the group consisting of PT150, PT155, PT156, PT157, PT158, TCY1, combinations thereof, and pharmaceutically acceptable salts thereof; wherein the mycobacterial infection is *Mycobacterium tuberculosis* (MTB) and leprosy, identified by routine screening in the absence of clinical signs or symptoms of mycobacterial infection, identified by serologic studies, identified in cultured tissue, identified on histochemical or immunostains in tissue biopsy or resection specimens, or presenting with clinical signs or symptoms of mycobacterial infection, in order to antagonize physiologic cortisol-mediated suppression of the immune system and thereby facilitating immune-clearance of infection.

The invention provides a method of treating immunocompetent patients who have mycobacterial infection comprising: selecting a patient in need of treating and/or preventing the condition; administering to the patient at least one active agent selected from the group consisting of PT150, PT155, PT156, PT157, PT158, TCY1, combinations thereof, and pharmaceutically acceptable salts thereof, wherein the mycobacterial infection including, but not limited to *Mycobacterium tuberculosis* (MTB), leprosy, *Mycobacterium avium intracellulare* (MAI), *Mycobacterium kansasii, Mycobacterium fortuitum*, identified by routine screening in the absence of clinical signs or symptoms of mycobacterial infection, identified by serologic studies, identified in cultured tissue, identified on histochemical or immunostains in tissue biopsy or resection specimens, or presenting with clinical signs or symptoms of mycobacterial infection, in order to antagonize physiologic cortisol-mediated suppression of the immune system and thereby facilitating immune-clearance of infection.

The invention provides a pharmaceutical composition comprising: at least one glucocorticoid antagonist, selected from the group consisting of PT150, PT155, PT156, PT157, PT158, TCY1, combinations thereof, and pharmaceutically acceptable salts thereof; optionally, antibiotics with antimycobacterial infection (including, but not limited to rifamycins, isoniazid, pyrazinamide, ethambutol, fluoroquinolones, aminoglycosides, ethionamide, cycloserine, capreomycin, dapsone, clofazimine, minocycline, clarithromycin, macrolides; at least one pharmaceutically acceptable excipient.

The invention provides a method of treating and/or preventing addiction in a patient comprising: selecting a patient in need of treating and/or preventing addiction; continuously or intermittently administering to the patient at least one active agent selected from the group consisting of PT150, PT155, PT156, PT157, PT158, TCY1, combinations thereof, and pharmaceutically acceptable salts thereof, wherein the at least one active agent prevents triggering of Pavlovian sign-tracking and thereby diminish or eliminate likely relapse in response to cues originally associated with the use of the addictive compound.

The invention provides a method of treating and/or preventing addiction in a patient comprising: selecting a patient in need of treating and/or preventing the addiction; continuously or intermittently administering to the patient at least one active agent selected from the group consisting of PT150, PT155, PT156, PT157, PT158, TCY1, combinations thereof, and pharmaceutically acceptable salts thereof, wherein the at least one active agent prevents development of Pavlovian sign-tracking and thereby diminishing or prevent progression from regular (recreational or medicinal) use to physical addiction.

The invention provides a method of treating or preventing Addison's Disease in a patient, the method comprising: selecting a patient in need of treating and/or preventing Addison's Disease; administering to the patient a pharmaceutical composition comprising: i) a first therapeutic agent which is at least one antiviral agent or pharmaceutically acceptable salt thereof; ii) a second therapeutic agent which is a GCR antagonist selected from the group consisting of PT150, PT155, PT156, PT157, PT158, TC Y1, combinations thereof, and pharmaceutically acceptable salts thereof; and iii) at least one pharmaceutically acceptable carrier, wherein the pharmaceutical composition is formulated or manufactured as a liquid, an elixir, an aerosol, spray, a powder, a tablet, a pill, a capsule, a gel, a gel type, a nano suspension, a nanoparticle, and extended release dosage form, or at topical formulation, further wherein the antiviral agent and the GCR antagonists are each present in an amount which, in combination, is a therapeutically effective amount for treating or preventing a viral infection in a patient, wherein the antiviral agent is selected from the group consisting of Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof, as a way of preventing or minimizing development of Addisonian symptoms from ongoing, high level systemic GCR blockade of endogenous, physiologic cortisol, thereby treating and/or preventing Addison's Disease. The invention provides a method of treating and/or preventing reactivation of viral infection in a patient comprising: selecting a patient in need of treating and/or preventing viral infection; administering to the patient prior to or receiving therapeutic doses of glucocorticoids at least one active agent selected from the group consisting of PT150, PT155, PT156, PT157, PT158, TCY1, combinations thereof, and pharmaceutically acceptable salts thereof.

The invention provides a method of treating and/or preventing reactivation of latent viral infection in a patient comprising: selecting a patient in need of treating and/or preventing latent viral infection; administering to the patient prior to or receiving therapeutic doses of glucocorticoids at least one active agent selected from the group consisting of PT150, PT155, PT156, PT157, PT158, TCY1, combinations thereof, and pharmaceutically acceptable salts thereof, wherein the administration diminish intensity of viral reactivation, to diminish length of viral reactivation, to speed time to resolution and healing of viral reactivation, to speed time to suppression of viral reactivation, to increase likelihood of viral eradication, and/or to diminish infectivity of viral reactivation.

The invention provides a method of treating and/or preventing reactivation of viral infection in a patient comprising: selecting a patient in need of treating and/or preventing viral infection; administering to the patient prior to or receiving therapeutic doses of glucocorticoids at least one active agent selected from the group consisting of PT150, PT155, PT156, PT157, PT158, TCY1, combinations thereof, and pharmaceutically acceptable salts thereof, wherein the administration diminishes intensity of viral infection, to diminish length of viral infection, to speed time to resolution and healing of viral infection, to speed time to suppression of viral infection, to increase likelihood of viral eradication, and/or to diminish infectivity of viral infection.

The invention provides a method of treating and/or preventing reactivation of viral infection in a patient comprising: selecting a patient in need of treating and/or preventing viral infection; administering to the patient prior to or during travel to environments in which viruses are endemic at least one active agent selected from the group consisting of PT150, PT155, PT156, PT157, PT158, TCY1, combinations thereof, and pharmaceutically acceptable salts thereof.

The invention provides a method of treating and/or preventing dementia in a patient comprising: selecting a patient in need of treating and/or preventing dementia; administering to the patient at least one active agent selected from the group consisting of PT150, PT155, PT156, PT157, PT158, TCY1, combinations thereof, and pharmaceutically acceptable salts thereof; administering to the patient at least one additional therapeutic agent which is selected from the group consisting of cholinesterase inhibitors, Aricept, Exelon, Razadyne, and memantine, thereby treating and/or preventing dementia in the patient.

The invention provides a pharmaceutical composition made by combining at least one antiviral agent or pharmaceutically acceptable salt thereof, at least one a GCR antagonist selected from the group consisting of PT150, PT155, PT156, PT157, PT158, TCY1, combinations thereof, and pharmaceutically acceptable salts thereof, and a pharmaceutically acceptable carrier.

The invention provides a pharmaceutical active substance combination comprising: i) a first therapeutic agent which is at least one antiviral agent or pharmaceutically acceptable salt thereof; ii) a second therapeutic agent which is a GCR antagonist selected from the group consisting of PT150, PT155, PT156, PT157, PT158, TCY1, combinations thereof, and pharmaceutically acceptable salts thereof, as a combination product for simultaneous, separate, or sequential use.

The invention provides a pharmaceutical dosage form comprising: i) a first therapeutic agent which is at least one antiviral agent or pharmaceutically acceptable salt thereof; ii) a second therapeutic agent which is a GCR antagonist selected from the group consisting of PT150, PT155, PT156, PT157, PT158, TCY1, combinations thereof, and pharmaceutically acceptable salts thereof, wherein the first and second agents are in multiple separated dosage units or in a single dosage unit of a combination of the therapeutic agents.

The invention provides a kit for the treatment, amelioration or prevention of a viral infection condition in a patient in need of such treatment comprising: (a) the pharmaceutical composition herein; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition.

The invention provides a pharmaceutical packaging system comprising: i) a first therapeutic agent which is an antiviral agent, or pharmaceutically acceptable salts thereof; ii) a second therapeutic agent which is a GCR antagonist, or pharmaceutically acceptable salts thereof, wherein the means for containing said therapeutic dosages is selected from the group consisting of the first and second agents are in a single dosage form; the first and second agents are packaged together in a single package or packette; the first and second agents are packaged separately in a plurality of packages or packettes; a blister packet; a lidded blister; or blister card or packets; a shrink wrap, and with both drugs released upon opening of the single package or packette; a plurality of packages or packettes; blister packet; lidded blister or blister card or packets; or shrink wrap; a blister pack; a container; and a device, and wherein the dosages are separated from each other within the pharmaceutical packaging system.

The invention provides a process for making a pharmaceutical composition comprising combining at least one antiviral agent or pharmaceutically acceptable salts thereof, at least one GCR antagonist selected from the group consisting of PT150, PT155, PT156, PT157, PT158, TCY1, combinations thereof, and pharmaceutically acceptable salts thereof, and at least one pharmaceutically acceptable carrier.

The invention provides a method of treating or preventing viral infection in a patient, comprising: selecting a patient in need of treating or preventing viral infection; administering to the patient a composition comprising: i) a first therapeutic agent which is a antiviral agent, or pharmaceutically acceptable salts thereof; ii) a second therapeutic agent which is a GCR antagonist or pharmaceutically acceptable salts thereof; and iii) at least one a pharmaceutically acceptable carrier, wherein the antiviral agent and the GCR antagonist are each present in an amount which, in combination, is a therapeutically effective amount for treating or preventing viral infection in a patient.

The invention provides a method wherein the antiviral agent is selected from the group consisting of: Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu). Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir, Zidovudine, and combinations thereof.

The invention provides a method wherein the GCR antagonist is selected from the group consisting of is selected from the group consisting of PT150, PT155, PT156, PT157, PT158, TCY1, combinations thereof, and pharmaceutically acceptable salts thereof.

The present invention relates to a method for detecting the presence of a biological substance in a test sample, comprising the steps of providing a test sample consisting of, for example, saliva, or a bodily fluid sample from a subject with, for example, a lollipop-like apparatus including a stem integrated with the base and a head integrated with the stem. The stem head including a receptor of a sponge like carrier to ensure a high void volume to absorb sufficient saliva, oral fluid or a bodily fluid sample.

Combining the test sample with a buffering system (Reagent 1) containing viscosity controllers and stabilizers into a reaction vessel, mixing the solution well, and expressing all the liquid from the sample carrier apparatus into Reagent 1 in the reaction vessel and discarding. Reading the reaction vessel with sample and buffer for a fluorescence polarization blank and then combining the test sample and buffer mixture with a fluorescence-labeled ligand (Reagent 2) to said biological substance in the reaction vessel, mix solution well, to produce an assay solution. Furthermore, Reagent 2 may be delivered to the reaction vessel without further dilution volume of the assay solution.

The invention provides a method for screening a patient for a disease state suitable for GCR (glucocorticoid receptor) antagonist therapy, comprising the steps of: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; and h) comparing the patient's measured cortisol levels to a predetermined reference range cortisol levels, wherein when the level of cortisol is elevated relative to the predetermined reference range, then the patient has a disease state which involves elevated cortisol, and thus has a disease state which is a potential candidate for GCR antagonist or active agent therapy. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of about hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method further comprising the steps of i) determining a patient's elevated cortisol level; and j) providing a therapeutic for such elevated cortisol level, wherein the therapeutic comprises GCR antagonist or active agent therapy. The invention further provides a method wherein the patient has changed patterns of cortisol levels that have been observed in connection with abnormal Adrenocorticotropic hormone (ACTH) levels. The invention further provides a method wherein the patient has non-normal cortisol levels produced by the adrenal cortex or disordered circadian rhythms, as a method for selecting subjects for GCR antagonist or active agent therapy wherein the patient has cortisol levels selected from the group consisting abnormally high cortisol levels but maintained circadian rhythm, over responsiveness to normal levels, and high night time cortisol levels as a feature of disrupted circadian rhythm. The invention further provides a method wherein the disease state is selected from the group consisting of cancer, clinical depression, psychological stress, and physiological stressors such as hypoglycemia, illness, fever, trauma, surgery, fear, pain, physical exertion, or temperature extremes.

The invention provides a method for monitoring changes in cortisol levels in response to treatment, in patients who have non-normal cortisol levels produced by the adrenal cortex, comprising: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) administering a GCR antagonist; i) repeating steps a) to f) after the therapy has been administered; and j) determining the patient's circulating cortisol levels post-therapy, wherein when the cortisol levels change in response to treatment to indicate responsiveness to the GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one day, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means.

The invention provides a method for monitoring changes in cortisol levels in response to treatment and adjusting the treatment in response to these changes in a patient who has non-normal cortisol levels produced by the adrenal cortex, comprising: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) administering a GCR antagonist; i) repeating steps a) to f) after the therapy has been administered; j) determining the patient's circulating cortisol levels post-therapy; and k) adjusting the GCR antagonist or active agent therapy in response to changes in the patient's cortisol levels post-therapy, wherein the adjustment in GCR antagonist or active agent therapy is to enhance therapeutic efficacy.

The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of compounds which are selective for GCR, compounds which non-specifically bind steroid hormone receptors, and compounds which cross-react to both GCR and other steroid hormone receptors. The invention further provides a method wherein a decision to adjust the GCR antagonist or active agent therapy in response to changes in the cortisol levels, post-therapy, is made by a medical professional. The invention further provides a method further comprising the step of monitoring changes in biomarker expression using a nucleic acid microarray. The invention further provides a method wherein in the patients having normal baseline cortisol at the start of treatment, and changing cortisol levels during treatment indicate responsiveness to the GCR antagonist. The invention further provides a method wherein the combined system of salivary cortisol quantification as an enabling device for its paired GCR antagonist will identify patients for whom GCR antagonism has a likely benefit. The invention further provides a method wherein the GCR antagonist is selected from the group consisting of PT150, PT155, PT156, PT157, PT158, TCY1, combinations thereof, and pharmaceutically acceptable salts thereof. The invention further provides a method wherein the buffering system comprises additional components selected form the group consisting of viscosity controllers, stabilizers, and combinations thereof. The invention further provides a method wherein the fluorescence-labeled ligand which binds cortisol is selected from the group consisting of an aptamer, an antibody, an antibody fragment, a receptor, a receptor fragment, a binding polypeptide, a binding peptide, and combinations thereof. The invention further provides a method wherein the test sample is collected from the patient with a lollipop-like apparatus, including a stem integrated with the base and a head integrated with the stem, and further wherein the stem head including a receptor of a sponge like carrier to ensure a high void volume to absorb sufficient sample.

The invention provides a method of treating major depressive disorder in a patient in need thereof by determining whether the patient has major depressive disorder suitable for GCR (glucocorticoid receptor) antagonist therapy, comprising the steps of: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the a predetermined reference range, then the patient has major depressive disorder which involves elevated cortisol, and thus has major depressive disorder suitable for GCR (glucocorticoid receptor) antagonist therapy; and i) when the patient has major depressive disorder suitable for GCR antagonist or active agent therapy, a administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR (glucocorticoid receptor) antagonist is selected from the group consisting of PT150, PT155, PT156, PT157, PT158, TCY1, combinations thereof, and pharmaceutically acceptable salts thereof.

The invention provides a method of treating psychotic depression in a patient in need thereof by determining whether the patient has psychotic depression suitable for GCR (glucocorticoid receptor) antagonist therapy, comprising the steps of a) obtaining a test sample from the patient, optionally at a predetermined time using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has psychotic depression which involves elevated cortisol, and thus has psychotic depression suitable for GCR antagonist or active agent therapy; and i) when the patient has psychotic depression suitable for GCR antagonist or active agent therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of PT150, PT155, PT156, PT157, PT158, TCY1, combinations thereof, and pharmaceutically acceptable salts thereof.

The invention provides a method of treating stress-induced cortisol elevation in a patient in need thereof by determining whether the patient has stress-induced cortisol elevation suitable for GCR (glucocorticoid receptor) antagonist therapy, comprising the steps of a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has stress-induced cortisol elevation which involves elevated cortisol, and thus has stress-induced cortisol elevation suitable for GCR antagonist or active agent therapy; and i) when the patient has stress-induced cortisol elevation suitable for GCR antagonist or active agent therapy, administering at least one GCR antagonist.

The invention further provides a method wherein the patient's test sample is selected from the group consisting of saliva, blood, plasma, serum, urine, other bodily fluids, and combinations thereof. The invention further provides a method wherein the stress-related cortisol elevation is related to a hospital stay, medical treatment, an institutional stay, clinical depression, psychological stress, physiological stressors, hypoglycemia, illness, fever, trauma, surgery, fear, pain, physical exertion, or temperature extremes. The invention further provides a method wherein the patient is an elderly individual. The invention further provides a method wherein the patient has autism or Asperger's syndrome. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of PT150, PT155, PT156, PT157, PT158, TCY1, combinations thereof, and pharmaceutically acceptable salts thereof.

The invention provides a method of treating post-traumatic stress disorder in a patient in need thereof by determining whether the patient has post-traumatic stress disorder suitable for GCR (glucocorticoid receptor) antagonist therapy, comprising the steps of: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has post-traumatic stress disorder which involves elevated cortisol, and thus has post-traumatic stress disorder suitable for GCR (glucocorticoid receptor) antagonist therapy; and i) when the patient has post-traumatic stress disorder suitable for GCR antagonist or active agent therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of PT150, PT155, PT156, PT157, PT158, TCY1, combinations thereof, and pharmaceutically acceptable salts thereof.

The invention provides a method of prevention of weight gain in patients using anti-psychotic or anti-depressant medications in a patient in need thereof, wherein the weight gain is suitable for GCR (glucocorticoid receptor) antagonist therapy, comprising the steps of: a) obtaining a test sample from the patient, optionally at a predetermined time using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has weight gain which involves elevated cortisol, which is suitable for GCR (glucocorticoid receptor) antagonist therapy; and i) when the patient has weight gain suitable for GCR antagonist or active agent therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of PT150, PT155, PT156, PT157, PT158, TCY1, combinations thereof, and pharmaceutically acceptable salts thereof.

The invention provides a method of treating Cushing's syndrome in a patient in need thereof by determining whether the patient has Cushing's syndrome suitable for GCR (glucocorticoid receptor) antagonist therapy, comprising the steps of a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has Cushing's syndrome which involves elevated cortisol, which is suitable for GCR (glucocorticoid receptor) antagonist therapy; and i) when the patient has Cushing's syndrome suitable for GCR antagonist or active agent therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patients previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of PT150, PT155, PT156, PT157, PT158, TCY1, combinations thereof, and pharmaceutically acceptable salts thereof.

The invention provides a pharmaceutical composition comprising: (a) GCR (glucocorticoid receptor) antagonist; (b) the pharmaceutical composition of (a), further comprising at least one pharmaceutically acceptable excipient; (c) the pharmaceutical composition of (a) or (b), wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The invention provides a method for treating a condition selected from the group consisting of major depressive disorder, psychotic depression, stress-induced cortisol elevation, post-traumatic stress disorder, preventing weight gain in patients using anti-psychotic and anti-depressant medications, or having Cushing's syndrome, in a patient in need of such treatment comprising administering the pharmaceutical composition to the patient.

The invention provides a kit for the treatment, amelioration or prevention of a condition selected from the group consisting of major depressive disorder, psychotic depression, stress-induced cortisol elevation, post-traumatic stress disorder, preventing weight gain in patients using anti-psychotic and anti-depressant medications, or having Cushing's syndrome, in a patient in need of such treatment comprising: (a) the pharmaceutical composition; and (b) at least one blister package; a lidded blister; a blister card or packet; a clamshell; an intravenous (IV) package, N packette or IV container; a tray or a shrink wrap comprising the pharmaceutical composition of (a) and instructions for use of the pharmaceutical composition.

The invention provides a product of manufacture comprising a blister package; a lidded blister; a blister card or packet; a clamshell; an intravenous (N) package, IV packette or N container; a tray or a shrink wrap comprising the pharmaceutical composition and instructions for use of the pharmaceutical composition. The invention further provides a method wherein the GCR (glucocorticoid receptor) antagonist selected from the group consisting of PT150, PT155, PT156, PT157, PT158, TCY1, combinations thereof, and pharmaceutically acceptable salts thereof.

The invention provides a method for treating neoplasia characterized by expression of a glucocorticoid receptor, in a patient in need of such treatment, comprising: administering to said animal or human therapeutically effective amounts of each of at least one neoplasia-treating agent and a GCR (glucocorticoid receptor) antagonist selected from the group consisting of PT150, PT155, PT156, PT157, PT158, TCY1, combinations thereof, and pharmaceutically acceptable salts thereof. The invention further provides a method wherein PT150, PT155, PT156, PT157, PT158, TCY1, combinations thereof, and pharmaceutically acceptable salts thereof is administered as an agent which directly effects tumor growth, independent of other administered treatment modalities, for palliation, remission, or cure. The invention further provides a method wherein said neoplasia treating agent is radiation. The invention further provides a method wherein said neoplasia treating agent is a biotherapy agent. The invention further provides a method wherein said neoplasia treating agent is a chemotherapy agent. The invention further provides a method wherein said neoplasia treating agent is a radionuclide. The invention further provides a method wherein the neoplasia is selected for the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention further provides a method wherein the neoplasia expresses multidrug resistance genes when GR is activated through binding by endogenous cortisol. The invention further provides a method wherein the neoplasia expresses proteins of cell survival pathway (including inhibition of apoptosis) genes when GR is activated through binding by endogenous cortisol. The invention further provides a method wherein the neoplasia expresses genes responsible for epithelial-mesenchymal transition and cell shape maintenance are repressed when GR is activated through binding by endogenous cortisol. The invention further provides a method wherein the neoplasia expresses genes involved in signal transduction pathways, lipid/fatty acid metabolism, inflammation and macrophage regulation, transcriptional regulation and chromatin remodeling, and cell metabolic pathways. The invention further provides a method wherein tumor stem cells (TSC) express GR, blockade of which by PT150, PT155, PT156, PT157, PT158, TCY1, combinations thereof, and pharmaceutically acceptable salts thereof results in anti-TSC therapy. The invention further provides a method wherein TSC express multidrug resistance genes when GR is activated through binding by endogenous cortisol. The invention further provides a method wherein TSC express proteins of cell survival pathways (including inhibition of apoptosis) genes when GR is activated through binding by endogenous cortisol. The invention further provides a method wherein TSC express genes responsible for epithelial-mesenchymal transition and cell shape maintenance are repressed when GR is activated through binding by endogenous cortisol. The invention further provides a method wherein TSC express genes involved in signal transduction pathways, lipid/fatty acid metabolism, inflammation and macrophage regulation, transcriptional regulation and chromatin remodeling, and cell metabolic pathways. The invention further provides a method wherein the neoplasia is chemo-resistant ER/GR+ breast cancer. The invention further provides a method wherein the administration of PT150, PT155, PT156, PT157, PT158, TCY1, combinations thereof, and pharmaceutically acceptable salts thereof for GR-blockade, reduces toxicities and side effects when given systemically. The invention further provides a method wherein the PT150, PT155, PT156, PT157, PT158, TCY1, combinations thereof, and pharmaceutically acceptable salts thereof given systemically through oral or intravenous routes. The invention further provides a method wherein the PT150, PT155, PT156, PT157, PT158, TCY1, combinations thereof, and pharmaceutically acceptable salts thereof is targeted to tumor by intra-arterial infusion to reduce systemic side effects of GR blockade. The invention further provides a method wherein the PT150, PT155, PT156, PT157, PT158, TCY1, combinations thereof, and pharmaceutically acceptable salts thereof is given to accomplish cure or remission of tumor. The invention further provides a method wherein the PT150, PT155, PT156, PT157, PT158, TCY1, combinations thereof, and pharmaceutically acceptable salts thereof is given to accomplish reduction of tumor burden to enhance effectiveness of subsequent surgical resection. The invention further provides a method wherein the PT150, PT155, PT156, PT157, PT158, TCY1, combinations thereof, and pharmaceutically acceptable salts thereof is given to accomplish reduction of tumor burden to make an unresectable tumor resectable.

The invention provides a method for treatment of neoplasia in a patient comprising targeted delivery of PT150, PT155, PT156, PT157, PT158, TCY1, combinations thereof, and pharmaceutically acceptable salts thereof, wherein the neoplasia expresses multidrug resistance genes when GR is activated through binding by endogenous cortisol. The invention further provides a method wherein the HCC patient is not a candidate to undergo surgical intervention because tumor is too large or encroaches on liver anatomy in a manner that prevents resection, delivery of PT150, PT155, PT156, PT157, PT158, TCY1, combinations thereof, and pharmaceutically acceptable salts thereof prior to ablative or chemotherapy to shrink the tumor and make it resectable. The invention further provides a method wherein the HCC is present in cirrhosis and the patient is not a candidate for transplantation because of large tumor size, administration of PT150, PT155, PT156, PT157, PT158, TCY1, combinations thereof, and pharmaceutically acceptable salts thereof making the tumor amenable to ablative or chemotherapy to shrink the tumor and allow the patient to be eligible for liver transplant. The invention further provides a method wherein the HCC is present in cirrhosis and the patient is a candidate for transplantation, administration of PT150, PT155, PT156, PT157, PT158, TCY1, combinations thereof, and pharmaceutically acceptable salts thereof making the tumor amenable to ablative therapy to manage tumor while patient remains on the liver transplant waitlist.

The invention provides a method for low toxicity chemoprevention by targeted liver infusion in patients with forms of established cirrhosis that are high risk for emergence of HCC, including those with premalignant lesions diagnosed on biopsy or by radiology, comprising targeted delivery of PT150, PT155, PT156, PT157, PT158, TCY1, combinations thereof, and pharmaceutically acceptable salts thereof to intrahepatic lesions, wherein the targeted delivery of ORG g34517 to intrahepatic lesions prevents emergence of HCC. The invention further provides a method wherein the patient with HCC is not a candidate for undergo surgical intervention. The invention further provides a method wherein the HCC resides in locations where surgical or ablative interventions are not available. The invention further provides a method wherein the patient with HCC has cirrhosis that is too advanced to make partial hepatectomy safe. The invention further provides a method wherein the patient with HCC is too early in their chronic liver disease to qualify for transplantation. The invention further provides a method wherein the HCC is too advanced for localized treatments. The invention provides a method for treatment of HCC comprising: a) targeted delivery of PT150, PT155, PT156, PT157, PT158, TCY1, combinations thereof, and pharmaceutically acceptable salts thereof to intrahepatic lesions, wherein the targeted delivery of PT150, PT155, PT156, PT157, PT158, TCY1, combinations thereof, and pharmaceutically acceptable salts thereof to intrahepatic lesions improves outcomes of localized chemo-ablative therapies. The invention further provides a method wherein the treatment is to help patients qualify for liver transplantation.

The invention provides a method for low toxicity chemoprevention by targeted liver infusion in patients with forms of established cirrhosis that are high risk for emergence of HCC, including those with premalignant lesions diagnosed on biopsy or by radiology comprising targeted delivery of PT150, PT155, PT156, PT157, PT158, TCY1, combinations thereof, and pharmaceutically acceptable salts thereof to intrahepatic lesions, wherein the targeted delivery of PT150, PT155, PT156, PT157, PT158, TCY1, combinations thereof, and pharmaceutically acceptable salts thereof to intrahepatic lesions prevents emergence of HCC. The invention further provides a method wherein the neoplasia is eSCC.

The invention provides a method for treatment of eSCC in a patient with unresectable eSCC where systemic or targeted administration of PT150, PT155, PT156, PT157, PT158, TCY1, combinations thereof, and pharmaceutically acceptable salts thereof makes tumor responsive to ablative or chemotherapies as palliative or curative treatment.

The invention provides method for treatment of eSCC in a patient with unresectable eSCC where systemic or targeted administration of PT150, PT155, PT156, PT157, PT158, TCY1, combinations thereof, and pharmaceutically acceptable salts thereof makes tumor responsive to ablative or chemotherapies to shrink the tumor and enhance resectability. The invention further provides a method wherein the neoplasia-treating agent is a chemotherapeutic agent including but not limited to gemcitabine, paclitaxel, carboplatin, cisplatin, and 5-fluorouracil. The invention further provides a method wherein the therapeutic effective amount of glucocorticoid administered is about 100 to 400 microg/kg body weight per day when administered intravenously.

The invention provides a method for treating neoplasia, in an animal or human in need of such treatment, wherein said neoplasia comprises neoplastic stem cells characterized by expression of a glucocorticoid receptor, and further characterized by expression of multidrug resistance genes or other stem cell related means of survival when GR is activated through binding by endogenous cortisol, the method comprising: a) administering to said animal or human a therapeutically effective amount of PT150, PT155, PT156, PT157, PT158, TCY1, combinations thereof, and pharmaceutically acceptable salts thereof; and b) administering to said animal or human a therapeutically effective amount of the at least one neoplasia-treating agent, wherein said therapeutically effective amount of PT150, PT155, PT156, PT157, PT158, TCY1, combinations thereof, and pharmaceutically acceptable salts thereof is an amount sufficient to promote susceptibility of the neoplastic stem cells to at least one neoplasia-treating agent. The invention further provides a method wherein said neoplasia-treating agent is radiation selected from the group consisting of external beam or radionuclide therapy. The invention further provides a method wherein said neoplasia-treating agent is a biotherapy agent. The invention further provides a method wherein said neoplasia-treating agent is a chemotherapy agent. The invention further provides a method wherein said neoplasia-treating agent is a radionuclide. The invention further provides a method wherein the neoplasia is selected from the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention further provides a method wherein the neoplasia expresses multidrug resistance genes when GR is activated through binding by endogenous cortisol.

The invention provides a pharmaceutical composition for treating neoplasia in a patient which is characterized by expression of a glucocorticoid receptor, comprising: a) therapeutically effective amounts of at least one neoplasia-treating agent; b) a GCR (glucocorticoid receptor) antagonist selected from the group consisting of PT150, PT155, PT156, PT157, PT158, TCY1, combinations thereof, and pharmaceutically acceptable salts thereof; and c) optionally, at least one pharmaceutically acceptable carrier. The invention further provides a method wherein said neoplasia-treating agent is selected from the group consisting of a chemotherapeutic agent, a biotherapeutic agent, a radionuclide agent, and combinations thereof. The invention further provides a method wherein the neoplasia is selected from the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention further provides a method, wherein the neoplasia is chemo-resistant ER-GR+ breast cancer. The invention further provides a method wherein the neoplasia expresses multidrug resistance genes when GR is activated through binding by endogenous cortisol. The invention further provides a method wherein the chemotherapeutic agent is selected from the group comprising: busulfan, cisplatin, carboplatin, chlorambucil, cyclophosphamide, ifosfamide, dacarbazine (DTIC), mechlorethamine (nitrogen mustard), melphalan carmustine (BCNU) lomustine (CCNU), 5-FU, capecitabine, methotrexate, gemcitabine, cytarabine (ara-C), fludarabine dactinomycin, daunorubicin, doxorubicin (Adriamycin), idarubicin, mitoxantrone, paclitaxel, docetaxel, etoposide (VP-16), vinblastine, vincristine, vinorelbine prednisone, dexamethasone, tamoxifen, fulvestrant, anastrozole, letrozole, megestrol acetate, bicalutamide, flutamide, leuprolide, goserelin, L-asparaginase, and tretinoin, gemcitabine, paclitaxel, carboplatin, 5-FU, and combinations thereof.

The invention provides a diagnostic kit comprises the following components: a) test sample collection unit; b) the buffer system unit; c) the reaction unit; and d) the label unit, wherein the components are in a blister package; a lidded blister; a blister card or packet; a clamshell; a tray, or a shrink wrap, and instructions for use of the kit. The invention further provides test sample collection unit wherein the test sample collection unit comprises a stem integrated with a base, and a head integrated with the stem. The invention further provides a test sample collection unit wherein the stem head comprises a receptor of a sponge-like carrier sufficient to ensure a high void volume to absorb sufficient saliva, oral fluid or a bodily fluid sample. The invention further provides a buffer system unit wherein the buffer system unit comprises additional components selected from the group consisting of viscosity controllers, stabilizers, and combinations thereof. The invention further provides a reaction unit wherein the reaction unit is adapted to fit in a fluorescent polarization reader. The invention further provides a label unit wherein the label unit comprises a fluorescence-labeled ligand which binds cortisol, wherein the fluorescence-labeled ligand which binds cortisol is selected from the group consisting of an aptamer, an antibody, an antibody fragment, a receptor, a receptor fragment, a binding polypeptide, a binding peptide, and combinations thereof. The invention further provides a diagnostic kit wherein the reader apparatus provides temperature control and on-board mixing as an aid in viscosity control of the reaction to ensure better accuracy and precision. The invention further provides a diagnostic kit wherein the reader is a miniaturized, portable apparatus for measuring fluorescence polarization of a liquid sample by direct or indirect methods. The invention further provides a diagnostic kit wherein system also enables continual monitoring of the patient during treatment for assessment of responsiveness to treatment.

The invention provides a method for treating or preventing addiction, addiction induced anxiety, and/or withdrawal symptoms wherein said method comprises administering to a patient in need of such therapy at least one glucocorticoid receptor antagonist in a therapeutically effective amount. The invention provides a method wherein the at least one glucocorticoid receptor antagonist and/or active agent is in a pharmaceutical preparation. The invention provides a method wherein the glucocorticoid receptor antagonist and/or active agent is selected from the group consisting of PT150, PT155, PT156, PT157, PT158, TCY1, combinations thereof, and pharmaceutically acceptable salts thereof.

The invention provides a method of treating or preventing addiction, addiction induced anxiety, and/or withdrawal symptoms in a patient in need thereof, comprising: administering a composition comprising: i) a first therapeutic agent which is a GCR antagonist, or pharmaceutically acceptable salts thereof; ii) at least one or possibly more additional therapeutic agent(s) selected from the group consisting of anxiolytics, antidepressants, neuroleptics, or other psychotropic medications and combinations thereof; and iii) at least one pharmaceutically acceptable carrier, wherein the first and second therapeutic agents are each present in an amount which, in combination, is a therapeutically effective amount for treating or preventing addiction, addiction induced anxiety, and/or withdrawal symptoms.

The invention provides a method wherein the second therapeutic agent is selected from the group consisting of at least one anti-anxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof.

The invention provides a method wherein the GCR antagonist is selected from the group consisting of PT150, PT155, PT156, PT157, PT158, TCY1, combinations thereof, and pharmaceutically acceptable salts thereof.

The invention provides a method of treating or preventing addiction, addiction induced anxiety, and/or withdrawal symptoms in a patient, comprising the steps of: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the a predetermined reference range, then the patient has elevated cortisol, and thus is suitable for GCR (glucocorticoid receptor) antagonist therapy; and i) when the patient is suitable for GCR antagonist or active agent therapy, administering at least one GCR antagonist, thereby treating or preventing addiction, addiction induced anxiety, and/or withdrawal symptoms in the patient.

The invention provides a method wherein the patient's test sample is selected from the group consisting of saliva, blood, plasma, serum, urine, other bodily fluids, and combinations thereof. The invention provides a method wherein the sample is obtained from the patient one time, selected from the group consisting of morning, noon, and evening. The invention provides a method wherein the sample is obtained from the patient over more than one time, and the predetermined time is selected to determine the nature of the cortisol circadian rhythm (including its possible disruption or elimination) from the group consisting of morning, noon, and evening. The invention provides a method wherein the sample is obtained from the patient over consecutive days. The invention provides a method wherein the method is to determine the circadian cycle of the cortisol levels in the patient, and the predetermined time is selected from the group consisting of hourly, every 4 hours, every 6 hours, every 8 hours, and every 12 hours. The invention provides a method wherein the predetermined reference range is a medically standard reference range. The invention provides a method wherein the predetermined reference range is the patient's previously measured level. The invention provides a method wherein the ligand is detectably labeled with a moiety selected from the group consisting of a radioisotope, a fluorophore, a quencher of fluorescence, an enzyme, an affinity tag, and an epitope tag. The invention provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means.

The invention provides a method wherein the GCR (glucocorticoid receptor) antagonist is selected from the group consisting of PT150, PT155, PT156, PT157, PT158, TCY1, combinations thereof, and pharmaceutically acceptable salts thereof.

The invention provides a kit for treating or preventing addiction, addiction induced anxiety, and/or withdrawal symptoms comprising: (a) a pharmaceutical composition comprising at least one glucocorticoid receptor antagonist and/or active agent in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing addiction, addiction induced anxiety, and/or withdrawal symptoms.

The invention provides a product of manufacture for treating or preventing addiction, addiction induced anxiety, and/or withdrawal symptoms comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist and/or active agent, and instructions for treating or preventing addiction, addiction induced anxiety, and/or withdrawal symptoms.

The invention provides a method for treating bone fracture and/or a bone related injury wherein said method comprises administering, to a patient in need of such therapy, at least one glucocorticoid receptor antagonist and/or active agent in a therapeutically effective amount. The invention provides a method wherein the at least one glucocorticoid receptor antagonist and/or active agent is in a pharmaceutical preparation. The invention provides a method wherein the GCR (glucocorticoid receptor) antagonist is selected from the group consisting of PT150, PT155, PT156, PT157, PT158, TCY1, combinations thereof, and pharmaceutically acceptable salts thereof. The invention provides a method wherein the GCR antagonist is administered intravenously, intradermally, intraarterially, intraperitoneally, intralesionally, intracranially, intraarticularly, intraprostaticaly, intrapleurally, intratracheally, intranasally, intrathecally, intravitreally, intravaginally, intrarectally, intratumorally, intramuscularly, intraperitoneally, intraocularly, subcutaneously, subconjunctival, intravesicularlly, mucosally, intrapericardially, intraumbilically, intraocularally, orally, topically, locally, by inhalation, by injection, by infusion, by continuous infusion, by localized perfusion, by direct application during surgery, via a catheter, via a lavage, or through catheterization, immersion, absorption, or adsorption. The invention provides a method wherein the method comprises administering the pharmaceutical composition to tissue surrounding the fracture. The invention provides a method wherein administration of the pharmaceutical composition comprises injecting the pharmaceutical composition into tissue surrounding the fracture. The invention provides a method wherein the glucocorticoid receptor antagonist is selected from the group consisting of PT150, PT155, PT156, PT157, PT158, TCY1, combinations thereof, and pharmaceutically acceptable salts thereof.

The invention provides a kit for treating bone fracture and/or a bone related injury comprising: (a) a pharmaceutical composition comprising at least one glucocorticoid receptor antagonist and/or active agent in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating bone fracture and/or a bone related injury.

The invention provides a product of manufacture for treating bone fracture and/or a bone related injury comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist and/or active agent, and instructions for treating bone fracture and/or a bone related injury.

The invention provides a method for treating or preventing osteoporosis, whether stress induced or related to dysregulated or elevated cortisol of the elderly, wherein said method comprises administering, to a patient in need of such therapy, at least one glucocorticoid receptor antagonist and/or active agent in a therapeutically effective amount. The invention provides a method wherein the at least one glucocorticoid receptor antagonist and/or active agent is in a pharmaceutical preparation.

The invention provides a method wherein the glucocorticoid receptor antagonist and/or active agent is selected from the group consisting of PT150, PT155, PT156, PT157, PT158, TCY1, combinations thereof, and pharmaceutically acceptable salts thereof. The invention provides a method wherein the GCR antagonist is administered intravenously, intradermally, intraarterially, intraperitoneally, intralesionally, intracranially, intraarticularly, intranasally, intrarectally, intramuscularly, subcutaneously, orally, topically, locally, by inhalation, by injection, by infusion, by continuous infusion, by localized perfusion, by direct application during surgery, via a catheter, via a lavage, or through catheterization, immersion, absorption, or adsorption.

The invention provides a kit for treating or preventing osteoporosis, whether stress induced or related to dysregulated or elevated cortisol of the elderly, comprising: (a) a pharmaceutical composition comprising at least one glucocorticoid receptor antagonist and/or active agent in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing stress induced osteoporosis.

The invention provides a product of manufacture for treating or preventing osteoporosis, whether stress induced or related to dysregulated or elevated cortisol of the elderly, comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist and/or active agent, and instructions for treating or preventing osteoporosis, whether stress induced or related to dysregulated or elevated cortisol of the elderly.

The invention provides a method for enhancing post-transplant functioning of stem cells in a patient in need of such treatment comprising the steps of: providing stem cells, whether embryonic stem cells, stem cells derived from embryonic stem cells or their differentiated progeny, induced pluripotent stem cells or their progeny, fetal stem cells or their differentiated progeny, and post-natal (adult) stem cells or their differentiated progeny, or of tissues derived from any of these, treating the stem cells or stem cell-derived, differentiated progeny with at least one GCR antagonist in preparation for transplantation; and introducing the treated stem cells into the patient.

The invention provides a method wherein the glucocorticoid receptor antagonist and/or active agent is selected from the group consisting of PT150, PT155, PT156, PT157, PT158, TCY1, combinations thereof, and pharmaceutically acceptable salts thereof. The invention provides a method wherein the treated stem cells are administered intravenously, intradermally, intraarterially, intraperitoneally, intralesionally, intracranially, intraarticularly, intraprostatically, intrapleurally, intratracheally, intranasally, intrathecally, intravitreally, intravaginally, intrarectally, intratumorally, intramuscularly, intraperitoneally, intraocularly, subcutaneously, subconjunctival, intravesicularly, mucosally, intrapericardially, intraumbilically, intraocularly, orally, topically, locally, by inhalation, by injection, by infusion, by continuous infusion, by localized perfusion, by direct application during surgery, via a catheter, via a lavage, or through catheterization, immersion, absorption, or adsorption.

The invention provides a pharmaceutical composition for enhancing post-transplant functioning of stem cells in mammals, comprising: a therapeutically effective amount of the treated stem cells, whether embryonic stem cells, stem cells derived from embryonic stem cells or their differentiated progeny, induced pluripotent stem cells or their progeny, fetal stem cells or their differentiated progeny, and post-natal (adult) stem cells or their differentiated progeny, or of tissues derived from any of these; and a pharmaceutically acceptable medium or carrier.

The invention provides a method for reducing post-transplant rejection of a transplanted organ and/or improving graft functioning and survival comprising the steps of: providing an organ to be transplanted; treating the organ with a GCR antagonist prior to transplantation: and implanting the organ to a patient in need of such treatment. The invention provides a method wherein the glucocorticoid receptor antagonist is selected from the group consisting of PT150, PT155, PT156, PT157, PT158, TCY1, combinations thereof, and pharmaceutically acceptable salts thereof. The invention provides a method for reducing post-transplantation rejection and/or improving graft functioning and survival comprising treating a patient in need of such treatment with a GCR antagonist. The invention provides a method wherein the glucocorticoid receptor antagonist and/or active agent is selected from the group consisting of PT150, PT155, PT156, PT157, PT158, TCY1, combinations thereof, and pharmaceutically acceptable salts thereof.

The invention provides a method wherein the GCR antagonist is administered to the organ graft, prior to transplantation, intravascularly, intraarterially, intravenously or in a tissue or immersion of the whole or part of the organ.

The invention provides a kit for reducing post-transplantation rejection and/or improving graft functioning and survival comprising: (a) a pharmaceutical composition comprising at least one glucocorticoid receptor antagonist in a therapeutically effective amount; and (b) organ preservation fluid.

The invention provides a kit for reducing post-transplantation rejection and/or improving graft functioning and survival comprising: (a) a pharmaceutical composition comprising at least one glucocorticoid receptor antagonist in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for reducing post-transplantation rejection.

The invention provides a product of manufacture for reducing post-transplantation rejection comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for reducing post-transplantation rejection and/or improving post-transplant graft functioning and survival.

The invention provides a method for improving wound healing and preventing excessive scar formation in a patient in need thereof, comprising administering to a mammal a therapeutically effective amount of glucocorticoid receptor antagonist. The invention provides a method wherein the glucocorticoid receptor antagonist is selected from the group consisting of PT150, PT155, PT156, PT157, PT158, TCY1, combinations thereof, and pharmaceutically acceptable salts thereof. The invention provides a method wherein the wound is treated with glucocorticoid receptor antagonist whereby the glucocorticoid receptor antagonist and/or active agent is administered intravenously, intradermally, intraarterially, intraperitoneally, intralesionally, intracranially, intraarticularly, intraprostaticaly, intrapleurally, intratracheally, intranasally, intrathecally, intravitreally, intravaginally, intrarectally, intratumorally, intramuscularly, intraperitoneally, intraocularly, subcutaneously, subconjunctival, intravesicularlly, mucosally, intrapericardially, intraumbilically, intraocularally, orally, topically, locally, by inhalation, by injection, by infusion, by continuous infusion, by localized perfusion, by direct application during surgery, via a catheter, via a lavage, or through catheterization, immersion, absorption, or adsorption, or by topical application of bandage, gauze or sutures impregnated with antagonist.

The invention provides a pharmaceutical composition for improving wound healing and prevention of excessive scarring, comprising: a therapeutically effective amount of the glucocorticoid receptor antagonist, selected from the group consisting of PT150, PT155, PT156, PT157, PT158, TCY1, combinations thereof, and pharmaceutically acceptable salts thereof; and a pharmaceutically acceptable medium or carrier.

The invention provides a pharmaceutical composition for treating or preventing treatment resistant prostate cancer, comprising: (a) therapeutically effective amounts of at least one androgen receptor antagonist selected from the group consisting of ARN-509, flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, MDV3100, Cyproterone acetate, Spironolactone, flutamide, hydroxyflutamide, and combinations thereof; (b) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof, and combinations thereof; and (c) optionally, at least one pharmaceutically acceptable carrier.

The invention provides a kit for treating or preventing treatment resistant prostate cancer comprising: (a) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof, and combinations thereof; (b) therapeutically effective amounts of at least one androgen receptor antagonist selected from the group consisting of ARN-509, flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, MDV3100, Cyproterone acetate, Spironolactone, flutamide, hydroxyflutamide, and combinations thereof; (c) optionally, at least one pharmaceutically acceptable carrier; and (d) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing treatment resistant prostate cancer.

The invention provides a product of manufacture for treating or preventing treatment resistant prostate cancer comprising a blister package; a lidded blister; a blister card or packet; a clamshell; an intravenous (IV) package, IV packette or IV container; a tray or a shrink wrap comprising the pharmaceutical composition of claim 1, and instructions for use of the pharmaceutical composition for treating or preventing treatment resistant prostate cancer.

The invention provides a method for treating or preventing treatment resistant prostate cancer, in a patient in need of such treatment or prevention, comprising: administering to said patient therapeutically effective amounts of each of: (a) therapeutically effective amounts of at least one androgen receptor antagonist selected from the group consisting of ARN-509, flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, MDV3100, Cyproterone acetate, Spironolactone, flutamide, hydroxyflutamide, and combinations thereof; and (b) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof, and combinations thereof. The invention provides a method wherein the GCR (glucocorticoid receptor) antagonist is PT150, PT155, PT156, PT157, PT158, TCY1, combinations thereof, and pharmaceutically acceptable salts thereof. The invention provides a method wherein PT150, PT155, PT156, PT157, PT158, TCY1, combinations thereof, and pharmaceutically acceptable salts thereof is administered as an agent which directly effects tumor growth, independent of other administered treatment modalities, for palliation, remission, or cure. The invention provides a method wherein the PT150, PT155, PT156, PT157, PT158, TCY1, combinations thereof, and pharmaceutically acceptable salts thereof given systemically through oral or intravenous routes. The invention provides a method wherein the PT150, PT155, PT156, PT157, PT158, TCY1, combinations thereof, and pharmaceutically acceptable salts thereof is targeted to tumor by intra-arterial infusion to reduce systemic side effects of GR blockade. The invention provides a method wherein the PT150, PT155, PT156, PT157, PT158, TCY1, combinations thereof, and pharmaceutically acceptable salts thereof is given to accomplish cure or remission of tumor. The invention provides a method wherein the PT150, PT155, PT156, PT157, PT158, TCY1, combinations thereof, and pharmaceutically acceptable salts thereof is given to accomplish reduction of tumor burden to enhance effectiveness of subsequent surgical resection. The invention provides a method wherein the PT150, PT155, PT156, PT157, PT158, TCY1, combinations thereof, and pharmaceutically acceptable salts thereof is given to accomplish reduction of tumor burden to make an unresectable tumor resectable.

The invention provides a pharmaceutical composition for treating neoplasia in a patient in need thereof, comprising: (a) therapeutically effective amounts of at least one PARP inhibitor selected from the group consisting of 4-[[3-[4-(cyclopropanecarbonyl)piperazine-1-carbonyl]-4-fluoro-phenyl]-met-hyl]-2H-phthalazin-1-one (Compound B, i.e., Olaparib), 4-iodo-3-nitrobenzamide (Iniparib), 2-[(2R)-2-methylpyrrolidin-2-yl]-1H-benzimidazole-4-carboxamide (AB T-888), 8-Fluoro-2-{4-[(methylamino)methyl]-phenyl}-1,3,4,5-tetrahydro-6H-azepino-[5,4,3-cd]indol-6-one (AG014699), 4-methoxy-carbazole (CEP 9722), 2-[4-[(3S)- piperidin-3-yl]phenyl]indazole-7-carboxamide hydrochloride (MK 4827), and 3-aminobenzamide, Iniparib, Olaparib, Rucaparib, Veliparib, CEP-9722, MK4827, BMN-673, pharmaceutically acceptable salts thereof, and combinations thereof (b) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof; and (c) optionally, at least one pharmaceutically acceptable carrier.

The invention provides a kit for treating or preventing neoplasia comprising: (a) therapeutically effective amounts of at least one PARP inhibitor selected from the group consisting of 4-[[3-[4-(cyclopropanecarbonyl)piperazine-1-carbonyl]-4-fluorophenyl]-methyl]-2H-phthalazin-1-one (Compound B, i.e., Olaparib), 4-iodo-3-nitrobenzamide (Iniparib), 2-[(2R)-2-methylpyrrolidin-2-yl]-1H-benzimidazole-4-carboxamide (AB T-888), 8-Fluoro-2-{4-[(methylamino)methyl]-phenyl}-1,3,4,5-tetrahydro-6H-azepino-[5,4,3-cd]indol-6-one (AG014699), 4-methoxy-carbazole (CEP 9722), 2-[4-[(3 S)-piperidin-3-yl]phenyl]indazole-7-carboxamide hydrochloride (MK 4827), and 3-aminobenzamide, Iniparib, Olaparib, Rucaparib, Veliparib, CEP-9722, MK4827, BMN-673, pharmaceutically acceptable salts thereof, and combinations thereof; and (b) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof; and (c) optionally, at least one pharmaceutically acceptable carrier; and (d) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing neoplasia. The invention provides a product of manufacture for treating or preventing neoplasia comprising a blister package; a lidded blister; a blister card or packet; a clamshell; an intravenous (IV) package, IV packette or IV container; a tray or a shrink wrap comprising the pharmaceutical composition of claim 12, and instructions for use of the pharmaceutical composition for treating or preventing neoplasia.

The invention provides a method for treating or preventing neoplasia in a patient in need of such treatment or prevention, comprising: administering to said patient: (a) therapeutically effective amounts of at least one PARP inhibitor selected from the group consisting of 4-[[3-[4-(cyclopropanecarbonyl)piperazine-1-carbonyl]-4-fluorophenyl]-met-hyl]-2H-phthalazin-1-one (Compound B, i.e., Olaparib), 4-iodo-3-nitrobenzamide (Iniparib), 2-[(2R)-2-methylpyrrolidin-2-yl]-1H-benzimidazole-4-carboxamide (ABT-888), 8-Fluoro-2-{4-[(methylamino)methyl]-phenyl}-1,3,4,5-tetrahydro-6H-azepino-[5,4,3-cd]indol-6-one (AG014699), 4-methoxy-carbazole (CEP 9722), 2-[4-[(3S)-piperidin-3-yl]phenyl]indazole-7-carboxamide hydrochloride (MK 4827), and 3-aminobenzamide, Iniparib, Olaparib, Rucaparib, Veliparib, CEP-9722, MK4827, BMN-673, pharmaceutically acceptable salts thereof, and combinations thereof; (b) therapeutically effective amounts of at least one GCR (glucocorticoid receptor) antagonist or active agent selected from the group consisting of PT150, PT155, PT156, PT157, PT158, TCY1, combinations thereof, and pharmaceutically acceptable salts thereof; and (c) optionally, at least one pharmaceutically acceptable carrier. The invention provides a method wherein the GCR (glucocorticoid receptor) antagonist is PT150, PT155, PT156, PT157, PT158, TCY1, combinations thereof, and pharmaceutically acceptable salts thereof. The invention provides a method wherein PT150, PT155, PT156, PT157, PT158, TCY1, combinations thereof, and pharmaceutically acceptable salts thereof is administered as an agent which directly effects tumor growth, independent of other administered treatment modalities, for palliation, remission, or cure. The invention provides a method wherein the PT150, PT155, PT156, PT157, PT158, TCY1, combinations thereof, and pharmaceutically acceptable salts thereof given systemically through oral or intravenous routes. The invention provides a method wherein the neoplasia is selected for the group consisting of Adenocarcinomas of the head and neck (including salivary glands and oral cavity), gastrointestinal tract (including pharynx, esophagus, stomach, small intestine, large intestine, anus), lung, liver (including hepatocellular carcinoma, cholangiocarcinoma, and mixed tumors), extrahepatic biliary tract and gallbladder, pancreas (including ductal and acinar types), genitourinary tracts (ovaries, fallopian tubes, endometrium, cervix, and vagina, ureters, urinary bladder, testicles, epididymis, prostate), and skin adnexa; squamous cell carcinomas of the head and neck (including salivary glands and oral cavity), gastrointestinal tract (including pharynx, esophagus, anus), lung, intrahepatic and extrahepatic biliary tree (including gallbladder), pancreas, genitourinary tracts (including endometrium, cervix, vagina, ureters, urinary bladder, testicles, epididymis, prostate), and skin adnexa; germ cell tumors (including malignant teratoma, embryonal carcinoma, struma ovarii, yolk sac tumor, seminoma, choriocarcinoma); sarcomas (including leiomyosarcomas, rhabdomyosarcomas, angiosarcomas, hemangioendotheliomas, liposarcomas, chondosarcomas, fibrosarcomas, Ewing sarcoma, malignant nerve sheathe tumors, alveolar soft part sarcomas, clear cell sarcomas, synovial sarcoma, osteosarcomas); malignancies of the central nervous system (including astrocytomas, oligodendroglioma, glioblastoma, medulloblastoma); salivary gland malignancies (including adenoid cystic carcinoma, adenosquamous carcinoma, clear cell carcinoma, cystadenocarcinoma, mucoepidermoid carcinoma); mixed type carcinomas (including hepatocellular-cholangiocarcinomas, carcinosarcomas, mixed adenoneurondocrine carcinomas, adenosquamous carcinomas); hepatocellular carcinoma; blastic malignancies (including hepatoblastoma, neuroblastoma, ganglioneuroblastoma, nephroblastoma); renal cell carcinomas; neuroendocrine carcinomas; thyroid carcinomas (including papillary, follicular, medullary, anaplastic carcinomas); parathyroid gland carcinomas, pituitary gland carcinomas, adrenal gland carcinomas (including adrenocortical carcinomas, pheochromocytoma), and combinations thereof. The invention provides a method wherein the PT150, PT155, PT156, PT157, PT158, TCY1, combinations thereof, and pharmaceutically acceptable salts thereof is targeted to tumor by intra-arterial infusion to reduce systemic side effects of GR blockade. The invention provides a method wherein the PT150, PT155, PT156, PT157, PT158, TCY1, combinations thereof, and pharmaceutically acceptable salts thereof is given to accomplish cure or remission of tumor. The invention provides a method wherein the PT150, PT155, PT156, PT157, PT158, TCY1, combinations thereof, and pharmaceutically acceptable salts thereof is given to accomplish reduction of tumor burden to enhance effectiveness of subsequent surgical resection. The invention provides a method wherein the PT150, PT155, PT156, PT157, PT158, TCY1, combinations thereof, and pharmaceutically acceptable salts thereof is given to accomplish reduction of tumor burden to make an unresectable tumor resectable.

The invention provides a pharmaceutical composition for treating or preventing infection related to acute or chronic injury or disease in a patient in need thereof, comprising: (a) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof; and (b) optionally, at least one pharmaceutically acceptable carrier.

The invention provides a method for treating or preventing infection related to acute or chronic injury or disease in a patient in need of such treatment, comprising: administering to said animal or human therapeutically effective amounts of each of: (a) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof; (b) optionally, at least one pharmaceutically acceptable carrier.

The invention provides a method for treating or preventing infection related to acute or chronic injury or disease wherein said method comprises administering to a patient in need of such therapy at least one glucocorticoid receptor antagonist in a therapeutically effective amount.

The invention provides a method wherein the at least one glucocorticoid receptor antagonist and/or active agent is in a pharmaceutical preparation.

The invention provides a method wherein the glucocorticoid receptor antagonist and/or active agent is selected from the group consisting of PT150, PT155, PT156, PT157, PT158, TCY1, combinations thereof, and pharmaceutically acceptable salts thereof.

The invention provides a method wherein the acute or chronic injury or disease is selected from the group consisting of vascular events, stroke, cardiac arrest, acute limb infarction accident/battle field trauma, traumatic limb, hip, brain injuries, post-surgical trauma, major orthopedic, thoracic, abdominal, neurological surgeries.

The invention provides a kit for treating or preventing infection related to acute or chronic injury or disease comprising at least one blister package; a lidded blister; a blister card or packet; a clamshell; an intravenous (IV) package, IV packette or IV container; a tray or a shrink wrap comprising a pharmaceutical composition comprising at least one active agent selected from the group consisting of PT150, PT155, PT156, PT157, PT158, TCY1, combinatinos thereof, and pharmaceutically acceptable salts thereof, and instructions for use of the pharmaceutical composition for treating or preventing infection related to acute or chronic injury or disease.

The invention provides a product of manufacture for treating or preventing infection related to acute or chronic injury or disease comprising a blister package; a lidded blister; a blister card or packet; a clamshell; an intravenous (IV) package, IV packette or IV container; a tray or a shrink wrap comprising a pharmaceutical composition comprising a pharmaceutical composition comprising at least one active agent selected from the group consisting of PT150, PT155, PT156, PT157, PT158, TCY1, combinatinos thereof, and pharmaceutically acceptable salts thereof, and instructions for use of the pharmaceutical composition for treating or preventing infection related to acute or chronic injury or disease.

The invention provides a pharmaceutical composition for treating or preventing impaired short term memory performance in a patient in need thereof, comprising: (a) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof; and (b) optionally, at least one pharmaceutically acceptable carrier.

The invention provides a method for treating or preventing impaired short term memory performance in a patient in need thereof, comprising: administering to said animal or human therapeutically effective amounts of each of: (a) therapeutically effective amounts of at least one GCR (glucocorticoid receptor) antagonist selected from the group consisting of PT150, PT155, PT156, PT157, PT158, TCY1, combinations thereof, and pharmaceutically acceptable salts thereof; (b) optionally, at least one pharmaceutically acceptable carrier.

The invention provides a kit for treating or preventing infection related to acute or chronic injury or disease comprising at least one blister package; a lidded blister; a blister card or packet; a clamshell; an intravenous (IV) package, IV packette or IV container; a tray or a shrink wrap comprising the pharmaceutical composition comprising: i) a first therapeutic agent which is at least one antiviral agent or pharmaceutically acceptable salt thereof; ii) a second therapeutic agent which is a GCR antagonist selected from the group consisting of PT150, PT155, PT156, PT157, PT158, TCY1, combinations thereof, and pharmaceutically acceptable salts thereof; and iii) at least one pharmaceutically acceptable carrier, wherein the pharmaceutical composition is formulated or manufactured as a liquid, an elixir, an aerosol, spray, a powder, a tablet, a pill, a capsule, a gel, a gel type, a nano suspension, a nanoparticle, and extended release dosage form, or at topical formulation, further wherein the antiviral agent and the GCR antagonists are each present in an amount which, in combination, is a therapeutically effective amount for treating or preventing a viral infection in a patient, wherein the antiviral agent is selected from the group consisting of Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof, as a way of preventing or minimizing development of Addisonian symptoms from ongoing, high level systemic GCR blockade of endogenous, physiologic cortisol, and instructions for use of the pharmaceutical composition for treating or preventing infection related to acute or chronic injury or disease.

The invention provides a product of manufacture for treating or preventing infection related to acute or chronic injury or disease comprising a blister package; a lidded blister; a blister card or packet; a clamshell; an intravenous (IV) package, IV packette or IV container; a tray or a shrink wrap comprising a pharmaceutical composition comprising the pharmaceutical composition comprising: i) a first therapeutic agent which is at least one antiviral agent or pharmaceutically acceptable salt thereof; ii) a second therapeutic agent which is a GCR antagonist selected from the group consisting of PT150, PT155, PT156, PT157, PT158, TCY1, combinations thereof, and pharmaceutically acceptable salts thereof; and iii) at least one pharmaceutically acceptable carrier, wherein the pharmaceutical composition is formulated or manufactured as a liquid, an elixir, an aerosol, spray, a powder, a tablet, a pill, a capsule, a gel, a gel type, a nano suspension, a nanoparticle, and extended release dosage form, or at topical formulation, further wherein the antiviral agent and the GCR antagonists are each present in an amount which, in combination, is a therapeutically effective amount for treating or preventing a viral infection in a patient, wherein the antiviral agent is selected from the group consisting of Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof, as a way of preventing or minimizing development of Addisonian symptoms from ongoing. high level systemic GCR blockade of endogenous, physiologic cortisol, and instructions for use of the pharmaceutical composition for treating or preventing infection related to acute or chronic injury or disease.

The invention provides for the use of the compositions of the invention for the production of a medicament for treating the indications as set forth herein.

In accordance with a further embodiment, the present invention provides a use of the pharmaceutical compositions described above, an amount effective for use in a medicament, and most preferably for use as a medicament for treating a disease or disorder in a subject.

In accordance with yet another embodiment, the present invention provides a use of the pharmaceutical compositions described above, and at least one additional therapeutic agent, in an amount effective for use in a medicament, and most preferably for use as a medicament for treating a disease or disorder associated with disease in a subject.

The invention provides a method for treating or preventing infection after ischemic stroke wherein said method comprises administering to a patient in need of such therapy at least one glucocorticoid receptor antagonist in a therapeutically effective amount.

The invention provides a method wherein the at least one glucocorticoid receptor antagonist and/or active agent is in a pharmaceutical preparation.

The invention provides a method wherein the glucocorticoid receptor antagonist and/or active agent is selected from the group consisting of PT150, PT155, PT156, PT157, PT158, TCY1, combinations thereof, and pharmaceutically acceptable salts thereof.

The invention provides a method of treating or preventing infection secondary to CNS injury in a patient in need thereof, comprising administering at least one GCR antagonist in a therapeutically effective amount.

The invention provides a method wherein the CNS injury is selected from the group consisting of stroke, neuronal damage resulting from head trauma, epilepsy, pain, migraine, a mood disorder, schizophrenia, a neurodegenerative disorder, depression, anxiety, a psychosis, hypertension or cardiac arrhythmia, and combinations thereof.

The invention provides a kit for treating or preventing infection after ischemic stroke comprising: (a) a pharmaceutical composition comprising at least one glucocorticoid receptor antagonist in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing infection after ischemic stroke.

The invention provides a product of manufacture for treating or preventing infection after ischemic stroke comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for use of the pharmaceutical composition for treating or preventing infection after ischemic stroke.

The invention provides a method for reducing infarct severity and improving long term outcome after ischemic stroke wherein said method comprises administering, to a patient in need of such therapy, at least one glucocorticoid receptor antagonist in a therapeutically effective amount.

The invention provides a method wherein the at least one glucocorticoid receptor antagonist and/or active agent is in a pharmaceutical preparation.

The invention provides a method wherein the glucocorticoid receptor antagonist and/or active agent is selected from the group consisting of PT150, PT155, PT156, PT157, PT158, TCY1, combinations thereof, and pharmaceutically acceptable salts thereof.

The invention provides a method of treating or preventing infection secondary to CNS injury in a patient in need thereof, comprising administering at least one GCR antagonist in a therapeutically effective amount.

The invention provides a method for improving long term outcome secondary to CNS injury in a patient in need thereof, comprising administering at least one GCR antagonist.

The invention provides a method wherein the CNS injury is selected from the group consisting of stroke, neuronal damage resulting from head trauma, epilepsy, pain, migraine, a mood disorder, schizophrenia, a neurodegenerative disorder, depression, anxiety, a psychosis, hypertension or cardiac arrhythmia, and combinations thereof.

The invention provides a kit for reducing infarct severity and improving long term outcome after ischemic stroke comprising: (a) a pharmaceutical composition comprising at least one GCR antagonist; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing infection after ischemic stroke.

The invention provides a product of manufacture for reducing infarct severity and improving long term outcome after ischemic stroke comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for use of the pharmaceutical composition for treating or preventing infection after ischemic stroke.

The invention provides a glucocorticoid receptor antagonist selected from the group consisting of PT150, PT155, PT156, PT157, PT158, TCY1, combinations thereof, and pharmaceutically acceptable salts thereof for use in the preparation of a medicament for use in treating or preventing a disease or condition as set forth herein in a patient. The invention provides a pharmaceutical composition comprising a glucocorticoid receptor antagonist selected from the group consisting of PT150, PT155, PT156, PT157, PT158, TCY1, combinations thereof, and pharmaceutically acceptable salts thereof, for use in the preparation of a medicament for use in topical application to treat and/or prevent a disease or condition as set forth herein in a patient. The invention provides a method for treating and/or preventing a disease or condition as set forth herein in a patient, wherein said method comprises: selecting a patient in need of treating and/or preventing said disease or condition as set forth herein; administering to the patient a composition of the invention in a therapeutically effective amount, thereby treating and/or preventing said disease in said patient.

BRIEF DESCRIPTION OF SEVERAL VIEWS OF THE DRAWINGS

The invention will be described in conjunction with the following drawings in which like reference numerals designate like elements and wherein:

FIG. 7(A) Schematic representation of the 3'-NCR of West Nile virus demonstrating the arrangement of stem-loops (SL) and pseudoknots (PK) and the sfRNA 5'-terminus. FIG. 7(B) Schematic representation demonstrating the predicted conservation of the SL-II/PK1-like RNA structure within the 3'-NCR of divergent members of the genus Flavivirus

DETAILED DESCRIPTION OF THE INVENTION

Figure 1:
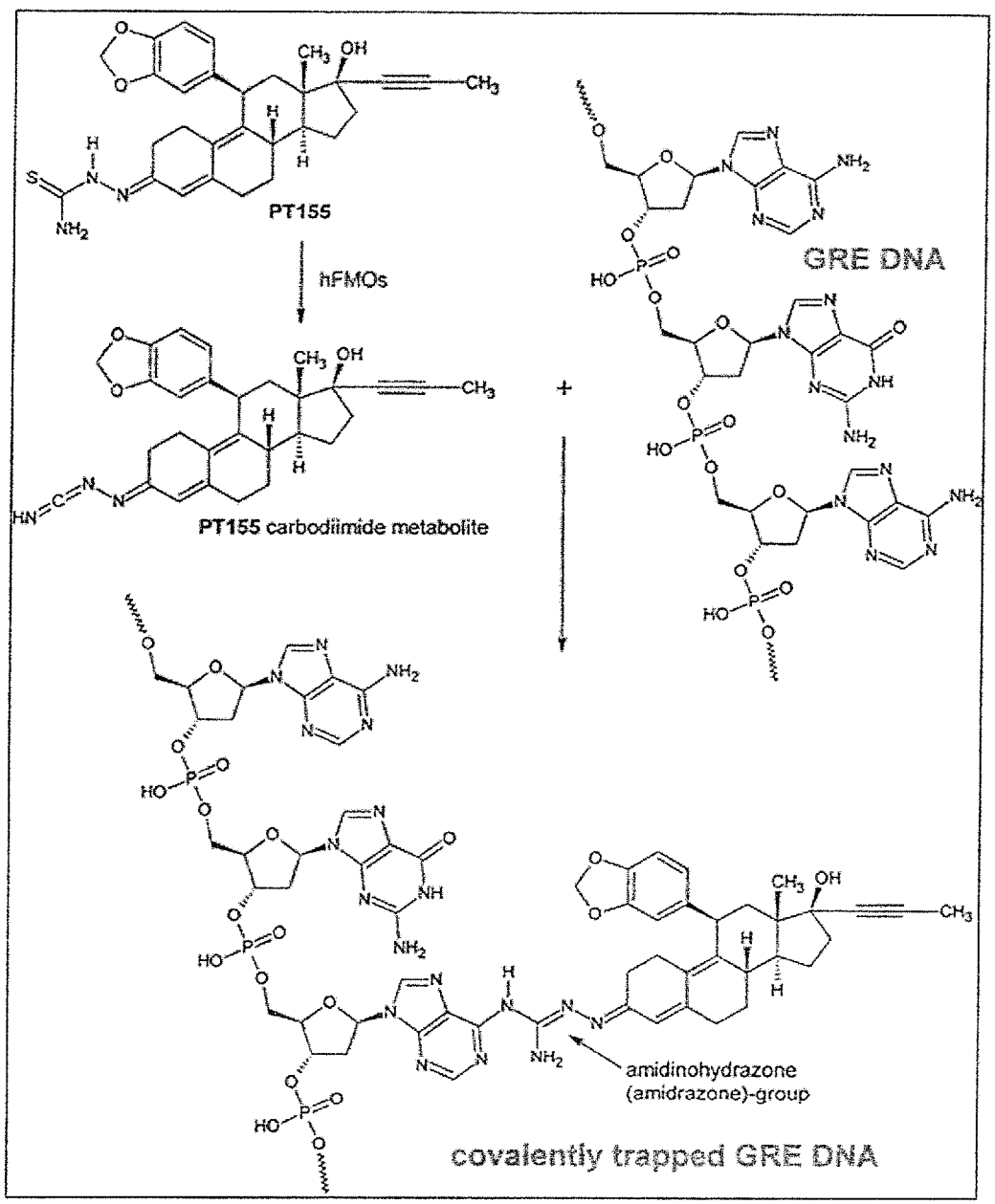
FIG. 1 shows Bio-activation by human flavin-dependent monooxygenases (hFMOs) and GRE DNA-trapping of PT155. The thiosemicarbazone moiety in PT155 can be oxidized by hFMOs (hFMO1, hFMO2.1, hFMO3) with molecular oxygen over the sulfenic acid to the PT155 carbodiimide metabolite which could be co-transported into the host cell nucleus by hGRalpha: hGRalphasubunit 1-(PT155 carbodiimide metabolite)=hGRalphasubunit 2-PT150. The carbodiimide moiety adds to one amino group of proviral GRE DNA yielding an N-amidinohydrazone (amidrazone)-group, thereby inducing proviral DNA damage.
Figure 2:
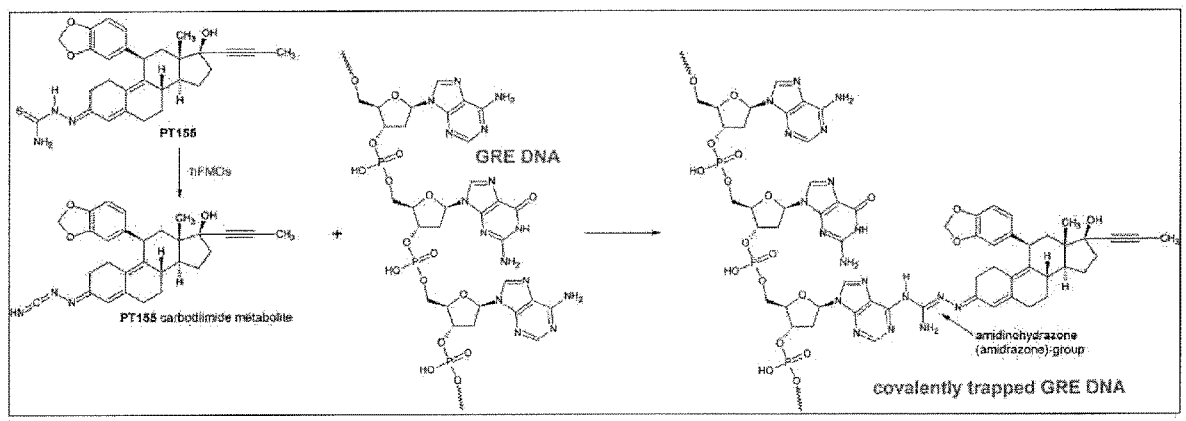
FIG. 2 shows Covalent Inactivation of HIV-1 host DNA-integrated proviral GRE DNA.
Figure 3:
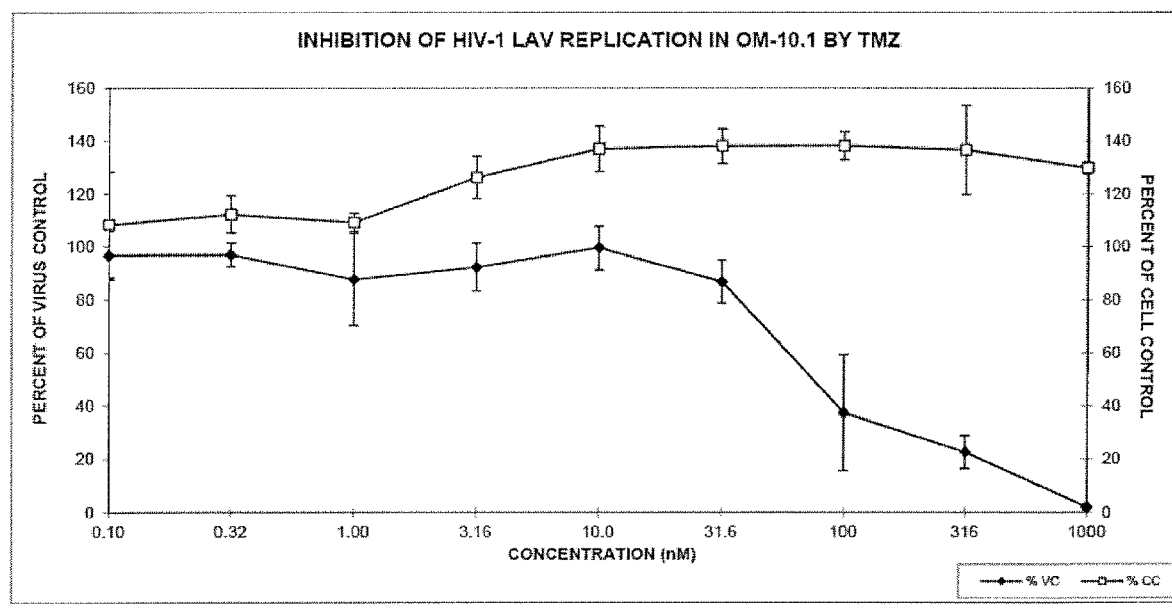
FIG. 3 is a chart showing Inhibition of HIV-1 LAV Replication in OM-10.1 by TMZ.
Figure 4:
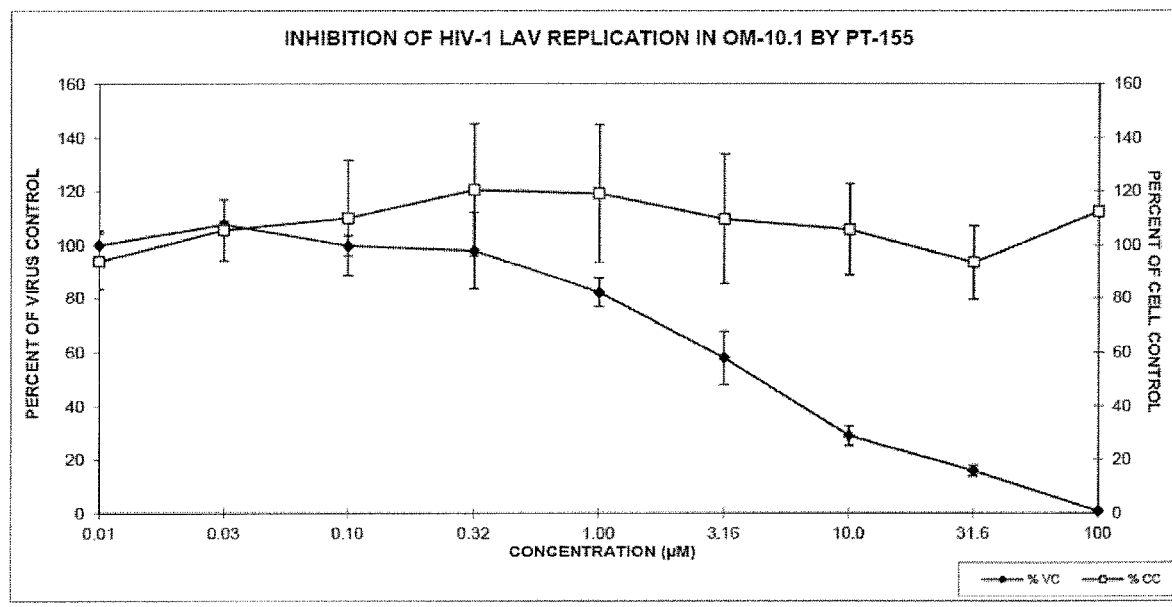
FIG. 4 is a chart showing Inhibition of HIV-1 LAV Replication in OM-10.1 by PT155.
Figure 5:
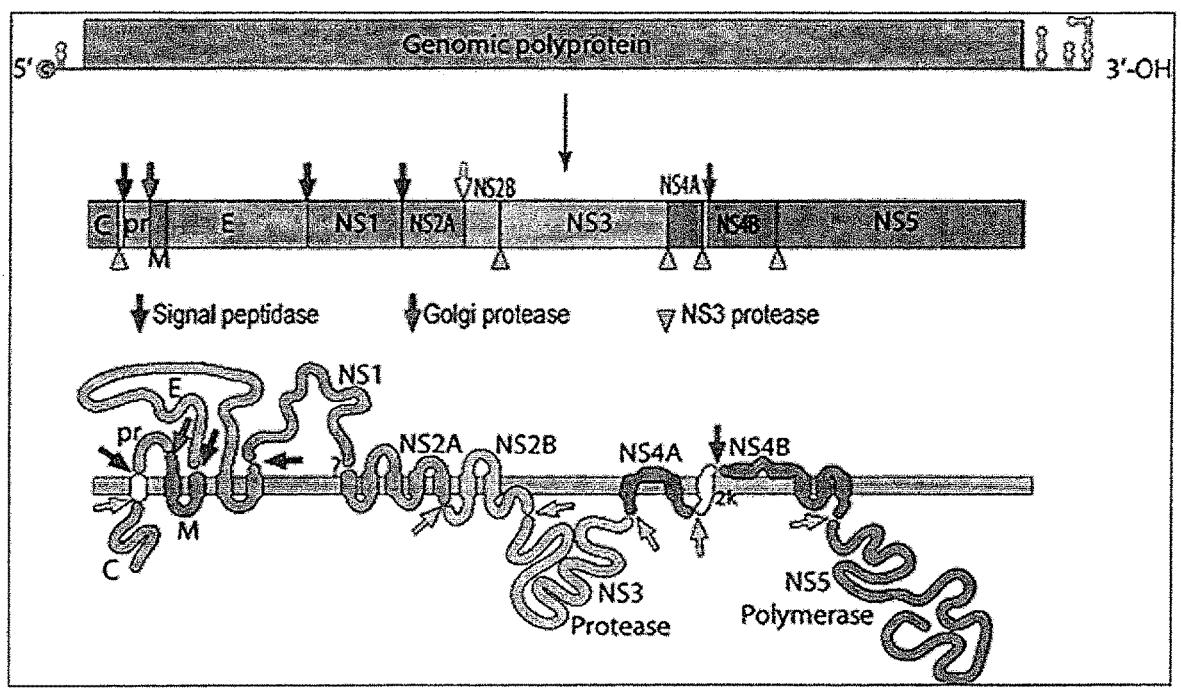
FIG. 5 shows Flavivirus (+)-ssRNA genome-encoded polyprotein with the locations of 5'-noncoding region (5'-NCR) and 3'-noncoding region (3'-NCR at 3'-OH). This graphic shows a typical Flavivirus positive-sense single-stranded RNA [(+)-ssRNA] (length about 11,000 nucleotides) genome encoding a polyprotein. The (+)-ssRNA genome is shown with short 5'-capped (left) 5'-noncoding region (5'-NCR), and the 3'-noncoding region [3'-NCR; in green at the right end (3'-OH) of the genome]. The host cell and viral protease cleavage sites in the polyprotein leading to mature flaviviral proteins are indicated (host cell signal peptidase; host cell Golgi protease; viral NS3 protease).
Figure 6:
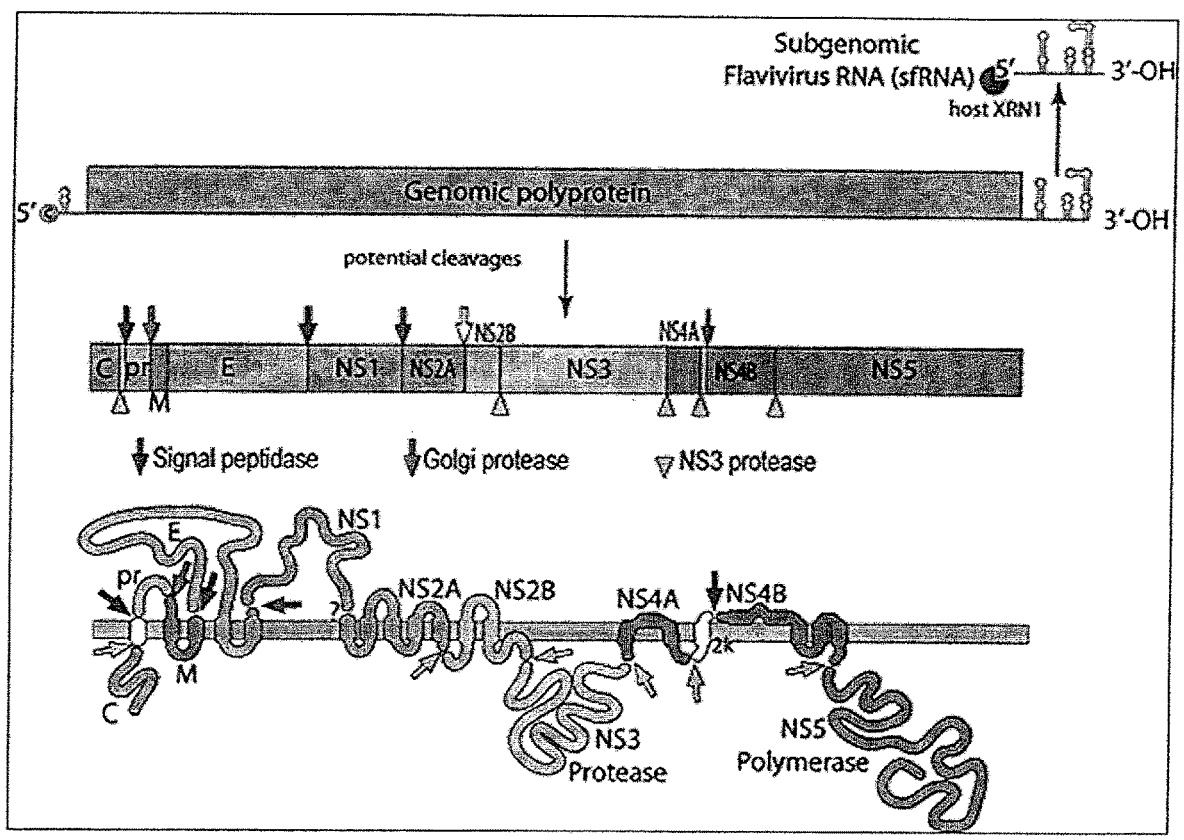
FIG. 6 shows Zika virus (+)-ssRNA genome-encoded polyprotein with the locations of 3'-noncoding region (3'-NCR at 3'-OH) and the origin of sfRNA. This graphic shows Zika virus (isolate Zika virus/M.mulatta-tc/UGA/1947/MR-766) positive-sense single-stranded RNA [(+)-ssRNA] (10, 795 nt) genome (GenBank: KU955594.1) encoding a polyprotein. The (+)-ssRNA genome is shown with the 3'-noncoding region [3'-NCR; in green at the right end (3'-OH) of the genome]. The origin of the subgenomic flavivirus RNA (sfRNA) by human host cell XRN1 5'→3'-exoribonuclease is indicated.
Figure 7:
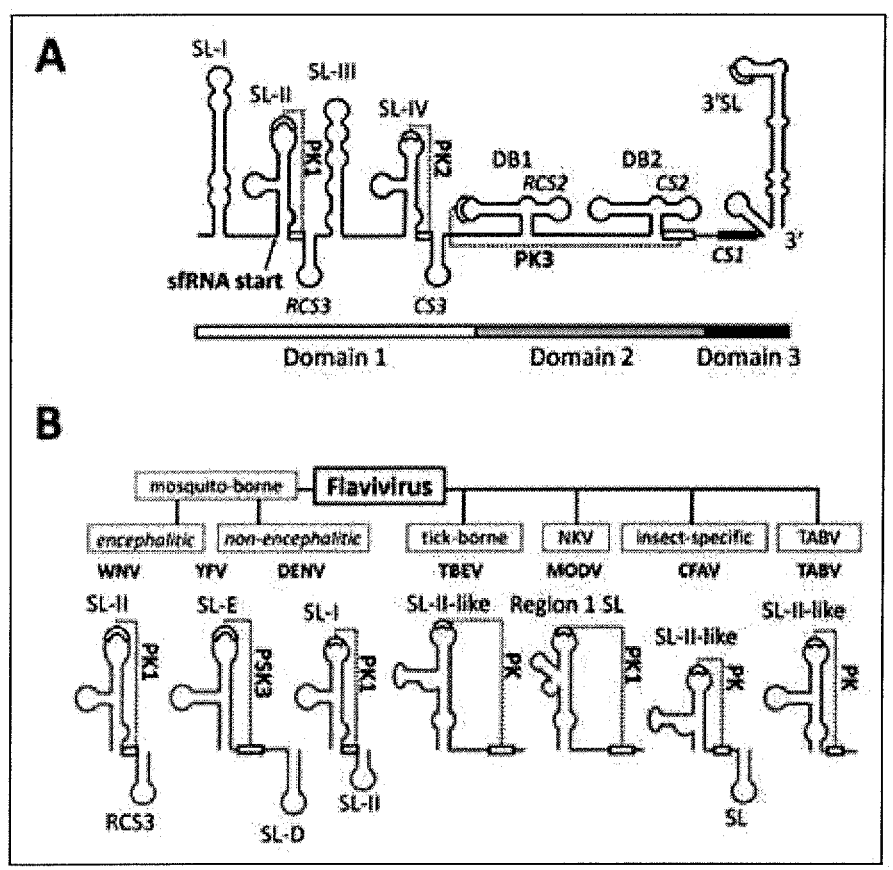
FIG. 7 is a Schematic representation of the 3'-NCR of West Nile virus.
Figure 8:
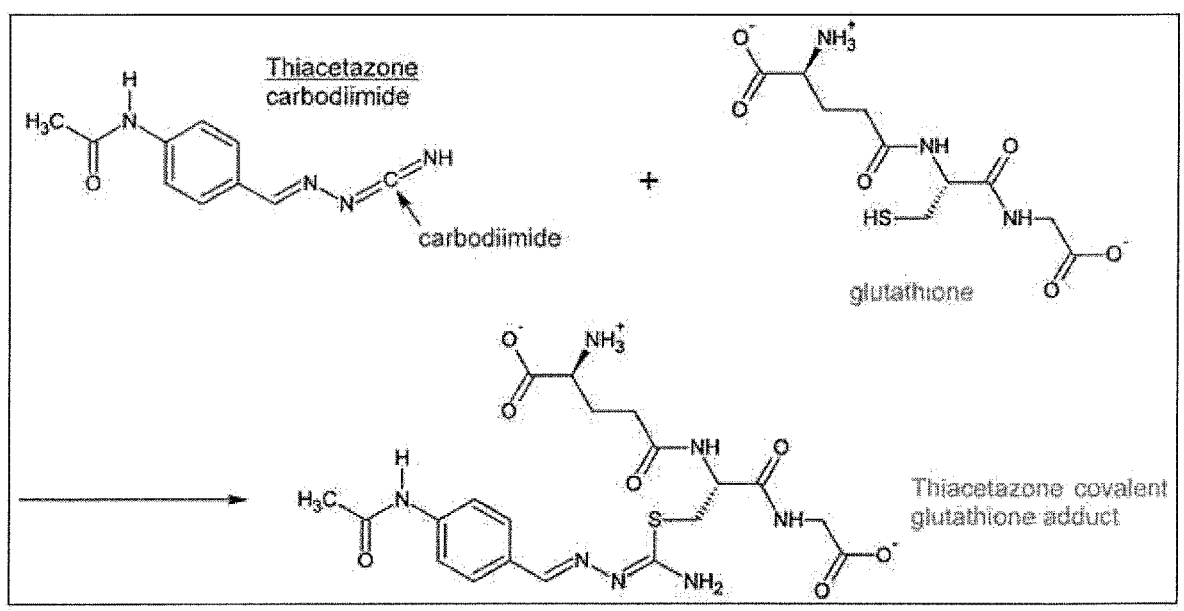
FIG. 8 shows carbodiimide metabolite can react with amino acid residues in target proteins of, for example, *Mycobacterium tuberculosis* (refs 11, 14), or with human hepatic/extrahepatic glutathione R—SH thiol group for metabolic detoxification.
Figure 9:
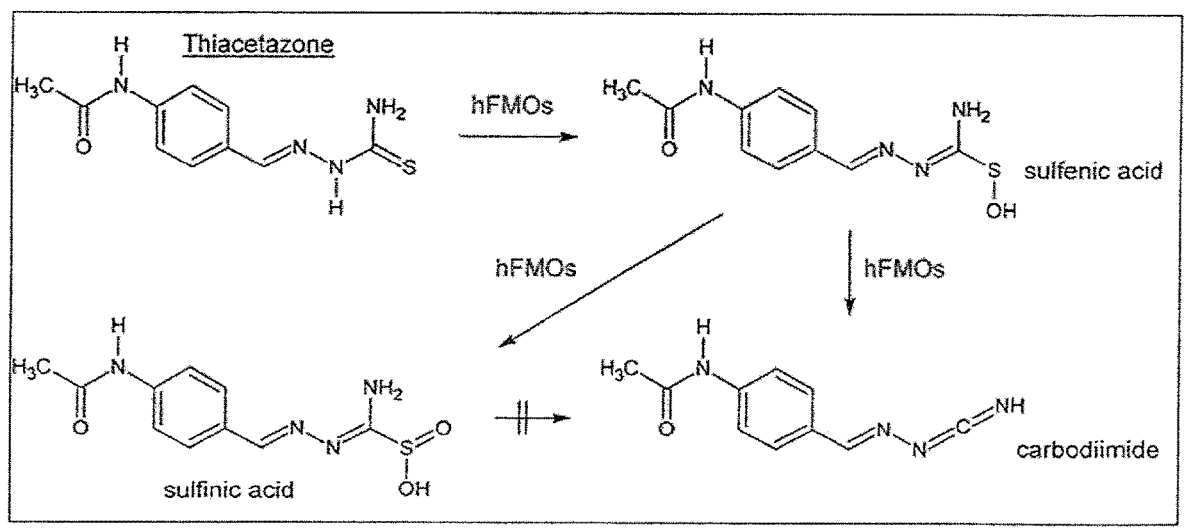
FIG. 9 shows thiosemicarbazones like thiacetazone (p-acetamidobenzaldehyde thiosemicarbazone), a cheap, second-line antitubercular substance discovered by Nobel laureate Gerhard Domagk in 1946 (ref 13), are bio-activated by human flavin-containing monooxygenases (hFMO1, hFMO2.1, hFMO3) into a sulfenic acid (R—S—OH), a sulfinic acid [R—(S=O)—OH], and a carbodiimide derivative (R—N=C=N—H).
Figure 10:
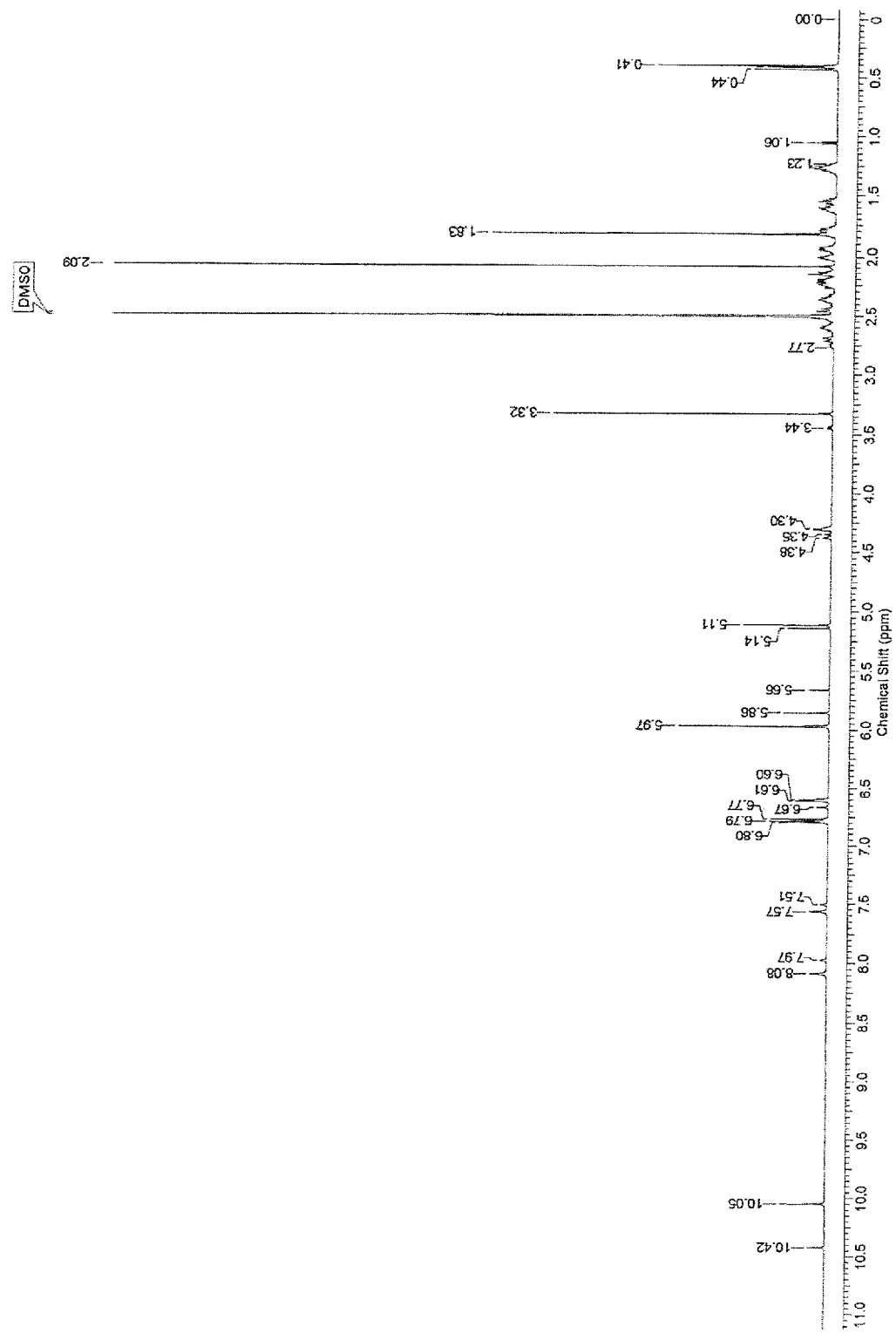
FIG. 10 shows the 700.35 MHz proton (1H) nuclear magnetic resonance (NMR) spectrum of PT155 dissolved in DMSO-d6.
Figure 11:
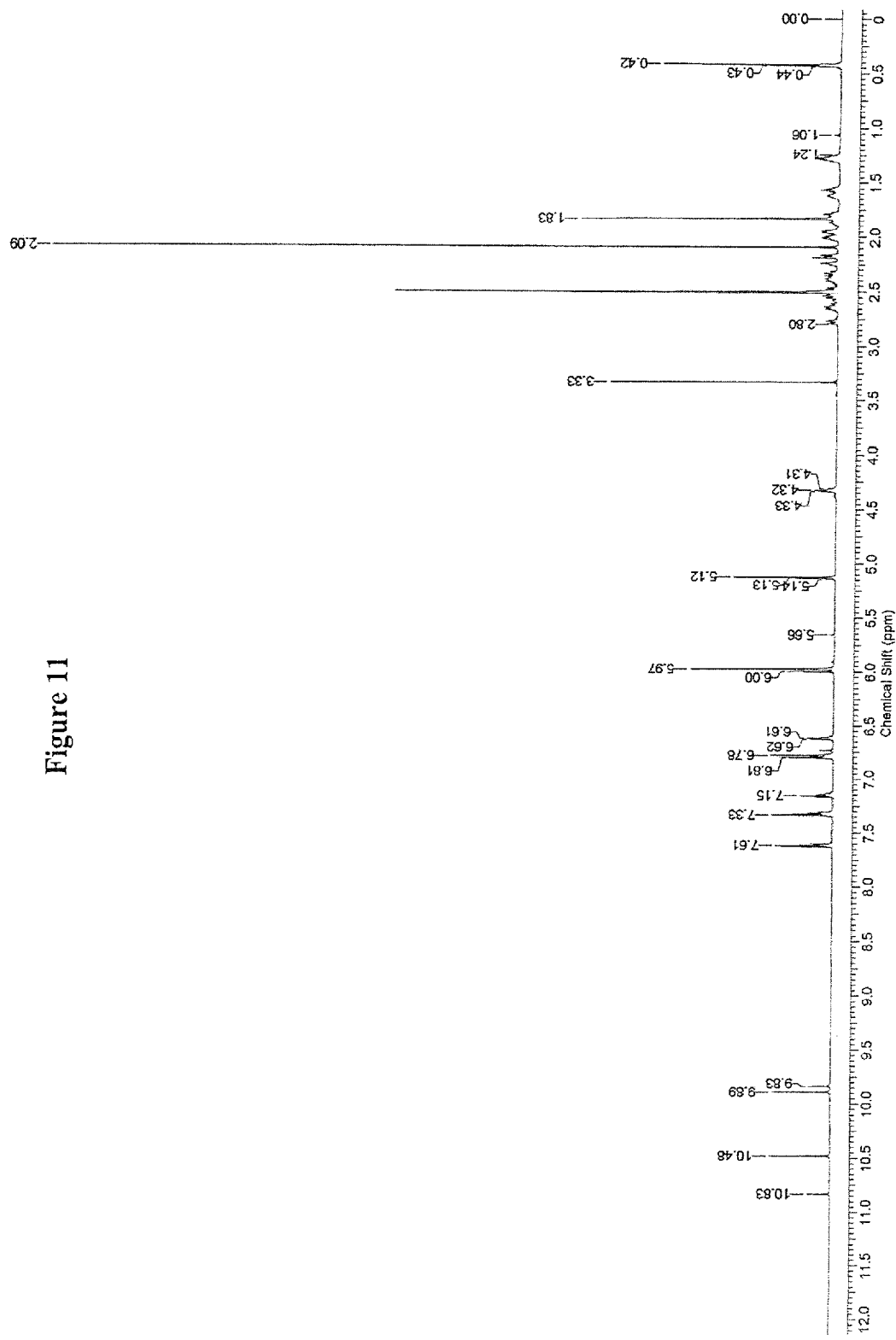
FIG. 11 shows the 700.35 MHz proton (1H) nuclear magnetic resonance (NMR) spectrum of PT156 dissolved in DMSO-d6.
Figure 12:
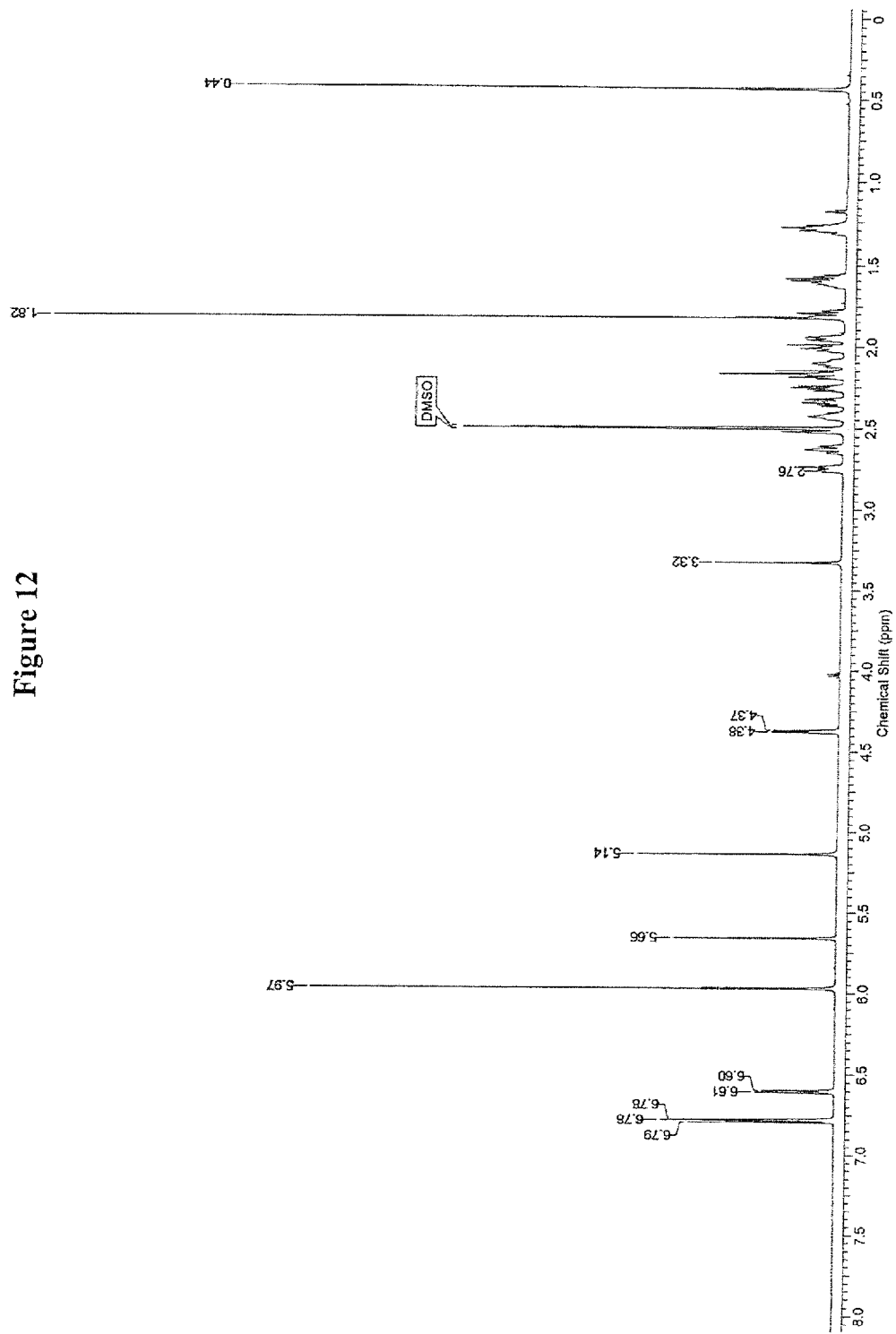
FIG. 12 shows the 700.35 MHz proton (1H) nuclear magnetic resonance (NMR) spectrum of highly purified ORG34517 (PT150) dissolved in DMSO-d6.
Figure 13:
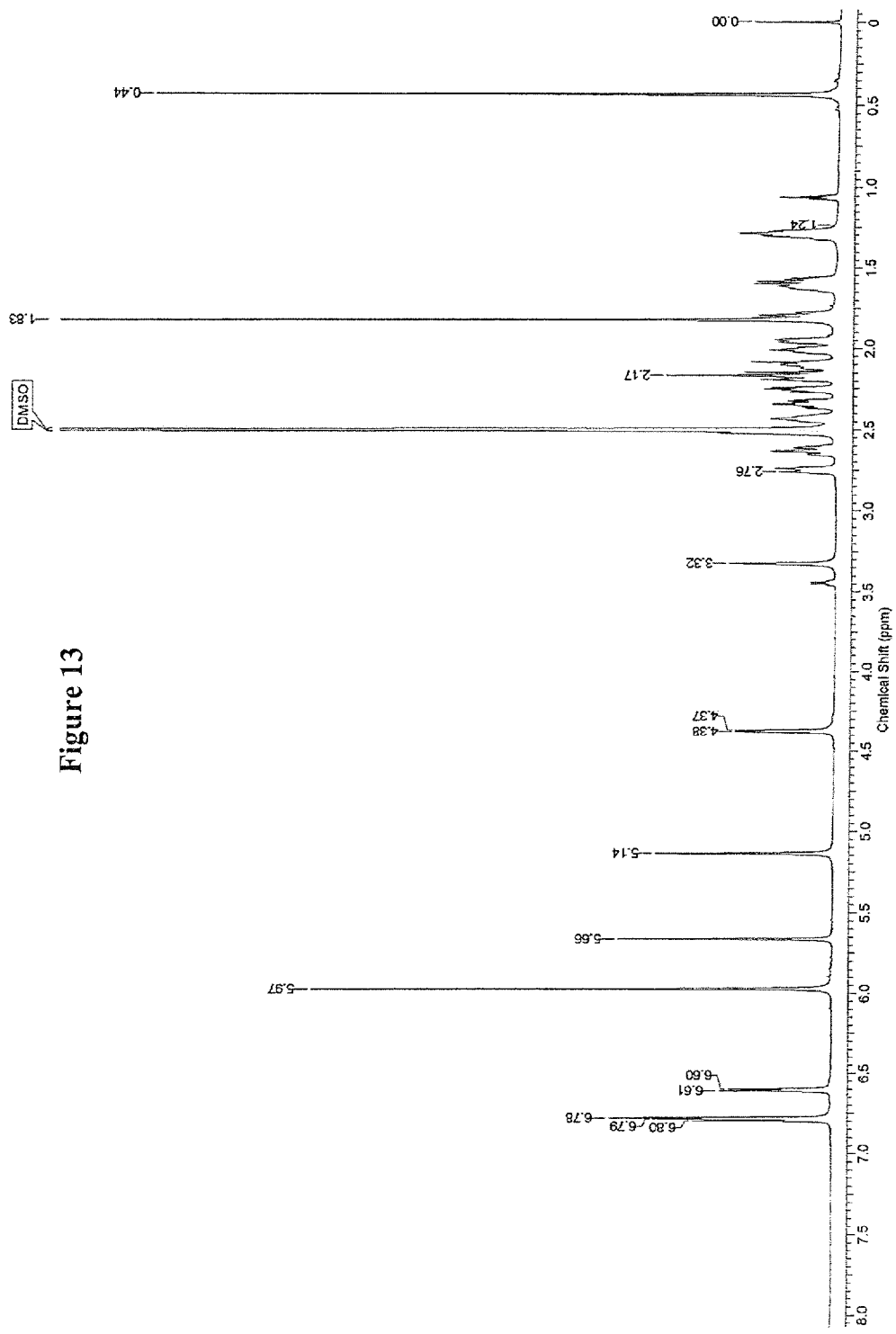
FIG. 13 shows the 700.35 MHz proton (1H) nuclear magnetic resonance (NMR) spectrum of PT157 dissolved in DMSO-d6.
Figure 14:
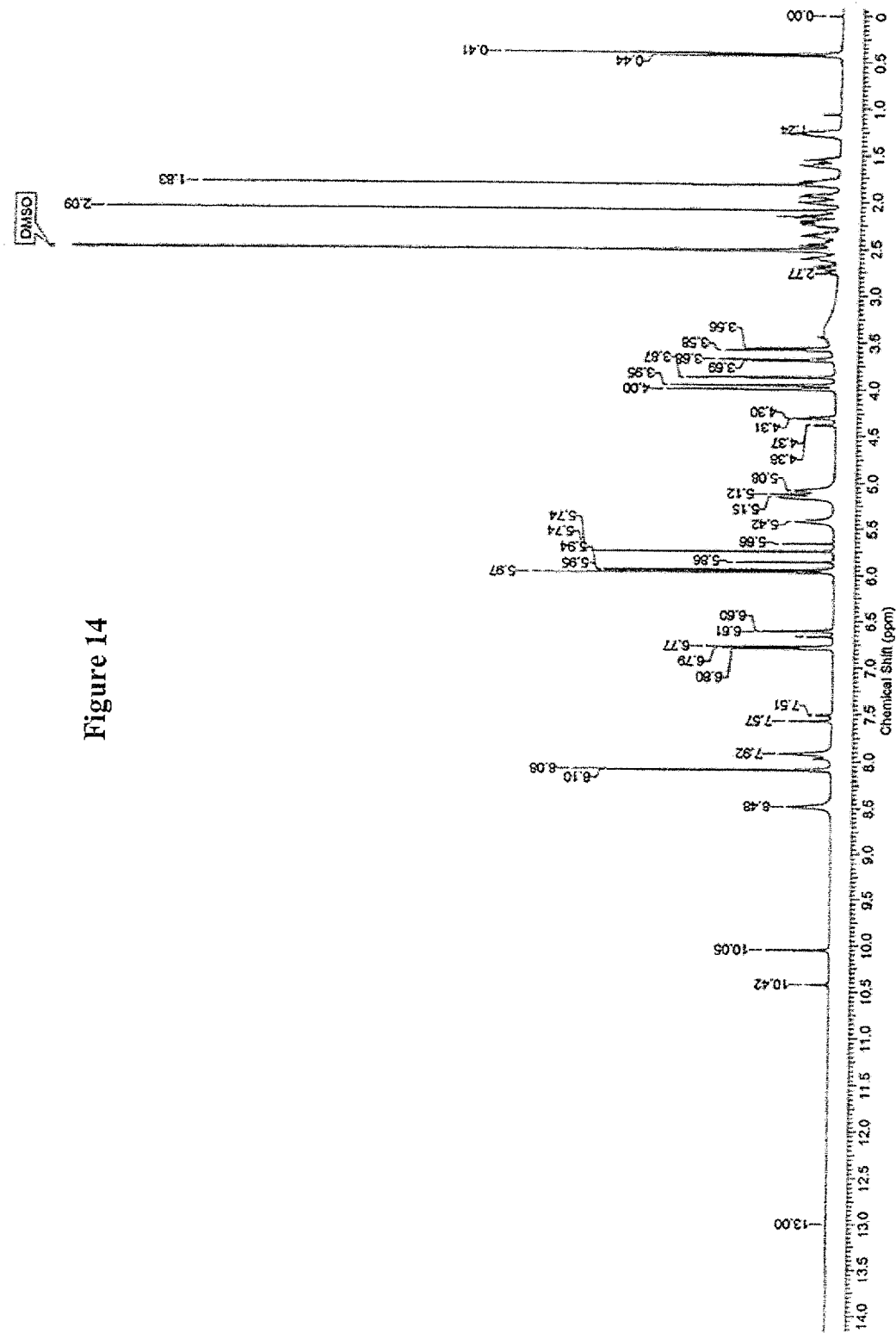
FIG. 14 shows the 700.35 MHz proton (1H) nuclear magnetic resonance (NMR) spectrum of PT158 dissolved in DMSO-d6.
Figure 15:
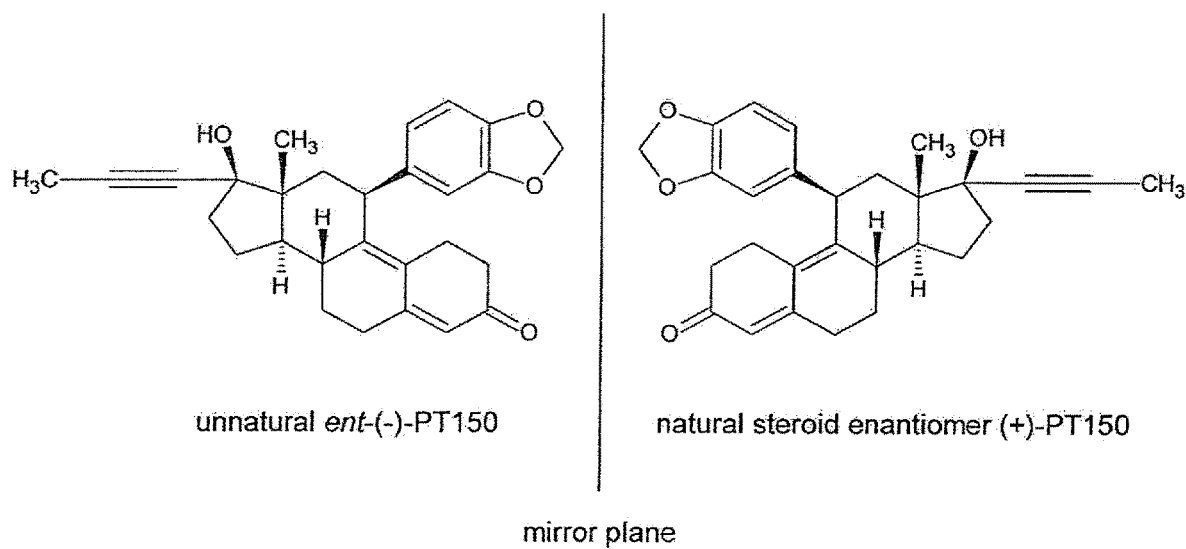
FIG. 15 shows enantiomers of ORG34517 (PT150).
Figure 16:
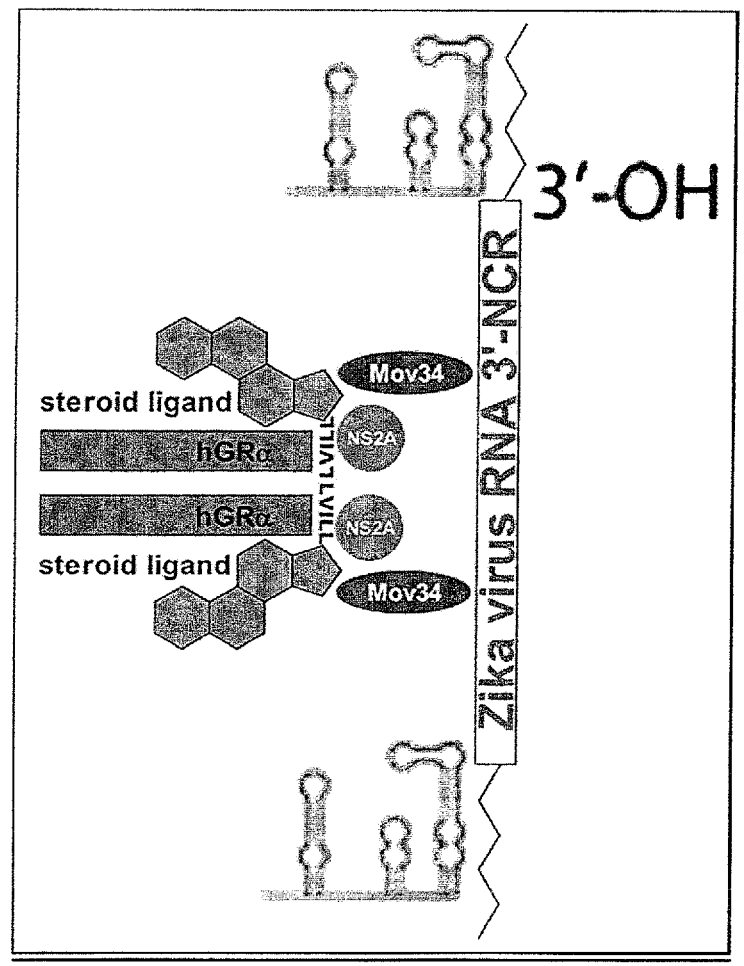
FIG. 16 shows Zika virus NS2A protein contains the LXXLL glucocorticoid receptor coactivator sequence. A ternary complex Mov34-NS2A$_{zika}$-hGRα can be formed in case of Zika virus infection, which in turn is essential to Zika virus RNA replication. Zika virus 3'-NCR requires the Mov34-NS2A$_{zika}$-hGRα axis to replicate optimally in human cells, that means forming a functional replicase complex at the 3'-NCR for negative-strand (−)-ssRNA synthesis. This also requires the physiological human glucocorticosteroid cortisol (hydrocortisone) bound to hGRα in this axis. Glucocorticoid antagonists, especially PT155, prevent activation of Zika virus 3'-NCR required for negative-strand (−

The invention is directed to the use of, for example, a glucocorticoid receptor antagonist, optionally in combination with another agent, for treating or preventing treatment resistant prostate cancer, treating or preventing neoplasia, and/or treating or preventing infection related to acute or chronic injury or disease.

As used herein, the term "effective amount" refers to the amount of a therapy that is sufficient to result in the prevention of the development, recurrence, or onset of a disease or condition, such as neoplasia or infection, and one or more symptoms thereof, to enhance or improve the prophylactic effect(s) of another therapy, reduce the severity, the duration of a disease or condition, such as neoplasia or infection, ameliorate one or more symptoms of a disease or condition such as neoplasia or infection, prevent the advancement of a disease or condition, such as neoplasia or infection, cause regression of a disease or condition, such as neoplasia or infection, and/or enhance or improve the therapeutic effect(s) of another therapy. An amount is "effective" as used herein, when the amount provides an effect in the subject. As used herein, the term "effective amount" means an amount of a compound or composition sufficient to significantly induce a positive benefit, including independently or in combinations the benefits disclosed herein, but low enough to avoid serious side effects, i.e., to provide a reasonable benefit to risk ratio, within the scope of sound judgment of the skilled artisan. For those skilled in the art, the effective amount, as well as dosage and frequency of administration, may easily be determined according to their knowledge and standard methodology of merely routine experimentation based on the present disclosure.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, such as neoplasia, viral infection, latent viral infections, or a symptom thereof in a subject resulting from the administration of a therapy (e.g., a prophylactic or therapeutic agent), or a combination of therapies (e.g., a combination of prophylactic or therapeutic agents).

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the terms "therapies" and "therapy" can refer to any method(s), composition(s), and/or agent(s) that can be used in the prevention, treatment and/or management of a disease or condition, such as neoplasia or viral infection, or one or more symptoms thereof.

As used herein, the terms "treat," "treatment," and "treating" in the context of the administration of a therapy to a subject refer to the reduction or inhibition of the progression and/or duration of a disease or condition, such as neoplasia or viral infection, the reduction or amelioration of the severity of a disease or condition, such as neoplasia or infection, and/or the amelioration of one or more symptoms thereof resulting from the administration of one or more therapies.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "androgenergic antagonist" refers to agents that can prevent androgens from expressing their biological effects on responsive tissues. These agents alter the androgen pathway by blocking the appropriate receptors, competing for binding sites on the cell's surface, or affecting androgen production. Androgenergic antagonist can be prescribed to treat an array of diseases and disorders. In men, these agents are most frequently used to treat prostate cancer. In women, these agents are used to decrease levels of male hormones causing symptoms of hyperandrogenism. Androgenergic antagonist present in the environment have become a topic of concern. Many industrial chemicals, pesticides and insecticides exhibit antiandrogenic effects. Non-limiting examples of the androgenergic antagonist include, but not limited to, allylestrenol, oxendolone, osaterone acetate, bicalutamide, steroidal, anti-androgergic agents, medroxyprogesterone (MPA), cyproterone, cyproterone acetate (CPA), dienogest, flutamide, nilutamide, spironolactone, 5alpha-reductase inhibitors, dutasteride, finasteride, salts thereof, gold nanoparticles thereof, combinations thereof, and the like. In some embodiments of the present invention, examples of the androgenergic antagonist includes, but not limited to a gold nanoparticle of alpha-bicalutamide, or a gold nanoparticle of beta-bicalutamide.

The present invention relates to the use of GR antagonists (e.g., ORG 34517, PT150, PT155, PT156, PT157, PT158, TCY1, combinations thereof, and pharmaceutically acceptable salts) for the prevention or addiction induced anxiety and withdrawal side effects as a therapeutic, for wound healing and transplants, for the prevention or treatment of stress induced osteoporosis and for the rapid healing of bone related injuries, and regenerative therapy.

This invention relates to a low cost rapid response diagnostic system to determine salivary cortisol levels in patients selected as potential candidates for GCR (glucocorticoid receptor) antagonist therapy utilizing a GCR antagonist, such as ORG 34517, PT150, PT155, PT156, PT157, PT158, TCY1, combinations thereof, and pharmaceutically acceptable salts. The rapid, sensitive, and inexpensive test can be used to determine patients who have non-normal cortisol production or disordered circadian rhythms as a method for selecting subjects for GCR antagonist or active agent therapy for whom it is likely to have beneficial and/or therapeutic effects, and can also be used to monitor changes in cortisol levels in response to treatment.

As used herein, the term "agent" refers to any molecule, compound, methodology and/or substance for use in the prevention, treatment, management and/or diagnosis of viral infection or cancer. Non-limiting examples of cancer therapies include chemotherapies, radiation therapies, hormonal therapies, anti-angiogenesis therapies, targeted therapies, and/or biological therapies including immunotherapies and surgery.

As used herein, the term "cancer cells" refer to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cell" is meant to encompass both pre-malignant and malignant cancer cells.

As used herein, the term "cancer stem cell(s)" refers to a cell that can be a progenitor of a highly proliferative cancer cell. A cancer stem cell has the ability to re-grow a tumor as demonstrated by its ability to form tumors in immunocompromised mice, and typically to form tumors upon subsequent serial transplantation immunocompromised mice. Cancer stem cells are also typically slow-growing relative to the bulk of a tumor; that is, cancer stem cells are generally quiescent. In certain embodiments, but not all, the cancer stem cell may represent approximately 0.1 to 10% of a tumor.

As used herein, the phrase "diagnostic agent" refers to any molecule, compound, and/or substance that is used for the purpose of diagnosing a disease or condition. Non-limiting examples of diagnostic agents include antibodies, antibody fragments, or other proteins, including those conjugated to a detectable agent. As used herein, the term "detectable agents" refer to any molecule, compound and/or substance that is detectable by any methodology available to one of skill in the art. Non-limiting examples of detectable agents include dyes, gases, metals, or radioisotopes. As used herein, diagnostic agent and "imaging agent" are equivalent terms.

In an embodiment of the invention, the amount of a therapy is effective to achieve one, two, three, or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

As used herein, the term "predetermined reference range" refers to a reference range for the particular biological entity, e.g., cortisol, for a subject or a population of subjects. Each laboratory may establish its own reference range for each particular assay, or a standard reference range for each assay may be made available and used locally, regionally, nationally, or worldwide or may be patient-specific. In one specific embodiment, the term refers to a reference range for the amount of cortisol in a patient or a specimen from a patient. In another specific embodiment, the term refers to a reference range for the amount of cortisol in a patient or a specimen from a patient.

As used herein, the term "therapeutic agent" refers to any molecule, compound, and/or substance that is used for the purpose of treating and/or managing a disease or disorder. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), proliferation-based therapy, radiation, chemotherapy, anti-angiogenic agents, and small molecule drugs.

As used herein, the terms "therapies" and "therapy" can refer to any method(s), composition(s), and/or agent(s) that can be used in the prevention, treatment and/or management of a disease or condition, such as cancer or viral infection, or one or more symptoms thereof. In certain embodiments, the terms "therapy" and "therapies" refer to chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or a combination of the foregoing and/or other therapies useful in the prevention, management and/or treatment of a cancer or one or more symptoms thereof. As used herein, the terms "treat," "treatment," and "treating" in the context of the administration of a therapy to a subject refer to the reduction or inhibition of the progression and/or duration of a disease or condition, such as cancer or viral infection, the reduction or amelioration of the severity of a disease or condition, such as cancer, and/or the amelioration of one or more symptoms thereof resulting from the administration of one or more therapies. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to a stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The invention is directed to the use of, for example, a glucocorticoid receptor antagonist for preventive anti-infective therapy after, for example, stroke, and for the production of medicines and/or pharmaceutical preparations for preventive anti-infective therapy after stroke. Respiratory tract infections ranged from 1-33% after stroke and urinary tract infections ranged from 2-27%. These infections have a high impact on morbidity and mortality. The 30-day-mortality rate in patients with pneumonia is 27% while the mortality rate is 4% in stroke patients without pneumonia. Also, the disability in stroke patients with pneumonia is higher than in patients without, resulting in increased medical costs and a lower quality of life. It is ethically and medically preferred to prevent or treat the post-stroke infections. Presently, trials of antibiotics for the prevention and treatment of post-stroke infections are underway.

The term "early preventive, anti-infective therapy after stroke" means that the treatment is started within 72 hours after the stroke event.

Glucocorticoid Receptor

The glucocorticoid receptor is widely distributed and expressed in many cultured cell lines, and the control of gene expression by glucocorticoids, therefore, has been widely studied as a model for transcriptional regulation.

A number of glucocorticoid-responsive transcription units, including mouse mammary tumor virus (MMTV) (Ringold, et al., 1975; Parks, et al., 1974), mouse and human metallothionein (Eager, et al., 1981; Karin, et al., 1980), rat alpha2M-globulin (Kurtz, et al., 1977) and rat and human growth hormone (Spindler, et al., 1982; Evans, et al., 1982; Robins, et al., 1982) genes have been identified. DNA sequences mediating transcriptional stimulation of several of these genes have been localized. For MMTV, these sequences are discrete genomic regions upstream of the transcriptional start site which appear to exert their actions independently of orientation and position (Chandler, et al., 1983; Ostrowski, et al., 1984). The steroid/receptor complex appears to bind to these regulatory sequences and purified receptor has been used to define the specific binding sites (Govinda, et al., 1982; Scheidereit, et al., 1983; Pfahl, 1982; Payvar, et al., 1983). The ability of the glucocorticoid-responsive element (GRE) to alter its position and orientation yet still maintain promoter inducibility suggests that it resembles the class of cis-acting regulatory sequences termed enhancers (Chandler, et al., 1983). First discovered in viruses and subsequently in cellular genes, these sequences are necessary for efficient transcription in vivo (Laimonis, et al., 1982; Benoist, et al., 1981; Baerji, et al., 1983). It has been suggested that enhancers are recognized by trans-acting factors that mediate regulatory effects by tissue-specific transcriptional control. Although the enhancer factors have not been well characterized, the glucocorticoid receptor may serve as a paradigm for these putative gene activator proteins.

It is generally accepted that the unliganded glucocorticoid receptor (GR) resides in the cytoplasm, and that hormone activation leads both to nuclear accumulation and gene activation. (Gasc, J.-M. & Baulieu, E. E. (1987) in Steroid Hormone Receptors: Their Intracellular Localisation, ed. Clark, C. R. (Ellis Horwood Ltd., Chichester, England), pp. 233-250; Beato, M. (1989) Cell 56, 335-344; Carson-Jurica, M. A., Schrader, W. T. & OMalley, B. W. (1990) Endocr. Rev. 11, 201-220; Gronemeyer, H. (1993) in Steroid Hormone Action, ed. Parker, M. G. (Oxford University Press, New York), pp. 94-117; Tsai, M. J. & OMalley, B. W. (1994) Annu. Rev. Biochem. 63, 451-486; Akner, G., Wikstrom, A. C. & Gustafsson, J. A. (1995) J. Steroid Biochem. Mol. Biol. 52, 1-16), and references therein. However, the mechanisms involved in nuclear translocation and targeting of steroid receptors to regulatory sites in chromatin have been poorly understood. It has previously been difficult to discriminate between the ability of a given receptor mutant, or a given receptor/ligand combination, to participate in the separate processes of receptor activation, nuclear translocation, sequence-specific binding, and promoter activation.

The glucocorticoid receptor (GR) is expressed in a subset of both ERalpha-positive and -negative human breast cancers as well as in other malignancies such as some ovarian cancers, hepatocellular carcinoma, and esophageal squamous cell carcinoma. In vitro and in vivo experiments suggest that activation of the GR in ER-negative pre-malignant breast epithelial and cancer cells initiates cell survival pathways under stress conditions that normally induce significant cell death (e.g. chemotherapy, radiation, growth factor deprivation).

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFkappa-B. Such interactions result in inhibition of API- and NFkappa-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisolone.

Glucocorticoid Receptor Antagonists

Glucocorticoid receptor antagonists bind to the receptor and prevent glucocorticoid receptor agonists from binding and eliciting GR mediated events, including transcription. RU486 is an example of a non-selective glucocorticoid receptor antagonist.

Compounds having high glucocorticoid receptor binding affinity and, in addition, high in vivo anti-glucocorticoid activity, while having, for example, low androgenic and progestagenic activities are disclosed in U.S. Pat. No. 6,011,025, incorporated herein by reference in its entirety. ORG 34517 (PT150) is an example of a compound with high glucocorticoid receptor binding affinity while having low androgenic and progestagenic activities, show specific and high glucocorticoid receptor binding affinity and are highly active in vivo showing predominant anti-glucocorticoid activity. The compounds lack appreciable affinity for mineralocorticoid, progesterone, estrogen and androgen receptors, indicating a clean side effect profile.

ORG 34517, PT150, PT155, PT156, PT157, PT158, TCY1, combinations thereof, and pharmaceutically acceptable salts thereof derivatives of the invention can be used in the prevention and treatment of glucocorticoid dependent diseases or symptoms, like Cushing syndrome, diabetes, glaucoma, sleep disturbances, depression, anxiety, atherosclerosis, hypertension, adiposity, osteoporosis and withdrawal symptoms from narcotics and their mixtures.

Preferred compounds according to this invention are ORG 34517, PT150, PT155, PT156, PT157, PT158, TCY1, combinations thereof, and pharmaceutically acceptable salts thereof. Preferred active agents according to this invention are ORG 34517, PT150, PT155, PT156, PT157, PT158, TCY1, combinations thereof, and pharmaceutically acceptable salts thereof.

GR antagonists from the following structural classes are presented: octahydrophenanthrenes, spirocyclic dihydropyridines, triphenylmethanes and diaryl ethers, chromenes, dibenzyl anilines, dihydroisoquinolines, pyrimidinediones, azadecalins, and aryl pyrazolo azadecalins. Exemplary glucocorticoid receptor antagonists include, but are not limited to, mifepristone, RU486, 11β-(4-dimethylaminoethoxypheny)-17α-propynyl-17β-hydroxy-4,9 estradien-3-one, 17β-hydroxy-17α-19-(4-methylphenyl)androsta-4,9(11)-dien-3-one-4α(S)-Benzyl-2(R)-prop-1-ynyl-1,2,3,4,4α,9,10,10α (R)-o-ctahydro-phenanthrene-2,7-diol and 4.alpha. (S)-Benzyl-2(R)-chloroethynyl-1,2,3,4,4α,9,10,10α(R)-octahydro-phenanthrene-2,7-diol, and (11β,17β)-11-(1,3-benzodioxo-5-yl)-17-hydroxy-17-(1-propynyl)es-tra-4,9-dien-3-one. Examples include, but are not limited to, beclometasone, betamethasone, budesonide, ciclesonide, flunisolide, fluticasone, mifepristone, mometasone, and triamcinolone. In further embodiments it may be CORT 0113083 or CORT 00112716.

Examples of steroidal glucocorticoid receptor antagonists include, without limitation, mifepristone, cortexolone, dexamethasone-oxetanone, 19-nordeoxycorticosterone, 19-norprogesterone, cortisol-21-mesylate; dexamethasone-21-mesylate, 11(-(4-dimethylaminoethoxyphenyl)-17(-propynyl-17(-hydroxy-4,9-estradien-3one, and 17(-hydroxy-17(-19-(4-methylphenyl)androsta-4,9(11)-dien-3-one.

Examples of non-steroidal glucocorticoid receptor antagonists include, without limitation, N-(2-[4,4',441-trichlorotrityl]oxyethyl)morpholine; 1-(2-[4,4',4"-trichlorotrityl]oxyethyl)-4-(2-hydroxyethyl)piperazine dimaleate; N-([4,4', 4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-1,2,4-triazole; 1,S-bis(4,4',4"-trichlorotrityl)-1,2,4-triazole-3-thiol; 4. alpha. (S)-Benzyl-2(R)-chloroethynyl-1,2,3,4, 4.alpha.,9,10,10alpha(R)-octahydro-phenanthrene-2,7-diol ("CP 394531"), 4alpha(S)-Benzyl-2(R)-prop-1-ynyl-1,2,3, 4,4.alpha.,9,10,10alpha(R)-oc-tahydro-phenanthrene-2,7-diol ("CP-409069"), trans-(1R,2R)-3,4-dichloro-N-methyl-N-[2-1pyrrolidinyl)cyclohexy]benzene-acetamide, bremazocine, ethylketocyclazocine and naloxone.

The specificity of ORG 34517, PT150, PT155, PT156, PT157, PT158, TCY1, combinations thereof, and pharmaceutically acceptable salts thereof for GR blockade, without significant cross-binding to other related steroidal hormone receptors (such as those for estrogen and progesterone), eliminates the likelihood of significant toxicities and side effects. Indeed, none were identified in all the substantial phase I and phase II clinical trials that already have been performed with the PT150 compound. Because the drug is envisioned as being used in limited dosing over time, coordinated with the intermittent dosing strategies typical for chemotherapeutic agents, the GR blockade also would not lead to significant alteration of HPA-axis functioning, with rapid restitution of the HPA-axis to baseline following dosing.

ORG 34517/PT150

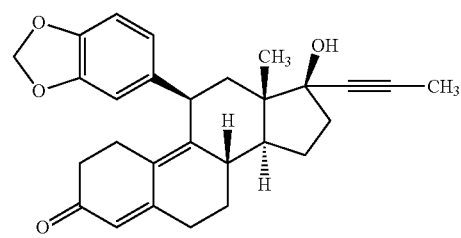

The (-)-enantiomer of PT150 (ent-PT150) and of PT155 (ent-PT155) stand as being representative for the corresponding unnatural enantiomers of the steroid parts in PT155, PT156, PT157 and PT158. We claim the unnatural (—)-enantiomers, and all possible existing steroidal diastereomers, of the steroid parts in PT155, PT156, PT157 and PT158 as a subject of the art.

PT153

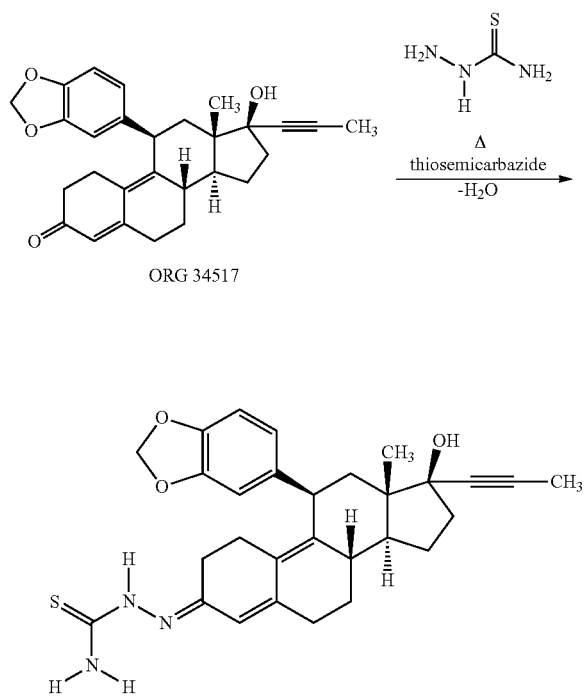

PT153 is an inclusion complex of one molecule ORG34517 (guest) with two molecules ORG34517 thiosemicarbazone (host). PT153 is formed by refluxing ORG34517 in 90% (v/v) aqueous ethanol with an excess of thiosemicarbazide [H2N—NH—(C=S)—NH2]. The product is precipitated by addition of water or freezing.

In-depth analysis of the reaction product revealed that the product PT153 consisted of two molecules ORG34517 thiosemicarbazone and one unreacted molecule of ORG34517 in conjunction with the solvents ethanol (1.52×) and water (1.25×) which could not being removed by prolonged vacuum drying over anhydrous calcium chloride (CaCl2):

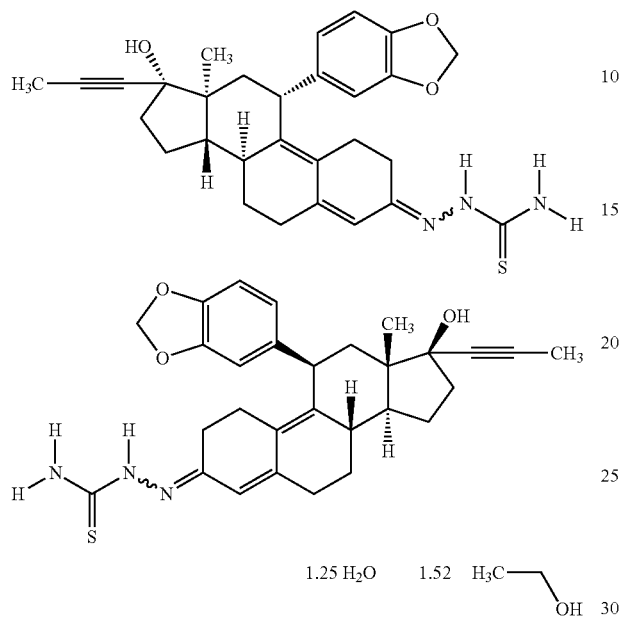

The ORG34517 thiosemicarbazone part is a cis/trans stereoisomeric mixture [(Z/E)-mixture] with 71.8% (E)-stereoisomer (trans) and 28.2% (Z)-stereoisomer (cis):

The proton nuclear magnetic resonance ($^1$H-NMR) spectrum clearly resolved the three molecular species [(E)-thiosemicarbazone, (Z)-thiosemicarbazone, ORG34517] contained in PT153. This composition was clearly confirmed by elemental analysis (combustion analysis of elemental CHNS/O content):

| Compound: | PT153 | |
|---|---|---|
| Molecular formula: | $C_{28}H_{30}O_4 \times 2\ C_{29}H_{33}N_3O_3S \times 1.52\ C_2H_5OH \times 1.25\ H_2O$ | |
| Molecular weight: | 1530.39 g/mol | |
| Elemental analysis: | calculated: | C 69.88% H 7.09% N 5.49% |
| | | S 4.19% O 13.35% |
| | found: | C 69.91% H 7.25% N 5.69% |
| | | S 3.85% O 13.09% |
| | | C 69.87% H 7.29% N 5.69% |
| | | S 3.91% O 13.16% |

The (E/Z)-stereoisomerism resulting from hindered rotation about thioamide groups ($H_2N$—$C$=$S$) is well-known for thiosemicarbazones. The nature of the inclusion complex will be revealed in the discussion of the structure of PT154.

An important feature of PT153 is the strongly electrostatic nature of its powder form. The powder of PT153 is so inductively magnetic that it poses considerable difficulties in grounding, powdering and dosage. The powder jumps from every spatula when grounded. Taken together, this magnetic nature of PT153 poses considerable difficulties in pharmaceutical formulation. As will be shown, PT154 does not exhibit this peculiar phenomenon in such intensity.

PT154

PT154 is a purified inclusion complex of one molecule ORG34517 (guest) with two molecules ORG34517 thiosemicarbazone (host).

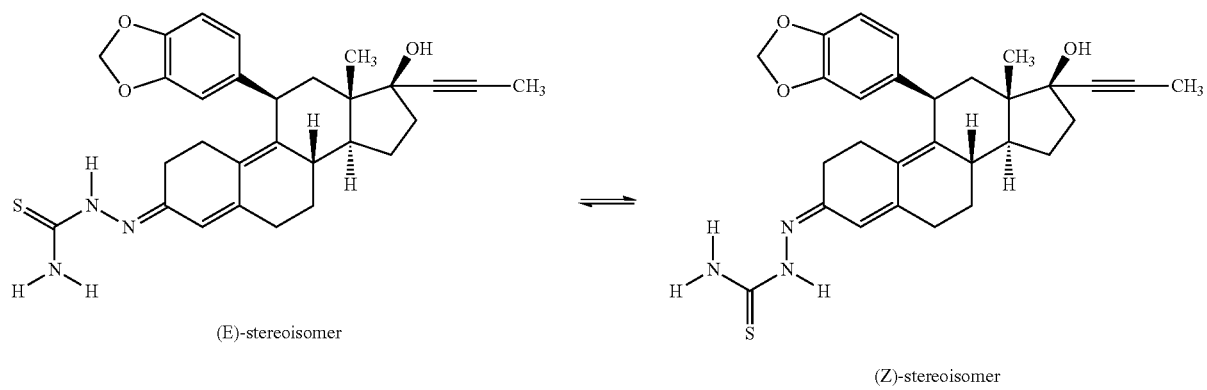

(E)-stereoisomer ⇌ (Z)-stereoisomer

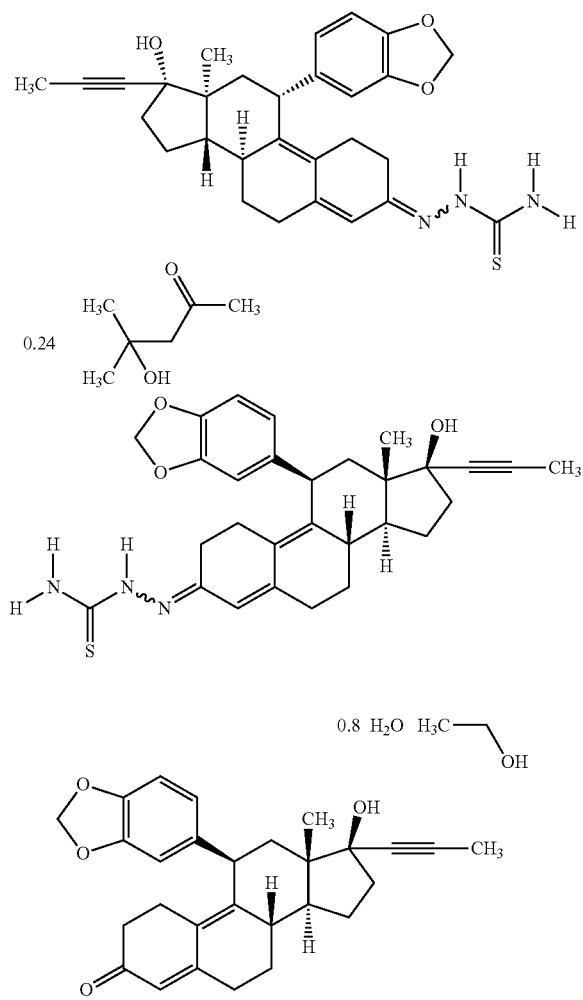

To synthesize a putative dimer, PT153 was treated with a molar excess of aqueous sodium hydroxide (NaOH) in acetone at room temperature. The product PT154 was precipitated by addition of water and freezing. The model reaction for this experiment was the dimerization of a retinoid thiosemicarbazone published in 2011.

In-depth analysis of the reaction product revealed that the product PT154 consisted of two molecules ORG34517 thiosemicarbazone and one unreacted molecule of ORG34517 in conjunction with the solvents ethanol (1×), diacetone alcohol (0.24×) and water (0.8×) which could not being removed by prolonged vacuum drying over anhydrous calcium chloride ($CaCl_2$)). The diacetone alcohol resulted from the well-known base-catalysed dimerization of the reaction solvent acetone [$2H_3C$—(C=O)—$CH_3$→$(H_3C)_2C$(OH)—$CH_2$—(C=O)—$CH_3$]. Diacetone alcohol is a relatively non-toxic solvent also found as a natural product in sleepy grass (*Achnatherum robustum, Poaceae*; syn. *Stipa robusta*).

The ORG34517 thiosemicarbazone part in PT154 was analyzed to be exactly the same cis/trans stereoisomeric mixture as in PT153 [(Z/E)-mixture with 71.8% (E)-stereoisomer (trans) and 28.2% (Z)-stereoisomer (cis)].

The proton nuclear magnetic resonance ($^1$H-NMR) spectrum clearly resolved the three molecular species [(E)-thiosemicarbazone, (Z)-thiosemicarbazone, ORG34517] contained in PT154 (see Experimental section). This composition was clearly confirmed by elemental analysis (combustion analysis of elemental CHNS/O content):

| Compound: | PT154 | |
|---|---|---|
| Molecular formula: | $C_{28}H_{30}O_4$ × 2 $C_{29}H_{33}N_3O_3S$ × $C_2H_5OH$ × 0.24 $C_6H_{12}O_2$ × 0.8 $H_2O$ | |
| Molecular weight: | 1526.21 g/mol | |
| Elemental analysis: | calculated: | C 70.39% H 7.03% N 5.51% S 4.20% O 12.87% |
| | found: | C 70.23% H 7.10% N 5.62% S 4.13% O 12.78% |
| | | C 69.98% H 7.16% N 5.59% S 4.11% O 12.78% |

This striking analogy of PT154 to PT153 is remarkable, since complete dissolution, treatment with base and precipitation leads almost invariantly to a change in composition and stereoisomeric proportions. Furthermore, a sodium salt should have been formed from the ORG34517 thiosemicarbazone. Nothing of these changes happened at all. This strongly pointed to a complex formation (inclusion compound) of ORG34517 in an ORG34517 thiosemicarbazone molecular lattice. The ORG34517 thiosemicarbazone exhibits a thiourea grouping, and thiourea is well-known for its ability to build macromolecular inclusion compounds[9-11], so-called clathrates. Therefore, it is assumed that PT153 and PT154 are, in fact, stable inclusion compounds of one molecule ORG34517 (guest) with two molecules ORG34517 thiosemicarbazone (host).

The reasons for this assumption are (i) the exactly analogous composition of PT153 and PT154, despite of PT153's treatment with base and re-precipitation to yield PT154, (ii) the thiourea structural element in PT153 and PT154 enables thiourea-like inclusion compounds as exemplified by the hexamethylenetetramine inclusion complex with thiourea (ratio 1:2)[11], and (iii) the existence of steroidal inclusion compounds as exemplified by cholesterol (guest) with deoxycholate (host) according to Nobel laureate Heinrich Wieland.

The most suitable explanation for the interaction of one molecule ORG34517 (guest) with two molecules ORG34517 thiosemicarbazone (host) is the published observation of complex formation of testosterone with hippuric acid (or also phenyl urethane, acetanilide, acetamide) (all in ratio 1:2). Also deoxycorticosterone (21-hydroxypregn-4-ene-3,20-dione) or dehydro-epi-androsterone 3-O-acetate [(3β)-3-(acetyloxy)androst-5-en-17-one] form complexes with hippuric acid (both in ratio 1:2). This means that 3-keto-$Δ^4$-steroids like ORG34517 can form addition compounds with amide (or thioamide)-presenting compounds in ratio 1:2.

Very interestingly, thiourea complexes with pyridinium halides (2:1)[14,15] can exhibit ferroelectric/dielectric properties in the case of pyridinium iodide/thiourea (1:2)[15]. This might be an explanation for the electrostatic/magnetic nature of PT153.

PT155

PT155: ⅓(11β,17β)-17-Hydroxy-11-[3,4-(methylenedioxy)phenyl]-17-(1-propyn-1 yl)estra-4,9-dien-3-one (ORG34517)×(2EZ)-2-{(11β,17β)-17-hydroxy-11-[3,4-(methylenedioxy)phenyl]-17-(1-propyn-1-yl)estra-4,9-dien-3 ylidene}hydrazinecarbothioamide [71.8% (E), 28.2% (Z)]hemihydrate×¾ acetone×⅛ ethanol (PT155)

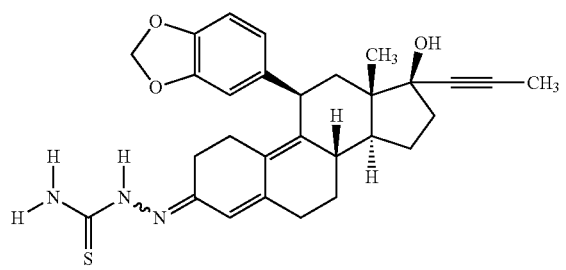

x 0.333

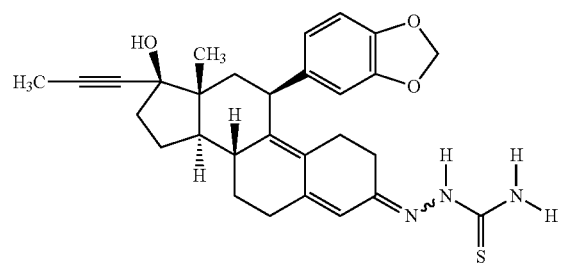

x 0.333

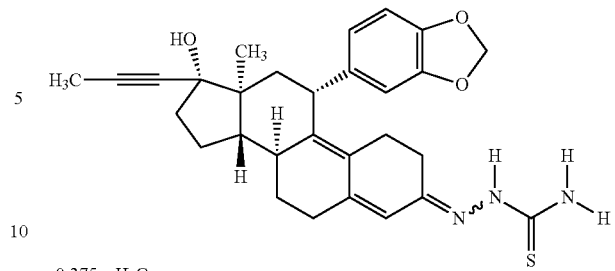

0.375  H₃C—CH₂—OH 1.5  H₂O

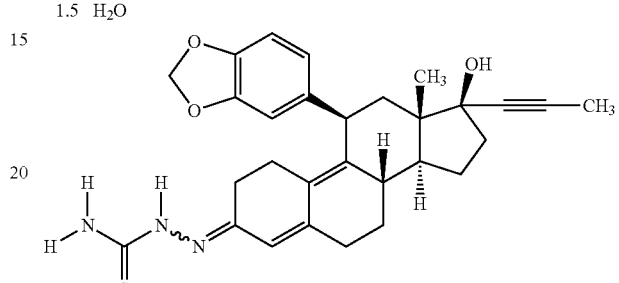

2.25  H₃C—C(=O)—CH₃

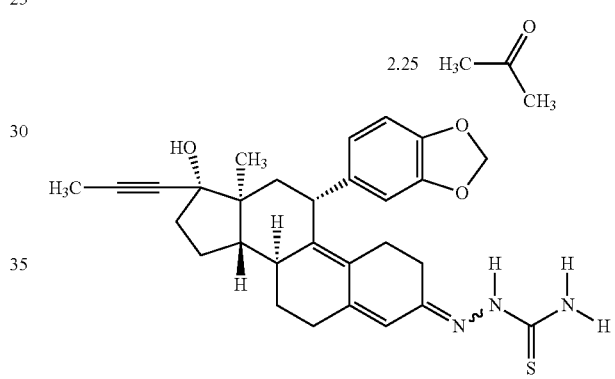

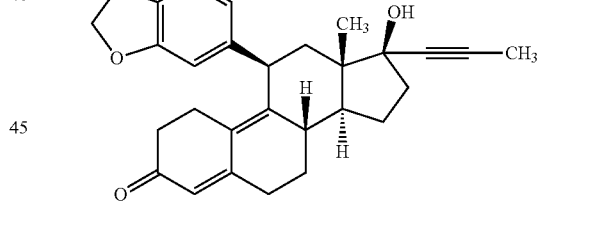

| Compound: | PT155 |
|---|---|
| Molecular formula: | ⅓ C₂₈H₃₀O₄ × C₂₉H₃₃N₃O₃S × ¾ C₃H₅O × ⅛ C₂H₅OH × ½ H₂O |
| Molecular weight: | 705.49 g/mol |
| Elemental analysis: | calculated: C 69.52% H 7.04% N 5.96% S 4.55% O 12.95% |
| | found: C 69.81% H 7.17% N 5.82% S 4.25% O 12.90% |
| | C 69.40% H 7.13% N 5.91% S 4.48% O 12.70% |

PT155 is an inclusion complex of choice of, for example, one molecule ORG34517 (guest) on three molecules ORG34517 thiosemicarbazone (host). In exemplary embodiments, the ratio of ORG34517 thiosemicarbazone to ORG34517 is, for example, 6:1, 5:1, 4:1, 3:1, 2:1, or 1:1.

In an experiment aimed at forcing the reaction in direction of ORG34517 thiosemicarbazone, the reflux time was doubled from 30 min to 1 h. Only a similar inclusion complex as contained in PT153 and PT154 could be isolated. It is concluded that ORG34517 thiosemicarbazone and ORG34517 interact strongly as previously postulated.

The ORG34517 thiosemicarbazone part of PT155 is a (Z/E)-mixture with 71.8% (E)-stereoisomer and 28.2% (Z)-stereoisomer. This material PT155 is the complex of choice to be used in antiviral studies in vitro. The metabolic activation of ORG34517 thiosemicarbazone contained in PT153-155:
S-Oxidation by Human Flavin-Containing Monooxygenases (hFMOs).

It is well-known that thiosemicarbazones like thiacetazone (p-acetamidobenzaldehyde thiosemicarbazone), a cheap second-line antitubercular substance discovered by Nobel laureate Gerhard Domagk in 1946, are bio-activated by human flavin-containing monooxygenases (hFMO1, hFMO2.1, hFMO3) into a sulfenic acid (R—S—OH), a sulfinic acid [R—(S=O)—OH], and a carbodiimide derivative (R—N=C=N—H)23,24:

Both the sulfenic acid and the carbodiimide derivative are the active antitubercular metabolites. The sulfinic acid (bottom left) does not form the carbodiimide, and represents an inactive metabolite. Especially the carbodiimide derivative can react with amino acid residues in target proteins of, for example, *Mycobacterium tuberculosis*, or with human hepatic/extrahepatic glutathione R—SH thiol/mercapto group for metabolic detoxification:

Therefore, ORG34517 thiosemicarbazone will be bio-activated (S-oxidized) in the same manner as thiacetazone by hFMOs under consumption of molecular oxygen (O2), and will be able to bind covalently to HBV and HIV proviral GRE DNA after being shuttled to the host cell nucleus by hGR. The thiosemicarbazone moiety in ORG34517 thiosemicarbazone can be oxidized by hFMOs (hFMO1, hFMO2.1, hFMO3) with molecular oxygen over the sulfenic acid to the ORG34517 thiosemicarbazone carbodiimide which could be co-transported into the host cell nucleus by hGR: hGRsubunit 1-(ORG34517 thiosemicarbazone carbodiimide)=hGRsubunit 2-ORG34517. The carbodiimide moiety adds to one amino group of proviral GRE DNA yielding an N-amidinohydrazone (amidrazone)-group, thereby inducing proviral DNA damage.

Human flavin-dependent monooxygenases (hFMOs) (EC 1.14.13.8) are the second important type of monooxygenases in the human body, the other well-known type being the cytochrome P450 monooxygenases (CYP450 monooxygenases). Both are localized in microsomes and dependent on molecular oxygen (O2), and hFMOs need also the cofactors flavin-adenine dinucleotide (FAD) and nicotinamide-adenine dinucleotide phosphate (NADPH), whereas CYP450 monooxygenases are heme-dependent. hFMO1 is mainly expressed in human kidney, and, to a smaller extent, in small intestine and lung. hFMO2 is expressed to a very high level in human lung and kidney, and, to a smaller extent, in liver and small intestine28. hFMO3 and hFMO5 are highly expressed in human liver, but are also expressed in lung and, to a smaller extent, in human kidney. hFMO4 is mainly expressed in kidney and, to a smaller extent, in liver and small intestine. hFMO5 is also expressed to a high level in small intestine. FMO2 is additionally expressed in human brain, but at low abundance (<1% of lung).

Slightly modified citation: "The hFMOs oxygenate nucleophilic heteroatom-containing chemicals and drugs and generally converts them into harmless, polar, readily excreted metabolites. Sometimes, however, FMO bioactivates chemicals into reactive materials that can cause toxicity. Most of the interindividual differences of hFMOs are due to genetic variability and allelic variation, and splicing variants may contribute to interindividual and interethnic variability observed for hFMO-mediated metabolism. In contrast to cytochrome P450 monooxygenases (CYP450 monooxygenases), hFMOs are not easily induced nor readily inhibited, and potential adverse drug-drug interactions are minimized for drugs prominently metabolized by hFMOs. These properties may provide advantages in drug design and discovery, and by incorporating hFMO detoxication pathways into drug candidates, more drug-like materials may be forthcoming. Although exhaustive examples are not available, physiological factors can influence hFMO function, and this may have implications for the clinical significance of hFMOs and a role in human disease."

PT155 exhibits magnetism is of electrostatic type, and is called the triboelectric effect. The triboelectric effect (also known as triboelectric charging) is a type of contact electrification in which certain materials become electrically charged after they come into frictional contact with a different material. Rubbing glass with fur, or a comb through the hair, can build up triboelectricity. Most everyday static electricity is triboelectric. The polarity and strength of the charges produced differ according to the materials, surface roughness, temperature, strain, and other properties.

PT-156

PT156: $^{1}/_{17}$(11β,17β)-17-Hydroxy-11-[3,4-(methylenedioxy)phenyl]-17-(1-propyn-1-yl)estra-4,9-dien-3-one (ORG34517)×(2EZ)-2-{(11β,17β)-17-hydroxy-11-[3,4-(methylenedioxy)phenyl]-17-(1-propyn-1-yl)estra-4,9-dien-3-ylidene}-N-phenylhydrazinecarbothioamide [74.1% (E), 25.9% (Z)]$^{11}/_{17}$ hydrate (PT156)

PT156: ORG34517 4-Phenylthiosemicarbazone Containing Traces of ORG34517:

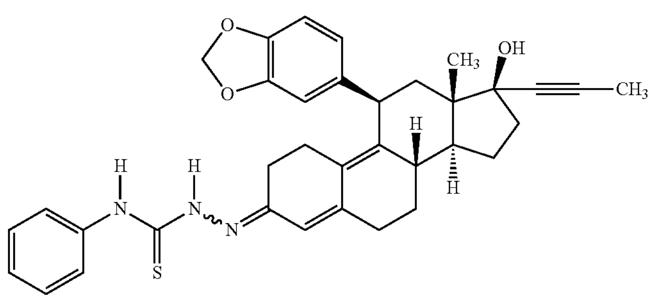

x 0.059

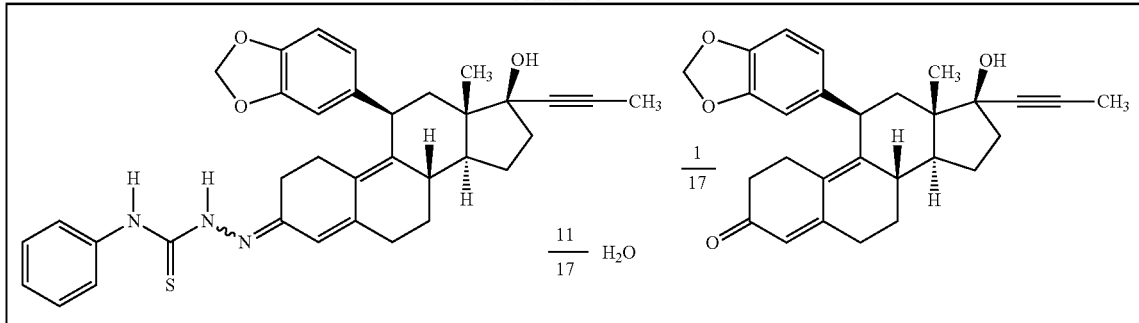

In exemplary embodiments, PT156 is (2EZ)-2-{(11β,17β)-17-hydroxy-11-[3,4-(methylenedioxy)phenyl]-17-(1-propyn-1-yl) estra-4,9-dien-3-ylidene}-N-phenylhydrazinecarbothioamide without the presence of (11β,17β)-17-Hydroxy-11-[3,4-(methylenedioxy)phenyl]-17-(1-propyn-1-yl) estra-4,9-dien-3-one (ORG34517). In exemplary embodiments, the ratio of PT156 to ORG34517 is 30:1, 20:1, 17:1, 16:1, 15:1, 14:1, 13:1, 12:1, 11:1, 10:1, 9:1, 8:1, 7:1, 6:1, 5:1, 4:1, 3:1, 2:1, or 1:1.

The elemental analysis confirmed the results obtained by 1H NMR spectroscopy:

| Compound: | PT156 | |
|---|---|---|
| Molecular formula: | $1/17\ C_{28}H_{30}O_4 \times C_{35}H_{37}N_3O_3S \times {}^{11}/_{17}\ H_2O$ | |
| Molecular weight: | 616.73 g/mol | |
| Elemental analysis: | calculated: | C 71.37% H 6.55% N 6.81% S 5.20% O 10.07% |
| | found: | C 71.47% H 6.83% N 6.83% S 5.58% O 10.05% |
| | | C 71.18% H 6.88% N 6.87% S 5.45% O 10.07% |

PT156 is formed by refluxing ORG34517 in 90% (v/v) aqueous ethanol with a slight excess of 4-phenylthiosemicarbazide [H2N—NH—(C=S)—NH—C6H5]. The product is precipitated by addition of water and freezing. Analysis of the reaction product revealed that the present invention PT156 contained 17 1 of an unreacted molecule of ORG34517 in conjunction with the solvent water (17 11×) which could not being removed by prolonged vacuum drying over anhydrous calcium chloride (CaCl2). The ORG34517 4-phenylthiosemicarbazone part is a cis/trans stereoisomeric mixture [(Z/E)-mixture] with 74.1% (E)-stereoisomer (trans) and 25.9% (Z)-stereoisomer (cis).

The Metabolic Activation of ORG34517 4-Phenylthiosemicarbazone Contained in PT156: Para-Oxidation by Human Cytochrome P450 Monoxygenases It is well-known that acetanilide is oxidized by human cytochrome P450 monooxygenase 1A2 (CYP1A2) isoenzyme in para-position of the phenyl ring to yield paracetamol (acetaminophen) 29, and is further oxidized by CYP3A4 to N-acetyl-p-benzoquinone imine:

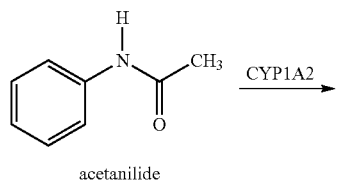

acetanilide

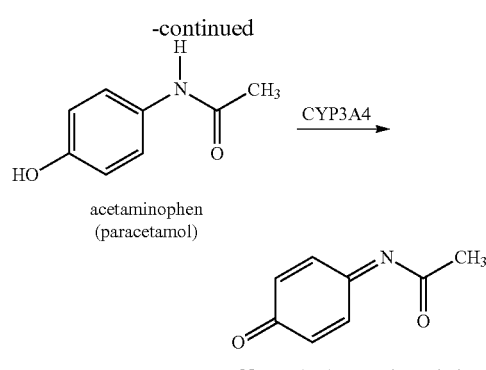

acetaminophen (paracetamol)

N-acetyl-p-benzoquinone imine

Analogously, PT156 could be activated by CYP1A2 and CYP3A4 in T lymphocytes to:

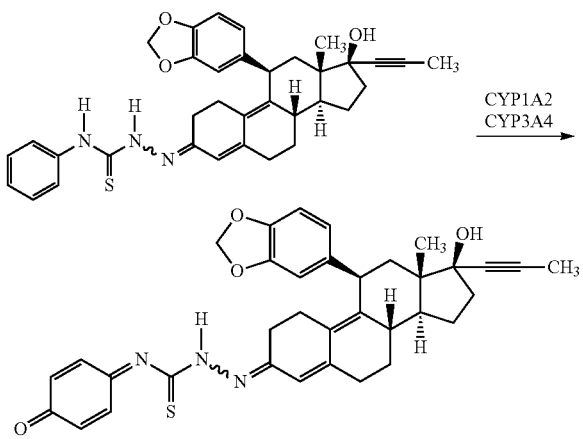

Analogously, PT156 could be activated by CYP1A2 and CYP3A4 in T lymphocytes to:

This represents an additional activation mechanism for PT156 which is not achieved with and incorporated in PT155. It is especially important for the potential treatment of acquired immunodeficiency syndrome (AIDS) with PT compounds, since in human blood lymphocytes only very low levels of human flavin-containing monooxygenases (only hFMO4 and hFMO5) could be detected. Even in absence of human flavin-containing monooxygenases PT156 could be activated in human T lymphocytes, since microsomal cytochrome P450 isoenzymes 1A2 and 3A4 were readily detected in human blood lymphocytes. Historically, the overall metabolism of acetanilide was elucidated by Brodie & Axelrod in 1948.

PT-157

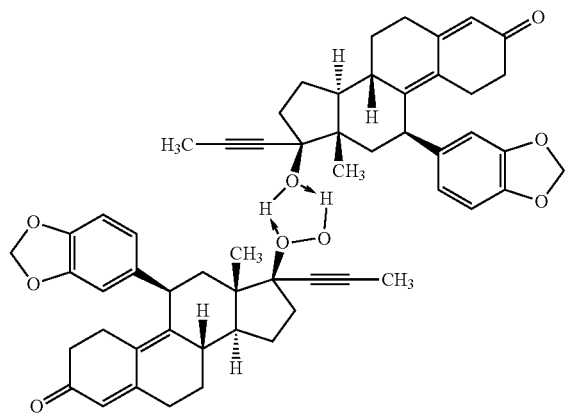

PT-158

⅓(11β,17β)-17-Hydroxy-11-[3,4-(methylenedioxy) phenyl]-17-(1-propyn-1-yl)estra-4,9-dien-3-one-(2)-2-{(11β,17β)-17-hydroxy-11-[3,4-(methylenedioxy) phenyl]-17-(1-propyn-1-yl)estra-4,9-dien-3-ylidene}hydrazinecarbothioamide [71.8% (E), 28.2% (Z)]-bis[6-amino-2-oxo-3-(β-D-ribofuranosyl)-2,3-dihydropyrimidin-1-ium-1-yl]methanediide monohydrochloride×½ acetone (PT158)

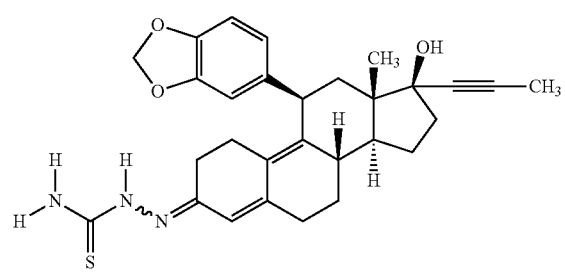

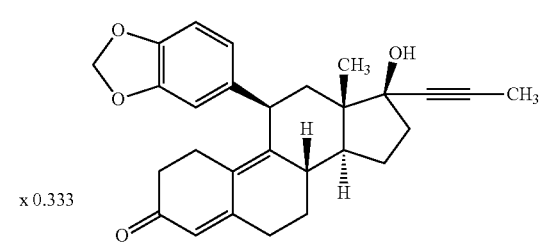

-continued

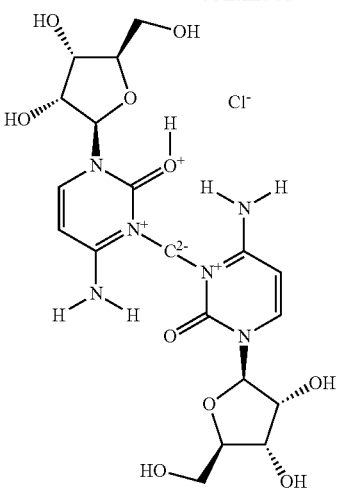

In exemplary embodiments, PT-158 is:

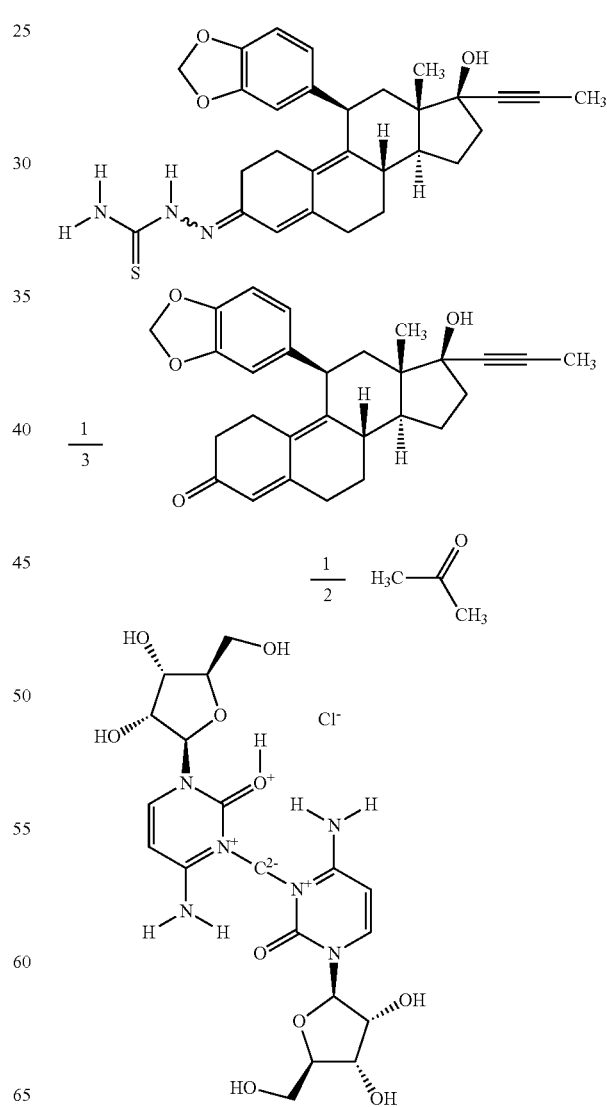

Materials:

PT155 (.C28H30O4×C29H33N3O3S×¾C3H6O× .C2H5OH×½H2O) [Pop Test Oncology LLC, Cliffside Park, NJ, USA; first batch synthesized by Andreas J. Kesel at Thursday, Oct. 8, 2015; w (n/n). 99% (1H NMR and elemental analysis)]

TCY-1 (C19H26N6O10×HCl×1.25 H2O) [synthesized by Andreas J. Kesel at Saturday, Dec. 26, 2015; w (n/n). 99% (1H NMR and elemental analysis)]=bis(cytidin-3-ium-3-yl)methanediide monohydrochloride×1.25 H2O=bis[6-amino-2-oxo-3-(â-D-ribofuranosyl)-2,3-dihydropyrimidin-1-ium-1-yl]methanediide monohydrochloride×1.25 H2O Instruction: PT155 (M=705.49 g/mol, 151 mg, 214.0356 µmol) and TCY-1 (M=557.42 g/mol, 121 mg, 217.0715 µmol) (this complete mixture had M=1270.82 g/mol before drying) were carefully weighed and thoroughly mixed as solid powders with a spatula. The mixture was then carefully dried over CaCl2 in vacuo to yield PT158 as light yellow amorphous powder.

| Compound: | PT158 |
|---|---|
| Molecular formula: | (. C28H30O4 × C29H33N3O3S) × (C19H26N6O10 × HCl) × ½ C3H6O |
| Molecular weight: | 1211.11 g/mol |
| Yield: | 260 mg (100%) |
| 1H-NMR: (DMSO-d6, ppm) | 0.41 (3 H, s; 18-CH3, (E)-TSC*), 0.42 (1.18 H, s; 18-CH3, (Z)-TSC**), 0.44 (1.393 H, s; 18-CH3, ORG34517), 1.20-2.77 (m; steroid CH and CH2), 1.83 (5.58 H, br s; R—C≡C—CH3 methyl, all three species), 2.09 (4.18 H, s; acetone CH3), 3.57 (dd, 2 H; 2J = −11.9 Hz, 3J = 2.2 Hz; H-5', pro-R, TCY-1), 3.68 (dd, not resolved, 2 H; 2J = −12.2 Hz; H-5', pro-S, TCY-1), 3.86 (dt, 2 H; 3J = 5.6 Hz, 3J = 2.6 Hz; H-4', TCY-1), 3.95 (t, 2 H; 3J = 5.1 Hz; H-3', TCY-1), 4.00 (t, 2 H, 3J = 4.5 Hz; H-2', TCY-1), 4.28 (0.393 H, m; 11á-CH, (Z)-TSC), 4.30 (1 H, d; 3J (H, H) = 7.1 Hz; 11á-CH, (E)-TSC), 4.38 (0.464 H, d; 3J (H, H) = 7.1 Hz; 11á-CH, ORG34517), 5.08-5.16 (1.857 H + 4 H, br m; 17á-OH, all three species; 3'-OH, 5'-OH, TCY-1), 5.42 (br s, 2 H; 2'-OH,TCY-1), 5.66 (0.464 H, s; 4-CH, ORG34517), 5.74 (d, 2 H; 3J = 3.8 Hz; H-1', TCY-1), 5.86 (1 H, s; 4-CH, (E)-TSC), 5.94 (d, 2 H; 3J = 7.7 Hz; H-5, TCY-1), 5.97 (3.716 H, br s; O—CH2—O benzodioxole, all three species), 5.97 (0.393 H, s; 4-CH, (Z)-TSC), 6.60 (1.858 H, d; 3J (H, H) = 7.7 Hz; 5'-CH benzodioxole, all three species), 6.67 (0.393 H, s; 2'-CH benzodioxole, (Z)-TSC), 6.77 (1.464 H, s; 2'-CH benzodioxole, (E)-TSC and ORG34517), 6.79 (0.393 H, m; 6'-CH benzodioxole, (Z)-TSC), 6.79 (1.464 H, d; 3J (H, H) = 8.3 Hz; 6'-CH benzodioxole, (E)-TSC and ORG34517), 7.51 (0.393 H, br s; NH2, HA, (Z)-TSC), 7.57 (1 H, br s; NH2, HA, (E)-TSC), 7.92 (br s, 2 H; 4-NH2, HA, TCY-1), 7.97 (0.393 H, br s; NH2, HB, (Z)-TSC), 8.08 (1 H, br s; NH2, HB, (E)-TSC), 8.09 (d, 2 H; 3J = 7.7 Hz; H-6, TCY-1), 8.48 (br s, 2 H; 4-NH2, HB, TCY-1), 10.05 (1 H, br s; N—H, (E)-TSC), 10.42 (0.393 H, br s; N—H, (Z)-TSC), 13.00 (br s, 1 H; hydrochloride, TCY-1). |

*, **(E or Z)-TSC = (E or Z)-thiosemicarbazone.

TCY-1

Bis(cytidin-3-ium-3-yl)methanediide monohydrochloride×1.25 H2O=bis[6-amino-2-oxo-3-(β-D-ribofuranosyl)-2,3-dihydropyrimidin-1-ium-1-yl] methanediide monohydrochloride×1.25 H2O (TCY-1

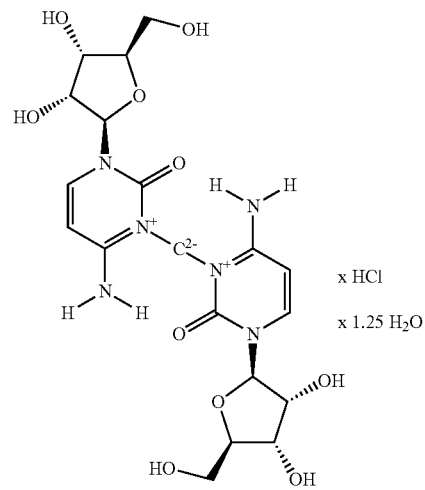 [SMILES: Nc1ccn([C@@H]2O[C@H](CO)[C@@H](O)[C@H]2O)c(=O)[n+]1[C-2][n+]1c(N)ccn([C@@H]2O[C@H](CO)[C@@H](O)[C@H]2O)c1=O]

In exemplary embodiments, TCY1 is:

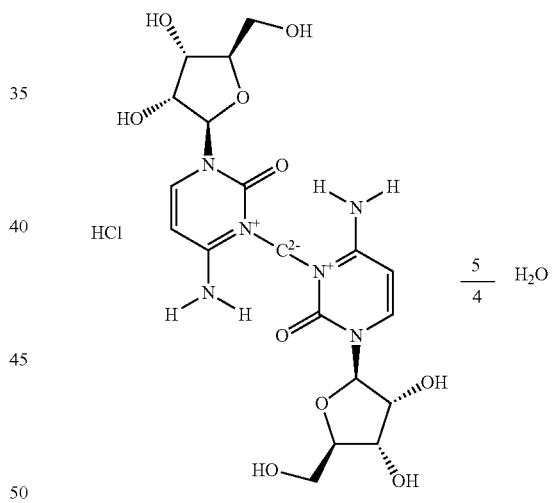

In exemplary embodiments, TCY1 is an HIV Integrase inhibitor. HIV integrase is an attractive target for the discovery of new therapeutics due to its important role in viral infections, particularly HIV infections. The compounds of the present invention exhibit advantages over previously disclosed integrase inhibitors, for example increased potency, metabolic stability, increased therapeutic index, or other pharmaceutical properties.

The methods, compounds, compositions, and uses described herein can be specifically directed to inhibiting HIV integrase in a patient in need thereof. Such methods and uses may prevent, treat or delay the onset of AIDS in a mammal in need thereof. The present invention also includes a compound of the present invention described herein, and/or a pharmaceutically-acceptable salt, hydrate, solvate, tautomer, optical isomer, E-isomer, Z-isomer, or combination thereof for use in, for use as a medicament for, and/or for use in the preparation of a medicament for: inhibiting HIV integrase, preventing or treating infection by HIV, or preventing, treating or delaying the onset of AIDS.

The compounds of the present invention may also be used with one or more agents useful in the treatment of HIV infection or AIDS. As the compounds of the present invention can be HIV integrase inhibitors, such compounds are also useful in salvage therapy for patients whose virus has mutated and acquired resistance to other drugs. Such inhibitors target a distinct step in the retroviral life cycle and therefore, may be taken in combination with other types of HIV drugs to minimize adaptation by the virus.

Materials:

Cytidine [Sigma-Aldrich Corp., St. Louis, MO, USA, Lot: BCBN7660V; w (n/n)=99.9% (HPLC, area %), =+29.7° (c=9 in H2O), =+33.0° (c=2 in H2O), mp 210-220° C. (dec.)]20D][a20D][a Thymol (5-methyl-2-isopropylphenol) cryst. Ph. Eur. 1997 [Caesar & Loretz (Caelo) GmbH, Hilden, Germany, Lot: 24252173; residue after evaporation <0.05% (m/m)]

3% (m/m) aqueous dihydrogen peroxide (H2O2) solution [according to DAC/NRF (Deutscher Arzneimittel-Codex/Neues Rezeptur-Formularium), NRF monograph № 11.103] stabilized with aqueous ortho-phosphoric acid (H3PO4) [0.0588% (m/m) of 85% (m/m) aqueous H3PO4; this corresponds to 0.05% (m/m) H3PO4 final concentration in the stabilized H2O2 solution (this solution showed pH 5.0 at.=19.8° C.)]

10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]

Ethyl acetate pro analysi [AppliChem GmbH, Lot: 0000518022; w (n/n)=99.9% (GC), w (H2O)=0.01% (m/m) (Karl Fischer titration), ethanol<0.1%, methanol<0.02%, methyl acetate<0.02%, trace elements (Cr, Fe, Ni, Pb, Zn, P, S, K, Mg)<0.00001%, Si<0.00002%, Na<0.0002%, non-volatile matter<0.001%, acidity/alkalinity<0.0005 meq/g]

Instruction:

Cytidine (M=243.22 g/mol, 10.355 g, 42.5746 mmol), the carbon source thymol Ph. Eur. 1997 (M=150.22 g/mol, 6.228 g, 41.4592 mmol), and sodium hydrogen carbonate NaHCO3 (3.646 g, 43.3996 mmol) were suspended in 90% (v/v) aqueous ethanol (100 ml). Then 3% (m/m) aqueous dihydrogen peroxide (H2O2) solution [48 ml, 1.440 g H2O2 (M=34.01 g/mol) 42.3405 mmol] was added at room temperature (RT, ϑ=15.6° C.). Solid sodium hydroxide NaOH (2.064 g, 51.6000 mmol) pearls, and water (80 ml), were added under stirring. The suspension became light purple during 10 min stirring at RT. Afterwards, the suspension was heated to 40-50° C. for 5 min (heatgun) until all solids had dissolved. The solution was left standing at RT for 5 min. Afterwards, the reaction was stopped by addition of 10.27 M [32% (m/m)] aqueous hydrochloric acid pro analysi (9.20 ml, 94.4840 mmol). The color changed from purple to light yellow. A floating yellow oil evolved soon. The solution (pH 4-5) with the floating yellow oil was cooled at +0-2° C. for 2 h. The mixture was then frozen at −25° C. for 2.5 h. Then sodium hydroxide (520 mg, 13.0000 mmol) dissolved in water (3 ml) was added (color change to purple). The mixture was then frozen at −25° C. for 30 min. Then 10.27 M [32% (m/m)] aqueous hydrochloric acid pro analysi (3.00 ml, 30.8100 mmol) was added under stirring (color change to yellow). The mixture was then frozen at −25° C. for 105 min. Then sodium hydroxide (740 mg, 18.5000 mmol) dissolved in water (5 ml) was added. The yellow solution was extracted with ethyl acetate pro analysi (EtOAc, 100 ml). The aqueous phase was isolated and frozen at −25° C. for 55 h (2 days 7 h). The evolved yield (1.932 g) of the white, crystalline, very odorous (caseous) product was filtered and dried over CaCl2 in vacuo.

| | |
|---|---|
| Compound: | TCY-1 |
| Molecular formula: | C19H26N6O10 × HCl × 1.25 H2O |
| Molecular weight: | 557.42 g/mol |
| Yield: | 1.932 g (16%) |
| Elemental analysis: | C 40.94% H 5.33% N 15.08% O 32.29% |
| calculated: | C 39.31% H 5.56% N 15.26% O 32.08% |
| found: | C 39.43% H 5.63% N 15.16% O 32.04% |
| 1H-NMR: (DMSO-d6, ppm) | 3.57 (dd, 2 H; 2J = −12.2 Hz, 3J = 3.2 Hz; H-5', pro-R), 3.68 (dd, 2 H; 2J = −12.2 Hz, 3J = 3.2 Hz; H-5', pro-S), 3.86 (dt, 2 H; 3J = 5.4 Hz, 3J = 3.0 Hz; H-4'), 3.95 (t, 2 H; 3.J = 5.1 Hz; H-3'), 3.99 (m, 2 H; H-2'), 5.07 (br s, 2 H; 3'-OH), 5.15 (br s, 2 H; 5'-OH), 5.41 (br s, 2 H; 2'-OH), 5.74 (d, 2 H; 3J = 3.8 Hz; H-1'), 5.93 (d, 2 H; 3J = 7.7 Hz; H-5), 7.89 (br s, 2 H; 4-NH2, HA), |

TABLE 1

The antiretroviral activity of TCY-1 versus HIV-1 strain LAI replication in PBMC:

| | Cytotoxicity $CC_{50}$ (µM) | | | Anti-HIV-$1_{LAI}$ activity $EC_{50}$ (µM)/ $EC_{90}$ (µM) in PBMC | | | |
|---|---|---|---|---|---|---|---|
| Drug | PBMC | CCRF-CEM | Vero | $EC_{50}$ | $EC_{90}$ | $SI_{50}$ | $r^2$ |
| TCY-1 | >100 | >100 | >100 | 0.29 | 1.00 | >345 | 0.94 |
| AZT* | >100 | 14.3 | 56.0 | 0.0044 ± 0.0039 | 0.0299 ± 0.0245 | >22,696 | 0.98 |

Legend:
PBMC, primary human peripheral blood mononuclear cells.
CCRF-CEM, human T-lymphoblastic acute T cell leukemia cells.
Vero, African green monkey (grivet) Chlorocebus aethiops (syn. Cercopithecus aethiops) kidney epithelial cells.
$CC_{50}$, cytotoxic concentration 50%.
$EC_{50}$, effective inhibitory concentration 50%.
$EC_{90}$, effective inhibitory concentration 90%.
$SI_{50}$, selectivity index $CC_{50}/EC_{50}$.
$r^2$, coefficient of determination ($r^2$ measure of goodness-of-fit) on $EC_{50}$ and $EC_{90}$.
AZT, zidovudine (3'-azido-3'-deoxythymidine).
*The given effective inhibitory concentrations (µM ± s.d.) for the positive control AZT were averaged and treated statistically from twenty (n = 20) independent determinations.

Method of Determination: HIV-1 Replication Reverse Transcriptase (RT) Assay with TCY-1

HIV-1$_{LAI}$(=HIV-1$_{BRU}$=LAV-1; for the origin and identity of HIV-1$_{LAI}$) was assayed in primary [freshly donated from healthy (tested HIV-negative, HBV-negative, and HCV-negative) blood donors, and isolated by single-step Ficoll-Hypaque centrifugation method] human peripheral blood mononuclear cells (PBMC) in the presence of a drug being evaluated. The parameter for antiviral activity was reduction of RT activity in the cell supernatant after Triton X-100-mediated lysis of released virions, as measured by [5alpha-$^3$H]dTTP (5alpha-tritiated thymidine 5'-triphosphate) incorporation into poly(rA)•poly(dT) directed by the primed RNA template poly(rA)•oligo(dT). It should be noted that the assay did not detect RT inhibition by potential RT inhibitors per se, but indirectly quantified the amount of released HIV-1 in the supernatant. The detailed assay methodology was reported by Schinazi et al., as based on an older assay system of Spira et al. The experiments were conducted in triplicate and treated statistically by regression curve analysis ($r^2$ coefficient of determination). The RT inhibitor AZT (zidovudine, 3'-azido-3'-deoxythymidine; RETROVIR™) served as a positive control. Cytotoxicity on PBMC exerted by the test compounds was determined as described by Stuyver et al., by application of the CellTiter 96® AQ$_{ueous}$ One Solution Cell Proliferation Assay (Promega Corp., Madison, WI). Briefly, the phenazine ethosulfate (PES)-coupled reduction of the tetrazolium salt 3-(4,5-dimethylthiazol-2-yl)-5-(3-carboxymethoxyphenyl)-2-(4-sulfophenyl)-2H-tetrazolium (MTS) to a purple, water-soluble formazan by living, undamaged cells was measured.

Antiviral Activity

PT150, formerly known as ORG34517, was first developed by Organon as a drug therapy for major depressive disorder (Gallagher & Young, 2006). In 2007, it was acquired by Schering-Plough, then by Merck & Co., and ultimately was acquired by Pop Test Cortisol LLC in December of 2010. As ORG34517, it has undergone two Phases of Clinical Trials for safety:

| ClinicalTrials.gov ID | |
|---|---|
| NCT00226278 (Phase I) | Safety Study of ORG 34517 for Major Depression With Psychotic Features |
| NCT00844922 (Phase II) | Safety of Org 34517 900 mg in Patients Who Received Org 34517 in a Previous Trial (Study 28133/P05842) |

PT155 was developed from PT150 based on observations that thiosemicarbazones exhibit considerable antiviral activities, including activities versus hepatitis C virus and Ebola virus Zaire (Kesel, 2011; Kesel et al. 2014).

Mechanism of Action

The 3' UTR is critical to viral replication in the host and interacts with a large number of host proteins (Roby, 2014) including Mov34, which has been demonstrated to be involved in transcription and translation in mouse (Ta & Vrati, 2000). The PMSD7 gene product (a Mov34 related gene) is a subunit in the proteasome. Mov34 has been demonstrated to bind to the genome of the Japanese Encephalitis Virus (Ta & Vrati, 2000). Alterations in the proteasomal processing of NF-κB is a major regulatory point for the production of pro-inflammatory cytokines and in controlling the immune response; microbial and viral pathogens have been documented to alter this pathway to promote infection (Rahman & McFadden, 2011). Additionally, Mov34 contains an MPN domain, which is highly conserved in eukaryotic initiation factors in the 3A family (Asano, 1997; Sanches, 2007).

Without being bound to any theory, one possible mechanism of action for compounds PT150 and PT155 is rooted in their activity as glucocorticoid receptor (GR) antagonists. The GR agonist dexamethasone and the GR antagonist mifepristone (RU38486) have been demonstrated to interact with Mov34 in HIV-1 infection (Ramanathan et al., 2002) and either promote or inhibit translocation to the nucleus. The disruption of interactions between Mov34-like proteins and the 3'-UTR region of Zika, and likely other Flavivirus, suppress viral replication and negate sfRNA-mediated cellular events necessary for successful viral infection. This hypothesis is further supported by the patents WO 2004/112720 A2 ND US 2007/0259844 A1 (Kim 2004; Kim, 2007) for antiviral compositions against the human hepatitis C virus.

Results

Justification of Readiness Level

PT150 is a new class of therapeutic agents designed to block the glutocorticoid receptor (GR), acting as an antagonist for endogenous cortisol. PT150 or (11β,17β)-11-(1,3-benzodioxol-5-yl)-17-hydroxy-17-(1-propynyl)-estra-4,9-dien-3-one is the first selective GR antagonist studied in a Phase I program in healthy human subjects (ClinicalTrials.gov, NCT00226278) for its safety, tolerability and pharmacodynamic/pharmacokinetic characteristics. It showed no prohibitive effects in the first in-human studies. It has significantly higher selectivity for the GR compared to mifeprestone (RU486). PT150 and mifepristone bound to cytosolic GRs with values of 365% and 193% respectively; values for the cytosolic progesterone receptors (PR), however, were 6.4% and 36% respectively. This suggests that PT150 has a selectivity ratio (GR/PR) of 57 compared to 5.4 for mifeprestone. In the pregnancy interruption test in rats, twice daily administration of 4 mg kg$^{-1}$ po PT150 and 1-2 mg kg$^{-1}$ po mifepristone produced similar results (nearly 100% embryos lost) confirming the lower anti-progestational activity of PT150 as compared to mifeprestone. Therefore, the specificity of PT150 for GR-blockade, without significant cross binding to other related steroidal hormone receptors (such as those for estrogen and, discretely, progesterone) eliminate the likelihood of significant toxicities and side effects. In contrast to mifeprestone, PT150 was able to block corticosterone-induced GR translocation. This suggests that PT150 is a true competitive GR antagonist without partial agonistic activities (Peeters et al., 2008).

GR expression has not shown prognostic value in Kaplan-Meier survival and residual survival analysis or overall survival in ovarian cancer patients (Woenchhaus et al., 2006). Nonetheless, administration of GC along with apoptosis-inducing chemotherapies to ovarian cancer patients inhibited cell death and activation of anti-apoptotic genes SGK1, MKP1/DUSP1, and caspase inhibitor cIAP2 in ovarian tissues, suggesting an overall decrease in the effectiveness of chemotherapy (Runnebaum & Bruning, 2005; Melhem et al., 2009).

Results from Viral Testing

The following virus taken from the NIAID Merging Pathogens List are Flavivirus which PT150 and PT155 have the potential to treat.

Problems with Obscured Activity in Existing Test Results

Test results to date have two identified problems that we believe are obscuring antiviral results. Firstly, many of the cell lines used in testing are immortal cell lines. Secondly, not all of the cell lines tested contain active glucocorticoid receptors, which play a role in compound interaction for antiviral activity.

Phase II Clinical of PT150 dosed patients at 900 mg per day for 2 weeks with no noted adverse indications of cell toxicity. Yet, cytotoxicity is showing up for in vitro models. PT discovered that PT150 has value as a chemosensitizing agent in the treatment of cancer. As such, it has a demonstrable effect on cancerous cells. Unfortunately, this includes most cell lines utilized for in vitro testing.

Take, for example, the observable differences in cytotoxicity when PT150 is used in the Zika assay in HeLa cells (breast tumor derived cell line), HUH7 (liver tumor cell line) and HFF (human foreskin fibroblasts, non-tumor derived). The 50% cellular toxicity in primary human foreskin fibroblasts is far greater than 150 µM, these cells are very sensitive sensors of toxicity on human tissue.

Vero-derived cell lines (Vero, Vero 76, Vero E6) do not contain human glucocorticoid receptors, as they are derived from African green monkey (*Chlorocebus aethiops*) epithelial kidney cells. They even do not even contain a *Chlorocebus* glucocorticoid receptor (Dreyer et al., 1989), and have been demonstrated to be completely unresponsive to dexamethasone. As such, seeing no activity on an antiviral assay for Flavivirus is not surprising. We believe the choice of cell line obscured potential positive results for PT150 and PT155 assays. Re-assay in a cell line that contains a glucocorticoid receptor (preferably a human one) is likely to yield compound activity Sexual Transmission of the Zika Virus The Zika virus has been demonstrated to be sexually transmissible through semen in multiple studies. The RNA virus can be detected in semen up to 62 days after the beginning of infection. (Hill et al., 2016; Mansuy et al., 2016; McCarthy, 2016). This provides not only an infection route for the virus which is independent of an arthropod vector but also exceeds the current WHO guidelines for engaging in protected sex for 30 days after returning from an endemically infected area (Turmel et al., 2016).

The persistence of Zika in semen offers an opportunity to conduct clinical testing in an arena which avoids the issues of birth defects with testing in pregnant women or women seeking to become pregnant.

ORG34517, PT150, PT155, PT156, PT157, PT158, TCY1, combinations thereof, and pharmaceutically acceptable salts thereof and other GCR-antagonist molecules necessarily thereby also interfere with the functions of viral GRE and can be used in accord with the following methods:

Administration of ORG34517, PT150, PT155, PT156, PT157, PT158, TCY1, combinations thereof, and pharmaceutically acceptable salts thereof or other GCR-antagonist molecules prior to or during physical, social, emotional or psychological conditions of stress that lead to elevations of circulating cortisol in order to diminish or prevent reactivation of latent viral infections;

Administration of ORG34517, PT150, PT155, PT156, PT157, PT158, TCY1, combinations thereof, and pharmaceutically acceptable salts thereof or other GCR-antagonist molecules prior to or during physical, social, emotional or psychological conditions of stress that lead to elevations of circulating cortisol in order to diminish or prevent susceptibility to viral infection;

Administration of ORG34517, PT150, PT155, PT156, PT157, PT158, TCY1, combinations thereof, and pharmaceutically acceptable salts thereof or other GCR-antagonist molecules in individuals prior to or receiving therapeutic doses of glucocorticoids in order to diminish or prevent reactivation of latent viral infections;

Administration of ORG34517, PT150, PT155, PT156, PT157, PT158, TCY1, combinations thereof, and pharmaceutically acceptable salts thereof or other GCR-antagonist molecules in individuals prior to or receiving therapeutic doses of glucocorticoids in to diminish or prevent susceptibility to viral infection.

Administration of ORG34517, PT150, PT155, PT156, PT157, PT158, TCY1, combinations thereof, and pharmaceutically acceptable salts thereof or other GCR-antagonist molecules in individuals during reactivation of latent viral infections to diminish intensity of viral reactivation, to diminish length of viral reactivation, to speed time to resolution and healing of viral reactivation, to speed time to suppression of viral reactivation, to increase likelihood of viral eradication, and/or to diminish infectivity of viral reactivation;

Administration of ORG34517, PT150, PT155, PT156, PT157, PT158, TCY1, combinations thereof, and pharmaceutically acceptable salts thereof or other GCR-antagonist molecules in individuals during acute viral infections to diminish intensity of viral infection, to diminish length of viral infection, to speed time to resolution and healing of viral infection, to speed time to suppression of viral infection, to increase likelihood of viral eradication, and/or to diminish infectivity of viral infection.

Administration of ORG34517, PT150, PT155, PT156, PT157, PT158, TCY1, combinations thereof, and pharmaceutically acceptable salts thereof or other GCR-antagonist molecules prior to or during travel to environments in which viruses are endemic in order to diminish or prevent susceptibility to viral infection Through interference with the functions of viral GRE, ORG34517, PT150, PT155, PT156, PT157, PT158, TCY1, combinations thereof, and pharmaceutically acceptable salts thereof and other GCR-antagonist molecules can prevent or reduce tissue damage in forms such as, but not limited to direct viral cytotoxicity, immune mediate destruction of virally infected cells and tissues, and malignant transformation.

ORG34517, PT150, PT155, PT156, PT157, PT158, TCY1, combinations thereof, and pharmaceutically acceptable salts thereof and other GCR-antagonist molecules may be combined with other, virus-targeted anti-viral medications (i.e. molecules that specifically bind to viral molecules and interfere with virus physiology) in the setting of acute infection, reactivation of latent viral infection or active chronic viral infection.

ORG34517, PT150, PT155, PT156, PT157, PT158, TCY1, combinations thereof, and pharmaceutically acceptable salts thereof and other GCR-antagonist molecules may be combined with other, non-specific anti-virus medications (i.e. immune system modulators that work non-specifically to modulate virus physiology) in the setting of acute infection, reactivation of latent viral infection or active chronic viral infection.

Viral Conditions

Virus families that infect humans (some of which also infect animals) include:

Adenoviridae, Papillomaviridae, Polyomaviridae, Herpesviridae and Poxviridae. These include, but are not limited to: adenovirus, herpes simplex-1, herpes simplex-2, Varicella-zoster, Epstein-Barr virus, *cytomegalovirus*, human herpes virus 8, human papilloma virus, BK virus, JC virus, chicken pox and small pox.

Hepadnaviridae, including, but not limited to hepatitis B virus.
Parvoviridae, including but not limited to human *bocavirus* and *parvovirus* B19.
Astroviridae, Caliciviridae, Picornaviridae, Coronoviridae, Flaviviridae, Retroviridae, Togaviridae, Hepeviridae. These include, but are not limited to human *astrovirus*, Norwalk virus, *coxsackievirus*, hepatitis A, *poliovirus, rhinovirus*, severe acute respiratory syndrome virus (SARS), hepatitis C virus, yellow fever virus, dengue virus, West Nile virus, Rubella virus, hepatitis E virus
Arenaviridae, Bunyaviridae, Filoviridae, Orthomyxoviridae, Paramyxoviridae and Rhabdoviridae. These include, but are not limited to influenza virus, Guanarito virus, Junín virus, Lassa virus, Machupo virus, Sabia virus, Cimean-Congo hemorrhagic fever virus, Ebola virus, Marburg virus, Measelse virus, Mumps virus, Parainfluenza virus Respiratory syncytial virus, human *metapneumovirus*, Hendra virus, Hipah virus, Rabies virus,
Reoviridae including but not limited to *Toravirus, Orbivirus, Coltivirus, Banna virus*.
Hepatitis D virus.
Additional viruses that infect animals include:
Rhabdoviridae, including, but not limited to vesicular stomatitis virus.
Picornaviridae, including, but not limited to Foot and mouth disease virus,
Pestiviridae including, but not limited to Classical swine fever and Bovine viral diarrhea.
Arteriviridae including, but not limited to equine arteritis virus, porcine reproductive and respiratory syndrome virus, lactate dehydrogenase elevating virus and simian haemorrhagic fever virus.
Coronaviridae including, but not limited to infectious bronchitis virus, transmissible gastroenteritis coronoavirus, bovine coronavirus, feline coronavirus, canine coronavirus, moust hepatitis virus,
Toroviridae including, but not limited to Berne virus, Breda virus.
Orthomyxoviridae including, but not limited to avian influenza virus, swine influenza virus.
Reoviridae including, but not limited to Bluetongue virus.
CIroviridae including, but not limited to chicken anemia virus, porcine circovirus-1, porcine cirovirus-2, psittacine beak and feather disease virus, pigeon circovirus, canary circovirus and goose circovirus.
Asfarviridae including, but not limited to African swin fever virus.
Retroviridae including, but not limited to Avian leucosis virus, Rous sarcoma virus, mouse mammary tumor virus, murine leukemia virus, feline leukemia virus, boine leukemia virus, Walleye dermal sarcoma virus, Simian and feline immunodeficiency viruses, simian foamy virus.
Flaviviridae including, but not limited to Tick-borne encephalitis virus, Japenese encephalitis virus, St. Louis encephalitis virus, Israel turkey meningoencephalomyelitis virus, Sitiawan virus, Wesselsbron virus and louping ill virus.
Paramyxoviridae including, but not limited to canine distemper virus, phocine distemper virus, cetacean *morbillivirus*, Newcastle disease virus, rinder pest virus.
Most Confirmed PS-Interception-Susceptible Enveloped Viruses are RNA Viruses:
Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amaparí virus, Pichindé virus, Tacaribe virus, Junín virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus)

Confirmed PS-Interception-Susceptible Enveloped DNA Viruses are:
vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); *Autographa californica nucleopolyhedrovirus* (Baculoviridae, Alphabaculoviridae) (an insect virus)

Prospected PS-Interception-Susceptible Important Enveloped RNA Viruses are:
Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amaparí virus, Pichindé virus, Tacaribe virus, Junín virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus)

Prospected PS-Interception-Susceptible Enveloped DNA Viruses are:
variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus)

Anti-PS binding of a molecule to viral envelope PS will therefore interfere with acute infection by any of the above named viruses, with acute reactivation of a latent chronic viral infection (in those PS-labeled viruses capable of maintaining latency), or with chronic viral infection with active viral replication of any of the above named viruses.

The anti-viral actions of PT150, PT155, PT156, PT157, PT158, TCY-1 or any further derivatives therefore may act on any viral infection through more than one mechanism of action, either through binding to GREs (with all the possible anti-viral activities noted above) or to PS (with all possible anti-viral activities noted above) in an additive or synergistic fashion.

TABLE 5

Anti-viral Activities of PT150

| Virus | Strain | Host cell | Antiviral activity (μM) $EC_{50}$ NR | Remarks | Cytotoxicity 50% (μM) $CC_{50}$ | Selectivity index 50% $SI_{50}$ |
|---|---|---|---|---|---|---|
| Influenza A H5N1 (avian) | A/duck/Minnesota/1525/81 | MDCK | 13.9 | Toxicity on MDCK | 17.0 | 1.2 |
| Rift Valley fever | MP-12 | Vero 76 | 12.8 | Toxicity on Vero 76 | 16.5 | 1.3 |
| Venezuelan equine encephalitis | TC-83 | Vero 76 | >34.8 | No activity | 34.8 | <1 |
| Chikungunya | S-27 | Vero 76 | >21.8 | No activity | 21.8 | <1 |
| Respiratory syncytial type A | A2 (VR-1540) | MA-104 | >32.5 | No activity | 32.5 | <1 |
| Enterovirus D68 | US/Kentucky/14-18953 | RD | >10.2 | No activity | 10.2 | <1 |
| Enterovirus 71 | Tainan/4643/98 | Vero 76 | 7.4 | Toxicity on Vero 76 | 7.4 | 1.0 |
| Poliovirus type 3 | WM-3 | Vero 76 | 5.6 | Toxicity on Vero 76 | 7.4 | 1.3 |
| Yellow fever | 17D vaccine | HeLa | 9.8 | With hGRα | 11.8 | 1.2 |
|  |  | Vero 76 | >10.9 | No hGRα | 10.9 | <1 |
| Zika | MR766 | HuH-7 | 7.4 | Toxicity on HuH-7 | 7.4 | 1.0 |
| Ebola | Zaire Mayinga | Vero | >7.9 | Toxicity on Vero | 7.9 | <1 |

TABLE 6

Anti-viral Activities of PT155

| Virus | Strain | Host cell | Antiviral activity (μM) $EC_{50}$ NR | Remarks | Cytotoxicity 50% (μM) $CC_{50}$ | Selectivity index 50% $SI_{50}$ |
|---|---|---|---|---|---|---|
| Influenza A H5N1 (avian) | A/duck/Minnesota/1525/81 | MDCK | 31.2 | — | >141.7 | >4.5 |
| Rift Valley fever | MP-12 | Vero 76 | 10.8 | Toxicity on Vero 76 | 70.9 | 6.6 |
| Venezuelan equine encephalitis | TC-83 | Vero 76 | >18.4 | No activity | 18.4 | <1 |
| Chikungunya | S-27 | Vero 76 | >12.8 | No activity | 12.8 | <1 |
| Respiratory syncytial type A | A2 (VR-1540) | MA-104 | >17.0 | No activity | 17.0 | <1 |
| Enterovirus D68 | US/Kentucky/14-18953 | RD | >5.8 | No activity | 5.8 | <1 |
| Enterovirus 71 | Tainan/4643/98 | Vero 76 | 0.51 | Toxicity on Vero 76 | 45.4 | 89.0 |
| Poliovirus type 3 | WM-3 | Vero 76 | 0.74 | Toxicity on Vero 76 | 45.4 | 61.4 |
| Yellow fever | 17D vaccine | HeLa | 2.1 | With hGRα | 6.0 | 2.9 |
|  |  | Vero 76 | >6.1 | No hGRα | 6.1 | <1 |
| Zika | MR766 | HuH-7 | 0.45 | Toxicity on HuH-7 | 39.7 | 88.2 |
| Ebola | Zaire Mayinga | Vero | 7.5 | Toxicity on Vero | 19.6 | 2.6 |

Influenza Virus

PT150 and PT155 are antivirally active versus influenza A virus replication at higher concentrations ($EC_{50} >> 10$ μM). PT150 is more potently active than PT155
This antiviral activity is very probably dependent on human glucocorticoid receptor-a (hGRa), since PT150 is more active than PT155, with the latter reasonably assumed being a weaker glucocorticoid antagonist than PT150, as was shown for the PT155-related compound PT150 oxime (ORG36174). The activity of both compounds is better against avian influenza A virus (H5N1) as compared towards swine-origin pandemic influenza A (H1N1) virus The probable mechanism-of-action of PT150 is the trapping of Hsp90 onto a non-nuclear-translocated complex (PT150-hGRa-Hsp90) hold back in the host cytosol. Therefore, the amount of free Hsp90 available for influenza A virus polymerase complex assembly and nuclear trafficking is diminished by PT150 and, at lower propensity, also by PT155, leading to antiviral effects.

In addition, inhibition of Hsp90 by small-molecule drugs (for example, geldanamycin/radicicol derivatives) represents an established antineoplastic chemotherapeutic strategy. Hsp90 client proteins (>300 cellular proteins are known currently to be Hsp90 clients) are important for cancer growth and malignant transformation. PT compounds, especially PT150, indirectly target Hsp90 by trapping Hsp90 in an inactive complex with human glucocorticoid receptor isoform alpha. This, in turn, leads to diminished availability of Hsp90 protein, required for stabilizing client proteins essential to cancer cell growth, maintenance of malignant cell phenotype, tumor angiogenesis, tumor spread and metastasis.

Rift Valley Fever

PT150 and PT155 are antivirally active versus Rift Valley fever virus replication at relatively low concentrations (EC50≈10 µM). PT150 is about as active as PT155 This antiviral activity is clearly independent of human glucocorticoid receptor a (hGRa), since Vero 76 cells do not express such a receptor, even not any monkey glucocorticoid receptor.

The mechanism-of-action is very probably inhibition of virus-cell fusion, since RVFV glycoprotein GC contains a binding pocket for lipophilic compounds.

This was substantiated by the observation that the RVFV accessory proteins (the 78 kDa protein, NSm1, NSm2 and NSs) are dispensable for virus replication in vitro, and the postulation that the PT compounds do not interact with the large RNA-dependent RNA polymerase L and the nucleocapsid protein N. Other gene expression products are not known, therefore PT compounds should bind to GN and/or GC RVFV envelope transmembrane glycoproteins mediating receptor binding and fusion Binding of PT compounds to the nucleocapsid N protein is not expected, since the RVFV N protein does not present hydrophobic binding sites, only a central RNA-binding core (hence, positively charged) and alternately charged N- and C-termini.

A binding pocket for highly lipophilic compounds in the X-ray crystallographic structure of RVFV GC protein was described. GC is the fusion-competent glycoprotein, and represents a class II viral fusion glycoprotein.

Polio Virus

PT150 and PT155 are antivirally active versus *poliovirus* type 3 replication at low concentrations (EC50≈1-5 µM). PT155 is slightly more active than PT150

Poliomyelitis is an old disease (see picture). *Poliovirus* can infect neurons and can lead to neuromuscular paralysis.

The term "poliomyelitis" is used to identify the disease caused by any of the three serotypes of *poliovirus*. Two basic patterns of polio infection are described: a minor illness which does not involve the central nervous system (CNS), sometimes called abortive poliomyelitis, and a major illness involving the CNS, which may be paralytic or nonparalytic. PT150 and PT155 are antivirally active versus *poliovirus* type 3 replication at low concentrations (EC50≈1-5 µM). PT155 is slightly more active than PT150

This antiviral activity is clearly independent of human glucocorticoid receptor-a (hGRa), since Vero 76 cells do not express such a receptor, even not any monkey glucocorticoid receptor. The mechanism-of-action is very probably inhibition of *poliovirus* capsid uncoating, since PT150 fits well into the picornaviral VP1 capsid protein hydrophobic pocket binder model like do the "canyon binders" compound 40, arildone, disoxaril, WIN 58084, pleconaril, and pirodavir. For a model of this hydrophobic binding of PT150 into the VP1 pocket of human *rhinovirus* 14 see next side. A similar fit of PT150 is expected into *poliovirus* type 3 VP1 capsid protein hydrophobic pocket.

Hepatitis Virus

ORG34517, PT150, PT155, PT156, PT157, PT158, TCY1 are a new class of therapeutic agents designed to block the glucocorticoid receptor (GR), acting as an antagonist for endogenous cortisol. The primary developmental pathway to date has been as a treatment for neuropsychiatric diseases characterized by dysregulation of the hypothalamic-pituitary-adrenal axis of signaling that are often associated with higher than normal circulating levels of endogenous cortisol.

Other possible uses include oncology, viral infection and other neuropsychiatric conditions including post-traumatic stress disorder, weight gain in patients requiring long term anti-psychotic medication, and hospital delirium of the elderly.

Human hepatitis B virus (HBV) and human immunodeficiency virus type 1 (HIV-1) integrate their retro-transcribed DNA proviruses into the human host genome. Existing antiretroviral drug regimens fail to directly target these intrachromosomal xenogenomes, leading to persistence of viral genetic information. Both HBV and HIV-1 harbor glucocorticoid response elements (GREs) in their proviral DNA genomes. This invention describes a potent glucocorticoid antagonist which binds to human glucocorticoid receptor isoform alpha (hGR-alpha), is translocated to the nucleus by the nuclear receptor dimer, and has the ability to covalently inactivate the intragenic and intraexonic viral GREs of HBV and HIV-1. The glucocorticoid antagonist ORG34517 dimeric thiosemicarbazone derivative" described by this invention represents the first reported antiviral agent capable of eradicating human immunodeficiency and hepatitis B proviruses from their human host. The anti-HBV effect of the glucocorticoid antagonist ORG34517 dimeric thiosemicarbazone derivative may be mediated by hGR-alpha, since the HBV genome contains at least two hGR-alpha trans-activation targets (GREs). The glucocorticoid antagonist ORG34517 dimeric thiosemicarbazone derivative binds to hGR-alpha, is transported through the nuclear pore complex to the intranuclear HBV genome by the (glucocorticoid antagonist ORG34517 dimeric thiosemicarbazone derivative)-liganded hGR-alpha, the liganded hGR-alpha complex binds to GREs, and, finally, the co-transported glucocorticoid antagonist ORG34517 dimeric thiosemicarbazone derivative switches to the HBV DNA and covalently modifies amine group-containing nucleobases (cytosine, guanine, adenine) by trans-thiocarbamoylation. This could also happen for host cellular GREs, but we think there is selectivity for intraexonic GREs, which are not typical for the human genome, since viral intraexonic GREs are subject to different epigenetic regulation involving chromatin remodeling events in comparison to host cellular GREs. Human GREs are located in the promoter regions upstream of transcription initiation sites, with only few exceptions where the GRE is found within a human gene intron. Additionally, it should be mentioned that human GREs are in most instances imperfect (GRE sequence degeneracy), i.e. their sequences do not match the perfect GRE consensus sequence given. In spite of these imperfect GRE sites, their glucocorticoid responsiveness is retained.

GRE 4 is proposed as a target of the glucocorticoid antagonist ORG34517 dimeric thiosemicarbazone derivative, since the 5'-LTR GREs are only partially functional negative enhancers (silencers) of HIV-1 gene expression, whereas the GRE 4 in the vif gene was shown to be fully functional as enhancer of HIV gene transcription.

The covalent modification of HIV-1$_{LAI}$ vif gene by the glucocorticoid antagonist ORG34517 dimeric thiosemicarbazone derivative, in close analogy to the already described mechanism-of-action on HBV ayw, would lead to loss of HIV-1$_{LAI}$ Vif protein (Vif=viral infectivity factor) function. Vif protein serves as an inherent retroviral inhibitor of the innate human apolipoprotein B mRNA-editing enzyme 3G (APOBEC3G)-dependent human antiretroviral defense system. As a consequence, Vif could not protect HIV-1 (−)-cDNA towards host APOBEC3G cytidine deaminase enzymatic activity (dC→dU mutation).

The covalently 'trapped' proviral DNA of HBV or HIV-1 is expected to induce p53-mediated apoptosis through an DNA damage signal mechanism sensored by p53 tumor suppressor protein and/or other DNA damage-induced sensor mechanisms [e.g. ataxia telangiectasia and Rad3-related protein (ATR)]. By proviral DNA damage-induced apoptosis the host organism of the viruses could be successively cleared from host genome-integrated proviral xeno-DNA. The synthesis of the glucocorticoid antagonist ORG34517 dimeric thiosemicarbazone derivative is performed by construction of the thiosemicarbazone of ORG34517 [20 min reflux of ORG34517 with equimolar thiosemicarbazide in 90% (v/v) aqueous ethanol], and its subsequent dimerization by treatment (in acetone, room temperature) with sodium hydroxide (NaOH, pre-dissolved in water). These transactions are based on general procedures already described in literature and known to those skilled in the art.

The hitherto claimed compounds of this invention could also be active versus human hepatitis C virus (HCV), which is indicated by a published proof-of-concept study. An antiviral mechanism-of-action of the glucocorticoid antagonist ORG34517 dimeric thiosemicarbazone derivative, and of the intermediate ORG34517 thiosemicarbazone, versus human hepatitis C virus subtype 1b strain Con1 (HCV-1b Con1 is proposed. It is inherently clear that it cannot being mediated by hGR-alpha, since HCV incorporates no DNA stage in its life cycle. Since the anti-HCV-1b activity of thiosemicarbazones described in this invention was determined with the HCV RNA replicon cell line Huh7ET (luc-ubi-neo/ET), which only codes for the non-structural HCV proteins NS3, NS4A, NS4B, NS5A and NS5B, the inhibiting action of the thiosemicarbazones described in this invention must be confined to these five genes and/or gene products. It was reported that thiosemicarbazones (5,6-dimethoxyindan-1-one thiosemicarbazone, DMI-TSC) target bovine viral diarrhea virus type 1 (BVDV-1 strain NADL, Flaviviridae, Pestivirus) NS5B protein RNA-dependent RNA polymerase (RdRp). BVDV-1 is commonly regarded as a suitable surrogate for HCV, because both Flaviviridae polyprotein sequences are closely related (maximal sequence identitiy 39%)

Since the claimed compounds of this invention could also be active versus Ebola virus Zaire strain 1976 Mayinga (EBOV Zaire 1976 Mayinga), which is indicated by a published proof-of-concept study, a sequence triple alignment between BVDV-1 NADL NS5B RdRp, HCV-1b Con1 NS5B RdRp, and EBOV Zaire 1976 Mayinga VP40 membrane-associated matrix protein is included in this invention. A compound similar to the claimed compounds of this invention is an inhibitor of EBOV Zaire 1976 Mayinga membrane-associated matrix protein VP40 octamerization, an event which is essential to EBOV Zaire 1976 Mayinga replication.

The invention provides the treatment of EBOV Zaire infections with the glucocorticoid antagonist ORG34517 dimeric thiosemicarbazone derivative, or the intermediate ORG34517 thiosemicarbazone, both embodiments of this invention, as the procedures described in this invention are known to those skilled in the art.

The invention provides the combination of ORG34517 dimeric thiosemicarbazone derivative with additional antiviral and anti-inflammatory compounds in a kit for the treatment or amelioration of a condition selected from the group consisting of HBV infection, HIV infection, and Ebola virus infection.

Cytosolic nuclear receptors translocate into the nucleus following ligand binding Liganded nuclear receptor dimers bind to hormone response cognate element DNA Glucocorticoids bind to human glucocorticoid receptor isoforms a/b (hGR-a/b)

Liganded hGR-a/bdimer binds to DNA glucocorticoid response elements (GREs)

PT155 is metabolically activated by human flavin-containing monoxygenases (hFMOs) through S-oxidation in the thiosemicarbazone part of PT155

The PT155 carbodiimide metabolite binds as ligand to the homodimeric hGR-a/b, in one half with ORG 34517, and the liganded complex translocates to the nucleus:

hGRsubunit 1-(ORG 34517 carbodiimide derivative)=hGR-subunit 2-ORG 34517

The hGRa/b-(PT155 carbodiimide metabolite) complex binds to GREs in intrachromosomal HBV or HIV-1 proviral DNA The HBV or HIV-1 host DNA-integrated proviral GRE DNA is thereby covalently inactivated over an amidrazone bond The covalently trapped proviral DNA of HBV or HIV-1 is expected to induce p53-mediated apoptos is through an DNA damage signal mechanism sensored by p53 tumor suppressor protein and/or other DNA damage-induced sensor mechanisms [e.g. ataxiatelangiectasia and Rad3-related protein (ATR)]

By proviral DNA damage-induced apoptosis the host organism of the viruses could be successively cleared from host genome-integrated proviral xeno-DNA Human hepatitis B virus (HBV) and human immunodeficiency virus type 1 (HIV-1) integrate the irretro-transcribed DNA proviruses into the human host genome. Existing antiretroviral drug regimens fail to directly target these intrachromosomal xeno genomes, leading to persistence of viral genetic information Existing HAART therapies target reverse transcriptase (HBV, HIV), protease (HIV) and integrase (HIV) proteins. These therapy options are not curative In a proof-of-concept study the PT155-similar compound retinazone was proved to work versus HBV, HIV-1, HCV, and the human herpes viruses HHV-3, HHV-6, and HHV-8 (Herpes viridae)

Retinazone's antiviral activity correlated exactly with the presence of intragenic and intraexonic GREs in virus-essential genes of retinazone-susceptible viruses The glucocorticoid antagonist ORG34517 thiosemicarbazone derivative PT155 described in this presentation might represent the first reported antiviral agent capable of eradicating human immunodeficiency and hepatitis B proviruses from their human host Human hepatitis C virus (HCV) NS5B RNA polymerase protein bears a common thiosemicarbazone-binding motif HCV-1b Con1 NS5B fingertip/finger domain RdRp motif I, 139-MAKNEV-144 (Hepaciviruscompletely conserved aa residues in bold), was identified as thiosemicarbazone-binding motif In a proof-of-concept study structurally diverse thiosemicarbazones were active as inhibitors of HCV replication PT155 is additionally proposed as HCV inhibitor

HIV

The Mechanism-of-Action of PT150 and PT155 Versus Human Immunodeficiency Virus Type 1 Strain LAI (Retroviridae, Lentivirus)

Results: PT150 and PT155 are active versus human immunodeficiency virus type 1 (HIV-1) strain LAI (HIV-1$_{LAI}$) in primary human peripheral blood mononuclear cells (PBMCs) which consist of T lymphocytes, B lymphocytes and monocytes. (=HIV-1$_{LAI}$(=HIV-1$_{BRU}$=LAV-1 was assayed in primary [freshly donated from healthy (tested HIV-1-negative, HBV-negative, and HCV-negative) blood donors, and isolated by single-step Ficoll-Hypaque centrifugation method] human peripheral blood mononuclear (PBM) cells in the presence of a drug being evaluated. The parameter for antiviral activity was reduction of reverse transcriptase (RT) activity in the cell supernatant after Triton X-100-mediated lysis of released virions, as measured by [5alpha-$^3$H]dTTP (5alpha-tritiated thymidine 5'-triphosphate) incorporation into poly(rA)•poly(dT) directed by the primed RNA template poly(rA)•oligo(dT). It should be noted that the assay did not detect RT inhibition by potential RT inhibitors per se, but indirectly quantified the amount of released HIV-1 in the supernatant. The detailed assay methodology was reported by Schinazi et al., as based on an older assay system of Spira et al. The experiments were conducted in triplicate and treated statistically by regression curve analysis ($r^2$ coefficient of determination). The RT inhibitor AZT (zidovudine, 3'-azido-3'-deoxythymidine; RETROVIR™) served as a positive control. Cytotoxicity on PBMC exerted by the test compounds was determined as described by Stuyver et al., by application of the CellTiter 96® AQ$_{ueous}$ One Solution Cell Proliferation Assay (Promega Corp., Madison, WI). Briefly, the phenazine ethosulfate (PES)-coupled reduction of the tetrazolium salt 3-(4,5-dimethylthiazol-2-yl)-5-(3-carboxymethoxyphenyl)-2-(4-sulfophenyl)-2H-tetrazolium (MTS) to a purple formazan by undamaged cells was measured.

Mechanism-of-action: The antiretroviral action of PT150 and PT155 is mediated via DNA glucocorticoid response elements (GREs) residing in the prolentivirus of HIV-1$_{LAI}$ integrated into the nuclear, chromosomal human host genome as xenogenomic prolentiviral DNA sequence:

Cytosolic nuclear receptors translocate into the nucleus following ligand binding Liganded nuclear receptor dimers bind to hormone response cognate element DNA Glucocorticoids bind to human glucocorticoid receptor isoform alpha (hGR-alpha)

Liganded hGRalpha dimer binds to DNA glucocorticoid response elements (GREs)

Glucocorticosteroid nuclear receptors target GRE DNA

HIV-1$_{LAI}$ provirus (9229 nt) harbors four GREs: GRE 1-4

HIV-1$_{LAI}$ vif intragenic GRE 4 is located in vif gene exon

HIV-1$_{LAI}$ proviral DNA contains 4 recognized GREs (GRE 1, GRE 2, GRE 3, GRE 4)

GRE 1 (−264 to −259), GRE 2 (−6 to −1) and GRE 3 (+15 to +20) are Located within the 5'-Long Terminal Repeat (5'-LTR)

PT155 is metabolically activated by human flavin-containing monoxygenases (hFMOs) through S-oxidation in the thiosemicarbazone part of PT155.

The PT155 carbodiimide metabolite binds as ligand to the homodimeric hGRalpha, in one half with PT150, and the liganded complex translocates to the nucleus:

hGRalpha subunit 1-(PT155 carbodiimide metabolite)=hGRalphasubunit 2-PT150

The hGRalpha-(PT155 carbodiimide metabolite) complex binds to GREs in intrachromosomal HIV-1 proviral DNA Consequences of Proviral DNA Trapping by the PT155 Carbodiimide Derivative:

The covalently trapped proviral DNA of HIV-1 is expected to induce p53-mediated apoptosis through an DNA damage signal mechanism sensored by p53 tumor suppressor protein and/or other DNA damage-induced sensor mechanisms [e.g. ataxia telangiectasia and Rad3-related protein (ATR)]

By proviral DNA damage-induced apoptosis the host organism of the viruses could be successively cleared from host genome-integrated proviral xeno-DNA Without being bound by any theory, it is believed that Human immunodeficiency viruses (HIVs) integrate their retro-transcribed DNA proviruses into the human host genome. Existing antiretroviral drug regimens fail to directly target these intrachromosomal xenogenomes, leading to persistence of viral genetic information. Existing HAART therapies target reverse transcriptase, protease and integrase proteins. These therapy options are not curative. In a proof-of-concept study the PT155-similar compound retinazone was proved to work versus HBV, HIV-1, HCV, and the human herpesviruses HHV-3, HHV-5, HHV-6, and HHV-8 (Herpesviridae). Retinazone's antiviral activity correlated exactly with the presence of intragenic and intraexonic GREs in virus-essential genes of retinazone-susceptible viruses. The glucocorticoid antagonist PT155 described in this presentation might represent the first reported antiviral agent capable of eradicating human immunodeficiency proviruses from their human host The metabolic activation of PT150 thiosemicarbazone contained in PT155: S-Oxidation by human flavin-containing monooxygenases (hFMOs): It is well-known that thiosemicarbazones like thiacetazone (p-acetamidobenzaldehyde thiosemicarbazone), a cheap, second-line antitubercular substance discovered by Nobel laureate Gerhard Domagk in 1946, are bio-activated by human flavin-containing monooxygenases (hFMO1, hFMO2.1, hFMO3) into a sulfenic acid (R—S—OH), a sulfinic acid [R—(S=O)—OH], and a carbodiimide derivative (R—N=C=N—H). Both the sulfenic acid and the carbodiimide metabolite are the active antitubercular metabolites. The sulfinic acid does not form the carbodiimide, and represents an inactive metabolite. Especially the carbodiimide metabolite can react with amino acid residues in target proteins of, for example, *Mycobacterium tuberculosis*, or with human hepatic/extrahepatic glutathione R—SH thiol group for metabolic detoxification:

Therefore, PT155 will be bio-activated (S-oxidized) in the same manner as thiacetazone by hFMOs under consumption of molecular oxygen ($O_2$), and will be able to bind covalently to HBV and HIV proviral GRE DNA after being shuttled to the host cell nucleus by hGRalpha.

Human flavin-dependent monooxygenases (hFMOs) (EC 1.14.13.8) are the second important type of monooxygenases in the human body, the other well-known type being the cytochrome P450 monooxygenases (CYP450 monooxygenases). Both are localized in microsomes and dependent on molecular oxygen ($O_2$), and hFMOs need also the cofactors flavin-adenine dinucleotide (FAD) and nicotinamide-adenine dinucleotide phosphate (NADPH), whereas CYP450 monooxygenases are heme-dependent. hFMO1 is mainly expressed in human kidney, and, to a smaller extent, in small intestine and lung. hFMO2 is expressed to a very high level in human lung and kidney, and, to a smaller extent, in liver and small intestine. hFMO3 and hFMO5 are highly expressed in human liver, but are also expressed in lung and, to a smaller extent, in human kidney. hFMO4 is mainly expressed in kidney and, to a smaller extent, in liver and small intestine. hFMO5 is also expressed to a high level in small intestine. hFMO2 is additionally expressed in human brain, but at low abundance (<1% of lung).

Slightly modified citation following: "The hFMOs oxygenate nucleophilic heteroatom-containing chemicals and drugs and generally converts them into harmless, polar, readily excreted metabolites. Sometimes, however, FMO bioactivates chemicals into reactive materials that can cause toxicity. Most of the interindividual differences of hFMOs are due to genetic variability and allelic variation, and splicing variants may contribute to interindividual and interethnic variability observed for hFMO-mediated metabolism. In contrast to cytochrome P450 monooxygenases (CYP450 monooxygenases), hFMOs are not easily induced nor readily inhibited, and potential adverse drug-drug interactions are minimized for drugs prominently metabolized by hFMOs. These properties may provide advantages in drug design and discovery, and by incorporating hFMO detoxication pathways into drug candidates, more drug-like materials may be forthcoming. Although exhaustive examples are not available, physiological factors can influence hFMO function, and this may have implications for the clinical significance of hFMOs and a role in human disease."

Implications of the structure of PT155 on nuclear receptor binding—Nuclear translocation as key to biological action of PT155: PT150 does not support nuclear translocation of the PT150-hGRalpha complex. It is a competitive antagonist to cortisol in the cytosol only. Therefore, to reach our goal to target HBV and HIV proviruses residing in eukaryotic cell nuclear chromatin we must force nuclear translocation. Nuclear translocation of glucocorticosteroid-hGR complexes relies on structural modalities. The RU38486 (RU486, mifepristone) RU486-hGRalpha complex is indeed translocated into the nucleus, since RU486 represents a partial agonist at hGRalpha. The residual agonist potency of RU486 is sufficient to induce nuclear translocation. This latter property can be viewed as being strictly dependent of hGRalpha protein conformation with bound RU486 which still enables steroid receptor coactivator 2 (SRC-2) [=nuclear receptor coactivator 2 (NCoA-2), =glucocorticoid receptor interacting protein 2 (GRIP2), =transcriptional intermediary factor 2 (TIF-2)] or SRC-1 binding as necessary condition for nuclear targeting. These conformational inductions of RU486 on hGRalpha protein structure are pictured [next page, top and bottom].

From these considerations of the three-dimensional hGRalpha protein structure it can be deduced that the dimer postulated before is indeed not able to bind to hGRalpha because its size is too large to fit in the hGRalpha ligand-binding domain (LBD) pocket. It certainly would not induce nuclear translocation.

TABLE 7

Antiviral Activity of PT155 against Inducible HIV-1LAV in OM-10.1 Cells

| Test Article | $EC_{90}$ (µM) | $EC_{50}$ (µM) | $CC_{50}$ (µM) | Selectivity Index ($CC_{50}/EC_{50}$) |
|---|---|---|---|---|
| PT155 | 49.4 | 4.33 | >100 | >23.1 |
| Temacrazine (TMZ) | 0.64 | 0.07 | >1.00 | >0.13 |

TABLE 8

Inhibition of HIV-1 LAV in OM-10.1 by TMA

RT Values (cpm)

| | CONC (nM) | | | | | | | | |
|---|---|---|---|---|---|---|---|---|---|
| | 0.0 | 0.10 | 0.32 | 1.00 | 3.16 | 10.0 | 31.6 | 100 | 316 | 1000 |
| SAMPLE 1 | 28674 | 30380 | 28496 | 32770 | 30588 | 27453 | 25515 | 18782 | 6512 | 1016 |
| SAMPLE 2 | 29640 | 31745 | 31013 | 23041 | 25259 | 31623 | 24677 | 9733 | 5272 | 471 |
| SAMPLE 3 | 33105 | 26409 | 29181 | 24504 | 28648 | 31990 | 29321 | 5790 | 8986 | 351 |
| MEAN | 30472.8 | 29511.5 | 29563.5 | 26771.8 | 28165.2 | 30355.5 | 26504.5 | 11435.2 | 6923.5 | 612.8 |
| % VC | 100.0 | 96.8 | 97.0 | 87.9 | 92.4 | 99.6 | 87.0 | 37.5 | 22.7 | 2.0 |
| STD DEV | 7.6 | 9.1 | 4.3 | 17.2 | 8.9 | 8.3 | 8.1 | 21.9 | 6.2 | 1.2 |

TOXICITY VALUES (Cell Titer 96 - O.D. @ 490/650 nm)

| | CONC (nM) | | | | | | | | |
|---|---|---|---|---|---|---|---|---|---|
| | 0.0 | 0.10 | 0.32 | 1.00 | 3.16 | 10.0 | 31.6 | 100 | 316 | 1000 |
| SAMPLE 1 | 0.740 | 0.727 | 0.729 | 0.781 | 0.830 | 0.882 | 0.967 | 0.917 | 0.977 | 0.897 |
| SAMPLE 2 | 0.715 | 0.895 | 0.827 | 0.744 | 0.933 | 0.999 | 0.902 | 0.990 | 1.037 | 0.910 |
| SAMPLE 3 | 0.614 | 0.621 | 0.768 | 0.736 | 0.849 | 0.954 | 0.988 | 0.952 | 0.813 | 0.879 |
| MEAN | 0.690 | 0.748 | 0.775 | 0.754 | 0.871 | 0.945 | 0.952 | 0.953 | 0.942 | 0.896 |
| % CC | 100.0 | 108.4 | 112.4 | 109.3 | 126.3 | 137.0 | 138.1 | 138.2 | 136.7 | 129.9 |
| STD DEV | 9.7 | 20.0 | 7.1 | 3.5 | 8.0 | 8.6 | 6.5 | 5.3 | 16.8 | 2.2 |

| DRUG: TMZ | 50% | 90% | 95% |
|---|---|---|---|
| TC (nM) | >1000 | >1000 | >1000 |
| IC (nM) | 74.8 | 641 | 847 |
| ANTIVIRAL INDEX (AI) | >13.4 | >1.56 | >1.18 |

TABLE 9

Inhibition of HIV-1 LAV Replication in OM-10.1 by PT155

RT Values (cpm)

| | CONC (µM) | | | | | | | | |
|---|---|---|---|---|---|---|---|---|---|
| | 0.0 | 0.01 | 0.03 | 0.10 | 0.32 | 1.00 | 3.16 | 10.0 | 31.6 | 100 |
| SAMPLE 1 | 28674 | 32320 | 33018 | 29801 | 29905 | 23474 | 16156 | 8592 | 4254 | 0 |
| SAMPLE 2 | 29640 | 29982 | 33056 | 29663 | 25409 | 26693 | 21122 | 7827 | 4765 | 247 |
| SAMPLE 3 | 33105 | 29144 | 32387 | 31726 | 34136 | 24955 | 15662 | 10011 | 5466 | 454 |
| MEAN | 30472.8 | 30482.2 | 32820.5 | 30396.8 | 29816.8 | 25040.8 | 17646.8 | 8810.2 | 4828.5 | 233.8 |
| % VC | 100.0 | 100.0 | 107.7 | 99.8 | 97.8 | 82.2 | 57.9 | 28.9 | 15.8 | 0.8 |
| STD DEV | 7.6 | 5.4 | 1.2 | 3.8 | 14.3 | 5.3 | 9.9 | 3.6 | 2.0 | 0.7 |

TOXICITY VALUES (Cell Titer 96 - O.D. @ 490/650 nm)

| | CONC (µM) | | | | | | | | |
|---|---|---|---|---|---|---|---|---|---|
| | 0.0 | 0.01 | 0.03 | 0.10 | 0.32 | 1.00 | 3.16 | 10.0 | 31.6 | 100 |
| SAMPLE 1 | 0.740 | 0.707 | 0.749 | 0.867 | 0.925 | 0.937 | 0.896 | 0.828 | 0.714 | 0.777 |
| SAMPLE 2 | 0.715 | 0.669 | 0.794 | 0.820 | 0.933 | 0.911 | 0.800 | 0.761 | 0.682 | 0.775 |
| SAMPLE 3 | 0.614 | 0.567 | 0.642 | 0.590 | 0.635 | 0.618 | 0.572 | 0.599 | 0.536 | 0.775 |
| MEAN | 0.690 | 0.648 | 0.728 | 0.759 | 0.831 | 0.822 | 0.756 | 0.729 | 0.644 | 0.776 |
| % CC | 100.0 | 93.9 | 105.6 | 110.0 | 120.5 | 119.2 | 109.6 | 105.7 | 93.4 | 112.5 |
| STD DEV | 9.7 | 10.5 | 11.4 | 21.5 | 24.7 | 25.7 | 24.2 | 17.1 | 13.8 | 0.1 |

| DRUG: PT-155 | 50% | 90% | 95% |
|---|---|---|---|
| TC (µM) | >100 | >100 | >100 |
| IC (µM) | 4.33 | 49.4 | 72.4 |
| ANTIVIRAL INDEX (AI) | >23.1 | >2.02 | >1.38 |

Zika and Flavivirus

The Flavivirus family (Flaviviridae) are single-stranded (+) RNA virus. Other pathogens of note in the Flaviviridae include Hepatitis C, Yellow Fever, West Nile, St. Louis Encephalitis, Japanese Encephalitis and Dengue Fever. They are vector-transmitted (mosquito or tick) and generally causes mild, flu-like infections lasting less than a week. The Flavivirus have a unique set of secondary structures in their 3' untranslated regions (UTRs) which play roles in their replication as well as in their ability to produce subgenomic flavivirus (sfRNAs) when digested by host exonucleases. sfRNAs are of particular interest, as they are believed to play roles in altering host metabolic pathways through alteration of host mRNA stability, RNAi and DICER activity (Roby, 2014). sfRNAs have been implicated in altering the immune response to promote viral pathogenicity (Chang et al., 2013) as well as a recently discovered potential link between Zika, microencephaly and Guillain-Barré Syndrome (Ricketson & Lyons-Weiller, 2016).

Zika originated in central western African and spread through parts of African, Asia and Micronesia through the early part of the 21$^{st}$ century. Introduction into the Americas raised concern when the virus began to spread rapidly in Brazil (2015). The large number of cases have co-occurring have demonstrated the additional dangers of Zika causing microcephaly and other birth defects in the fetuses of pregnant women (Johannson et al., 2016; Malkki, 2016) and in the increased incidence of Guillain-Barré Syndrome (Cao-Lormeau et al., 2016; Paploski, 2016).

Microcephaly results from both genetic and environmental factors. Genetic factors are estimated to occur in 1:30-50,000 live births, while environmental factors are more common, estimated to occur in 1:10,000 live births. The connection between ZIka and microencephaly was made in Brazil in 2015 (Moron et al., 2016; Saiz et al., 2016; Slavov et al., 2016), and although the data is preliminary and difficult to correlate, it appears that case of microcephaly rose in infected areas of Brazil as much as 4-5 times in the northeast states of that country in 2015 (Butler, 2016). The primary risk appears to coincide with infection during the first trimester of pregnancy; Cauchenez et al. (2016) modeled data from cases in French Polynesia and estimated an increased risk for microcephaly 47.5 times greater in the first trimester if Zika infection occurred.

The CDC reported 3,988,076 births in the United States in 2014 (CDC Vital Statistics Reports, 2015). Births per month remain fairly steady in the United States with the highest months being July and August each year (Live Science, 2010). Extrapolating from 2006 data, 56.64% of children in 2016 will be conceived between the months of March through September with Zika-infected mosquitoes spreading throughout the country. That would place a 2,258,846 births in the upcoming year at increased risk for microcephaly. Using a 1:10,000 ratio as a guide, that would mean a possible increase of microcephaly in the Unites States in the upcoming year of as much as 9.3%.

Guillain-Barré syndrome (GBS) is an autoimmune disorder of the peripheral nervous system. The causes of GBS are elusive but have been demonstrated to occur following bacterial of viral infections. It has been theorized that inappropriate stimulation of the immune system by some infections is key to the induction of GBS. GBS is treated by plasma exchange or immunoglobulin therapy to lessen its duration and severity. Glucocorticoid therapy, useful in other autoimmune conditions, has been demonstrated to increase the severity of GBS.

To date, only one research study (Cao-Lormeau et al., 2016) has demonstrated Zika Virus as the causative agent of GBS. Yung & Thoon (2016) have modeled the increased risk of GBS following Zika infection using data gathered from French Polynesia in 2015. They report in increased incidence of GBS from a baseline of 0.24 per 1000 to 0.41 per 1000. This equates to a 21-fold risk increase of GBS.

Using 2004 data from the CDC, Frenzen (2008) calculated the annual health care cost for GBS in the United States at $1.7B dollars annually. CDC 2015 data lists the frequency of GBS in the United States at approximately 1:100,000. The mortality of GBS has been estimated in several studies Alshekhlee et al. (2008) at 2.58% and at 3.9% (van den Berg, 2013) but can vary widely because of demographics such as age and access to health care. Extrapolation from these statistics presents a very chilling scenario, where a fast-spreading population of Zika infection can cause a cascade of reactions impacting the number of GBS cases, health care costs and mortality rates.

The adverse reaction of patients receiving glucocorticoids with GBS is of particular interest with the compounds of the invention, as they demonstrate not only in vitro antiviral activity but also glucocorticoid antagonism. This means the compound PT150, which has already been established as safe in Phase II Human Clinical Trials, and the compound PT155, are potentially able to treat not only the infection but decrease the risks of contracting GBS and/or mitigating its severity as a post-infection occurrence.

PT150 (formerly known as ORG34517) has activity versus Flaviviridae, including Zika virus and yellow fever virus, and, possibly, some Picornaviridae like *poliovirus*. The proposed mechanism-of-action is as follows: PT150 represents a known, and clinically validated, potent and selective glucocorticoid receptor antagonist. Most Flaviviridae (excluding the genus Flavivirus) and all Picornaviridae contain an internal ribosome entry site (IRES) at the 5'-end of their (+)-ssRNA genome, a 5'-noncoding region (5'-NCR). This IRES is in turn necessary for translation at human host cell ribosomes of the viral (+)-ssRNA genome into a polyprotein (which is cleaved by host cellular and virally-encoded proteases to yield mature viral proteins) However, there is also a highly conserved noncoding region (NCR) at the 3'-end of the (+)-ssRNA genome, the 3'-NCR which exhibits a highly conserved stem-loop-containing RNA secondary structure (refs 22, 23) (see graphic next side)

The 3'-NCR binds several host cell proteins, one being hVIP/Mov34 which is required for proper Flavivirus propagation (transcription/replication). hVIP/Mov34 (human Vpr-interacting protein) is a member of the eukaryotic initiation factor 3A (eIF3) family (ref 26), and is required for Flaviviridae 3'-NCR-controlled replication (the exact roles of the 3'-NCR in Flaviviridae replication are presently unknown and remain to be elucidated). This was specifically proved for the 3'-NCR of Japanese encephalitis virus (JEV), a typical Flavivirus like Zika virus.

A Mov34-homologous protein serves as a 26S proteasome S12 subunit p40 (the proteasome is the "waste container" of the human cell and degrades all overused, misfolded and "trash" proteins by protease digestion within an enormously large protein complex, called the 26S proteasome) Mov34-like proteins are an integral part of eukaryotic initiation factor 3 (eIF3) complex: eIF3 subunit F p47 (37.5 kDa) & eIF3 subunit H p40 (39.9 kDa). Therefore, Mov34-like proteins seem to be life-essential and multi-functional HIV-1 vpr accessory gene product protein Vpr interacts with the human Mov34 protein, therefore Mov34 was termed: human Vpr-interacting protein (hVIP/Mov34). Mov34 was linked to the G2/M phase transition of the mammalian cell cycle, that means that hVIP/Mov34 protein is essential for the transition from G2 to M phase of human cell division. The carboxyl terminus of hVIP/Mov34 is critical for HIV-1-Vpr interaction and glucocorticoid-mediated signaling. This defines the crucial interaction between human Mov34 protein and human glucocorticoid receptor alpha.

In the absence of Vpr or HIV-1 infection, full-length hVIP/Mov34 is expressed in the cytoplasm. The cytoplasmic localization pattern of full-length hVIP/Mov34 protein, however, is shifted to a clear nuclear localization pattern in cells expressing both hVIP/Mov34 and HIV-1 Vpr. In contrast, Vpr did not alter the localization pattern of hVIP/Mov34 mutants, which have their carboxyl-terminal domain deleted. The movement of hVIP/Mov34 supported prior work that suggested that Vpr triggers activation of the glucocorticoid receptor complex. It was observed that dexamethasone moves hVIP/Mov34 into the nucleus and that mifepristone (RU38486) inhibited this effect. Interestingly, the expression of an hVIP/Mov34 carboxyl-terminal mutant, which is not responsive to Vpr, is also not responsive to dexamethasone. These data illustrate that the carboxyl-terminal domain of hVIP/Mov34 is critical for mediating hVIP/Mov34-Vpr interaction as well as for its hGRa response. These results support the view that hVIP/Mov34 is a member of the complex array of nucleocytoplasmic shuttling proteins that are regulated by HIV-1 infection and hGRalpha. Mov34 protein from mouse brain interacts with the 3'-noncoding region (3'-NCR) of Japanese encephalitis virus. Therefore, as Mov34 is a hGRa-binding partner, the 3'-NCR of flaviviruses is human glucocorticoid receptor-regulated and, therefore, prone to inhibition by glucocorticoid antagonists. Flaviviruses need Mov34 to replicate optimally in human cells. The glucocorticoid antagonist mifepristone (RU38486) was shown to inhibit Mov34 function in the case of HIV-1 infection. PT150 and, presumably, also PT155 bind as antagonists to human glucocorticoid receptor isoform alpha (hGRalpha). Human glucocorticoid receptor isoform b (hGRb) is an inactive receptor. PT150 and/or PT155-liganded hGRa, also Hsp90-bound inactive complex, in turn sequesters human Mov34 protein. This leads to a block of Flavivirus replication, since Mov34 is made unavailable for binding to yellow fever and Zika virus 3'-noncoding region (3'-NCR). PT150 and PT155 act via hVIP/Mov34 protein on Flavivirus 3'-noncoding region, which is also the origin of subgenomic flavivirus RNA (sfRNA) important for pathogenicity and immune evasion. hVIP/Mov34 protein is human glucocorticoid receptor a-regulated, and binds both to hGRa and HIV-1 Vpr protein. hVIP/Mov34 protein is indispensable for optimal replication and host pathogenicity of flaviviruses, this effect requires binding of hVIP/Mov34 to 3'-NCR and to the 3'-NCR-derived sfRNA hVIP/Mov34 protein binds to Flavivirus 3'-NCR and sfRNA, the exact binding mode and further details are still unknown PT155 is more potent than PT150 regarding inhibition of Flavivirus replication, as is PT155 versus HIV-1 replication. The Filoviridae are a Family within the Order Mononegavirales The Filoviridae consist of (in 2014):
Genus Marburgvirus: Marburg virus, Ravn virus
Genus Ebolavirus: Taï Forest virus, Reston virus, Sudan virus, Ebola virus, Bundibugyo virus
Genus Cuevavirus: Lloviu virus
Filoviridae are enveloped, non-segmented negative sense single-stranded RNA viruses [(−)-ssRNA viruses]
Filoviridae exhibit similarities to the Rhabdoviridae, Paramyxoviridae and Bornaviridae. Together they build up the Order Mononegavirales.
The compounds retinazone (RTZ) and PT155 share structural elements (lipophilic core/thiosemicarbazone head)

required for the inhibition of EBOV matrix protein VP40 octamerization and ring-mediated RNA binding RTZ was already proved to act as an in vitro inhibitor of EBOV replication in Vero cells.

RTZ inhibits EBOV matrix protein VP40 octamerization

We show here now that PT155 also acts as an in vitro inhibitor of EBOV replication, and, analogously to RTZ, probably acts by inhibition of EBOV matrix protein VP40 octamerization and RNA binding in Vero cells (first antifiloviral mechanism-of-action)

In addition, PT150 and PT155 also antagonize Hsp90 in cells expressing hGRa (second antifiloviral mechanism-of-action).

Results: The compound PT155 is highly active versus the very first isolate of Zika virus (MR766) obtained from rhesus monkey 766 at Zika Forest (Uganda) in 1947. This activity is seen in HuH-7 human hepatocellular carcinoma (HCC, hepatoma) cells, established from a liver tumor in a 57-year-old Japanese male in 1982 by Nakabayashi & Sato). In cells not expressing functional human glucocorticoid receptor-alpha (hGRalpha) PT155 is generally not active versus Zika virus MR766. This strongly points to involvement of hGRalpha in the antiviral activity of PT155 versus Zika virus MR766.

Putative mechanism-of-action: Most Flaviviridae (excluding the genus Flavivirus) and all Picornaviridae contain an internal ribosome entry site (IRES) at the 5'-end of their (+)-ssRNA genome, a 5'-noncoding region (5'-NCR). This IRES is in turn necessary for translation at human host cell ribosomes of the viral (+)-ssRNA genome into a polyprotein (which is cleaved by host cellular and virally-encoded proteases to yield mature viral proteins). However, there is also a highly conserved noncoding region (NCR) at the 3'-end of the (+)-ssRNA genome, the 3'-NCR which exhibits a highly conserved stem-loop-containing RNA secondary structure.

The 3'-NCR binds several host cell proteins, one being hVIP/Mov34 which is required for proper Flavivirus propagation (transcription/replication). hVIP/Mov34 (human Vpr-interacting protein) is a member of the eukaryotic initiation factor 3A (eIF3) family, and is required for Flaviviridae 3'-NCR-controlled replication (the exact roles of the 3'-NCR in Flaviviridae replication are presently unknown and remain to be elucidated). This was specifically proved for the 3'-NCR of Japanese encephalitis virus (JEV), a typical Flavivirus like Zika virus.

Glucocorticoid receptor (GR) agonists (dexamethasone) and glucocorticoid antagonists (mifepristone, RU38486) interact with hVIP/Mov34. Specifically, GR agonists stimulate hVIP/Mov34 translocation into the nucleus, and mifepristone inhibits this translocation. Therefore, mifepristone can act as an hVIP/Mov34 antagonist, and this antagonism is able to suppress Flaviviridae replication, as was disclosed in an U.S. Pat. Appl. for the *Hepacivirus* human hepatitis C virus, by yet unknown detailed mechanism(s).

Vero cell derivatives (Vero, Vero 76, Vero E6) do not contain human glucocorticoid receptor, as they are derived from African green monkey (*Chlorocebus aethiops, Cercopithecus aethiops*) epithelial kidney cells. They even do not contain a *Chlorocebus* glucocorticoid receptor, and Vero cells do not respond to dexamethasone. Therefore, in all Vero cell derivatives (Vero, Vero 76, Vero E6) an antiviral effect of PT155 versus Flaviviridae will be obscured.

hVIP/Mov34 protein may be crucial to Flavivirus replication, infectivity and pathogenicity, and key to the antiflaviviral activity of PT compounds. Mov34 protein is named correctly: Moloney murine leukemia provirus insertion-disrupted protein of 36 kDa:

Mouse (murine) Mov34 gene was firstly identified in 1987 during mutation analysis of Moloney murine leukemia virus (MoMLV) provirus insertion mapping in mice: Retroviruses and insertional mutagenesis in mice: proviral integration at the Mov 34 locus leads to early embryonic death Mouse (murine) Mov34 gene was further investigated in 1990, including chromosome mapping of a human Mov34 homolog gene: Molecular analysis of the Mov 34 mutation: transcript disrupted by proviral integration in mice is conserved in *Drosophila*. Mouse (murine) Mov34 gene was cloned and sequenced in 1991 Mouse (murine) Mov34 protein expression is essential to embryonic development: Embryos homozygous at theMov34 locus develop normally to the blastocyst stage and die shortly after implantation, indicating that virus integration resulted in a recessive lethal mutation. A Mov34-homologous protein serves as a 26S proteasome S12 subunit p40 (the proteasome is the "waste container" of the human cell and degrades all overused, misfolded and "trash" proteins by protease digestion within an enormously large protein complex, called the 26S proteasome)

Mov34-like proteins are an integral part of eukaryotic initiation factor 3 (eIF3) complex: eIF3 subunit F p47 (37.5 kDa) & eIF3 subunit H p40 (39.9 kDa)

Therefore, Mov34-like proteins seem to be life-essential and multi-functional HIV-1 vpr accessory gene product protein Vpr interacts with the human Mov34 protein, therefore Mov34 was termed: human Vpr-interacting protein (hVIP/Mov34). Mov34 was linked to the G2/M phase transition of the mammalian cell cycle, that means that hVIP/Mov34 protein is essential for the transition from G2 to M phase of human cell division.

The carboxyl terminus of hVIP/Mov34 is critical for HIV-1-Vpr interaction and glucocorticoid-mediated signaling. This defines the crucial interaction between human Mov34 protein and hGRalpha.

In the absence of Vpr or HIV-1 infection, full-length hVIP/Mov34 is expressed in the cytoplasm. The cytoplasmic localization pattern of full-length hVIP/Mov34 protein, however, is shifted to a clear nuclear localization pattern in cells expressing both hVIP/Mov34 and HIV-1 Vpr. In contrast, Vpr did not alter the localization pattern of hVIP/Mov34 mutants, which have their carboxyl-terminal domain deleted. The movement of hVIP/Mov34 supported prior work that suggested that Vpr triggers activation of the glucocorticoid receptor complex. It was observed that dexamethasone moves hVIP/Mov34 into the nucleus and that mifepristone (RU38486) inhibited this effect. Interestingly, the expression of an hVIP/Mov34 carboxyl-terminal mutant, which is not responsive to Vpr, is also not responsive to dexamethasone. These data illustrate that the carboxyl-terminal domain of hVIP/Mov34 is critical for mediating hVIP/Mov34-Vpr interaction as well as for its hGRalpha response. These results support the view that hVIP/Mov34 is a member of the complex array of nucleocytoplasmic shuttling proteins that are regulated by HIV-1 infection and hGRalpha. Mov34 protein from mouse brain interacts with the 3'-noncoding region (3'-NCR) of Japanese encephalitis virus. Therefore, as Mov34 is a hGRalpha-binding partner, the 3'-NCR of flaviviruses is human glucocorticoid receptor-regulated and, therefore, prone to inhibition by glucocorticoid antagonists. Flaviviruses need Mov34 to replicate optimally in human cells. The glucocorticoid antagonist mifepristone (RU38486) was shown to inhibit Mov34 function in the case of HIV-1 infection. PT155 binds as antagonist to human glucocorticoid receptor isoform alpha (hGRalpha) [human glucocorticoid receptor isoform alpha (hGRalpha) is an inactive receptor being ligand-independent]. PT155-liganded hGRalpha, also Hsp90-bound inactive complex, in turn sequesters human Mov34 protein. This leads to a block of Flavivirus replication, since Mov34 is made unavailable for binding to yellow fever and Zika virus 3'-noncoding region (3'-NCR).

hVIP/Mov34 Protein Binds to Highly Secondary-Structured Stem-Loop RNA of Flavivirus 3'-NCR:

hVIP/Mov34 Protein Interacts with the 3'-Noncoding Region (3'-NCR)-Derived Subgenomic Flavivirus RNA (sfRNA) which is Generated by Human Host Cell XRN1 Exoribonuclease (5'→3'-exoRNase)

Summary of the Mechanism-of-Action of PT155 Versus the Flavivirus Congeners Yellow Fever Virus and Zika Virus:

PT155 acts via hVIP/Mov34 protein on Flavivirus 3'-noncoding region, which is also the origin of subgenomic flavivirus RNA (sfRNA) important for pathogenicity and immune evasion hVIP/Mov34 protein is hGR□-regulated, and binds both to hGRalpha and HIV-1 Vpr protein hVIP/Mov34 protein is indispensable for optimal replication and host pathogenicity of flaviviruses, this effect requires binding of hVIP/Mov34 to 3'-NCR and to the 3'-NCR-derived sfRNA hVIP/Mov34 protein binds to Flavivirus 3'-NCR and sfRNA, the exact binding mode and further details are still unknown PT155 is more potent than PT150 regarding inhibition of Flavivirus replication, as is PT155 versus HIV-1 replication Activity of PT150 and PT155 versus Flavivirus replication can only be demonstrated in cells expressing human glucocorticoid receptor-alpha Search for a hVIP/Mov34 cofactor: As HIV-1 Vpr protein acts as a coactivator for hGRalpha and is dependent on hVIP/Mov34 to exert this coactivator function, it is highly probable that hVIP/Mov34 analogously needs a cofactor for binding to Zika virus 3'-NCR in conjunction with hGRalpha. Since it was found that PT compounds, including PT155, are inactive versus dengue virus type 2 strain New Guinea C (NGC) replication in hGRalpha-expressing HuH-7 cells, a Basic Local Alignment Search Tool (BLAST®) BLASTP 2.3.1+ search was conducted for the viral protein product of maximal sequence difference between Zika virus MR766 and dengue virus type 2 NGC. This was anticipated to yield the hVIP/Mov34 cofactor required for hGRalpha recruitment to Zika virus 3'-NCR, since this putative Zika virus cofactor was expected to be dysfunctional in dengue virus type 2. In turn, this would explain the inactivity of PT compounds, including PT155, versus dengue virus type 2.

It was found that the flaviviral non-structural protein 2A (NS2A) exhibited least similarity, or evolutionary conservation, between Zika virus and dengue virus type 2. The absolute amino acid identity was only 29%, whereas overall polyprotein absolute amino acid identity was 56%. This clearly pointed to involvement of Zika virus NS2A protein in antiviral action of PT155. The inactivity of PT compounds versus dengue virus type 2 is caused by missing affinity of PT compounds to the divergent dengue virus type 2 NS2A protein.

This coincidence was proved by a report that found strong physical binding of flaviviral NS2A protein to the corresponding Flavivirus 3'-NCR. In a comprehensive recent tabulation of all viral and host cellular factors known to bind to Flavivirus 3'-NCR, both hVIP/Mov34 and NS2A are indicated as high-affinity ligands for flaviviral 3'-NCR The mechanism-of-action of PT155 and PT156 versus human hepatitis C virus (Flaviviridae, Hepacivirus) HuH-7 clone B (genotype 1a) replicon Results: PT155 and PT156 are active within human hepatitis C virus (HCV) genotype 1a (HCV-1a) HuH-7 cell-derived subgenomic replicon established by C. M Rice & colleagues in 2000. The sequence of this replicon is based on the HCV-1a (isolate H77) genome. PT156 is more active than PT155, and PT150 shows only marginal activity versus HCV-1a (isolate H77) HuH-7 cell-derived subgenomic replicon RNA replication.

Mechanism-of-action: The antihepaciviral action of PT155 and PT156 is mediated by the thiosemicarbazone motif, or the 4-phenylthiosemicarbazone motif, respectively:

Human hepatitis C virus (HCV) NS5B RNA-dependent RNA polymerase (RdRp) protein bears a common thiosemicarbazone-binding motif.

HCV-1a (isolate H77) NS5B fingertip/finger domain RdRp motif I, represents a thiosemicarbazone-binding motif.

5,6-Dimethoxyindan-1-one thiosemicarbazone (DMI-TSC) was reported to inhibit bovine viral diarrhea virus type 1 (BVDV-1 strain NADL, Flaviviridae, Pestivirus) NS5B RdRp.

In a proof-of-concept study structurally diverse thiosemicarbazones were found to be active as inhibitors of HCV genotype 1b (HCV-1b) (isolate Con1) replicon RNA replication.

The antihepaciviral pharmacophore in PT155 and PT156 is the thiosemicarbazone moiety, or the 4-phenylthiosemicarbazone moiety, respectively Regarding the antiviral mechanism-of-action of PT155 and PT156 versus HCV-1a (isolate H77) HuH-7 cell-derived subgenomic replicon RNA replication, it is inherently clear that it cannot being mediated by glucocorticoid receptors, since HCV incorporates no DNA stage in its life cycle. It was recently reported that thiosemicarbazones (DMI-TSC) target bovine viral diarrhea virus type 1 (BVDV-1 strain NADL, Flaviviridae, Pestivirus) NS5B RdRp protein. BVDV-1 is commonly regarded as a suitable surrogate for HCV, because both Flaviviridae polyprotein sequences are closely related (maximal sequence identity 32%) (see Appendix 1). Since the anti-HCV-1a activity of PT155 and PT156 was determined with the HCV-1a (isolate H77) HuH-7 cell-derived subgenomic replicon, which only codes for the non-structural HCV proteins NS3, NS4A, NS4B, NS5A and NS5B, the inhibiting action of PT155 and PT156 must be confined to these five genes and/or gene products (proteins).

Implications for antiviral chemotherapy of hepatitis C infections: HCV is one of the major causative agents for chronic hepatitis, cirrhosis and hepatocellular carcinoma. As reported by the WHO, HCV infects about 2.2% of the world's population, with over a million new cases occurring each year. Furthermore, 27% of these infected individuals eventually progress to liver cirrhosis among whom 25% finally develop hepatocellular carcinomas. HCV is a positive-sense RNA virus that exhibits extensive genetic heterogeneity and a high level of resistance to antiviral drugs in vivo and in vitro. As such, HCV genetic variation poses a huge problem for global public health.

As an essence, PT156 successfully targets human hepatitis C virus RNA-dependent RNA polymerase NS5B protein, a "hard" target involving viral RNA replication ["hard" targets represent indispensable and non-compensable intracellular aspects of the viral life cycle; "soft" targets represent dispensable and compensable extracellular aspects of the viral life cycle, for example attachment/entry/fusion inhibitors (or neuraminidase inhibitors)]. This qualifies PT156 as efficacious antihepaciviral compound worth further investigation.

TABLE 10

RNA viruses inhibited by PT compounds

| Virus | Virus strain | Cell line | Reference drug | PT150 | PT155 | PT156 |
|---|---|---|---|---|---|---|
| Caliciviridae, Norovirus | | | | | | |
| Norwalk virus (replicon) | GT1 | HG23 | 2'-C-methyl-cytidine (RS-446) | | | |
| $EC_{50}$ (μM) | | | 6.9 | 1.1 | 26.0 | >100 |
| $EC_{90}$ (μM) | | | 18.0 | 8.1 | 77.0 | >100 |
| $CC_{50}$ (μM) | | | >300 | 8.7 | 111.0 | >100 |
| $SI_{50}$ ($CC_{50}/EC_{50}$) | | | >43 | 7.9 | 4.3 | — |
| Flaviviridae, Flavivirus | | | | | | |
| Zika virus | MR766 | HuH-7 | 6-azauridine | | | |
| $EC_{50}$ (μM) | | | 13.1 | 7.4 | 0.45 | 6.8 |

TABLE 10-continued

RNA viruses inhibited by PT compounds

| Virus | Virus strain | Cell line | Reference drug | PT150 | PT155 | PT156 |
|---|---|---|---|---|---|---|
| $CC_{50}$ (μM) | | | >408 | 7.4 | 39.7 | 51.9 |
| $SI_{50}$ ($CC_{50}/EC_{50}$) | | | >31 | 1.0 | 88.2 | 7.6 |
| Picornaviridae, Enterovirus, Enterovirus C | | | | | | |
| Poliovirus type 3 | WM-3 | Vero 76 | pirodavir | | | |
| $EC_{50}$ (μM) | | | 0.87 | 5.6 | 0.74 | 51.9 |
| $CC_{50}$ (μM) | | | >27 | 7.4 | 45.4 | 51.9 |
| $SI_{50}$ ($CC_{50}/EC_{50}$) | | | >31 | 1.3 | 61.4 | 1.0 |
| Picornaviridae, Enterovirus, Enterovirus A | | | | | | |
| Enterovirus 71 | Tainan/ 4643/98 | Vero 76 | pirodavir | | | |
| $EC_{50}$ (μM) | | | 0.097 | 7.4 | 0.51 | 51.9 |
| $CC_{50}$ (μM) | | | >27 | 7.4 | 45.4 | 51.9 |
| $SI_{50}$ ($CC_{50}/EC_{50}$) | | | >278 | 1.0 | 89.0 | 1.0 |

TABLE 11

Blood Borne viruses (HIV-1, HCV) inhibited by PT Compounds

| Virus | Virus strain | Cell line | Reference drug | PT150 | PT155 | PT156 |
|---|---|---|---|---|---|---|
| Retroviridae, Lentivirus | | | zidovudine (AZT) | | | |
| HIV-1 | LAI (LAV-1) | PBMC | (RETROVIR ™) [averaged from 20 independent determinations (μM ± s.d.)] | | | |
| $EC_{50}$ (μM) | | | 0.0044 ± 0.0039 (n = 20) | 8.9 | 5.5 | 23.2 |
| $EC_{90}$ (μM) | | | 0.0299 ± 0.0245 (n = 20) | 21.6 | 16.2 | >100 |
| $CC_{50}$ (μM) | | PBMC | >100 | 20.6 | 82.6 | 73.5 |
| $SI_{50}$ ($CC_{50}/EC_{50}$) | | | >22,696 (n = 20) | 2.3 | 15.0 | 3.2 |
| Additional cytotoxicity on malignant cells | | CCRF-CEM | | | | |
| $CC_{50}$ (μM) | | | | 56.1 | 15.4 | 7.1 | 23.8 |
| Additional cytotoxicity on kidney cells | | Vero | | | | |
| $CC_{50}$ (μM) | | | | 39.5 | 44.3 | >100 | 68.6 |
| Additional cytotoxicity on primary cells | | HFF-1 | | | | |
| $CC_{50}$ (μM) | | | — | >150 | >150 | 13.44 |
| Flaviviridae, Hepacivirus | | | | | | |
| Hepatitis C virus (replicon) | clone B (genotype 1a) | HuH-7 | 2'-C-methylcytidine (RS-446) | | | |
| Inhibition of HCV replicon RNA synthesis at the fixed concentration of 10 μM of the test compound (%) | | | 98.08 | 16.71 | 59.03 | 73.91 |
| Inhibition of cellular ribosomal RNA (rRNA) synthesis at the fixed concentration of 10 μM of the test compound (%) | | | 31.09 | −39.51 | −13.71 | 3.88 |
| TaqMan ® RT-qPCR threshold cycle value difference ($\Delta C_T$) of HCV replicon RNA synthesis at the fixed concentration of 10 μM of the test compound | | | 5.72 | 0.26 | 1.29 | 1.94 |
| TaqMan ® RT-qPCR threshold cycle value difference ($\Delta C_T$) of cellular ribosomal RNA (rRNA) synthesis at the fixed concentration of 10 μM of the test compound | | | 0.54 | −0.48 | −0.19 | 0.06 |

TABLE 12

Compilation of in vitro animal screening

| Virus | Strain | Cell Line | Treatment | Assay Type | Conc Unit (+Range) | $EC_{50}$ | $CC_{50}$ | $SI_{50}$ |
|---|---|---|---|---|---|---|---|---|
| Norwalk virus | Norovirus/1968/US | HG23 | RS-446 | Replicon | 3.7-100 µM | 6.9 | >300 | >44 |
| Norwalk virus | Norovirus/1968/US | HG23 | PT150 | Replicon | 0.1-100 µM | 1.1 | 8.7 | 7.9 |
| Norwalk virus | Norovirus/1968/US | HG23 | PT155 | Replicon | 0.1-100 µM | 26 | 111 | 4.3 |
| Norwalk virus | Norovirus/1968/US | HG23 | PT156 | Replicon | 0.1-100 µM | >100 | >100 | 1 |
| Chikungunya virus | S27 (VR-67) | Vero 76 | INFERGEN ™ | Neutral red | 0.00001-0.01 µg/mL | 0.00006 | >0.01 | >167 |
| Chikungunya virus | S27 (VR-67) | Vero 76 | INFERGEN ™ | Visual | 0.00001-0.01 µg/mL | 0.00006 | >0.01 | >167 |
| Chikungunya virus | S27 (VR-67) | Vero 76 | PT150 | Neutral red | 0.1-100 µg/mL | >2.6 | 2.6 | 0 |
| Chikungunya virus | S27 (VR-67) | Vero 76 | PT150 | Visual | 0.1-100 µg/mL | >4.2 | 4.2 | 0 |
| Chikungunya virus | S27 (VR-67) | Vero 76 | PT155 | Neutral red | 0.1-100 µg/mL | >8.4 | 8.4 | 0 |
| Chikungunya virus | S27 (VR-67) | Vero 76 | PT155 | Visual | 0.1-100 µg/mL | 15 | 24 | 1.6 |
| Chikungunya virus | S27 (VR-67) | Vero 76 | PT156 | Neutral red | 0.1-100 µg/mL | >11 | 11 | 0 |
| Chikungunya virus | S27 (VR-67) | Vero 76 | PT156 | Visual | 0.1-100 µg/mL | 32 | 32 | 1 |
| Dengue virus type 2 | New Guinea C | HuH-7 | 6-Azauridine | Neutral red | 0.1-100 µg/mL | 4.6 | 21 | 4.6 |
| Dengue virus type 2 | New Guinea C | HuH-7 | 6-Azauridine | Visual | 0.1-100 µg/mL | 2.8 | >100 | >36 |
| Dengue virus type 2 | New Guinea C | HuH-7 | PT150 | Neutral red | 0.1-100 µg/mL | >2.5 | 2.5 | 0 |
| Dengue virus type 2 | New Guinea C | HuH-7 | PT150 | Visual | 0.1-100 µg/mL | 3.2 | 3.2 | 1 |
| Dengue virus type 2 | New Guinea C | HuH-7 | PT155 | Neutral red | 0.1-100 µg/mL | >3.3 | 3.3 | 0 |
| Dengue virus type 2 | New Guinea C | HuH-7 | PT155 | Visual | 0.1-100 µg/mL | >13 | 13 | 0 |
| Dengue virus type 2 | New Guinea C | HuH-7 | PT156 | Neutral red | 0.1-100 µg/mL | >7.4 | 7.4 | 0 |
| Dengue virus type 2 | New Guinea C | HuH-7 | PT156 | Visual | 0.1-100 µg/mL | 28 | 28 | 0 |
| Enterovirus D68 | US/KY/14-18953 | RD | Enviroxime | Neutral red | 0.1-100 µg/mL | 0.1 | 25 | 250 |
| Enterovirus D68 | US/KY/14-18953 | RD | Enviroxime | Visual | 0.1-100 µg/mL | <0.1 | 32 | >320 |
| Enterovirus D68 | US/KY/14-18953 | RD | PT150 | Neutral red | 0.1-100 µg/mL | >2.6 | 2.6 | 0 |
| Enterovirus D68 | US/KY/14-18953 | RD | PT150 | Visual | 0.1-100 µg/mL | 3.2 | 3.2 | 1 |
| Enterovirus D68 | US/KY/14-18953 | RD | PT155 | Neutral red | 0.1-100 µg/mL | >8.1 | 8.1 | 0 |
| Enterovirus D68 | US/KY/14-18953 | RD | PT155 | Visual | 0.1-100 µg/mL | 3.2 | 3.2 | 1 |
| Enterovirus D68 | US/KY/14-18953 | RD | PT156 | Neutral red | 0.1-100 µg/mL | >18 | 18 | 0 |
| Enterovirus D68 | US/KY/14-18953 | RD | PT156 | Visual | 0.1-100 µg/mL | 32 | 32 | 1 |
| Enterovirus 71 | Tainan/4643/98 | Vero 76 | Pirodavir | Neutral red | 0.1-100 µg/mL | 0.1 | >10 | >100 |
| Enterovirus 71 | Tainan/4643/98 | Vero 76 | Pirodavir | Visual | 0.1-100 µg/mL | 0.036 | >10 | >280 |
| Enterovirus 71 | Tainan/4643/98 | Vero 76 | PT150 | Neutral red | 0.1-100 µg/mL | >2.7 | 2.7 | 0 |
| Enterovirus 71 | Tainan/4643/98 | Vero 76 | PT150 | Visual | 0.1-100 µg/mL | 3.2 | 3.2 | 1 |
| Enterovirus 71 | Tainan/4643/98 | Vero 76 | PT155 | Neutral red | 0.1-100 µg/mL | 0.33 | 92 | 280 |
| Enterovirus 71 | Tainan/4643/98 | Vero 76 | PT155 | Visual | 0.1-100 µg/mL | 0.36 | 32 | 89 |
| Enterovirus 71 | Tainan/4643/98 | Vero 76 | PT156 | Neutral red | 0.1-100 µg/mL | 27 | 32 | 1.2 |
| Enterovirus 71 | Tainan/4643/98 | Vero 76 | PT156 | Visual | 0.1-100 µg/mL | 32 | 32 | 1 |
| Herpes simplex virus type 1 | E-377 | Primary HFF-1 | Aciclovir | CellTiter-Glo | 0.048-150 µM | 3.85 | >150 | >39 |
| Herpes simplex virus type 1 | E-377 | Primary HFF-1 | PT150 | CellTiter-Glo | 0.048-150 µM | >150 | >150 | 1 |
| Herpes simplex virus type 1 | E-377 | Primary HFF-1 | PT155 | CellTiter-Glo | 0.048-150 µM | >30 | 134.15 | <4 |
| Herpes simplex virus type 1 | E-377 | Primary HFF-1 | PT156 | CellTiter-Glo | 0.048-150 µM | >6 | 13.05 | <2 |
| Influenza A virus (H1N1) | California/Jul. 20, 2009 | MDCK | PT150 | Neutral red | 0.1-100 µg/mL | >29 | 29 | 0 |
| Influenza A virus (H1N1) | California/Jul. 20, 2009 | MDCK | PT150 | Visual | 0.1-100 µg/mL | >37 | 37 | 0 |

TABLE 12-continued

Compilation of in vitro animal screening

| Virus | Strain | Cell Line | Treatment | Assay Type | Conc Unit (+Range) | $EC_{50}$ | $CC_{50}$ | $SI_{50}$ |
|---|---|---|---|---|---|---|---|---|
| Influenza A virus (H1N1) | California/ Jul. 20, 2009 | MDCK | PT155 | Neutral red | 0.1-100 µg/mL | 36 | >100 | >2.8 |
| Influenza A virus (H1N1) | California/ Jul. 20, 2009 | MDCK | PT155 | Visual | 0.1-100 µg/mL | 32 | >100 | >3.1 |
| Influenza A virus (H1N1) | California/ Jul. 20, 2009 | MDCK | PT156 | Neutral red | 0.1-100 µg/mL | 34 | 62 | 1.8 |
| Influenza A virus (H1N1) | California/ Jul. 20, 2009 | MDCK | PT156 | Visual | 0.1-100 µg/mL | >42 | 42 | 0 |
| Influenza A virus (H1N1) | California/ Jul. 20, 2009 | MDCK | Ribavirin | Neutral red | 0.32-320 µg/ml | 14 | >320 | >23 |
| Influenza A virus (H1N1) | California/ Jul. 20, 2009 | MDCK | Ribavirin | Visual | 0.32-320 µg/ml | 13 | >320 | >25 |
| MERS coronavirus | HCoV-EMC/2012 | MA-104 | M128533 | Neutral red | 0.1-100 µg/mL | 0.8 | >100 | >125 |
| MERS coronavirus | HCoV-EMC/2012 | MA-104 | M128533 | Visual | 0.1-100 µg/mL | 0.86 | >100 | >116 |
| MERS coronavirus | HCoV-EMC/2012 | MA-104 | PT150 | Neutral red | 0.1-100 µg/mL | 3.1 | 3.9 | 1.3 |
| MERS coronavirus | HCoV-EMC/2012 | MA-104 | PT150 | Visual | 0.1-100 µg/mL | 3.2 | 3.6 | 1.1 |
| MERS coronavirus | HCoV-EMC/2012 | MA-104 | PT155 | Neutral red | 0.1-100 µg/mL | >24 | 24 | 0 |
| MERS coronavirus | HCoV-EMC/2012 | MA-104 | PT155 | Visual | 0.1-100 µg/mL | >18 | 18 | 0 |
| MERS coronavirus | HCoV-EMC/2012 | MA-104 | PT156 | Neutral red | 0.1-100 µg/mL | 3.2 | 9.7 | 3 |
| MERS coronavirus | HCoV-EMC/2012 | MA-104 | PT156 | Visual | 0.1-100 µg/mL | 3.2 | 8.6 | 2.7 |
| Poliovirus type 3 | WM-3 | Vero 76 | Pirodavir | Neutral red | 0.01-10 µg/mL | 0.41 | >10 | >24 |
| Poliovirus type 3 | WM-3 | Vero 76 | Pirodavir | Visual | 0.01-10 µg/mL | 0.32 | >10 | >31 |
| Poliovirus type 3 | WM-3 | Vero 76 | PT150 | Neutral red | 0.1-100 µg/mL | 2.1 | 3.2 | 1.5 |
| Poliovirus type 3 | WM-3 | Vero 76 | PT150 | Visual | 0.1-100 µg/mL | 2.4 | 3.2 | 1.3 |
| Poliovirus type 3 | WM-3 | Vero 76 | PT155 | Neutral red | 0.1-100 µg/mL | 0.56 | 31 | 55 |
| Poliovirus type 3 | WM-3 | Vero 76 | PT155 | Visual | 0.1-100 µg/mL | 0.52 | 32 | 62 |
| Poliovirus type 3 | WM-3 | Vero 76 | PT156 | Neutral red | 0.1-100 µg/mL | 28 | 32 | 1.1 |
| Poliovirus type 3 | WM-3 | Vero 76 | PT156 | Visual | 0.1-100 µg/mL | 32 | 32 | 1 |
| Respiratory syncytial virus | A2 (VR-1540) | MA-104 | PT150 | Neutral red | 0.1-100 µg/mL | 1.9 | 4.3 | 2.3 |
| Respiratory syncytial virus | A2 (VR-1540) | MA-104 | PT150 | Visual | 0.1-100 µg/mL | 2.4 | 4.2 | 1.8 |
| Respiratory syncytial virus | A2 (VR-1540) | MA-104 | PT155 | Neutral red | 0.1-100 µg/mL | 2.8 | 3.5 | 1.3 |
| Respiratory syncytial virus | A2 (VR-1540) | MA-104 | PT155 | Visual | 0.1-100 µg/mL | 3.2 | 3.7 | 1.2 |
| Respiratory syncytial virus | A2 (VR-1540) | MA-104 | PT156 | Neutral red | 0.1-100 µg/mL | >29 | 29 | 0 |
| Respiratory syncytial virus | A2 (VR-1540) | MA-104 | PT156 | Visual | 0.1-100 µg/mL | 32 | 32 | 1 |
| Respiratory syncytial virus | A2 (VR-1540) | MA-104 | Ribavirin | Neutral red | 0.32-320 µg/mL | 6.8 | >320 | >47 |
| Respiratory syncytial virus | A2 (VR-1540) | MA-104 | Ribavirin | Visual | 0.32-320 µg/mL | 6.7 | >320 | >48 |
| Rift Valley fever virus | MP-12 | Vero 76 | PT150 | Neutral red | 0.1-100 µg/mL | >4.1 | 4.1 | 0 |
| Rift Valley fever virus | MP-12 | Vero 76 | PT150 | Visual | 0.1-100 µg/mL | 3.2 | 4.2 | 1.3 |
| Rift Valley fever virus | MP-12 | Vero 76 | PT155 | Neutral red | 0.1-100 µg/mL | 6.4 | 15 | 2.3 |
| Rift Valley fever virus | MP-12 | Vero 76 | PT155 | Visual | 0.1-100 µg/mL | 2.2 | 8.6 | 3.9 |
| Rift Valley fever virus | MP-12 | Vero 76 | PT156 | Neutral red | 0.1-100 µg/mL | >27 | 27 | 0 |
| Rift Valley fever virus | MP-12 | Vero 76 | PT156 | Visual | 0.1-100 µg/mL | 10 | 10 | 1 |
| Rift Valley fever virus | MP-12 | Vero 76 | Ribavirin | Neutral red | 1-1000 µg/mL | 9.7 | >1000 | >100 |
| Rift Valley fever virus | MP-12 | Vero 76 | Ribavirin | Visual | 1-1000 µg/mL | 8.3 | >1000 | >120 |
| Tacaribe virus | TRVL 11573 | Vero | PT150 | Neutral red | 0.1-100 µg/mL | 3.1 | 3.5 | 1.1 |
| Tacaribe virus | TRVL 11573 | Vero | PT150 | Visual | 0.1-100 µg/mL | 3.2 | 4.2 | 1.3 |

TABLE 12-continued

Compilation of in vitro animal screening

| Virus | Strain | Cell Line | Treatment | Assay Type | Conc Unit (+Range) | $EC_{50}$ | $CC_{50}$ | $SI_{50}$ |
|---|---|---|---|---|---|---|---|---|
| Tacaribe virus | TRVL 11573 | Vero | PT155 | Neutral red | 0.1-100 µg/mL | >3.8 | 3.8 | 0 |
| Tacaribe virus | TRVL 11573 | Vero | PT155 | Visual | 0.1-100 µg/mL | >5.9 | 5.9 | 0 |
| Tacaribe virus | TRVL 11573 | Vero | PT156 | Neutral red | 0.1-100 µg/mL | >12 | 12 | 0 |
| Tacaribe virus | TRVL 11573 | Vero | PT156 | Visual | 0.1-100 µg/mL | >12 | 12 | 0 |
| Tacaribe virus | TRVL 11573 | Vero | Ribavirin | Neutral red | 1-1000 µg/mL | 7.9 | >1000 | >130 |
| Tacaribe virus | TRVL 11573 | Vero | Ribavirin | Visual | 1-1000 µg/mL | 7 | >1000 | >140 |
| Vaccinia virus | Copenhagen | Primary HFF-1 | Cidofovir | CellTiter-Glo | 0.048-150 µM | 7.34 | >150 | >20 |
| Vaccinia virus | Copenhagen | Primary HFF-1 | PT150 | CellTiter-Glo | 0.048-150 µM | >150 | >150 | 1 |
| Vaccinia virus | Copenhagen | Primary HFF-1 | PT155 | CellTiter-Glo | 0.048-150 µM | >150 | >150 | 1 |
| Vaccinia virus | Copenhagen | Primary HFF-1 | PT156 | CellTiter-Glo | 0.048-150 µM | >6 | 13.44 | <2 |
| Venez equine enceph virus | TC-83 | Vero 76 | INFERGEN™ | Neutral red | 0.00001-0.01 µg/mL | <0.00001 | >0.01 | >1000 |
| Venez equine enceph virus | TC-83 | Vero 76 | INFERGEN™ | Visual | 0.00001-0.01 µg/mL | 0.000012 | >0.01 | >833 |
| Venez equine enceph virus | TC-83 | Vero 76 | PT150 | Neutral red | 0.1-100 µg/mL | 3.1 | 3.5 | 1.1 |
| Venez equine enceph virus | TC-83 | Vero 76 | PT150 | Visual | 0.1-100 µg/mL | 3.2 | 3.2 | 1 |
| Venez equine enceph virus | TC-83 | Vero 76 | PT155 | Neutral red | 0.1-100 µg/mL | >20 | 20 | 0 |
| Venez equine enceph virus | TC-83 | Vero 76 | PT155 | Visual | 0.1-100 µg/mL | >28 | 28 | 0 |
| Venez equine enceph virus | TC-83 | Vero 76 | PT156 | Neutral red | 0.1-100 µg/mL | >16 | 16 | 0 |
| Venez equine enceph virus | TC-83 | Vero 76 | PT156 | Visual | 0.1-100 µg/mL | 32 | 32 | 1 |
| Zika virus | MR766 | HuH-7 | 6-Azauridine | Neutral red | 0.1-100 µg/mL | 11 | >100 | >9.1 |
| Zika virus | MR766 | HuH-7 | 6-Azauridine | Visual | 0.1-100 µg/mL | 3.2 | >100 | >31 |
| Zika virus | MR766 | HuH-7 | PT150 | Neutral red | 0.1-100 µg/mL | 3 | 3.3 | 1.1 |
| Zika virus | MR766 | HuH-7 | PT150 | Visual | 0.1-100 µg/mL | 3.2 | 3.2 | 1 |
| Zika virus | MR766 | HuH-7 | PT155 | Neutral red | 0.1-100 µg/mL | 0.81 | 7 | 8.6 |
| Zika virus | MR766 | HuH-7 | PT155 | Visual | 0.1-100 µg/mL | 0.32 | 28 | 88 |
| Zika virus | MR766 | HuH-7 | PT156 | Neutral red | 0.1-100 µg/mL | 21 | 31 | 1.5 |
| Zika virus | MR766 | HuH-7 | PT156 | Visual | 0.1-100 µg/mL | 4.2 | 32 | 7.6 |
| HIV-1 | LAI | PBMC | Zidovudine | RT $^3$H-dTTP | 0.00001-100 µM | 0.00079 | >100 | >126582 |
| HIV-1 | LAI | PBMC | PT150 | RT $^3$H-dTTP | 0.1-100 µM | 8.9 | 20.6 | 2.3 |
| HIV-1 | LAI | PBMC | PT155 | RT $^3$H-dTTP | 0.1-100 µM | 5.5 | 82.6 | 15 |
| HIV-1 | LAI | PBMC | PT156 | RT $^3$H-dTTP | 0.1-100 µM | 23.2 | 73.5 | 3.2 |
| Hepatitis B virus (HBV) | ayw | HepAD38 | Lamivudine | $^{32}$P dot blot | µM | 0.03 | — | — |
| Hepatitis B virus (HBV) | ayw | HepAD38 | PT150 | $^{32}$P dot blot | Fixed: 10 µM | >10 | HBV replication +188.4% | |
| Hepatitis B virus (HBV) | ayw | HepAD38 | PT155 | $^{32}$P dot blot | Fixed: 10 µM | >10 | HBV replication +147.4% | |

| Virus | Strain | Cell Line | Treatment | Assay Type | Conc Unit (+Range) | % Inhib replication | % Inhib rRNA (tox) |
|---|---|---|---|---|---|---|---|
| Hepatitis C virus (HCV) | Clone B genotype 1a | HuH-7 | RS-446 | Replicon | Fixed: 10 µM | 98.08 | 31.09 |
| Hepatitis C virus (HCV) | Clone B genotype 1a | HuH-7 | PT150 | Replicon | Fixed: 10 µM | 16.71 | −39.59 |
| Hepatitis C virus (HCV) | Clone B genotype 1a | HuH-7 | PT155 | Replicon | Fixed: 10 µM | 59.03 | −13.71 |
| Hepatitis C virus (HCV) | Clone B genotype 1a | HuH-7 | PT156 | Replicon | Fixed: 10 µM | 73.91 | 3.88 |

TABLE 12-continued

Compilation of in vitro animal screening

| Virus | Strain | Cell Line | Treatment | Assay Type | Conc Unit (+Range) | $EC_{50}$ | $CC_{50}$ | $SI_{50}$ |
|---|---|---|---|---|---|---|---|---|
| — | Cytotoxicity control | PBMC | Cycloheximide | CellTiter MTS | µM | — | 0.5 | |
| — | Cytotoxicity control | PBMC | PT150 | CellTiter MTS | µM | — | 20.6 | |
| — | Cytotoxicity control | PBMC | PT155 | CellTiter MTS | µM | — | 82.6 | |
| — | Cytotoxicity control | PBMC | PT156 | CellTiter MTS | µM | — | 73.5 | |
| — | Cytotoxicity control | CCRF-CEM | Cycloheximide | CellTiter MTS | µM | — | 0.1 | |
| — | Cytotoxicity control | CCRF-CEM | PT150 | CellTiter MTS | µM | — | 15.4 | |
| — | Cytotoxicity control | CCRF-CEM | PT155 | CellTiter MTS | µM | — | 7.1 | |
| — | Cytotoxicity control | CCRF-CEM | PT156 | CellTiter MTS | µM | — | 23.8 | |
| — | Cytotoxicity control | Vero | Cycloheximide | CellTiter MTS | µM | — | 0.2 | |
| — | Cytotoxicity control | Vero | PT150 | CellTiter MTS | µM | — | 44.3 | |
| — | Cytotoxicity control | Vero | PT155 | CellTiter MTS | µM | — | >100 | |
| — | Cytotoxicity control | Vero | PT156 | CellTiter MTS | µM | — | 68.6 | |
| — | Cytotoxicity control | HepG2 | Cycloheximide | CellTiter MTS | µM | — | 0.6 | |
| Cycloheximide = cellular toxin control | | | | | | | | |
| — | Cytotoxicity control | Primary HFF-1 | PT150 | CellTiter-Glo | µM | — | >150 | |
| — | Cytotoxicity control | Primary HFF-1 | PT155 | CellTiter-Glo | µM | — | >150 | |
| — | Cytotoxicity control | Primary HFF-1 | PT156 | CellTiter-Glo | µM | — | 13.4 | |

Legend:
Conc Unit (+Range), concentration unit (µM or µg/mL) and concentration range tested;
$EC_{50}$, effective antiviral concentration 50%;
$CC_{50}$, cytotoxic concentration 50%;
$SI_{50}$, selectivity index 50% ($CC_{50}/EC_{50}$);
RS-446, 2'-C-methylcytidine;
INFERGEN ™, interferon alfacon-1 = consensus interferon-α;
CellTiter-Glo, CellTiter-Glo ® Luminescent Cell Viability Assay (Promega) quantifying ATP with ATP-dependent Ultra-Glo ™ Recombinant Luciferase;
RT $^3$H-dTTP, measurement of [5α-$^3$H]dTTP incorporation into poly(rA) • poly(dT) directed by the primed RNA template poly(rA) • oligo(dT) by reverse transcriptase (RT);
$^{32}$P dot blot, hybridization assay with EcoRI-digested HBV ayw DNA 3.2 kb fragment, phosphorus-32 ($^{32}$P)-labeled by DNA polymerase I-mediated nick translation with [α-$^{32}$P]dCTP;
cycloheximide, eukaryotic protein synthesis inhibitor; CellTiter MTS, CellTiter 96 ® AQ$_{ueous}$ One Solution Cell Proliferation Assay (Promega) with tetrazolium salt MTS.

Phosphatidylserine Binding

PS (serine-cephalin) represents an important inner membrane lipid in all human cells. PS represents a phospholipid, together with phosphatidylcholine (lecithin) and phosphatidylethanolamine (colamine-cephalin). PS is constructed of 1,2-diacylglycerol phospho-L-serine. The 1,2-diacylglycerol-3-phosphate is also called phosphatidic acid, therefore the term "phosphatidyl". PS is normally exposed on human cells only in the case of apoptosis (programmed cell death, "voluntary cell suicide"). Enveloped viruses expose PS on their host-captured lipid bilayer membranes constantly. Enveloped viruses utilize this PS-exposure to evade attacks by the human immune system and to enter phagocytic cells like monocytes/macrophages.

3-O-sn-phosphatidyl-L-serine (PS)

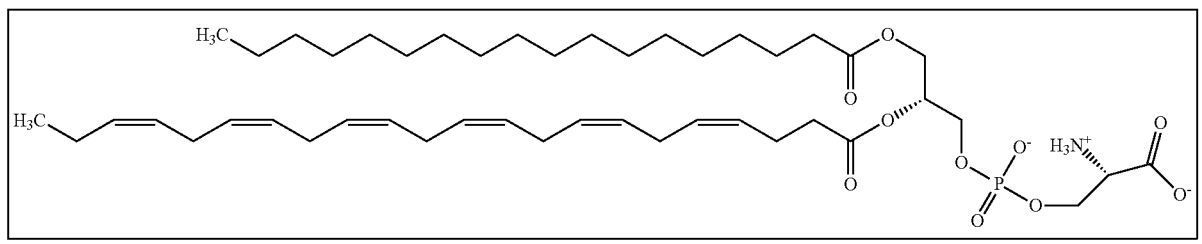 [SMILES: CC/C=C\C/C=C\C/C=C\C/C=C\C/C=C\C/C=C\CCC(=O)O[C@H](COC(=O)CCCCCCCCCCCCCCCCC)COP(=O)([O-])OC[C@H]([NH3+])C(=O)[O-]]

The structure of a typical PS, as shown with stearic acid at position 1-O, and docosa-4,7,10,13,16,19-hexaenoic acid at position 2-O. This represents a major serine-cephalin from bovine brain. Fatty acid composition at position 1-O and 2-O is subject of variation, depending e.g. on cell type. The polar head group (phosphoserine) is negatively charged. The phosphate anion charge and the cation charge of the ammonium group neutralize each other. Therefore, PS is net-negatively charged at physiological pH 7.4.

Sn-Phosphatidylcholine (PC)

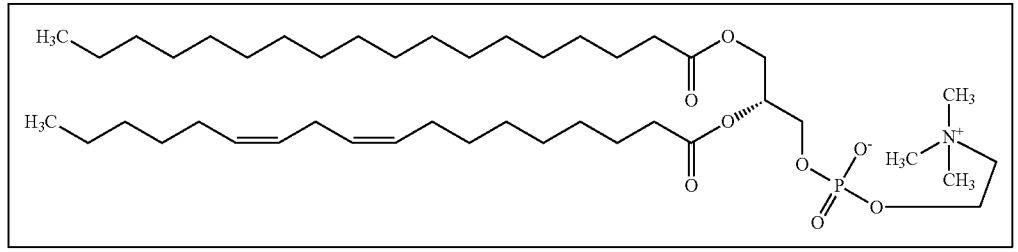 [SMILES: CCCCC/C=C\C/C=C\CCCCCCCC(=O)O[C@H](COC(=O)CCCCCCCCCCCCCCCCC)COP(=O)([O-])OCC[N+](C)(C)C]

The structure of a typical PC, as shown with stearic acid at position 1-O, and linoleic acid at position 2-O. This represents a major lecithin from egg yolk and human cell membranes. Fatty acid composition at position 1-O and 2-O is subject of variation, depending e.g. on cell type. The polar head group (phosphocholine) is zwitterionic. The phosphate anion charge and the cation charge of the ammonium group neutralize each other. Therefore, PC is net-neutral at physiological pH 7.4. Both ORG34517 and PT155 bind to PS, but not to PC. Weak (stereospecific!) binding to PC is only observed for the PT155-component (E)-ORG34517 thiosemicarbazone, which is contained in the three component mixture PT155. Therefore, the PS-binding of ORG34517 and PT155 is selective. ORG34517- and PT155-binding to PS is observed both in PS-micelles and non-micellar PS. The three components of PT155 [the two (E/Z)-ORG34517 thiosemicarbazones, and the residual (original) ORG34517] are readily resolved in the thin-layer chromatographic run.

Most Confirmed PS-Interception-Susceptible Enveloped Viruses are RNA Viruses:

Ebola and Marburg virus (Filoviridae)|Ross River virus, chikungunya virus, Sindbis virus, eastern equine encephalitis virus (Togaviridae, Alphavirus)|vesicular stomatitis virus (Rhabdoviridae, Vesiculovirus)|Amaparí virus, Pichindé virus, Tacaribe virus, Junín virus, Machupo virus (Arenaviridae, Mammarenavirus)|West Nile virus, dengue virus, yellow fever virus (Flaviviridae, Flavivirus)|human immunodeficiency virus type 1 (Retroviridae, Lentivirus) Moloney murine leukemia virus (Retroviridae, Gammaretrovirus)|influenza A virus (Orthomyxoviridae)|respiratory syncytial virus (Paramyxoviridae, Pneumovirinae, Pneumovirus)

Confirmed PS-Interception-Susceptible Enveloped DNA Viruses are:

vaccinia virus (Poxviridae, Chordopoxvirinae, Orthopoxvirus)|herpes simplex virus type 1, herpes simplex virus type 2 (Herpesviridae, Alphaherpesvirinae, Simplexvirus)|human cytomegalovirus (Herpesviridae, Betaherpesvirinae, Cytomegalovirus)|*Autographa californica* nucleopolyhedrovirus (Baculoviridae, Alphabaculoviridae) (an insect virus)

Prospected PS-interception-susceptible important enveloped RNA viruses are (important human viruses are highlighted in red):

Ebola and Marburg virus (Filoviridae)|Semliki Forest virus, Ross River virus, chikungunya virus, O'nyong-nyong virus, Sindbis virus, eastern/western/Venezuelan equine encephalitis virus (Togaviridae, Alphavirus)|rubella (German measles) virus (Togaviridae, Rubivirus)|rabies virus, Lagos bat virus, Mokola virus (Rhabdoviridae, Lyssavirus) |Amaparí virus, Pichindé virus, Tacaribe virus, Junín virus, Machupo virus, Guanarito virus, Sabia virus, Lassa virus (Arenaviridae, Mammarenavirus)|West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus)|human hepatitis C virus (Flaviviridae, Hepacivirus)|human immunodeficiency virus type 1 (Retroviridae, Lentivirus)|influenza A/B virus (Orthomyxoviridae, the common 'flu' virus)|respiratory syncytial virus (Paramyxoviridae, Pneumovirinae, Pneumovirus)|Hendra virus, Nipah virus (Paramyxoviridae, Paramyxovirinae, Henipavirus)|measles virus (Paramyxoviridae, Paramyxovirinae, Morbillivirus)

Prospected PS-interception-susceptible enveloped DNA viruses are:

variola major (smallpox) virus (Poxviridae, Chordopoxvirinae, Orthopoxvirus)|human hepatitis B virus (Hepadnaviridae, Orthohepadnavirus)|hepatitis delta virus (hepatitis D virus) (unassigned Family, Deltavirus)|herpes simplex virus type 1, herpes simplex virus type 2 (Herpesviridae, Alphaherpesvirinae, Simplexvirus)|human cytomegalovirus (Herpesviridae, Betaherpesvirinae, Cytomegalovirus)

*Norovirus*

*Norovirus* infect humans and many other mammals causing severe gastroenteritis. *Norovirus* causes approximately 90% of epidemic nonbacterial outbreaks of gastroenteritis around the world (Lindesmith et al., 2003). *Norovirus* have also been isolated from numerous other species including pigs, cattle, sheep, and mice. The zoonotic potential of *norovirus* is largely unstudied and may represent a reservoir from which new strains may emerge (Thorne & Goodfellow, 2014). Vaccines are not currently available and treatments which lessen the length of illness, severity of symptoms, period of infectiousness and loss of productivity and life are highly desirable.

The *norovirus* protein VP1 is unstable during capsid assembly and requires the host protein Hsp90 to assemble mature viral particles. Vaschist et al. (2012) have demonstrated that geldanamycin binds to Hsp90 and inhibits *norovirus* assembly and budding. Hsp90 complexes with GRα in the host cytosol and is, therefore, susceptible to the action of hGRα antagonists, such as PT15x compounds according to the predicted stoichiometry:

$$[hGR\alpha\text{-PT150-(Hsp90)}n]m(n=1,2,\ldots;m=2)$$

The compounds of the invention have demonstrated activity against both human and murine *norovirus*, suggesting broader applications among other *norovirus* in veterinary medicine, research applications involving mice and human medical applications.

Results: PT150 is highly active versus human Norwalk virus HuH-7-derived HG23 cell self-replicating RNA replicon replication [Norwalk virus (human *norovirus*) genotype 1 (GT1), 1968 original isolate, Hu/NV/Norwalk virus/1968/US (GenBank: M87661.2)].

Mechanism-of-action: Heat-shock protein 90 (Hsp90) was suggested as therapeutic target for noroviruses in 2015 by Vashist et al. The mechanism is clearly glucocorticoid receptor-dependent, since PT150, as high-affinity human glucocorticoid receptor-alpha (hGRalpha) ligand, is highly active against *norovirus* replicon RNA replication, whereas PT155 is marginally active and PT156 is inactive. PT150 can reduce availability of Hsp90 by trapping it in an transcriptionally inactive, dimeric complex:

$$[\text{hGRalpha-PT150-(Hsp90)}n]m(n=1,2,\ldots;m=2)$$

The *norovirus* capsid protein VP1 is a very unstable protein, and must be protected by the molecular chaperone Hsp90 to survive in the host cell cytosol. If Hsp90 is captured by PT150 in an inactive complex with hGRalpha, then *norovirus* VP1 is degraded quickly by unknown mechanisms. Vashist et al. used geldanamycin derivatives to prove this. Geldanamycin binds to Hsp90, also 17-allylamino-17-demethoxygeldanamycin [and water-soluble derivatives of geldanamycin used in this study like: 17-{N-[2-(dimethylamino)ethyl]amino}-17-demethoxygeldanamycin] which inhibited *norovirus* assembly and budding.

Taken together, PT150 reduces availabilty of Hsp90 for noroviruses by trapping Hsp90 into an inactive complex [hGRalpha-PT150-(Hsp90)n]m (n=1, 2, . . . ; m=2). This prevents stabilization of the sensitive viral capsid protein VP1, and leads to degradation of this viral capsid component by yet unknown mechanisms. In consequence, *norovirus* assembly and budding are abrogated by the hGRalpha high-affinity ligand PT150.

Implications for antiviral chemotherapy of *Norovirus* infections: The prototype *norovirus*, Norwalk virus, was first described in 1972 as the etiological agent responsible for an outbreak of acute gastroenteritis in an elementary school in Norwalk, OH, USA. Noroviruses are now accepted as a leading cause of gastroenteritis in developed and developing countries. Spread primarily via the faecal-oral route, *norovirus* infections are typically an acute self-limiting gastrointestinal infection. *Norovirus* gastroenteritis has recently been identified as a significant cause of morbidity and mortality in the immunocompromised, and can result in long-term persistent disease. *Norovirus* infection has also been associated with a number of more significant clinical outcomes: necrotizing enterocolitis, seizures in infants, encephalopathy, pneumatosis intestinalis and disseminated intravascular coagulation, to name but a few. In developing countries, an estimated 200,000 deaths in children $<5$ years of age are thought to be due to *norovirus* infections and they have recently been reported as the second leading cause of gastroenteritis-related deaths in the USA, typically resulting in 797 deaths per annum. Despite their significant impact, noroviruses remain one of the most poorly characterized groups of RNA viruses, due largely to the fact that, despite numerous attempts, human noroviruses have yet to be cultured efficiently in cell culture.

Noroviruses are members of the family Caliciviridae of small, positive-sense RNA viruses, which is divided currently into five genera: *Vesivirus, Lagovirus, Nebovirus, Sapovirus* and *Norovirus*. Members of the genera *Norovirus* and *Sapovirus* are able to infect humans and cause gastroenteritis. The genus *Norovirus* is subdivided into at least five genotypes (GT1-5). Genotypes GT1, GT2 and GT4 infect humans and cause acute gastroenteritis, but noroviruses have also been isolated from numerous other species including pigs (GT2), cattle and sheep (GT3), and mice (GT5). More recently, a novel *norovirus* identified in domestic dogs with diarrhoea has been proposed to represent a new genotype, GT6. To date, zoonotic *norovirus* infections have not been reported, but there is clear evidence of the potential for transmission. For example, human noroviruses can infect gnotobiotic piglets and there is serological evidence of human noroviruses in pigs. Whilst antibodies to GT6 noroviruses have been identified in veterinarians, it has yet to be determined whether infection results in clinical disease. Additional studies are required to further elucidate the zoonotic potential of noroviruses and whether animals represent a reservoir from which new strains may emerge.

Addiction

The invention provides Therapeutic Compositions and Methods to Mitigate Addiction. The present invention enables PT150 (formerly ORG34517), or its derivatives (e.g. PT-155, PT-156, PT-157) a highly potent and selective corticosteroid antagonist, to prevent the signs and symptoms of physical withdrawal when administered to someone with physical addiction at or near the time of withdrawal of the addictive compound. The mechanism underlying this effect is that the central nervous system (CNS) pathways governing physical withdrawal are dependent on cortisol or other glucocorticoid binding. When blockade is established by administration of PT150 or its derivatives (e.g. PT155, PT156, PT157, PT158, TCY1, combinations therof, and pharmaceutically acceptable salts thereof), the pathways fail to function and physical withdrawal symptoms are not produced. The broad field of addiction research has established that corticosteroids appear to play important roles in other aspects of addiction behaviors and mechanisms. They have a key role in promoting a shift from recreational (or medicinal in the case of opiates) to compulsive use, meaning use that is driven by physical addiction. The terminology of this shift is tricky, but simply put, goal-tracking in animal models indicates that animals pay more attentional and display behavior directly linked to obtaining a rewarding substance. For example, in a rat that is pressing a bar to receive food pellets with opiates in them, the rat initially will focus on the food delivery door and scratch the door, etc. However, when physical addiction occurs with repeated exposure to the opiates, animals shift their focus and behavior to the stimuli that predict drug delivery, namely the bar pressing. This is called "sign-tracking".

An analogous human condition would be an alcohol-dependent individual, for example, that initially experiences thoughts and subjective feelings of reward when drinking alcohol. With continued use of high doses of alcohol, physical addiction develops. At that point, alcohol cues (which may include, for example, drinking buddies, bar signs, emotional stress or tension, the time of day or day of the week when drinking usually takes place) provide "reward" to the addict, in a manner similar to the actual drug of abuse. This is a key signal that physical addiction has occurred. Abundant animal work and other studies exploring the translation of these findings to human subjects, suggest that increases in circulating corticosteroids, at the least, are highly correlated with sign-tracking.

Dementia

According to the Alzheimer's Association, Dementia is not a specific disease. It's an overall term that describes a wide range of symptoms associated with a decline in memory or other thinking skills severe enough to reduce a person's ability to perform everyday activities. Alzheimer's disease accounts for 60 to 80 percent of cases. Vascular dementia, which occurs after a stroke, is the second most common dementia type.

Glucocorticoid receptor activity, stimulated by administration of the steroid hormone corticosterone, perturbs neuronal function in the rodent hippocampus, a brain region which is critical to learning and the formation of memories in all mammals and which is known to be atrophied in those with Alzheimer's Disease or Major Depressive Disorder. Work conducted has demonstrated that such effects are dependent on over activation of glucocorticoid receptors (GRs; result of hypercortisolemia) and subsequent enhancement of glutamate receptor activity via effects at the level of transcription and/or trafficking of receptor subunits. Indeed, one medication federally approved for the treatment of Alzheimer's Disease, Namenda® (memantine), is a short-acting glutamate receptor inhibitor (reviewed in Zhou et al. 2016), supporting evidence of a role for these receptors in the initiation of brain atrophy.

The evidence discussed above also suggests that modulation of GRs may represent a therapeutic target in the treatment of dementing illnesses, as hypothesized by Dhikav and Anand (2007), though clinical research has not yet confirmed this possibility and this has not been tested with use of a selective GR antagonist or active agent, such as ORG34517, PT150, PT155, PT156, PT157, PT158, TCY1, combinations thereof, and pharmaceutically acceptable salts thereof. In a mouse model of Alzheimer's Disease, sub-chronic treatment with the non-selective GR/progesterone receptor antagonist mifepristone prevented losses in episodic memory. However, the lack pharmacological specificity observed with mifepristone use does not allow for a clear examination of GR signaling in this context.

Studies examined effects of selective and competitive inhibition of GRs, with use of PT150 or PT155, on corticosteroid-induced hippocampal neuronal loss using a validated organotypic slice culture model. Slice cultures of rat hippocampus are surgically harvested and maintained in vitro for 5 days prior to experimentation. After 5 days, slice cultures are transferred to treatment wells containing corticosterone (0.1-1 µM) or corticosterone vehicle (peanut oil), for a 5 day continuous treatment. Portions of these cultures, both corticosterone-exposed and -naïve cultures, are also co-exposed to PT150 or PT155 (1-100 nM), in cell culture medium for the duration of the 5 days. After 5 days, cultures were either harvested to measure cytotoxicity (propidium iodide uptake and immunoreactivity of neuron-specific nuclear protein) and glutamate receptor density or exposed to the glutamate receptor agonist NMDA for a period of 24-hr. In the latter cultures, measures of cytotoxicity and receptor density was assessed after NMDA exposure. It is revealed that 5 day corticosterone exposure, at concentrations greater than 1 nM, induced cytoxicity in the cornu ammonis 1 pyramidal cell layer and the co-exposure to PT150 and PT155 attenuate this cytotoxicity. This cell layer is a region that is critical for the formation of memory in mammals and is known to degenerate in dementias. It is determined that PT150 and PT155 produce effects of cellular integrity in corticosterone-naïve cultures. Additionally, corticosterone exposure upregulates NR2B subunits of ionotropic glutamate receptors and markedly enhance the neurotoxicity of NMDA itself, demonstrating a steroid hormone receptor-mediated elevation of glutamate signaling in a brain region that is critical to memory formation.

The present Invention provides for method of use claims and composition of matter formulation claims. In particular embodiments, the invention provides a composition of therapeutically effective amount of a GR antagonist (PT150 or PT155) and at least one additional therapeutic agent selected from the group consisting of at least one of cholinesterase inhibitors (Aricept, Exelon, Razadyne) and memantine (Namenda).

Amyloid beta (Aβ or Abeta) denotes peptides of 36-43 amino acids that are crucially involved in Alzheimer's disease as the main component of the amyloid plaques found in the brains of Alzheimer patients. The peptides result from the amyloid precursor protein (APP), which is cleaved by β and γ secretase to yield Aβ. Aβ is formed after sequential cleavage of the amyloid precursor protein (APP), a trans-membrane glycoprotein of undetermined function. APP can be cleaved by the proteolytic enzymes α-, β- and γ-secretase; Aβ protein is generated by successive action of the β and γ secretases. Aβ molecules can aggregate to form flexible soluble oligomers which may exist in several forms. Certain misfolded oligomers (known as "seeds") can induce other Aβ molecules to also take the misfolded oligomeric form, leading to a chain reaction akin to a prion infection. The seeds or the resulting amyloid plaques are toxic to nerve cells. The other protein implicated in Alzheimer's disease, tau protein, also forms such prion-like misfolded oligomers, and there is some evidence that misfolded Aβ can induce tau to misfold.

The triboelectric PT155 could form nanomagnets in the brain of Morbus Alzheimer patients, leading to disruption of Aβ amyloid fibrillar aggregates, restoring brain functions to more or lesser extent. Since Alzheimer fibrils are itself highly structured aggregates with polarized order inducing an electromagnetic field in the brain. By inserting a nano-magnetic material into the Aβ supramolecular ordered β-sheets could disrupt the polarized order (orientation polarization of permanent dipoles) of Alzheimer Aβ fibrils making them subject to degradation in the proteasome.

A nanomagnet is a submicrometric system that presents spontaneous magnetic order (magnetization) at zero applied magnetic field (remanence). The small size of nanomagnets prevents the formation of magnetic domains. The magnetization dynamics of sufficiently small nanomagnets at low temperatures, typically single-molecule magnets, presents quantum phenomena, such as macroscopic spin tunnelling. At larger temperatures, the magnetization undergoes random thermal fluctuations (superparamagnetism) which present a limit for the use of nanomagnets for permanent information storage.

Autism

Autism is a neurodevelopmental disorder characterized by impaired social interaction, verbal and non-verbal communication, and restricted and repetitive behavior. Parents usually notice signs in the first two years of their child's life. These signs often develop gradually, though some children with autism reach their developmental milestones at a normal pace and then regress. The diagnostic criteria require that symptoms become apparent in early childhood, typically before age three. While autism is highly heritable, researchers suspect both environmental and genetic factors as causes. In rare cases, autism is strongly associated with agents that cause birth defects. Controversies surround other proposed environmental causes. Autism affects information processing in the brain by altering how nerve cells and their synapses connect and organize; how this occurs is not well understood. In the DSM V it is one of three recognized disorders in the autism spectrum disorders (ASDs), the other two being Asperger syndrome, which lacks delays in cognitive development and language, and pervasive developmental disorder, not otherwise specified (commonly abbreviated as PDD-NOS), which is diagnosed when the full set of criteria for autism or Asperger syndrome are not met.

The triboelectric PT155 can form nanomagnets in the brain of autism patients, leading to unknown effects of nerve cells (neurons). It is believed that in autism spectrum disorders cortisol levels are elevated Therapeutic Compositions and Methods for Treating and Preventing Tuberculosis Tuberculosis (TB) is on the top of global infectious disease list, linked to 1.5 million deaths in 2014 and 9.6 million infected. TB is responsible for 1 in 3 deaths for HIV positive patients, and an estimated 480,000 cases of multi-drug resistant TB exist globally (WHO, 2016). There are no effective vaccines for TB. Existing chemotherapeutics have extensive side effects, and require prolonged treatment for success, discounting the possibilities of drug resistance (Gillespie & Murphy, 2011; Korb et al., 2016).

The causative agent, *Mycobacterium tuberculosis*, utilizes multiple strategies to manipulate the host immune response to entrench itself and avoid clearance. Following engulfment by macrophage, *M. tuberculosis* evades destruction by blocking full activation of the phagosome as well as altering the behaviors of signaling molecules that modulate inflammation and adaptive immunity (Russell, 2007; Sasindran & Torrelles, 2011; Korb et al., 2016). The Toll-like Receptor (TLR) family is partially responsible for modulating these responses (Hermoso et al., 2004; Coutinho & Chapman, 2011) through cascade-altering reactions using a counterbalance between the inflammatory effects of tumor necrosis factor alpha (TNF-α) and the immunosuppressive effects of glucocorticoids (GC).

Antagonism of the GC pathways offers a potential way to shift the cellular behaviors of infected cells to encourage a prolonged immune response and clearing of TB (Brown et al., 1993; Bottasso, 2007).

Combination Therapy

Compositions and methods for treating GC-responsive conditions, including for example, the prevention or addiction induced anxiety and withdrawal side effects as a therapeutic, for wound healing and transplants, for the prevention or treatment of stress induced osteoporosis and for the rapid healing of bone related injuries, and regenerative therapy, in a subject are provided by the present invention.

Methods of treating a GC-responsive condition in a subject are provided according to embodiments of the present invention which includes administering, in combination, a GR antagonist and at least one additional therapeutic agent selected from the group consisting of at least one anti-anxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof, in therapeutically effective amounts. In certain embodiments the agents are administered in the same dosage form. In certain embodiments the therapeutic agents are administered separately.

In particular embodiments, the invention provides a composition a therapeutically effective amount of a GR antagonist and at least one additional therapeutic agent selected from the group consisting of at least one antianxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof.

In certain embodiments the agents are in the same dosage form. In certain embodiments the therapeutic agents are in separate dosage forms.

The phrase "administering in combination" as used herein refers to any form of administration of one or more GR antagonists and at least one additional therapeutic agent selected from the group consisting of at least one anti-anxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof, in therapeutically effective amounts. In certain embodiments the agents are in the same dosage form. In certain embodiments the therapeutic agents are in separate dosage forms.

Addiction and Withdrawal

The present invention relates to methods of and compositions for treating and relieving symptoms associated with substance abuse and withdrawal. The present invention relates to methods of and compositions for treating addiction to, for example, alcohol, drugs, caffeine, sugar, food, nicotine, opiates, and/or marijuana, etc.

Substance addiction and abuse is a multi-factorial neurological disease. Over time, repeated exposure to various substances, both endogenous and exogenous, causes modification of the neurotransmission circuits and adaptations in post-receptor signaling cascades. There are several effects of this neuronal modification. Among them, there is a reduction in the ability of natural rewards to activate the reward pathways leading to depressed motivation and mood and an increased compulsion to compensate for the physiological change.

While the common perception underlying addiction is that of a "reward circuit", pleasure may not necessarily be a strong enough impetus to drive people towards their addictions. Rather, addictive behavior arises from an intense desire to manage and/or avoid the anxiety that arises when someone is experiencing withdrawal.

Traditional treatments for substance dependency, such as benzodiazepine abuse, have been based upon cognitive-behavioral therapy or drug therapy, or a combination thereof. Conventional methods of treatment fail, however, in that they do not address the physiochemical changes that occur with addiction and dependence. Thus, conventional treatments for controlling withdrawal symptoms and cravings for addictive substances have had limited success and often have undesirable side effects.

What is therefore needed are improved methods of, and compositions for, preventing addiction to, and physiological dependence upon addictive substances. What is also needed is an improved treatment methodology for controlling cravings and withdrawal symptoms caused by substance abuse.

Accordingly, the invention provides methods of, and compositions for, preventing addiction to, and physiological dependence upon addictive substances. Also provided are methods of and compositions for an improved treatment methodology for controlling cravings and withdrawal symptoms caused by substance abuse.

The present invention relates to the use of cortisol blockers (glucocorticoid receptor [GR] antagonists) for the prevention or addiction induced anxiety and withdrawal side effects as a therapeutic and in concert with a diagnostic.

The compounds of the invention may be administered enterally or parenterally. Mixed with pharmaceutically suitable auxiliaries, e.g. as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray. For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The compounds of the invention can be administered orally, topically, intravenously, etc. By means of pharmaceutically suitable liquids the compounds can be applied in the form of a solution, suspension, or emulsion. The compounds can also be formulated in a patch, ointment or can be enclosed in a device for local administration to the skin.

The present invention reflects the role of endogenous glucocorticoids (GCs) in withdrawal from substances of abuse and addictive substances (hereafter referred to as "drug" or "drugs", inclusive of, but not restricted to, alcohol, nicotine, caffeine, cocaine (including crack cocaine), *cannabis*, amphetamines (including crystal methamphetamine), opiates and opiate analogues (including heroine, oxycodone, hydrocodone, hydromorphone, methadone), dextromethorphan, benzodiazepines, ecstacy (MDMA), GHB, barbiturates, khat, kratom, PCP, LSD, ketamine, peyote, mescaline, psilocybin, rohypnol, *Salvia divinorum*, antidepressants, anti-anxiety 5 medications, sleep aids, allergy medications.

Increased circulating levels of GCs may relate to direct elevating effects of substances of abuse or from stress-associated GC elevations in response to neuropsychiatric and physical stresses of withdrawal.

The present invention relates to co-administration of a selective GC receptor antagonist, such as ORG 34517, PT150, PT155, PT156, PT157, PT158, TCY1, combinations thereof, and pharmaceutically acceptable salts thereof administered during the active intoxication phase of drug use, prior to drug use, or after cessation of drug use to reduce neuropsychiatric and physical symptoms of withdrawal, such as anxiety, hallucinations, dysphoria, depression, delirium tremens, chills, shakes, tremors, akathisia, restlessness, restless leg syndrome, musculoskeletal aches and pains, cramping, chills, weakness.

The present invention relates to single dose of GC receptor antagonist or sustained administration of GC receptor antagonist for hours, days, weeks, or months for prevention of and/or treatment of symptoms of drug withdrawal.

The present invention may be considered for co-administration with anti-anxiety drugs and anti-depressant drugs to better control sporadic episodes, flare-ups of anxiety or depression. Regular co-administration of the present invention with anti-anxiety and/or anti-depressant drugs.

The present invention may also be used in concert with a diagnostic (for example, a diagnostic test using saliva, blood, plasma, serum, urine or tears as substrate) for the specific constituent i.e.: alcohol, cocaine, caffeine, nicotine, etc. to monitor the specific level of said constituent in the individual to prevent from occurrences of anxiety and withdrawals.

The present invention may also be used in concert with a diagnostic (for example, a diagnostic test using saliva, blood, plasma, serum, urine or tears as substrate) for cortisol to determine which individuals have elevated circulating cortisol or dysregulated cortisol and may therefore be most likely to benefit from administration of GC receptor antagonist.

The present invention may be packaged for use alone, as a single dose (by prescription or over the counter), as a limited number of timed doses in packaging designed to specifically guide self-administration, and in combination with drug or cortisol diagnostic test (using saliva, blood, plasma, serum, urine or tears as substrate) for self-administration or administration by health care professional or technician.

Androgen Receptor Antagonists

The compositions and methods of the invention may also make use of one or more androgen receptor antagonists, such as in a combination with the glucocorticoid receptor antagonist of the invention. For example, the invention provides with at least one glucocorticoid receptor antagonist in combination with at least one androgen receptor antagonist, such as for example, ARN 509 (4-{7-[6-Cyano-5-(trifluoromethyl)-3-pyridinyl]-8-oxo-6-thioxo-5,7-diazaspiro[3.4]oct-5-yl}-2-fluoro-N-methylbenzamide). ARN-509 is a novel androgen receptor (AR) antagonist for the treatment of castration-resistant prostate cancer (CRPC). ARN-509 inhibits AR nuclear translocation and AR binding to androgen response elements and, unlike bicalutamide, does not exhibit agonist properties in the context of AR overexpression.

Another exemplary antiadrogen is bicalutamide, which has the chemical name (R,S)—N-(4-cyano-3-(4-fluorophenyl sulfonyl)-2-hydroxy-2-methyl-3-(triflu-oromethyl)propanamide, Flutamide (brand name Eulexin), nilutamide (brand names Anandron and Nilandron) and bicalutamide (brand name Casodex) are nonsteroidal, "pure" antiandrogens; 5-alpha-reductase inhibitors such as finasteride (brand names Proscar and Propecia), dutasteride (brand name Avodart), bexlosteride, izonsteride, turosteride, and episteride are antiandrogenic as they prevent the conversion of testosterone to dihydrotestosterone (DHT); Spironolactone (brand names Aldactone and Spirotone), a synthetic 17-spirolactone corticosteroid; Cyproterone acetate (brand names Androcur, Climen, Diane 35, and Ginette 35) is a synthetic steroid, a potent antiandrogen that also possesses progestational properties. Hydroxyflutamide.

In some embodiments, steroidal or nonsteroidal androgen receptor antagonists include but are not limited to flutamide, hydroxyflutamide, enzalutamide bicalutamide, nilutamide, or hydroxysteroid dehydrogenase inhibitor.

In one embodiment, the androgen receptor antagonist is enzalutamide (marketed as Xtandi®, Astellas Pharma US, Inc.), also known as and referred to herein as MDV3100, having the chemical name 4-(3-(4-cyano-3-(trifluoromethyl)phenyl)-5,5-dimethyl-4-oxo-2-thioxoimida-zolidin-1-yl)-2-fluoro-N-methylbenzamide.

The compositions and methods of the invention may also make use of one or more androgen receptor antagonist, such as in a combination with the glucocorticoid receptor antagonist of the invention. The androgen receptor antagonist may be selected from the group consisting of, for example, flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, MDV3100, Cyproterone acetate, Spironolactone, flutamide, hydroxyflutamide, enzalutamide and combinations thereof.

The selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Prostate cancer is one of the most common cancers in men around the world, and is one of the leading causes of cancer death in men in the United States. The androgen receptor antagonist drugs, such as flutamide and bicalutamide, were originally designed to avoid the side effects of HT but androgen agonism was observed for hydroxyfluamide (the active form of flutamide) and bicalutamide. The compositions of the present invention are combinations of GCRAs and, for example, androgen receptor antagonists, which can be used to alleviate any condition associated with inappropriate activation of the androgen receptor. In addition to prostate cancer, other examples of such conditions include acne, hirsutism, seborrhoea, excess sebum, and alopecia. In order to exhibit the therapeutic properties described above, the compounds need to be administered in a quantity sufficient to inhibit activation of the androgen receptor. In a typical embodiment, the compounds are administered topically, which is especially appropriate for hirsutism, alopecia, acne and hyperseborhhea. Androgens, having a profound effect on hair loss, stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. The compositions of the invention may also be used topically to decrease seborrhea production and more specifically to alleviate hyperseborrhoea (oily skin), which can be used topically alleviate acne.

Poly (ADP-Ribose) Polymerase (PARP)

The compositions and methods of the invention may also make use of one or more PARP inhibitors, such as in a combination with the glucocorticoid receptor antagonist of the invention. The poly (ADP-ribose) polymerase (PARP) is also known as poly (ADP-ribose) synthase and poly ADP-ribosyltransferase. PARP catalyzes the formation of mono- and poly (ADP-ribose) polymers which can attach to cellular proteins (as well as to itself) and thereby modify the activities of those proteins. The enzyme plays a role in regulation of transcription, cell proliferation, and chromatin remodeling (see D'amours et al., Biochem., 342: 249268, 1999).

Poly(ADP-ribose)polymerase has an essential role in facilitating DNA repair, controlling RNA transcription, mediating cell death, and regulating immune response. These actions makePARJP inhibitors targets for a broad spectrum of disorders. (Virag L., et al., Pharmacol. Rev. 2002 54(3):375-429). In various preclinical cancer models and human clinical trials, PARP inhibitors have been shown to potentiate radiation and chemotherapy by increasing apoptosis of cancer cells, limiting tumor growth, decreasing metastasis, and prolonging the survival of tumor-bearing subjects. (WO 2007-084532; Donawho C. K., et al., Clin Cancer Res 2007 13(9):2728-37; Kummar S., et al., J Clin Oncol. 2009 27(16):2705-11).

PARP comprises an N-terminal DNA binding domain, an automodification domain, and a C-terminal catalytic domain. Various cellular proteins interact with PARP. The N-terminal DNA binding domain contains two zinc finger motifs. Transcription enhancer factor-1 (TEF-1), retinoid X receptor a, DNA polymerase a, X-ray repair cross-complementing factor-1 (XRCC1) and PARP itself interact with PARP in this domain. The automodification domain contains a BRCT motif, one of the protein-protein interaction modules. This motif is originally found in the C-terminus of BRCA1 (breast cancer susceptibility protein 1) and is present in various proteins related to DNA repair, recombination and cell-cycle checkpoint control. POU-homeodomain-containing octamer transcription factor-1 (Oct-1), YinYang (YY)1, and ubiquitin conjugating enzyme 9 (ubc9) could interact with this BRCT motif in PARP.

More than 15 members of the PARP family of genes are present in the mammalian genome. PARP family proteins and poly(ADP-ribose) glycohydrolase (PARG), which degrades poly(ADP-ribose) to ADP-ribose, are involved in a variety of cell regulatory functions including DNA damage response and transcriptional regulation and associated with carcinogenesis and the biology of cancer. Several PARP family proteins have been identified. Tankyrase has been found as an interacting protein of telomere regulatory factor 1 (TRF-1) and is involved in telomere regulation. Vault PARP (VPARP) is a component in the vault complex, which acts as a nuclear-cytoplasmic transporter. PARP-2, PARP-3 and 2,3,7,8-tetrachlorodibenzo-p-dioxin inducible PARP (TiPARP) have also been identified. Therefore, poly(ADP-ribose) metabolism could be related to a variety of cell regulatory functions.

A member of this gene family is PARP-1. The PARP-1 gene product is expressed at high levels in the nuclei of cells and is dependent upon DNA damage for activation. It is believed that PARP-1 binds to DNA single or double-stranded breaks (DSBs) through an amino-terminal DNA-binding domain. The binding activates the carboxy-terminal catalytic domain and results in the formation of polymers of ADP-ribose on target molecules. PARP-1 is itself a target of poly ADP-ribosylation by virtue of a centrally located automodification domain. The ribosylation of PARP-1 causes dissociation of the PARP-1 molecules from the DNA. The entire process of binding, ribosylation, and dissociation occurs very rapidly. It has been suggested that this transient binding of PARP-1 to sites of DNA damage results in the recruitment of DNA repair machinery or may act to suppress the recombination long enough for the recruitment of repair machinery.

The source of ADP-ribose for the PARP reaction is nicotinamide adenosine dinucleotide (NAD). NAD is synthesized in cells from cellular ATP stores and thus high levels of activation of PARP activity can rapidly lead to depletion of cellular energy stores. It has been demonstrated that induction of PARP activity can lead to cell death that is correlated with depletion of cellular NAD and ATP pools. PARP activity is induced in many instances of oxidative stress or during inflammation. For example, during reperfusion of ischemic tissues reactive nitric oxide is generated and nitric oxide results in the generation of additional reactive oxygen species including hydrogen peroxide, peroxynitrate, and hydroxyl radical. These latter species can directly damage DNA and the resulting damage induces activation of PARP activity. Frequently, it appears that sufficient activation of PARP activity occurs such that the cellular energy stores are depleted and the cell dies. A similar mechanism is believed to operate during inflammation when endothelial cells and pro-inflammatory cells synthesize nitric oxide, which results in oxidative DNA damage in surrounding cells and the subsequent activation of PARP activity. The cell death that results from PARP activation is believed to be a major contributing factor in the extent of tissue damage that results from ischemia-reperfusion injury or from inflammation.

PARP (poly-ADP ribose polymerase) participates in a variety of DNA-related functions including cell proliferation, differentiation, apoptosis, DNA repair and also effects on telomere length and chromosome stability (d'Adda di Fagagna et al., Nature Gen., 23(1): 76-80, 1999). Oxidative stress-induced overactivation of PARP consumes NAD+ and consequently ATP, culminating in cell dysfunction or necrosis. This cellular suicide mechanism has been implicated in the pathomechanism of cancer, stroke, myocardial ischemia, diabetes, diabetes-associated cardiovascular dysfunction, shock, traumatic central nervous system injury, arthritis, colitis, allergic encephalomyelitis, and various other forms of inflammation. PARP has also been shown to associate with and regulate the function of several transcription factors.

PARP Inhibitors

Suitable PARP inhibitors for use in the compositions and methods of the invention include, but are not limited to, 4-[[3-[4-(cyclopropanecarbonyl)piperazine-1-carbonyl]-4-fluorophenyl]-met-hyl]-2H-phthalazin-1-one (Compound B, i.e., Olaparib), 4-iodo-3-nitrobenzamide (Iniparib), 2-[(2R)-2-methylpyrrolidin-2-yl]-1H-benzimidazole-4-carboxamide (ABT-888), 8-Fluoro-2-{4-[(methylamino)methyl]-phenyl}-1,3,4,5-tetrahydro-6H-azepino-[5,4,3-cd] indol-6-one (AGO 14699), 4-methoxy-carbazole (CEP 9722), 2-[4-[(3S)-piperidin-3-yl]phenyl]indazole-7-carboxamide hydrochloride (MK 4827), and 3-aminobenzamide, or a pharmaceutically acceptable salt thereof. In some embodiments, the Glucocorticoid receptor antagonists, e.g., ORG 34517, PT150, PT155, PT156, PT157, PT158, TCY1, combinations thereof, and pharmaceutically acceptable salts thereof composition described herein, is administered in combination with a poly ADP-ribose polymerase (PARP) inhibitor (e.g., BSI201, Olaparib (AZD-2281), ABT-888, AG014699, CEP 9722, MK 4827, KU-0059436 (AZD2281), LT-673,3-aminobenzamide). Other example PARP inhibitors include, i.e., pharmacological inhibitors of the enzyme poly ADP ribose polymerase (PARP). Suitable PARP inhibitors maybe iniparib, olaparib, rucaparib, veliparib, or CEP 9722.

Current PARP inhibitors in clinical trials include: Iniparib (Sanofi), Olaparib (AstraZeneca), Rucaparib (Pfizer), Veliparib (Abbott), CEP-9722 (Cephalon), MK4827 (Merck), BMN-673 (Biomarin), among others.

Treatment Resistant Prostate Cancer

The invention provides a method for treating and/or preventing treatment resistant prostate cancer in a patient in need of such treatment and/or prevention, comprising: administering to the patient therapeutically effective amounts of a GCR (glucocorticoid receptor) antagonist as exemplified herein, in combination with, for example, a neoplasia treating agent, including, for example, an androgen receptor (AR) antagonist. Prostate cancer is the most commonly diagnosed cancer in men and the second leading cause of death from cancer in North American and European males. New therapeutic approaches are needed to prevent and treat advanced and metastatic prostate cancer. Nutritional factors, particularly high intake of protein and calcium, as well as metabolic syndrome, are known to modify prostate cancer risk and progression, but the molecular mechanisms linking nutrition to prostate cancer are unknown. There are also links between prostate cancer and bone metabolism. Osteocalcin (OC), which encodes a vitamin-K dependent hormone predominantly produced by osteoblasts/osteocytes in bone, which functions to regulate energy metabolism, is also ectopically expressed by some prostate cancers that have a propensity to metastasize to bone. Polymorphisms in OC are also associated with prostate cancer progression. Recent evidence has also identified a correlation between the bone transcription factor Runx2 and advanced stages of prostate and breast cancer, as evidenced by the effects of depletion of Runx2 by RNA interference to inhibit migration and invasive properties of the cells and prevent metastatic bone disease. It is possible that OC secreted by bone may directly target prostate cancer cells. Finally, androgen deprivation therapy is the principal medical therapy for prostate cancer, but androgen ablation often becomes ineffective in controlling prostate cancer progression and castration-resistant metastatic disease, particularly to bone, becomes incurable. There is growing evidence for the presence of a putative membrane androgen sensing receptor that mediates the rapid, non-genomic effects of androgens, which also might be involved in prostate cancer growth and metastasis. Regardless, clues to possible new molecular targets to regulate prostate cancer growth and progression may be discovered from a better understanding of the molecular mechanisms underlying nutritional risk factors, OC effects and androgen resistance in prostate cancer.

Neoplasia, Cancer, Tumors, Proliferative Diseases, Malignancies and their Metastases The invention provides a method for treating neoplasia in a patient in need of such treatment, comprising: administering to the patient therapeutically effective amounts of a GCR (glucocorticoid receptor) antagonist as exemplified herein, such as ORG 34517, PT150, PT155, PT156, PT157, PT158, TCY1, combinations thereof, and pharmaceutically acceptable salts thereof, optionally in combination with, for example, a neoplasia treating agent. The term "neoplasia" as used herein refers also to tumors, proliferative diseases, malignancies and their metastases. Examples for cancer diseases are Adenocarcinomas of the head and neck (including salivary glands and oral cavity), gastrointestinal tract (including pharynx, esophagus, stomach, small intestine, large intestine, anus), lung, liver (including hepatocellular carcinoma, cholangiocarcinoma, and mixed tumors), extrahepatic biliary tract and gallbladder, pancreas (including ductal and acinar types), genitourinary tracts (ovaries, fallopian tubes, endometrium, cervix, and vagina, ureters, urinary bladder, testicles, epididymis, prostate), and skin adnexa; squamous cell carcinomas of the head and neck (including salivary glands and oral cavity), gastrointestinal tract (including pharynx, esophagus, anus), lung, intrahepatic and extrahepatic biliary tree (including gallbladder), pancreas, genitourinary tracts (including endometrium, cervix, vagina, ureters, urinary bladder, testicles, epididymis, prostate), and skin adnexa; germ cell tumors (including malignant teratoma, embryonal carcinoma, struma ovarii, yolk sac tumor, seminoma, choriocarcinoma); sarcomas (including leiomyosarcomas, rhabdomyosarcomas, angiosarcomas, hemangioendotheliomas, liposarcomas, chondosarcomas, fibrosarcomas, Ewing sarcoma, malignant nerve sheathe tumors, alveolar soft part sarcomas, clear cell sarcomas, synovial sarcoma, osteosarcomas); malignancies of the central nervous system (including astrocytomas, oligodendroglioma, glioblastoma, medulloblastoma); salivary gland malignancies (including adenoid cystic carcinoma, adenosquamous carcinoma, clear cell carcinoma, cystadenocarcinoma, mucoepidermoid carcinoma); mixed type carcinomas (including hepatocellular-cholangiocarcinomas, carcinosarcomas, mixed adenoneurondocrine carcinomas, adenosquamous carcinomas); hepatocellular carcinoma; blastic malignancies (including hepatoblastoma, neuroblastoma, ganglioneuroblastoma, nephroblastoma); renal cell carcinomas; neuroendocrine carcinomas; thyroid carcinomas (including papillary, follicular, medullary, anaplastic carcinomas); parathyroid carcinomas, pituitary gland carcinomas, adrenal gland carcinomas (including adrenocortical carcinomas, pheochromocytoma), and combinations thereof.

Cancer Therapies

Any therapy (e.g., therapeutic or prophylactic agent) which is useful, has been used, is currently being used, or may be used for the prevention, treatment and/or management of cancer can be used to prevent, treat, and/or manage the patient whose neoplasia and/or cancer stem cells are monitored in accordance with the methods of the invention. Also, such neoplasia and/or cancer stem cell monitoring can be employed in conjunction with any therapy for cancer according to the instant invention. Therapies (e.g., therapeutic or prophylactic agents) include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, anti-angiogenesis therapies, targeted therapies, and/or biological therapies including immunotherapies and surgery. In certain embodiments, a prophylactically and/or therapeutically effective regimen comprises the administration of a combination of therapies. In certain embodiments, ORG34517, PT150, PT155, PT156, PT157, PT158, TCY1, combinations thereof, and pharmaceutically acceptable salts thereof can be administered as an agent to treat or prevent neoplasia. In certain embodiments, RU486 (mifepristone) can be administered as an agent to treat or prevent neoplasia.

Examples of cancer therapies include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; histone deacetylase inhibitors (HDAC-Is) hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mifepristone; mitindomide; mitocarcin; mitocromin; mitogillin; mitomalcin; mitomycin; mitosper; mitotane; mitoxantrone hydrochloride; mycophenolic acid; nocodazole; nogalamycin; ORG 34517; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; RU486; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-I; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3 TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; oracin; oral cytokine inducer; ormaplatin; osaterone; oxaliplatin; oxaunomycin; paclitaxel;

paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; anti-integrin antibodies (e.g., anti-integrin $a_{vb3}$ antibodies); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaslitazar, muraglitazar, peliglitazar, lobeglitazone, balaglitazone, raglitazar, rosiglitazone, farglitazar, sodeiglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit disheveled/frizzled or beta catenin; anti-CD20 antibodies and conjugates (e.g. Rituxan, Bexxar, Zevalin) for novel use in multiple myeloma or melanoma; anti-CD133 antibody; anti-CD44 antibody; antibodies to IL-4; certain differentiation agents such as versnarinone; compounds that target CD33 such as an antibody or betulinic acid; compounds that target lactadherin such as an antibody; small molecules or antibodies that target CXCR4 or SDF-1; small molecules or antibodies that target multi-drug resistance pumps; inhibitors of survivin; inhibitors of XIAP; small molecules that target Bcl-2; antibodies to CLL-1; and furin inhibitors (such as cucurbitacins).

An additional non-limiting list of compounds that could also be used to target cancer and/or cancer stem cells includes: i) antibodies, antibody fragments, and proteins that are either naked or conjugated to a therapeutic moiety that target certain cell surface targets on cancer stem cells, or ii) small molecules known in the art including ones that can be further optimized (e.g., via chemistry) or identified via a cancer stem cell-based screen (e.g., such as one that would determine whether a compound impairs proliferation or viability of a cancer stem cell through standard methods, the cell surface and intracellular targets including (not meant to be exhaustive) are: Rex1 (Zfp42), CTGF, Activin A, Wnt, FGF-2, HIF-1, AP-2gamma, Bmi-1, nucleostemin, hiwi, Moz-TIF2, Nanog, beta-arrestin-2, Oct-4, Sox2, stella, GDF3, RUNX3, EBAF, TDGF-1, nodal, ZFPY, PTNE, Evi-1, Pax3, Mcl-1, c-kit, Lex-1, Zfx, lactadherin, aldehyde dehydrogenase, BCRP, telomerase, CD133, Bcl-2, CD26, Gremlin, and FoxC2.

In some embodiments, the therapy(ies) is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamides (e.g., leflunamide), T cell receptor modulators, cytokine receptor modulators, and modulators mast cell modulators. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) is an anti-angiogenic agent. Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab)2 fragments, and antigen-binding fragments thereof) such as antibodies that specifically bind to TNF-alpha, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) is not an anti-angiogenic agent.

In certain embodiments, the therapy(ies) is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, chlorambucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the *vinca* alkaloids (vinblastine, vincristine, and vinorelbine). In some embodiments of the invention, the therapy(ies) includes the administration cantharidin or an analog thereof. The invention includes the use of agents that target cancer stem cells. In certain embodiments, the agent acts alone. In other embodiments, the agent is attached directly or indirectly to another therapeutic moiety. Non-limiting examples of therapeutic moieties include, but are not limited to alkylating agents, antimetabolites, plant alkaloids, cytotoxic agents, chemotherapeutic agents (e.g., a steroid, cytosine arabinoside, fluoruracil, methotrexate, aminopterin, mitomycin C, demecolcine, etoposide, mithramycin, calicheamicin, CC-1065, chlorambucil or melphalan), radionuclides, therapeutic enzymes, cytokines, toxins including plant-derived toxins, fungus-derived toxins, bacteria-derived toxin (e.g., deglycosylated ricin A chain, a ribosome inactivating protein, alpha-sarcin, aspergillin, restirictocin, a ribonuclease, a diphtheria toxin, *Pseudomonas* exotoxin, a bacterial endotoxin or the lipid A moiety of a bacterial endotoxin), growth modulators and RNase. In some embodiments, the agent used is an agent that binds to a marker, e.g., an antigen on a cancer stem cell. In a specific embodiment, the agent binds to an antigen that is expressed at a greater level on cancer stem cells than on normal stem cells. In a specific embodiment, the agent binds specifically to a cancer stem cell antigen that is not a normal stem cell. In other embodiments, the therapy(ies) is an agent that binds to a marker on cancer stem cells. In one embodiment, the agent that binds to a marker on cancer stem cells is an antibody or an antibody conjugated to a therapeutic moiety or an antibody fragment conjugated to a therapeutic moiety.

For example, in a specific embodiment, the agent binds specifically to the IL-3 Receptor (IL-3R). In some embodiments, the agent that binds to the IL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the .alpha.-subunit of IL-3R (i.e., the CD123 antigen). In other embodiments, the antibody, antibody-conjugate, antibody fragment, or antibody fragment-conjugate binds to the IL-3R, containing both the .alpha. and .beta. subunits. Methods for preparing antibodies to IL-3R and mimetics of antibodies to IL-3R are described in U.S. Pat. No. 6,733,743 B2, which is incorporated herein by reference in its entirety.

In other embodiments, the agent that binds to a marker on cancer stem cells is a ligand. In some embodiments, the ligand is a cytokine that binds to a cytokine receptor on cancer stem cells. In a particular embodiment, the ligand is interleukin-3 (IL-3) which can be conjugated to a therapeutic moiety that includes a chemotherapeutic agent, a plant-, fungus-, or bacteria-derived toxin, or a radionuclide. The IL-3-conjugate prophylactic and/or therapeutic therapy or regimen can be in the form of a recombinant fusion protein in embodiments where the conjugate is a toxin and the toxin is a protein, such as diphtheria toxin. Methods for preparing and isolating an IL-3-diphtheria toxin fusion protein (IL3DT) are described in Frankel et al., "Diphtheria toxin fused to human interleukin-3 is toxic to blasts from patients with myeloid leukemias," Leukemia 14:576 (2000) and Urieto et al., Protein Expression and Purification 33: 123-133 (2004), the disclosures of which are incorporated by reference in their entireties.

In certain embodiments, antibodies or fragments thereof that bind to a marker on cancer stem cells are substantially non-immunogenic in the treated subject. Methods for obtaining non-immunogenic antibodies include, but are not limited to, chimerizing the antibody, humanizing the antibody, and isolating antibodies from the same species as the subject receiving the therapy. Antibodies or fragments thereof that bind to markers in cancer stem cells can be produced using techniques known in the art. See, for example, paragraphs 539-573 of U.S. Publication No. 2005/0002934, which is incorporated by reference in its entirety.

In some embodiments, the therapy comprises the use of X-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

In some embodiments, the therapy used is a proliferation based therapy. Non-limiting examples of such therapies include a chemotherapy and radiation therapy as described supra.

Currently available therapies and their dosages, routes of administration and recommended usage are known in the art and have been described in such literature as the Physician's Desk Reference (60th ed., 2006).

In a specific embodiment, cycling therapy involves the administration of a first cancer therapeutic for a period of time, followed by the administration of a second cancer therapeutic for a period of time, optionally, followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two prophylactically and/or therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first prophylactically and/or therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

Treating or Preventing Infection Related to Acute or Chronic Injury or Disease

The invention provides a method for treating or preventing infection related to acute or chronic injury or disease in a patient in need of such treatment, comprising: administering to the patient therapeutically effective amounts of a GCR (glucocorticoid receptor) antagonist as exemplified herein, such as ORG34517, PT150, PT155, PT156, PT157, PT158, TCY1, combinations thereof, and pharmaceutically acceptable salts thereof, alone or in combination with, for example, another agent. In particular, the invention has application to minimize life-threatening complications of persons suffering injury to cells, tissues or organs resulting from burns, shock, stroke, heart attack or other physical events, including complications from surgical or clinical interventions, as a consequence of trauma. Injured soldiers on the battlefield or civilians at a natural disaster site or injured from a terrorist attack are situations where such treatment may be useful.

The invention applies to protecting, preserving or stabilizing key organs such as the heart and brain, other neuronal tissues and cells, renal tissue, lung tissue, muscle tissue, liver and other tissues of the body.

In one form, the invention provides a method of reducing injury to the cells, tissues or organs of a body following trauma by administering a composition to the body following trauma including: (i) a glucocorticoid receptor antagonist; and optionally (ii) another pharmaceutical agent.

The term "trauma" is used herein in its broadest sense and refers to a serious or critical injury, wound or shock to the body. Trauma may be caused by unexpected physical damage (or injury) to the body as a result of, for example, transport or industrial accidents, birth, surgery, heart attack, stroke, burns, complications due to surgery or other medical interventions etc. Trauma may result from injury to a body, both in a hospital or out of hospital. Trauma is often associated with trauma medicine practiced in hospital (such as in hospital emergency rooms), during emergency transport or at out-of-hospital environments where a trauma has occurred, such as domestic or industrial accidents, transport accidents, the battlefield, and terrorist attacks. In many cases, trauma therapy may also include resuscitation therapy. Exemplary injuries include, for example, burns, shock, stroke, heart attack or other physical events, including complications from surgical or clinical interventions, as a consequence of trauma. Injured soldiers on the battlefield or civilians at a natural disaster site or injured from a terrorist attack are situations where such treatment may be useful. The invention provides a method for treating or preventing infection related to acute or chronic injury or disease wherein said method comprises administering to a patient in need of such therapy at least one glucocorticoid receptor antagonist in a therapeutically effective amount.

The activities of GR agonists and their alteration of cellular functions are variable, depending on complex intracellular molecular signaling that are cell and tissue specific. Amongst the cells that have glucocorticoid receptors are stem and progenitor cells of all tissues and organs of the body. Thus, binding of such molecules to normative, "in-tissue" stem cells and the progeny of these stem cells, so-called "transit amplifying" progenitor cells, results in variable, cell and tissue specific effects, inhibitory or enhancing of stem and progenitor cell functions, including activation, proliferation, migration and differentiation all of which are dependent on the tissue/organ in question.

GR antagonists or active agent, such as, for example, ORG 34517, PT150, PT155, PT156, PT157, PT158, TCY1, combinations thereof, and pharmaceutically acceptable salts thereof, will thus block the effects of GR-agonists in tissue specific fashion, enhancing stem/progenitor cell functioning in some, inhibiting it in others. GR-antagonists will have beneficial effects in specific clinical settings where regenerative medicine approaches to disease and wound healing may be of use, including: enhanced post-transplant functioning of autologous stem cell transplants (dependent on tissue of origin and/or target tissue).

Attenuation of the peri-surgical effects of catabolic stress hormones related to surgical or other physical traumas (e.g. combat wounds), wherein the acute or chronic injury or disease is selected from the group consisting of vascular events, stroke, cardiac arrest, acute limb infarction accident/battle field trauma, traumatic limb, hip, brain injuries, post-surgical trauma, major orthopedic, thoracic, abdominal, neurological surgeries.

Systemic GR blockade will be inappropriate, but direct application of ORG 34517, PT150, PT155, PT156, PT157, PT158, TCY1, combinations thereof, and pharmaceutically acceptable salts thereof to site of injury/wounding, either topically (for example, to prevent wound dehiscence) or by direct injection or intravascular infusion (for visceral organ injuries) will be beneficial.

CNS Injury

The invention provides a method for treating or preventing CNS injury in a patient in need of such treatment, comprising: administering to the patient therapeutically effective amounts of a GCR (glucocorticoid receptor) antagonist as exemplified herein, such as ORG34517, PT150, PT155, PT156, PT157, PT158, TCY1, combinations thereof, and pharmaceutically acceptable salts thereof, alone or in combination with, for example, another agent. Conditions suitable for treatment according to this invention include, for example, seizure disorders, pain syndromes, neurodegenerative diseases (including motor neuron diseases, myelopathies, radiculopathies, and disorders of the sympathetic nervous system), dementias, cerebrovascular conditions, movement disorders, brain trauma, cranial nerve disorders, neuropsychiatric disorders, and other disease neuropathies (including viral associated neuropathies, diabetes associated neuropathies, Guillain-Barre syndrome, dysproteinemias, transthyretin-induced neuropathies, and carpal tunnel syndrome). As used herein, seizure disorders include complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, mesial temporal lobe epilepsy, nocturnal frontal lobe epilepsy, progressive epilepsy with mental retardation, and progressive myoclonic epilepsy, as well as seizures associated with CNS mass lesions.

Pain syndromes include, for example, headaches (e.g., migraine, tension, and cluster), acute pain, chronic pain, neuropathic pain, nociceptive pain, central pain and inflammatory pain, drug-induced neuropathic pain, causalgia, complex regional pain syndrome types I and II, and reflex sympathetic dystrophy (RSDS).

Neurodegenerative diseases include Alzheimer's disease, Parkinson's Disease, multiple sclerosis, Huntington's Disease, ALS, spinal muscular atrophy, muscular dystrophies prion-related diseases, cerebellar ataxia, Friedrich's ataxia, SCA, Wilson's disease, RP, Gullian Barre syndrome, Adrenoleukodystrophy, Menke's Sx, cerebral autosomal dominant arteriopathy with subcortical infarcts (CADASIL), Charcot Marie Tooth diseases, neurofibromatosis, von-Hippel Lindau, Fragile X, spastic paraplegia, tuberous sclerosis complex, Wardenburg syndrome, spinal motor atrophies, Tay-Sachs, Sandoff disease, familial spastic paraplegia, myelopathies, radiculopathies, encephalopathies associated with trauma, radiation, drugs and infection, and disorders of the sympathetic nervous system (e.g., Shy Drager (familial dysautonomia), diabetic neuropathy, drug-induced and alcoholic neuropathy).

Dementias include Alzheimer's disease, Parkinson's disease, Pick's disease, frontotemporal dementia, vascular dementia, normal pressure hydrocephalus, Huntington's disease, and MCI. Cerebrovascular conditions amenable to treatment according to the present invention include cerebrovascular disease and strokes (e.g., thrombotic, embolic, thromboembolic, hemorrhagic [including AVM and berry aneurysms], venoconstrictive, and venous).

Included in movement disorders are Parkinson's disease, dystonias, benign essential tremor, tardive dystonia, tardive dyskinesia, and Tourette's syndrome. Brain trauma as used herein includes traumatic brain and spinal cord injuries as well as brain injuries from radiation. Cranial nerve disorders include trigeminal neuropathy, trigeminal neuralgia, Menier's syndrome, glossopharangela neuralgia, dysphagia, dysphonia, cranial nerve palsies and Bell's palsy.

Neuropsychiatric disorders include panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence/addiction (e.g., alcohol, psychostimulants (e.g., crack, cocaine, speed, meth), opioids, and nicotine), and drug-induced psychiatric disorders.

Other disease neuropathies that may be treated with the compositions and methods described herein include Guillain-Barre, diabetes associated neuropathies, dysproteinemias, transthyretin-induced neuropathies, neuropathy associated with HIV, herpes viruses (including herpes zoster) or other viral infection, neuropathy associated with Lyme disease, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy, postmeningitis syndrome, post-polio syndrome, prion diseases, and radiation associated neuropathic syndromes. Other diseases amenable to treatment with the present invention include fatigue syndromes (e.g., chronic fatigue syndrome and fibromyalgia), ataxic syndromes, olivopontoicerebellar degeneration, striatonigral degeneration, and axonic brain damage.

The present invention is particularly useful in the treatment of neuropsychiatric disorders such as depression, agitation, anxiety, seizure disorders such as grand mal seizures, status epilepticus, migraine pain treatment and prophylaxis, Alzheimer's disease, Parkinson's disease, and traumatic brain and spinal cord injury.

Also, the higher doses enabled by the present invention are expected to be of particular importance for dementias including Alzheimer's disease, Parkinson's disease, and vascular dementia, pain syndromes, including headaches and migraines, seizure disorders, movement disorders, and brain trauma.

Furthermore, the ease of use and convenience of a dosage form provided developed to be delivered at once per day or less frequent administration at a therapeutically effective quantity from the onset of therapy is of value in the treatment of dementias including Alzheimer's disease and Parkinson's disease, seizure disorders, pain syndromes, and cerebrovascular conditions.

Enhanced Memory and/or Performance. Situational stress can lead to elevated circulating levels of cortisol which, in turn, can impair short term memory formation. For example, student exam periods in high school, college, as well as graduate school and professional certification and licensing exams can lead to such stress and, therefore, to a self-defeating, cortisol associated deficit in learning that may impair formation of study-based memories and lead to poorer than expected test results. The present invention is particularly useful in the treatment and/or prevention of short term memory performance by, for example, single or sequential dosing with a glucocorticoid blocking compound or composition of the invention, before and during the examination study period, that will prevent suppression of short term memory formation and improve study and subsequent examination performance.

Immunomodulatory Effect

The inventive pharmaceutical composition may additionally contain one or more auxiliary substances in order to further increase its immunomodulatory effect, for example, ORG 34517, PT150, PT155, PT156, PT157, PT158, TCY1, combinations thereof, and pharmaceutically acceptable salts thereof alone or in combination with immune system regulators (e.g., EL-1R antagonist) for prevention of post-traumatic or disease-associated systemic immunosuppression at high risk for bacterial infections (e.g., wound infections, pneumonia, colitis, pyelonephritis, hepatic and splenic abscesses) and sepsis. New compositions and methods are provided which advantageously employ compounds having a newly defined immune modulating function, or which have the ability to mimic that immune modulating function, or a combination of such compounds. For the purposes of the present disclosure, the terms "immune mimic," "immune modulating," "immune modulator," "immune modulation," "immune control," "immune inhibition," "immune suppressor," and the like, refer in most instances to the newly identified cancer cell growth (i.e., proliferation) inhibitory effect of the secretory immune system (i.e., dimeric/polymeric IgA and pentameric IgM) that is mediated by a newly identified Poly-Ig receptor or Poly-Ig-like receptor (also classified as an Fc-like receptor), and not to the usual antibody/antigen recognition based immune function of the immune system. In this context, the terms "immune modulation" or "immune enhancement" refer especially to the modulation or enhancement of these cell growth inhibitory immunoglobulins of the secretory immune system. The term "immune mimic" refers to a substance (e.g., tamoxifen) that can function in a similar manner to an immunoglobulin inhibitor of cell growth. In some instances, however, reference is also made herein to "natural immune inhibition," "immune enhancer," "immune modulator," "immune system," "immune therapy," and "immune response," and the like, in which the conventional meanings of those terms are intended and the context so indicates, especially when prior art methods, compounds and compositions are described. Hereinafter, an indication has been made in appropriate instances whether a conventional definition or the "new" meaning, or both, is intended. A synergistic action of the compounds of the invention, e.g., ORG 34517, PT150, PT155, PT156, PT157, PT158, TCY1, combinations thereof, and pharmaceutically acceptable salts thereof or a derivative thereof as defined according to the present invention, and of an auxiliary substance, which may be optionally contained in the inventive pharmaceutical composition as described above, is preferably achieved thereby. Depending on the various types of auxiliary substances, various mechanisms can come into consideration in this respect. In general, it is possible to use as auxiliary substance any agent that influences the immune system in the manner of a "danger signal" (LPS, GP96, etc.) or cytokines, such as GM-CSF, which allow for an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-1 receptor antagonist, IL-2, EL-3, EL-4, IL-5, IL-6, EL-7, IL-8, EL-9, ELIO, IL-12, EL-13, EL-14, EL-15, EL-16, IL-17, EL-18, IL-19, EL-20, EL-21, EL-22, DL-23, EL-24, IL-25, EL-26, EL-27, EL-28, EL-29, EL-30, EL-31, EL-32, EL-33, INF-alpha, EFN-beta, INF-gamma, GM-CSF, G-CSF, M-CSF, LT-beta or TNF-alpha, growth factors, such as hGH.

The inventive pharmaceutical composition can also additionally or alternatively contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Immunoinflammatory Disorder

Another aspect of the present invention is directed to the use of the inventive compound and/or combination as a therapeutic agent for the prophylaxis and/or treatment of immunoinflammatory disorder. The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acne vulgaris; acute respiratory distress syndrome; Addison's disease; allergic rhinitis; allergic intraocular inflammatory diseases, antineutrophil cytoplasmic antibody (ANCA)-associated small-vessel vasculitis; ankylosing spondylitis; arthritis, asthma; atherosclerosis; atopic dermatitis; autoimmune hepatitis; autoimmune hemolytic anemia; autoimmune hepatitis; Behcet's disease; Bell's palsy; bullous pemphigoid; cerebral ischemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; erythema nodosum; exfoliative dermatitis; fibromyalgia; focal glomerulosclerosis; focal segmental glomerulosclerosis; giant cell arteritis; gout; gouty arthritis; graft versus host disease; hand eczema; Henoch-Schonlein purpura; herpes gestationis; hirsutism; idiopathic cerato-scleritis; idiopathic pulmonary fibrosis; idiopathic thrombocytopenic purpura; immune thrombocytopenic purpura inflammatory bowel or gastrointestinal disorders, inflammatory dermatoses; lichen planus; lupus nephritis; lymphomatous tracheobronchitis; macular edema; multiple sclerosis; myasthenia gravis; myositis; non-specific fibrosing lung disease; osteoarthritis; pancreatitis; pemphigoid gestationis; pemphigus vulgaris; periodontitis; polyarteritis nodosa; polymyalgia rheumatica; pruritus scroti; pruritis/inflammation, psoriasis; psoriatic arthritis; pulmonary histoplasmosis; rheumatoid arthritis; relapsing polychondritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; shoulder tendinitis or bursitis; Sjogren's syndrome; Still's disease; stroke-induced brain cell death; Sweet's disease; systemic lupus erythematosus; systemic sclerosis; Takayasu's arteritis; temporal arteritis; toxic epidermal necrolysis; transplant-rejection and transplant-rejection-related syndromes; tuberculosis; type-1 diabetes; ulcerative colitis; uveitis; vasculitis; and Wegener's granulomatosis.

As used herein, "non-dermal inflammatory disorders" include, for example, rheumatoid arthritis, inflammatory bowel disease, asthma, and chronic obstructive pulmonary disease. By "dermal inflammatory disorders" or "inflammatory dermatoses" is meant an inflammatory disorder selected from psoriasis, guttate psoriasis, inverse psoriasis, pustular psoriasis, erythrodermic psoriasis, acute febrile neutrophilic dermatosis, eczema, asteatotic eczema, dyshidrotic eczema, vesicular palmoplantar eczema, acne vulgaris, atopic dermatitis, contact dermatitis, allergic contact dermatitis, dermatomyositis, exfoliative dermatitis, hand eczema, pompholyx, rosacea, rosacea caused by sarcoidosis, rosacea caused by scleroderma, rosacea caused by Sweet's syndrome, rosacea caused by systemic lupus erythematosus, rosacea caused by urticaria, rosacea caused by zoster-associated pain, Sweet's disease, neutrophilic hidradenitis, sterile pustulosis, drug eruptions, seborrheic dermatitis, pityriasis rosea, cutaneous kikuchi disease, pruritic urticarial papules and plaques of pregnancy, Stevens-Johnson syndrome and toxic epidermal necrolysis, tattoo reactions, Wells syndrome (eosinophilic cellulitis), reactive arthritis (Reiter's syndrome), bowel-associated dermatosis-arthritis syndrome, rheumatoid neutrophilic dermatosis, neutrophilic eccrine hidradenitis, neutrophilic dermatosis of the dorsal hands, balanitis circumscripta plasmacellularis, balanoposthitis, Behcet's disease, erythema annulare centrifiigum, erythema dyschromicum perstans, erythema multiforme, granuloma annulare, hand dermatitis, lichen nitidus, lichen planus, lichen sclerosus et atrophicus, lichen simplex chronicus, lichen spinulosus, nummular dermatitis, pyoderma gangrenosum, sarcoidosis, subcorneal pustular dermatosis, urticaria, and transient acantholytic dermatosis.

By "proliferative skin disease" is meant a benign or malignant disease that is characterized by accelerated cell division in the epidermis or dermis. Examples of proliferative skin diseases are psoriasis, atopic dermatitis, nonspecific dermatitis, primary irritant contact dermatitis, allergic contact dermatitis, basal and squamous cell carcinomas of the skin, lamellar ichthyosis, epidermolytic hyperkeratosis, premalignant keratosis, acne, and seborrheic dermatitis. As will be appreciated by one skilled in the art, a particular disease, disorder, or condition may be characterized as being both a proliferative skin disease and an inflammatory dermatosis. An example of such a disease is psoriasis.

Symptoms and signs of inflammation associated with specific conditions include: rheumatoid arthritis:—pain, swelling, warmth and tenderness of the involved joints; generalized and morning stiffness; insulin-dependent diabetes mellitus-insulitis; this condition can lead to a variety of complications with an inflammatory component, including:—retinopathy, neuropathy, nephropathy; coronary artery disease, peripheral vascular disease, and cerebrovascular disease; autoimmune thyroiditis:—weakness, constipation, shortness of breath, puffiness of the face, hands and feet, peripheral edema, bradycardia; multiple sclerosis:—spasticity, blurry vision, vertigo, limb weakness, paresthesias; uveoretinitis:—decreased night vision, loss of peripheral vision; lupus erythematosus:—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis; scleroderma:—Raynaud's disease; swelling of the hands, arms, legs and face; skin thickening; pain, swelling and stiffness of the fingers and knees, gastrointestinal dysfunction, restrictive lung disease; pericarditis; renal failure; other arthritic conditions having an inflammatory component such as rheumatoid spondylitis, osteoarthritis, septic arthritis and polyarthritis:—fever, pain, swelling, tenderness; other inflammatory brain disorders, such as meningitis, Alzheimer's disease, AIDS dementia encephalitis:—photophobia, cognitive dysfunction, memory loss; other inflammatory eye inflammations, such as retinitis:—decreased visual acuity; inflammatory skin disorders, such as, eczema, other dermatites (e.g., atopic, contact), psoriasis, burns induced by UV radiation (sun rays and similar UV sources):—erythema, pain, scaling, swelling, tenderness; inflammatory bowel disease, such as Crohn's disease, ulcerative colitis:—pain, diarrhea, constipation, rectal bleeding, fever, arthritis; asthma:—shortness of breath, wheezing; other allergy disorders, such as allergic rhinitis:—sneezing, itching, runny nose conditions associated with acute trauma such as cerebral injury following stroke-sensory loss, motor loss, cognitive loss; heart tissue injury due to myocardial ischemia:—pain, shortness of breath; lung injury such as that which occurs in adult respiratory distress syndrome:—shortness of breath, hyperventilation, decreased oxygenation, pulmonary infiltrates; inflammation accompanying infection, such as sepsis, septic shock, toxic shock syndrome:—fever, respiratory failure, tachycardia, hypotension, leukocytosis; other inflammatory conditions associated with particular organs or tissues, such as: (i) nephritis (e.g., glomeralonephritis):—oliguria, abnormal urinalysis; (ii) inflamed appendix:—fever, pain, tenderness, leukocytosis; (iii) gout:—pain, tenderness, swelling and erythema of the involved joint, elevated serum and/or urinary uric acid; (iv) inflamed gall bladder:—abdominal pain and tenderness, fever, nausea, leukocytosis; (v) congestive heart failure:—shortness of breath, rales, peripheral edema; (vi) Type II diabetes:—end organ complications including cardiovascular, ocular, renal, and peripheral vascular disease; (vii) lung (pulmonary) fibrosis:—hyperventilation, shortness of breath, decreased oxygenation; (viii) vascular disease, such as atherosclerosis and restenosis:—pain, loss of sensation, diminished pulses, loss of function; and (ix) alloimmunity leading to transplant rejection:—pain, tenderness, fever.

Neurodegenerative Disease

Another aspect of the present invention is directed to the use of the inventive compound and/or combination as a therapeutic agent for the prophylaxis and/or treatment of Neurodegenerative Disease. Exemplary active agents include, for example, ORG34517, PT150, PT155, PT156, PT157, PT158, TCY1, combinations thereof, and pharmaceutically acceptable salts thereof.

The present invention also relates generally to the fields of neurology and psychiatry and to methods of protecting the cells of a mammalian central nervous system from damage or injury. Injuries or trauma of various kinds to the central nervous system (CNS) or the peripheral nervous system (PNS) can produce profound and long-lasting neurological and/or psychiatric symptoms and disorders. One form that this can take is the progressive death of neurons or other cells of the central nervous system (CNS), i.e., neurodegeneration or neuronal degeneration. Neuronal degeneration as a result of, for example; Alzheimer's disease, multiple sclerosis, cerebral-vascular accidents (CVAs)/stroke, traumatic brain injury, spinal cord injuries, degeneration of the optic nerve, e.g., ischemic optic neuropathy or retinal degeneration and other central nervous system disorders is an enormous medical and public health problem by virtue of both its high incidence and the frequency of long-term sequelae. Animal studies and clinical trials have shown that amino acid transmitters (especially glutamate), oxidative stress and inflammatory reactions contribute strongly to cell death in these conditions. Upon injury or upon ischemic insult, damaged neurons release massive amounts of the neurotransmitter glutamate, which is excitotoxic to the surrounding neurons. Glutamate is a negatively charged amino acid that is an excitatory synaptic transmitter in the mammalian nervous system. Although the concentration of glutamate can reach the millimolar range in nerve terminals its extracellular concentration is maintained at a low level to prevent neurotoxicity. It has been noted that glutamate can be toxic to neurons if presented at a high concentration. The term "excitotoxicity" has been used to describe the cytotoxic effect that glutamate (and other such excitatory amino acids) can have on neurons when applied at high dosages.

Patients with injury or damage of any kind to the central (CNS) or peripheral (PNS) nervous system including the retina may benefit from neuroprotective methods. This nervous system injury may take the form of an abrupt insult or an acute injury to the nervous system as in, for example, acute neurodegenerative disorders including, but not limited to; acute injury, hypoxia-ischemia or the combination thereof resulting in neuronal cell death or compromise. Acute injury includes, but is not limited to, traumatic brain injury (TBI) including, closed, blunt or penetrating brain trauma, focal brain trauma, diffuse brain damage, spinal cord injury, intracranial or intravertebral lesions (including, but not limited to, contusion, penetration, shear, compression or laceration lesions of the spinal cord or whiplash shaken infant syndrome).

In addition, deprivation of oxygen or blood supply in general can cause acute injury as in hypoxia and/or ischemia including, but not limited to, cerebrovascular insufficiency, cerebral ischemia or cerebral infarction (including cerebral ischemia or infarctions originating from embolic occlusion and thrombosis, retinal ischemia (diabetic or otherwise), glaucoma, retinal degeneration, multiple sclerosis, toxic and ischemic optic neuropathy, reperfusion following acute ischemia, perinatal hypoxic-ischemic injury, cardiac arrest or intracranial hemorrhage of any type (including, but not limited to, epidural, subdural, subarachnoid or intracerebral hemorrhage).

Trauma or injury to tissues of the nervous system may also take the form of more chronic and progressive neurodegenerative disorders, such as those associated with progressive neuronal cell death or compromise over a period of time including, but not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases (amyotrophic lateral sclerosis), multiple sclerosis, degenerative ataxias, cortical basal degeneration, ALS-Parkinson's-dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease or spinocerebellar ataxia type 3 and olivopontocerebellar degenerations, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome) or prion diseases (including, but not limited to Creutzfeld-Jakob disease, Gerstmann-Strussler-Scheinker disease, Kuru disease or fatal familial insomnia).

In addition, trauma and progressive injury to the nervous system can take place in various psychiatric disorders, including but not limited to, progressive, deteriorating forms of bipolar disorder or schizoaffective disorder or schizophrenia, impulse control disorders, obsessive compulsive disorder (OCD), behavioral changes in temporal lobe epilepsy and personality disorders. In one preferred embodiment the compounds and/or compositions of the invention would be used to provide neuroprotection in disorders involving trauma and progressive injury to the nervous system in various psychiatric disorders. These disorders would be selected from the group consisting of; schizoaffective disorder, schizophrenia, impulse control disorders, obsessive compulsive disorder (OCD) and personality disorders.

In addition, trauma and injury make take the form of disorders associated with overt and extensive memory loss including, but not limited to, neurodegenerative disorders associated with age-related dementia, vascular dementia, diffuse white matter disease (Binswanger's disease), dementia of endocrine or metabolic origin, dementia of head trauma and diffuse brain damage, dementia pugilistica or frontal lobe dementia, including but not limited to Pick's Disease.

Other disorders associated with neuronal injury include, but are not limited to, disorders associated with chemical, toxic, infectious and radiation injury of the nervous system including the retina, injury during fetal development, prematurity at time of birth, anoxic-ischemia, injury from hepatic, glycemic, uremic, electrolyte and endocrine origin, injury of psychiatric origin (including, but not limited to, psychopathology, depression or anxiety), injury from peripheral diseases and plexopathies (including plexus palsies) or injury from neuropathy (including neuropathy selected from multifocal, sensory, motor, sensory-motor, autonomic, sensory-autonomic or demyelinating neuropathies (including, but not limited to Guillain-Barre syndrome or chronic inflammatory demyelinating polyradiculoneuropathy) or those neuropathies originating from infections, inflammation, immune disorders, drug abuse, pharmacological treatments, toxins, trauma (including, but not limited to compression, crush, laceration or segmentation traumas), metabolic disorders (including, but not limited to, endocrine or paraneoplastic), Charcot-Marie-Tooth disease (including, but not limited to, type 1a, 1b, 2,4a or 1-X linked), Friedreich's ataxia, metachromatic leukodystrophy, Refsum's disease, adrenomyeloneuropathy, ataxia-telangiectasia, Djerine-Sottas (including, but not limited to, types A or B), Lambert-Eaton syndrome or disorders of the cranial nerves).

Further indications are cognitive disorders. The term "cognitive disorder" shall refer to anxiety disorders, delirium, dementia, amnestic disorders, dissociative disorders, eating disorders, mood disorders, schizophrenia, psychotic disorders, sexual and gender identity disorders, sleep disorders, somatoform disorders, acute stress disorder, obsessive-compulsive disorder, panic disorder, posttraumatic stress disorder, specific phobia, social phobia, substance withdrawal delirium, Alzheimer's disease, Creutzfeldt-Jakob disease, head trauma, Huntington's disease, HTV disease, Parkinson's disease, Pick's disease, learning disorders, motor skills disorders, developmental coordination disorder, communication disorders, phonological disorder, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, pica, rumination disorder, tic disorders, chronic motor or vocal tic disorder, Tourette's disorder, elimination disorders, encopresis, enuresis, selective mutism, separation anxiety disorder, dissociative amnesia, depersonalization disorder, dissociative fugue, dissociative identity disorder, anorexia nervosa, bulimia nervosa, bipolar disorders, schizophreniform disorder, schizoaffective disorder, delusional disorder, psychotic disorder, shared psychotic disorder, delusions, hallucinations, substance-induced psychotic disorder, orgasmic disorders, sexual pain disorders, dyspareunia, vaginismus, sexual dysfunction, paraphilias, dyssomnias, breathing-related sleep disorder, circadian rhythm sleep disorder, hypersomnia, insomnia, narcolepsy, dyssomnia, parasomnias, nightmare disorder, sleep terror disorder, sleepwalking disorder, parasomnia, body dysmorphic disorder, conversion disorder, hypochondriasis, pain disorder, somatization disorder, alcohol related disorders, amphetamine related disorders, caffeine related disorders, *cannabis* related disorders, cocaine related disorders, hallucinogen related disorders, inhalant related disorders, nicotine related disorders, opioid related disorders, phencyclidine-related disorder, abuse, persisting amnestic disorder, intoxication, withdrawal.

The term "bipolar and clinical disorders" shall refer to adjustment disorders, anxiety disorders, delirium, dementia, amnestic and other cognitive disorders, disorders usually first diagnosed in infancy (e.g.), childhood, or adolescence, dissociative disorders (e.g. dissociative amnesia, depersonalization disorder, dissociative fugue and dissociative identity disorder), eating disorders, factitious disorders, impulse-control disorders, mental disorders due to a general medical condition, mood disorders, other conditions that may be a focus of clinical attention, personality disorders, schizophrenia and other psychotic disorders, sexual and gender identity disorders, sleep disorders, somatoform disorders, substance-related disorders, generalized anxiety disorder (e.g. acute stress disorder, posttraumatic stress disorder), panic disorder, phobia, agoraphobia, obsessive-compulsive disorder, stress, acute stress disorder, anxiety neurosis, nervousness, phobia, posttraumatic stress disorder, posttraumatic stress disorder (PTSD), abuse, obsessive-compulsive disorder (OCD), manic depressive psychosis, specific phobias, social phobia, adjustment disorder with anxious features.

Examples for disorders usually first diagnosed in infancy, childhood, or adolescence are: mental retardation, learning disorders, mathematics disorder, reading disorder, disorder of written expression, motor skills disorders, developmental coordination disorder, communication disorders, expressive language disorder, phonological disorder, mixed receptive-expressive language disorder, stuttering, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, feeding disorder of infancy or early childhood, pica, rumination disorder, tic disorders, chronic motor or vocal tic disorder, Tourette's syndrome, elimination disorders, encopresis, enuresis, selective mutism, separation anxiety disorder, reactive attachment disorder of infancy or early childhood, stereotypic movement disorder.

Examples for substance-related disorders are: alcohol related disorders, amphetamine related disorders, caffeine related disorders, *cannabis* related disorders, cocaine related disorders, hallucinogen related disorders, inhalant related disorders, nicotine related disorders, opioid related disorders, psychotic disorder, psychotic disorder, phencyclidine-related disorder, abuse, persisting amnestic disorder, anxiety disorder, persisting dementia, dependence, intoxication, intoxication delirium, mood disorder, psychotic disorder, withdrawal, withdrawal delirium, sexual dysfunction, sleep disorder.

The term "neuroprotection" as used herein shall mean; inhibiting, preventing, ameliorating or reducing the severity of the dysfunction, degeneration or death of nerve cells, axons or their supporting cells in the central or peripheral nervous system of a mammal, including a human. This includes the treatment or prophylaxis of a neurodegenerative disease; protection against excitotoxicity or ameliorating the cytotoxic effect of a compound (for example, a excitatory amino acid such as glutamate; a toxin; or a prophylactic or therapeutic compound that exerts an immediate or delayed cytotoxic side effect including but not limited to the immediate or delayed induction of apoptosis) in a patient in need thereof.

The term "a patient in need of treatment with a neuroprotective drug" as used herein will refer to any patient who currently has or may develop any of the above syndromes or disorders, or any disorder in which the patient's present clinical condition or prognosis could benefit from providing neuroprotection to prevent the development, extension, worsening or increased resistance to treatment of any neurological or psychiatric disorder.

The term "treating" or "treatment" as used herein, refers to any indicia of success in the prevention or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluations.

In some embodiments this invention provides methods of neuroprotection. In certain embodiments, these methods comprise administering a therapeutically effective amount of the composition and/or combination of the invention to a patient who has not yet developed overt, clinical signs or symptoms of injury or damage to the cells of the nervous system but who may be in a high risk group for the development of neuronal damage because of injury or trauma to the nervous system or because of some known predisposition either biochemical or genetic or the finding of a verified biomarker of one or more of these disorders.

Thus, in some embodiments, the methods and compositions of the present invention are directed toward neuroprotection in a subject who is at risk of developing neuronal damage but who has not yet developed clinical evidence. This patient may simply be at "greater risk" as determined by the recognition of any factor in a subject's, or their families, medical history, physical exam or testing that is indicative of a greater than average risk for developing neuronal damage. Therefore, this determination that a patient may be at a "greater risk" by any available means can be used to determine whether the patient should be treated with the methods of the present invention.

Accordingly, in an exemplary embodiment, subjects who may benefit from treatment by the methods and the composition and/or combination of this invention can be identified using accepted screening methods to determine risk factors for neuronal damage. These screening methods include, for example, conventional work-ups to determine risk factors including but not limited to: for example, head trauma, either closed or penetrating, CNS infections, bacterial or viral, cerebrovascular disease including but not limited to stroke, brain tumors, brain edema, cysticercosis, porphyria, metabolic encephalopathy, drug withdrawal including but not limited to sedative-hypnotic or alcohol withdrawal, abnormal perinatal history including anoxia at birth or birth injury of any kind, cerebral palsy, learning disabilities, hyperactivity, history of febrile convulsions as a child, history of status epilepticus, family history of epilepsy or any seizure related disorder, inflammatory disease of the brain including lupis, drug intoxication either direct or by placental transfer, including but not limited to cocaine poisoning, parental consanguinity, and treatment with medications that are toxic to the nervous system including psychotropic medications.

The determination of which patients may benefit from treatment with a neuroprotective drug in patients who have no clinical signs or symptoms may be based on a variety of "surrogate markers" or "biomarkers".

As used herein, the terms "surrogate marker" and "biomarker" are used interchangeably and refer to any anatomical, biochemical, structural, electrical, genetic or chemical indicator or marker that can be reliably correlated with the present existence or future development of neuronal damage. In some instances, brain-imaging techniques, such as computer tomography (CT), magnetic resonance imaging (MRI) or positron emission tomography (PET), can be used to determine whether a subject is at risk for neuronal damage. Suitable biomarkers for the methods of this invention include, but are not limited to: the determination by MRI, CT or other imaging techniques, of sclerosis, atrophy or volume loss in the hippocampus or overt mesial temporal sclerosis (MT S) or similar relevant anatomical pathology; the detection in the patient's blood, serum or tissues of a molecular species such as a protein or other biochemical biomarker, e.g., elevated levels of ciliary neurotrophic factor (CNTF) or elevated serum levels of a neuronal degradation product; or other evidence from surrogate markers or biomarkers that the patient is in need of treatment with a neuroprotective drug.

It is expected that many more such biomarkers utilizing a wide variety of detection techniques will be developed in the future. It is intended that any such marker or indicator of the existence or possible future development of neuronal damage, as the latter term is used herein, may be used in the methods of this invention for determining the need for treatment with the compounds and methods of this invention.

A determination that a subject has, or may be at risk for developing, neuronal damage would also include, for example, a medical evaluation that includes a thorough history, a physical examination, and a series of relevant bloods tests. It can also include an electroencephalogram (EEG), CT, MRI or PET scan. A determination of an increased risk of developing neuronal damage or injury may also be made by means of genetic testing, including gene expression profiling or proteomic techniques. For psychiatric disorders that may be stabilized or improved by a neuroprotective drug, e.g., bipolar disorder, schizoaffective disorder, schizophrenia, impulse control disorders, etc. the above tests may also include a present state exam and a detailed history of the course of the patients symptoms such as mood disorder symptoms and psychotic symptoms over time and in relation to other treatments the patient may have received over time, e.g., a life chart. These and other specialized and routine methods allow the clinician to select patients in need of therapy using the methods and formulations of this invention. In some embodiments of the present invention compounds and/or compositions suitable for use in the practice of this invention will be administered either singly or concomitantly with at least one or more other compounds or therapeutic agents, e.g., with other neuroprotective drugs or antiepileptic drugs, anticonvulsant drugs. In these embodiments, the present invention provides methods to treat or prevent neuronal injury in a patient. The method includes the step of; administering to a patient in need of treatment, an effective amount of the compounds and/or compositions disclosed herein in combination with an effective amount of one or more other compounds or therapeutic agents that have the ability to provide neuroprotection or to treat or prevent seizures or epileptogenesis or the ability to augment the neuroprotective effects of the compounds of the invention.

As used herein the term "combination administration" of a compound, therapeutic agent or known drug with the combination of the present invention means administration of the drug and the one or more compounds at such time that both the known drug and/or combination will have a therapeutic effect. In some cases this therapeutic effect will be synergistic. Such concomitant administration can involve concurrent (i.e. at the same time), prior, or subsequent administration of the drug with respect to the administration of the composition and/or combination of the present invention. A person of ordinary skill in the art would have no difficulty determining the appropriate timing, sequence and dosages of administration for particular drugs of the present invention.

The said one or more other compounds or therapeutic agents may be selected from compounds that have one or more of the following properties: antioxidant activity; NMDA receptor antagonist activity, augmentation of endogenous GABA inhibition; NO synthase inhibitor activity; iron binding ability, e.g., an iron chelator; calcium binding ability, e.g., a Ca (II) chelator; zinc binding ability, e.g., a Zn (II) chelator; the ability to effectively block sodium or calcium ion channels, or to open potassium or chloride ion channels in the CNS of a patient.

Heart and Vascular Disease

Another aspect of the present invention is directed to the use of the inventive compound and/or combination such as for example, ORG34517, PT150, PT155, PT156, PT157, PT158, TCY1, combinations thereof, and pharmaceutically acceptable salts thereof, as a therapeutic agent for the prophylaxis and/or treatment of heart disease. Heart disease is a general term used to describe many different heart conditions. For example, coronary artery disease, which is the most common heart disease, is characterized by constriction or narrowing of the arteries supplying the heart with oxygen-rich blood, and can lead to myocardial infarction, which is the death of a portion of the heart muscle. Heart failure is a condition resulting from the inability of the heart to pump an adequate amount of blood through the body. Heart failure is not a sudden, abrupt stop of heart activity but, rather, typically develops slowly over many years, as the heart gradually loses its ability to pump blood efficiently. Risk factors for heart failure include coronary artery disease, hypertension, valvular heart disease, cardiomyopathy, disease of the heart muscle, obesity, diabetes, and/or a family histoiy of heart failure.

Examples of cardiovascular diseases and disorders are: aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive card iomyopathy, hypertrophic cardiomyopathy, restrictive cardiomyopathy, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, cardiac hypertrophy, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, Sneddon syndrome, superior vena cava syndrome, syndrome X, tachycardia, Takayasu's arteritis, hereditary hemorrhagic telangiectasia, telangiectasis, temporal arteritis, tetralogy of Fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Vascular diseases are often the result of decreased perfusion in the vascular system or physical or biochemical injury to the blood vessel.

Peripheral vascular disease (PVD) is defined as a disease of blood vessels often encountered as narrowing of the vessels of the limbs. There are two main types of these disorders, functional disease which doesn't involve defects in the blood vessels but rather arises from stimuli such as cold, stress, or smoking, and organic disease which arises from structural defects in the vasculature such as atherosclerotic lesions, local inflammation, or traumatic injury. This can lead to occlusion of the vessel, aberrant blood flow, and ultimately to tissue ischemia.

One of the more clinically significant forms of PVD is peripheral artery disease (PAD). PAD is often treated by angioplasty and implantation of a stent or by artery bypass surgery. Clinical presentation depends on the location of the occluded vessel. For example, narrowing of the artery that supplies blood to the intestine can result in severe postprandial pain in the lower abdomen resulting from the inability of the occluded vessel to meet the increased oxygen demand arising from digestive and absorptive processes. In severe forms the ischemia can lead to intestinal necrosis. Similarly, PAD in the leg can lead to intermittent pain, usually in the calf, that comes and goes with activity. This disorder is known as intermittent claudication (IC) and can progress to persistent pain while resting, ischemic ulceration, and even amputation.

Peripheral vascular disease is also manifested in atherosclerotic stenosis of the renal artery, which can lead to renal ischemia and kidney dysfunction.

One disease in which vascular diseases and their complications are very common is diabetes mellitus. Diabetes mellitus causes a variety of physiological and anatomical irregularities, the most prominent of which is the inability of the body to utilize glucose normally, which results in hyperglycemia. Chronic diabetes can lead to complications of the vascular system which include atherosclerosis, abnormalities involving large and medium size blood vessels (macroangiopathy) and abnormalities involving small blood vessels (microangiopathy) such as arterioles and capillaries. Patients with diabetes mellitus are at increased risk of developing one or more foot ulcers as a result of established long-term complications of the disease, which include impaired nerve function (neuropathy) and/or ischemia. Local tissue ischemia is a key contributing factor to diabetic foot ulceration.

In addition to large vessel disease, patients with diabetes suffer further threat to their skin perfusion in at least two additional ways. First, by involvement of the non-conduit arteries, which are detrimentally affected by the process of atherosclerosis, and secondly, and perhaps more importantly, by impairment of the microcirculatory control mechanisms (small vessel disease). Normally, when a body part suffers some form of trauma, the body part will, as part of the body's healing mechanism, experience an increased blood flow. When small vessel disease and ischemia are both present, as in the case of many diabetics, this natural increased blood flow response is significantly reduced. This fact, together with the tendency of diabetics to form blood clots (thrombosis) in the microcirculatory system during low levels of blood flow, is believed to be an important factor in ulcer pathogenesis.

Neuropathy is a general term which describes a disease process which leads to the dysfunction of the nervous system, and is one of the major complications of diabetes mellitus, with no well-established therapies for either its symptomatic treatment or for prevention of progressive decline in nerve function.

The thickening and leakage of capillaries caused by diabetes primarily affect the eyes (retinopathy) and kidneys (nephropathy). The thickening and leakage of capillaries caused by diabetes are also associated with skin disorders and disorders of the nervous system (neuropathy).

The eye diseases associated with diabetes are nonproliferative diabetic retinopathy, proliferative diabetic retinopathy, diabetic maculopathy, glaucoma, cataracts and the like. Other diseases, although not known to be related to diabetes are similar in their physiological effects on the peripheral vascular system. Such diseases include Raynaud syndrome, CREST syndrome, autoimmune diseases such as erythematosis, rheumatoid disease, and the like.

As used herein, the term "peripheral vascular diseases" comprises any peripheral vascular disease including peripheral and autonomic neuropathies. Examples of "peripheral vascular disease" include peripheral arterial disease, such as chronic arterial occlusion including arteriosclerosis, arteriosclerosis obliterans and thromboangiitis obliterans (Buerger's disease), macroangiopathy, microangiopathy, diabetes mellitus, thrombophlebitis, phlebemphraxis, Raynaud's disease, Raynaud's syndrome, CREST syndrome, health hazard due to vibration, Sudeck's syndrome, intermittent claudication, cold sense in extremities, abnormal sensation in extremities, sensitivity to the cold, Meniere's disease, Meniere's syndrome, numbness, lack of sensation, anesthesia, resting pain, causalgia (burning pain), disturbance of peripheral circulation function, disturbance of nerve function, disturbance of motor function, motor paralysis, diabetic peripheral circulation disorder, lumbar spinal canal stenosis, diabetic neuropathy, shock, autoimmune disease such as erythematosis, rheumatoid disease and rheumatoid arthritis, autonomic neuropathy, diabetic autonomic neuropathy, autonomic imbalance, orthostatic hypotension, erectile dysfunction, female sexual dysfunction, retrograde ejaculation, cystopathy, neurogenic bladder, defective vaginal lubrication, exercise intolerance, cardiac denervation, heat intolerance, gustatory sweating, diabetic complication, hyperglycemia, hypoglycemia unawareness, hypoglycemia unresponsiveness; glaucoma, neovascular glaucoma, cataract, retinopathy, diabetic retinopathy, diabetic maculopathy, occlusion of retinal artery, obstruction of central artery of retina, occlusion of retinal vein, macular edema, aged macular degeneration, aged disciform macular degeneration, cystoid macular edema, palpebral edema, retinal edema, chorioretinopathy, neovascular maculopathy, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, damage of skin, skin ulcer including foot ulcer, diabetic ulcer, burn ulcer, lower leg ulcer, postoperative ulcer, traumatic ulcer, ulcer after herpes zoster, radiation ulcer, drug induced ulcer, frostbite (cold injury), chilblain, gangrene and sudden gangrene, angina pectoris/variant angiitis, coronary arteriosclerosis (chronic ischemic heart disease, asymptomatic ischemic heart disease, arteriosclerotic cardiovascular disease), myocardial infarction, heart failure, congestive heart failure and painless ischemic heart disease, pulmonary edema, hypertension, pulmonary hypertension; portal hypertension, diabetic nephropathy, decubitus, renal failure.

Formulations

The compounds and compositions of the invention, such as for example, ORG34517, PT150, PT155, PT156, PT157, PT158, TCY1, combinations thereof, and pharmaceutically acceptable salts thereof, may be administered at a dose of less than 400 mg/day. In some embodiments, the compounds and compositions of the invention are administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 190 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. In certain embodiments, the compounds of the invention are administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 190 mg/day, less than 200 mg/day, less than 225 mg/day, less than 250 mg/day, less than 275 mg/day, less than 300 mg/day, less than 325 mg/day, less than 350 mg/day, less than 375 mg/day, less than 400 mg/day, less than 425 mg/day, less than 450 mg/day, less than 475 mg/day, or less than 500 mg/day. In some embodiments, the compounds of the invention are administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 190 mg/day, more than 200 mg/day, more than 225 mg/day, more than 250 mg/day, more than 275 mg/day, more than 300 mg/day, more than 325 mg/day, more than 350 mg/day, more than 375 mg/day, more than 400 mg/day, more than 425 mg/day, more than 450 mg/day, more than 475 mg/day, or more than 500 mg/day.

The compounds and compositions of the invention may be administered enterally or parenterally. Mixed with pharmaceutically suitable auxiliaries, e.g., as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g., tablets, the use of conventional additives such as fillers, colorants, polymeric binders and the like is contemplated, hi general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The activities of GR agonists and their alteration of cellular functions are variable, depending on complex intracellular molecular signaling that are cell and tissue specific. Amongst the cells that have glucocorticoid receptors are stem and progenitor cells of all tissues and organs of the body. Thus, binding of such molecules to normative, "in-tissue" stem cells and the progeny of these stem cells, so-called "transit amplifying" progenitor cells, results in variable, cell and tissue specific effects, inhibitory or enhancing of stem and progenitor cell functions, including activation, proliferation, migration and differentiation all of which are dependent on the tissue/organ in question.

GR antagonists or active agents, such as, for example, ORG 34517, PT150, PT155, PT156, PT157, PT158, TCY1, combinations thereof, and pharmaceutically acceptable salts thereof, will thus block the effects of GR-agonists in tissue specific fashion, enhancing stem/progenitor cell functioning in some, inhibiting it in others. GR-antagonists will have beneficial effects in specific clinical settings where regenerative medicine approaches to disease and wound healing may be of use, including: enhanced post-transplant functioning of autologous stem cell transplants (dependent on tissue of origin and/or target tissue).

Attenuation of the peri-surgical effects of catabolic stress hormones related to surgical or other physical traumas (e.g. combat wounds), wherein the acute or chronic injury or disease is selected from the group consisting of vascular events, stroke, cardiac arrest, acute limb infarction accident/battle field trauma, traumatic limb, hip, brain injuries, post-surgical trauma, major orthopedic, thoracic, abdominal, neurological surgeries.

Systemic GR blockade will be inappropriate, but direct application of ORG 34517, PT150, PT155, PT156, PT157, PT158, TCY1, combinations thereof, and pharmaceutically acceptable salts thereof to site of injury/wounding, either topically (for example, to prevent wound dehiscence) or by direct injection or intravascular infusion (for visceral organ injuries) will be beneficial.

Cortisol

The estimated daily cortisol production rate in normal subjects varies between 4-15 mg/m.sup.2 per day or, according to more recent studies between 9 and 11 mg/m.sup.2 per day. In order to describe the 24-hour variation in serum cortisol levels adequately, the day may be divided into, for example, four phases. Phase 1 is a 6-hours period of minimal secretory activity 4 h before and 2 h after onset of sleep. Phase 2 refers to the 3rd to 5th hours of sleep when there is a preliminary nocturnal secretory episode. Phase 3 is a 4-hour main secretory phase during the last 3 h of sleep and the first hour after wakening. Phase 4 is an 11-hour phase of intermittent secretory activity when there is a slow decline in serum levels of cortisol.

In a study by Mah et al. (Clinical Endocrinology (2004) 61, 367-375) the circadian rhythm of serum cortisol of normal subjects is described. Peak levels of about 400-800 mmol/1, about 150-300 mmol/1 and about 150 mmol/1 are observed at about 6 am, 2 pm and 9 pm, respectively, and the lowest level is about midnight. In this study it is observed that the endogenous cortisol levels reach their highest levels within 30 minutes after wake-up. In order to mimic the circadian rhythm, Mah et al. recommend a thrice-daily treatment regimen of hydrocortisone, the first dose taken in the fasted state and delaying the breakfast 1-3 hours and the other two doses taken 15-60 min before food. A trice-daily regimen is also recommended in a recent review by Czock et al. (Clin. Pharmacokinet (2005) 44, 61-98) due to the short half-life of hydrocortisone, and for prednisolone a twice-daily regimen is preferred over a once-daily regimen.
Cortisol Test The absence of rapid response and inexpensive testing for cortisol has, heretofore, prevented the linking of GCR antagonists or active agents (e.g., ORG 34517, PT150, PT155, PT156, PT157, PT158, TCY1, combinations thereof, and pharmaceutically acceptable salts thereof) to a cortisol pre-test for entry into clinical trials for GCR antagonists and will inhibit the ability to select the patients most likely to receive the benefit of treatment with the compounds when available for clinical use. The invention provides the pairing of an affordable, real-time cortisol test (e.g., PopTest Cortisol) which will enable the successful completion of clinical trials for this class of drugs as well as form the basis for their future, anticipated therapeutic use(s).

Conditions that may be treated using, for example, a linked salivary cortisol quantification test and GCR antagonist or active agent (e.g., ORG 34517, PT150, PT155, PT156, PT157, PT158, TCY1, combinations thereof, and pharmaceutically acceptable salts thereof) system include, but are not limited to the following:
Major Depressive Disorder (MDD).

MDD is a psychiatric disorder which has a lifetime prevalence of around 8%. One of the most consistent findings in psychiatry is that patients with major depression present with alterations in the hypothalamic-pituitary-adrenal (HPA) axis. A significant percentage of depressed patients exhibit hypersecretion cortisol, as manifested by elevated plasma, cerebrospinal fluid, and salivary concentrations of cortisol and increased urinary free cortisol. In addition, many depressed patients exhibit a clear inability to switch off endogenous cortisol release following exogenous challenge with the potent synthetic glucocorticoid dexamethasone (the so-called dexamethasone non-suppressors) (Gold P. W., et al., Clinical and biochemical manifestations of depression: relation to neurobiology of stress. New England J. Med. 319, 413-420, 1988). This 'sub-group' of severely compromised patients are most often the ones in whom depression becomes a life-threatening illness that warrants hospitalization.

Other abnormalities of the HPA axis found in depressed patients are increased cortisol response to corticotrophin, a blunted corticotrophin response to CRH (corticotrophin releasing hormone), and adrenal and pituitary enlargement (for a review see Holsboer, F. and Barden, N.: Endocrine Reviews 1996, 17, 187-205).

These observations have been interpreted to suggest a causal relationship between disturbed functioning of the HPA axis and the pathology of depression (Murphy, B. E. P. J. of Steroid Biochem. and Mol. Biol. 1991, 38, 537-559). Therapeutic efficacy of classical antidepressants has been shown to be preceded by or to coincide with restoration of the disturbed HPA axis in depression (Holsboer and Barden, 1996, supra). It has been postulated that any intervention which can restore this HPA dysfunction may have antidepressant potential.

One type of such intervention, studies of which support the impression that HPA-axis functioning and high circulating cortisol is a major instigator of major depression is the administration of glucocorticoid synthesis inhibitors, as has been shown in patients suffering from Cushing's Syndrome, which is a condition in which high cortisol levels are reported as a result of adrenal gland malfunction (due to a pituitary tumour or a secondary tumour, both producing the cortisol secretagogue ACTH). The depressive symptoms associated with Cushing's disappear relatively quickly with the return of cortisol levels to normal. Such treatment may involve removal of the offending tumour or treatment with cortisol synthesis inhibitors such as metyrapone, ketoconozole, or aminoglutethimide (Murphy, B. E. P, Steroids and Depression. J. Steroid Biochem & Mol. Biol. 38, 537-558, 1991). Similarly, relatively recent clinical trials have demonstrated that cortisol synthesis inhibitors can be used to ameliorate depressive symptoms in severe, treatment-resistant non-Cushing depressives (Murphy, B. E. P, Can. J. Psych. 43, 279-286, 1998; see also U.S. Pat. No. 4,814,333 (Ravaris, C. L.)).

Another type of intervention is the use of direct GCR antagonists, which have much more specific pharmacological effects as compared to synthesis inhibitors and which may help restore HPA activity. Small scale pilot clinical studies have been conducted in order to study the antidepressant activity of the non-selective glucocorticoid receptor antagonist RU 486 (mifepristone; Murphy, B. E. P. et al. J. Psychiat. Neurosc. 18, 209-213, 1993). More recently (Nemeroff, C., Remeron Scientific Expert Meeting, Budapest, Mar. 29-Apr. 1, 2001) it was demonstrated in a Phase IIB continuation of this study, that both the number of responders as well as the efficacy of the psychosis treatment increased with increasing daily dose of mifepristone as measured by the change in Brief Psychiatric Rating Scale (50 mg-33% change; 600 mg-40% change and 1200 mg-52% change). These data indicate that a higher dose of glucocorticoid receptor antagonist and/or active agent is correlated with a higher clinical efficacy.

Non-response to standard treatments, however, reach levels as high as 50%. (Connolly K R, Drugs. 2011; 71: 43-64.) Frequently, extra interventions are necessary to get patients to achieve remission. Various augmentation and combination strategies have been described in the literature for difficult to treat major MMD patients.

Use of an HPA-axis modulating drug in these patients has not been studied in spite of the fact that there is clear evidence that at least a sub-group of MDD patients have significant HPA-axis dysfunction, as noted above. Biological symptoms, indicative of excessive activity of the HPA-axis, have been reported with great consistency. In parallel, there is a body of evidence suggesting that there is an association between HPA-axis functioning and treatment response, where high HPA-axis activation at baseline, or post-treatment, is associated with a poorer response to SSRI treatment or a higher relapse risk.

Preclinical studies indicate that HPA-axis dysfunction of the type seen in affective disorders can attenuate the neurochemical effects of a selective serotonin re-uptake inhibitor (SSRI) antidepressant. Conversely, in animals with normal HPA axis function, co-administration of GR antagonists augmented the neurochemical effects of an SSRI. These data provide a mechanistic underpinning of the GR antagonist augmentation strategy, and moreover indicate that the strategy may prove efficacious in patients both with and without HPA axis dysfunction.

Small scale pilot clinical studies were conducted in order to study the antidepressant activity of the non-selective glucocorticoid receptor antagonist RU 486 (mifepristone; Murphy, B. E. P. et al. J. Psychiat. Neurosc. 18, 209-213, 1993). A double blind, 4 week, paroxetine controlled study of PT150 (ORG 34517) in depressed patients was carried out. Paroxetine is a selective serotonin re-uptake inhibitor which is recognized as an effective antidepressant for major depression. Patients were selected which had a primary depressive disorder fulfilling the diagnostic criteria of a MDD as defined by the DSM-IV for recurrent (296.3) episodes, and who had a severity of depression which resulted in a total score of at least 22 on the HAMD-21 (Hamilton Rating Scale for Depression; see Hamilton, M. "A rating scale for depression." J. Neurol. Neurosurg. Psychiat. 1960, 23, 56-62) scale at baseline. Patients had an episode of depression which had lasted at least 2 weeks before baseline. In this study, patients were randomly allocated to one of three treatment groups. Group I patients (50 patients) received 2 capsules with 75 mg of PT150 and one placebo (total daily dose 150 mg) for the first 2 weeks and 2 capsules with 75 mg PT150 and 1 capsule with 150 mg (total daily dose 300 mg) the next 2 weeks; Group II patients (46 patients) received 3 capsules with 150 mg PT150 (total daily dose 450 mg) in the first 2 weeks and 4 capsules of PT150 (total daily dose 600 mg) in the next 2 weeks; Group III patients (44 patients) received 2 capsules with 10 mg paroxetine and one placebo capsule (total daily dose 20 mg) for the first 2 weeks, followed by 2 capsules of 10 mg and one capsule of 20 mg paroxetine (total daily dose 40 mg) in the next 2 weeks. Medication was administered orally in the morning. Efficacy assessment was done on days 4, 7, 10, 14, 21, 28 and 35 by using the 21-item HAMD scale.

Thus, GCR antagonist or active agent therapy could prove a useful mechanism for treatment of selected individuals who fail to respond to current anti-depressant therapies such as SSRIs, providing a way to enhance responsiveness or as an alternate means of achieving a maintained euthymia.

Psychotic Depression.

The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of psychotic depression. Psychotic major depression has long been recognized as a distinct psychiatric illness, having both psychotic and depressive components in a differential diagnosis. Psychotic major depression is very common. It has been estimated that twenty five percent of depressed patients admitted to the hospital have psychotic major depression (Coryell (1984) J. Nerv. Ment. Dis. 172: 521). Like major depression, psychotic depression is often also a result of high circulating cortisol levels. Various evidence supports this concept. Psychosis has been associated with Cushing's syndrome (Gerson (1985) Can. J. Psychiatry 30:223-224; Saad (1984) Am. J. Med. 76:759-766). A GR antagonist has been used to treat acute psychiatric disturbances secondary to Cushing's syndrome. One study showed that a relatively high dose of such a GR antagonist (400 to 800 mg per day) was useful in rapidly reversing acute psychosis in patients with severe Cushing's' Syndrome due to adrenal cancers and ectopic secretion of ACTH from lung cancer (Van der Lely (1991) Ann. Intern. Med. 114:143; Van der Lely (1993) Pharmacy World & Science 15:89-90; Sartor (1996) supra). Relatively high dose mifepristone, in the range of 8-12 mg/kg/day, over a relatively short period of time (4 days), was also shown to be effective in the treatment of psychosis associated with psychotic major depression (International Patent Application WO 99/17779; Schatzberg and Belanoff).

Surgery-Associated Immune Suppression in the Elderly.

In healthy, young to middle aged subjects suffering from stress, there is a physiological balance between pro-inflammatory and anti-inflammatory mediators. In the elderly, the immune response is blunted as a result of the decline in several components of the immune system (immune senescence) and a shifting to a chronic pro-inflammatory status (the so-called "inflammaging" effect (Butcher and Lord, (2004) Aging Cell, pp. 151-160).

As production of cortisol remains reasonably constant with age, whereas summed levels of DHEA and DHEAS decrease gradually from the third decade, reaching 10-20% of their maximum by the eighth decade, Butcher and Lord (2004, supra) propose a model for age and stress, in which the age-related increase in the ratio of cortisol to DHEAS, combined with an elevated cortisol release during stress, leads to a significant reduction of immunity in aging subjects. This is proposed to explain that aging subjects are far more prone to infections under conditions of stress. (Butcher and Lord (2004, supra); Butcher et al. (2005, Aging Cell 5, pp. 319-324).

The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of infections or infectious conditions, in an aging patient, such as a human subject. The beneficial effects of said GCR antagonists may be explained on the basis of their correcting influence on the cortisol/DHEA(S) ratio. It is believed that the effect in selected subjects, found to have high circulating cortisol by a saliva test as provided for by this invention, can be explained by the unbalanced immunosuppressive role of the increased cortisol/DHEAS ratio in the aged group in comparison to the balanced influence of cortisol and DHEAS on the immune system in normal subjects.

The meaning of the term 'aging subject' or 'aged subject' will be well understood in the context of the use according to this invention. Although it is not linked to an exact lower age limit this general notion refers in the human situation usually to a person of at least 55 years old, but it is more clear with a lowest age limit set at 60, 65, 70 or 75 years.

In the context of the invention, the infection or infectious condition can be caused by any of several agents, e.g., by bacteria, by viruses or by fungi. Also in the context of the present invention, the expression "infectious conditions" means silent or subclinical infections as well as conditions not resulting in a manifest infectious disease, but in which at least one parameter associated with an infectious disease, such as the white blood (e.g., neutrophil, basophil or eosinophil) cell counts or the level of some antibodies or some cytokines is higher than normal. Normal values are known to the expert and may be found in standard medical manuals.

Particular uses according to the invention relate to aging subjects suffering from an infection or an infectious condition concomitant to stress resulting from a trauma. The invention particularly relates to uses wherein the subject suffers from the consequences of a bone fracture and/or bone surgery, either for such injury or for joint replacement for osteoarthritis or rheumatoid arthritis. The invention also relates to uses wherein the subject suffers from an infection or an infectious condition concomitant to psychological stress, particularly acute emotional stress.

Post Traumatic Stress Disorder (PTSD).

PTSD is a severe anxiety disorder that can develop after exposure to any event that results in psychological trauma. This event may involve the threat of death to oneself or to someone else, or to one's own or someone else's physical, sexual, or psychological integrity, overwhelming the individual's ability to cope. As an effect of psychological trauma, PTSD is less frequent and more enduring than the more commonly seen acute stress response. Diagnostic symptoms for PTSD include re-experiencing the original trauma(s) through flashbacks or nightmares, avoidance of stimuli associated with the trauma, and increased arousal, such as difficulty falling or staying asleep, anger, and hyper-vigilance. Formal diagnostic criteria (both DSM-IV-TR and ICD-9) require that the symptoms last more than one month and cause significant impairment in social, occupational, or other important areas of functioning. (Diagnostic and statistical manual of mental disorders: DSM-IV. American Psychiatric Association. 1994. Washington, D.C.: American Psychiatric Association.) PTSD displays biochemical changes in the brain and body that differ from other psychiatric disorders such as major depression. Abundant evidence suggests derangement of HPA-axis physiology in individuals diagnosed with PTSD, though the nature of the derangements is variable: some have low cortisol, some have normal levels, others have high levels of cortisol and for some, levels may be normal, but circadian rhythm is lost. It is postulated that these reflect different baseline mechanisms, but that when cortisol is high, either in a sustained way through the day or by loss of circadian rhythm with elevated night time levels, it is likely to be an important component of the clinical symptomatology (Lindley S E, et al. Basal and dexamethasone suppressed salivary cortisol concentrations in a community sample of patients with posttraumatic stress disorder. Biol. Psychiatry 2004; 55: 940-5). In such patients, determined by salivary cortisol testing, administration of a GCR antagonist is expected to be therapeutic or beneficial for the symptoms of PTSD. Prevention of Weight Gain in Patients Using Anti-Psychotic and Anti-Depressant Medications. Anti-psychotic and some anti-depressant medications (e.g., SSRIs) are amongst the most important tools for treating psychiatric conditions of all kinds. However, management of patients on who take many of these medications for chronic, long term disease is made difficult by their significant side effect profiles. One of the most important of these is weight gain and the attendant metabolic syndrome that follows. For example, it is estimated that 40-80% of patients who are under chronic anti-psychotic administration experience substantial weight gain, often exceeding 20% or more over their ideal body weights (Umbricht et al. J. Clin. Psychiatry 1994; 55: 157-160; Khan A Y, et al. J Psychiatr Pract. 2010; 16: 289-96; Pramyothin P, Khaodhiar L. Curr Opin Endocrinol Diabetes Obes. 2010; 17: 460-6; Rummel-Kluge C et al. Schizophr Res. 2010; 123: 225-33). Such weight gain is one of the most common causes of poor compliance with anti-psychotic and anti-depressant regimens and, therefore, of long term failure of therapy. Furthermore, anti-psychotic medications specifically are commonly associated with development of insulin resistance and metabolic syndrome (with development of type 2 diabetes mellitus and hyper/dyslipidemia states) and the potentially and significantly increased risks for cardiovascular disease; these conditions are of tremendous medical consequence for patients who are thereby caught in a "can't live with them, can't live without them" treatment scenario. While weight gain is potentially seen with all anti-psychotic medications, they are particularly common and tend to more severe with the newer or "atypical" AP drugs (Allison et al. Am J Psychiatry 1999; 156:1686-1696; Rummel-Kluge C et al. Schizophr Res. 2010; 123: 225-33).

Elevations in cortisol are associated with changes in body fat and insulin resistance. Several years ago, in a proof of principle clinical experiment, it was reported that one GCR anatogonist (mifepristone) was a highly effective treatment for multiple medical complications in a patient with Cushing's disease whose illness had not responded to surgery and radiation, including reversal of insulin dependent diabetes: the patient was able to stop insulin within a month (Chu et al., J. Clin. Endocrinol. Metab. 2001; 86, 3568-3573). These data suggest that a GCR antagonist could be useful for blocking and reversing the insulin resistance and weight changes seen in some patients treated with atypical antipsychotic agents. To this end, this compound was tested in rats who had olanzapine-induced weight gain and increases in abdominal fat; reversal of weight gain was seen and reduction of abdominal fat was obtained (Beebe et al. Behav. Brain Res. 2006; 171, 225-229). A clinical trial with this compound then confirmed this benefit in humans with a 2 week study of 600 mg/day of mifepristone that reduced olanzapine-induced weight gain in 57 non-overweight healthy males with Body Mass Indices less than 25 (Gross et al., Adv Ther. 2009; 26: 959-69). Thus, GCR antagonist or active agent therapy could prove a useful mechanism to target in treating psychotic patients with atypical antipsychotic agents. The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of PTSD.

Cushing's Syndrome

Cushing's Syndrome is a set of conditions in which high levels of circulating cortisol or other GCR agonists cause a set of seriously debilitating and sometimes life threatening signs and symptoms including, but not limited to, psychiatric disturbances (e.g. anxiety, depression, psychosis), immunosuppression, insulin resistance and metabolic syndrome, skin conditions, hypertension and osteoporosis. Endogenous cortisol may be produced by ACTH-secreting, benign or malignant tumors of the pituitary gland ("Cushing's Disease") or of the adrenal cortex. These are rare conditions and therefore Cushing's Syndrome is considered an "orphan disease."

A proof of concept trial using RU486 to treat patients with tumor-related Cushing's Syndrome demonstrated efficacy in remitting symptoms such as glucose metabolic abnormalities (i.e., glucose intolerance; (group 1) and hypertension (group 2). Statistically significant improvement was achieved for both groups: with 60% responding in the glucose intolerant group and 43% in the hypertensive group (Corcept Therapeutics Press Release Dec. 22, 2010). Thus, GCR antagonist or active agent therapy can be expected to provide clinical benefits for patients with Cushing's Syndrome administered prior to tumor surgery to improve surgical outcomes and/or post-surgery to mitigate symptoms in patients for whom surgical cure is not achievable.

In addition, GCR antagonist or active agent therapy can be expected to provide clinical benefits for patients, for example, in hospitals, nursing homes, nurseries, daycares, schools, work environments, public transportation, healthcare settings, psychiatric institutions, and long-term nursing facilities.

The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of Cushing's Syndrome.

Diagnostic Systems and Kits

A diagnostic kit may comprise some or all of the following components: 1) one or more standards comprised of one or more of the biomarker(s) of the invention, such as cortisol; 2) a ligand, such as an antibody or a plurality of antibodies, that are specific for the biomarker(s) that are to be assayed for using the kit; 3) written instructions; 4) diluents for samples and the standards; 5) a wash buffer; 6) color reagents; 7) stop solution; and 8) a ligand carrier, such as an antibody carrier, for example, a lateral flow device, or a microplate with bound antibody, or polystyrene beads. An example of such a kit is a quantitative ELISA (enzyme-linked immunosorbent assay) that determines the concentration or concentrations of the biomarker or biomarker(s) in accordance with methods embodied by the invention. The principle of the assay is to use the quantitative sandwich enzyme immunoassay technique wherein a monoclonal or polyclonal antibody selective for a biomarker is pre-coated onto a carrier such as a microplate into its wells. The standards and sample are then pipetted into the wells and any of the biomarker that is present is bound to this immobilized antibody. Next, the wells are washed with washing buffer, and an enzyme-linked monoclonal or polyclonal antibody that is specific for the biomarker is added to the wells.

Washing is again performed, then a substrate solution is added to the wells. Color subsequently develops in proportion to the amount of polypeptide of the invention that is bound in the first step. The color development is stopped using a stop solution, and the intensity of the color is measured by a microplate reader.

The methods of the invention may be carried out using, for example, a lateral flow assay. Such lateral flow assays have the potential to be a cost-effective, fast, simple, and sensitive method, for instance for on-site screening assays. The lateral flow assay comprises a carrier that allows a lateral flow to occur wherein either the sample or the detection reagent is displaced form one location on the carrier to another. There are many formats of lateral flow assays suitable for use in a method embodied by the invention, and the skilled person will readily know how to select and optimize a particular format. An example of a lateral flow test strip of the invention comprises, for example, the following components:

Sample pad—an absorbent pad onto which the test sample is applied.

Conjugate or reagent pad—this contains antibodies specific to the target analyte conjugated to colored particles (usually colloidal gold particles, or latex microspheres).

Reaction membrane—typically a hydrophobic nitrocellulose or cellulose acetate membrane onto which antitarget analyte antibodies are immobilized in a line across the membrane as a capture zone or test line (a control zone may also be present, containing antibodies specific for the conjugate antibodies).

Wick or waste reservoir—a further absorbent pad designed to draw the sample across the reaction membrane by capillary action and collect it.

Double Antibody Sandwich Assays—

In this format the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result.

A single line in the control zone is a negative result. Double antibody sandwich assays are most suitable for larger analytes, such as bacterial pathogens and viruses, with multiple antigenic sites. Competitive assays are primarily used for testing small molecules and differ from the double antibody sandwich format in that the conjugate pad contains antibodies that are already bound to the target analyte, or to an analogue of it. If the target analyte is present in the sample it will therefore not bind with the conjugate and will remain unlabelled.

As the sample migrates along the membrane and reaches the capture zone, an excess of unlabelled analyte will bind to the immobilized antibodies and block the capture of the conjugate, so that no visible line is produced.

The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. Competitive assays are most suitable for testing for small molecules, such as mycotoxins, unable to bind to more than one antibody simultaneously. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed. Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory. However, their sensitivity is limited without additional concentration or culture procedures.

Quantitative Tests—

While most lateral flow immunoassays are only capable of providing a qualitative result, it is possible to obtain some degree of quantification by measuring the amount of conjugate bound to the capture zone. This can be done using a dedicated reader to measure the intensity of the colored test line. For example, the Neogen Corporation has developed the Accuscan™ lateral flow reader for use with its range of Reveal® assay kits and Charm Sciences also supplies a reader for its Rosa® range of mycotoxin test strips. More sophisticated techniques, such as fluorescent dye labeled conjugates, have also been developed to improve the quantitative potential of lateral flow assays. Applications in the 20 years since the first lateral flow test was launched have expanded to include a huge range of different tests that have been developed based on the same technology. The first commercially available kits were aimed at the clinical diagnostics field, but there are now products with applications in almost every branch of microbiology. Clinical microbiology—lateral flow tests have been developed for bacterial pathogens, respiratory and enteric viruses, intestinal parasites and bacterial toxins. Many of the lateral flow immunoassay products designed for the clinical sector were intended to be used at the point-of-care for direct testing of fecal, blood and urine samples and nose and throat swabs, where the simple operation and speed of the tests is key to their use outside of the laboratory. However, the same test strips may also be useful as a quick confirmatory test following laboratory culture of clinical samples. Food and agricultural microbiology—test strips are available for food borne bacterial pathogens, bacterial and fungal toxins. In the food microbiology sector, the main applications are more likely to be in the laboratory, although there are field test kits for mycotoxins in grain samples. Testing for food borne bacterial pathogens generally involves at least one enrichment stage before the assay strip is used to confirm the presence or absence of the pathogen. Some manufacturers, such as Dupont®, have developed enrichment media and methods specifically designed for use with lateral flow test strips. Test strips may also be useful for rapid confirmation of the identity of bacterial isolates from conventional microbiological testing.

A diagnostic system in kit form of the present invention includes, for example, in an amount sufficient for at least one assay, a polypeptide, antibody composition or monoclonal antibody composition of the present invention, as a packaged reagent. Instructions for use of the packaged reagent are also typically included.

A diagnostic system in kit form of the present invention may include, for example, a means for detecting the presence of a biological substance in a test sample, comprising for example, a lollipop-like apparatus including a stem integrated with the base and a head integrated with the stem, for collecting a test sample consisting of, for example, saliva, or a bodily fluid sample from a subject. The stem head may include a receptor of a sponge like carrier to ensure a high void volume to absorb sufficient saliva, or bodily fluid sample. See U.S. Pat. No. 7,993,283, incorporated by reference herein in its entirety.

A diagnostic system in kit form of the present invention may include, for example, a means for combining the test sample with a buffering system (Reagent 1) containing viscosity controllers and stabilizers into a reaction vessel and mixing the solution. A diagnostic system in kit form of the present invention may include, for example, a means for reading the a parameter of the reaction vessel with sample and buffer, and further means for combining the test sample and buffer mixture with a fluorescence-labeled ligand (Reagent 2) to said biological substance in the reaction vessel, mixing the solution to produce an assay solution. Furthermore, Reagent 2 may be delivered to the reaction vessel without further dilution volume of the assay solution.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such .sup.11lindium or ,sup.3H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfire et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of cortisol in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif., in 1982 and in U.S. Pat. Nos. 3,654,090; 3,850,752; and 4,016,043, which are all incorporated herein by reference.

Thus, for example, a polypeptide, antibody molecule composition or monoclonal antibody molecule composition of the present invention can be affixed to a solid matrix to form a solid support that comprises a package in the subject diagnostic systems. The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. In one embodiment a diagnostic system of the present invention is useful for assaying for the presence of, for example, cortisol. Such a system comprises, in kit form, a package containing an antibody to, for example, cortisol.

"Sample" refers to, for example, essentially any source from which materials of interest to be analyzed (e.g., ligands and antiligands, such as antibodies and antigens, and nucleic acids and their complements) can be obtained. A sample may be acquired from essentially any organism, including animals and plants, as well as cell cultures, recombinant cells and cell components. Samples can be from a biological tissue, fluid or specimen and may be obtained from a diseased or healthy organism. Samples may include, but are not limited to, saliva, sputum, amniotic fluid, blood, blood cells (e.g., white cells), urine, semen, peritoneal fluid, pleural fluid, tissue or fine needle biopsy samples, and tissue homogenates. Samples may also include sections of tissues such as frozen sections taken for histological purposes. Typically, samples are taken from a human. However, samples can be obtained from other mammals also, including by way of example and not limitation, dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

Biological samples can be derived from patients using well known techniques such as venipuncture, lumbar puncture, fluid sample such as saliva or urine, or tissue biopsy and the like. When the biological material is derived from non-humans, such as commercially relevant livestock, blood and tissue samples are conveniently obtained from livestock processing plants. Alternatively, a biological sample may be obtained from a cell or blood bank where tissue and/or blood are stored, or from an in vitro source, such as a culture of cells.

Techniques for establishing a culture of cells for use as a source for biological materials are well known to those of skill in the art.

In one embodiment the sample is selected from or is derived from, for example, microbial products or biological products.

Although the above described example relates to the antigens relating to disease, the immunoassay apparatus could be used, for example, as an allergy test kit, as a test kit for drugs of abuse or for analyzing non-human derived samples e.g. bovine, porcine, and veterinary tests. Specific reagents used in the assay device will be selected so as to ensure that the particular target analyte is detected as is well known in the art. The target analyte may be any analyte for example a chemical reagent which may be organic or inorganic, and which optionally comprises a hapten, a protein, a polypeptide, a microorganism or a nucleic acid sequence.

In particular, the analyte is a hormone such as a fertility hormone like progesterone or a stress hormone such as cortisol. However, there is a wide range of applications of these types of tests across the entire field of diagnostics and analysis. Detection of marker proteins or hormones can be diagnostic of certain disease conditions in humans or animals, and the presence of drugs or drug residues may also be required to be detected, for example, in animal husbandry, forensic medicine or in the testing for banned or prohibited drug substances.

Alternatively, the analyte is a chemical reagent, for instance a small molecule, which suitably comprises a hapten. Small molecules will generally comprise a single recognizable binding site. Typically they will have a molecular weight of less than 1 kDa.

Where the assay utilizes a labelled binding partner for the analyte and the analyte is a chemical reagent, the binding partner may comprise any other reagent which reacts with or otherwise becomes associated with the chemical reagent, either because it forms covalent or ionic bonds with the reagent, or by the formation of other interactions, such as hydrogen bonding or Van der Waals interactions. For example, where the chemical reagent is an acid, the binding partner may comprise an alcohol or an amine that forms an ester or amide with the acid under the sorts of conditions found in the test. Alternatively the binding partner may comprise a base that forms a salt with the acid. Conversely, where the binding partner may comprise the acid part of the reactive pair.

Where the analyte is or comprises a hapten or a protein antigen, the binding partner may comprise an antibody or a binding fragment thereof, which may be monoclonal, polyclonal or recombinant, but preferably is monoclonal. Where the analyte is a hormone or enzyme, the labelled binding partner may comprise a labelled receptor for the analyte. However, where the analyte is itself an immunoglobulin, and in particular, an antibody, the labelled binding partner may also comprise for instance, an antigen or recombinant antigen, as well as antiantibody immunoglobulin such as antisera.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

For example, where the analyte is a biologically active material such as an active agrochemical as discussed above, specific reagents used in the assay device will be selected so as to ensure that the particular target biologically active material is detected as is well known in the art. The biologically active material may be any active chemical such as an agrochemical, for example a chemical reagent which may be organic or inorganic, and which optionally comprises a hapten, a protein, a polypeptide, a microorganism or a nucleic acid sequence. Most preferably the biologically active material is a chemical reagent, for instance a small molecule, which suitably comprises a hapten. Small molecules will generally have a single antibody binding site. Typically they will have a molecular weight of less that 1 kDa.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

Microarrays

The method of the invention is particularly useful in combination with the analysis of gene expression profiles. In some embodiments, a gene expression profile, such as a collection of transcription rates of a number of genes, is converted to a projected gene expression profile. The projected gene expression profile is a collection of expression values. The conversion is achieved, in some embodiments, by averaging the transcription rate of the genes. In some other embodiments, other linear projection processes may be used.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natd. Acad. Sci. 93:10614-10619; Baldeschweiler et al. (1995) PCT application WO95/251116; Shalon et al. (1995) PCT application WO95/35505; Heller et al. (1997) Proc. Natl. Acad. Sci. 94:2150-2155; and Heller et al. (1997); U.S. Pat. No. 5,605,662.) Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome DNA libraries.

Using the methods of the invention a skilled artisan can readily select and prepare probes for a microarray wherein the microarray contains specific individual probes for less than all the genes in the genome and less than all the genes in the genome. In such embodiments, the microarray contains one or two or more individual probes, each of which hybridizes to an expression product (e.g., mRNA, or cDNA or cRNA derived therefrom) for a desired number of genes. Thus, for example, changes in the expression of all or most of the genes in the entire genome of a cell or organism can thereby be monitored by use of a surrogate and on a single microarray by measuring expression of the group of genes that are representative of all or most of the genes of the genome. Such microarrays can be prepared using the selected probes and are therefore part of the present invention.

Stroke

Stroke (also referred to herein as acute stroke, ischemic stroke and/or cerebrovascular ischemia) is often cited as the third most common cause of death in the industrial world, ranking behind ischemic heart disease and cancer. Strokes are responsible for about 300,000 deaths annually in the United States and are a leading cause of hospital admissions and long-term disabilities. Accordingly, the socioeconomic impact of stroke and its attendant burden on society is practically immeasurable.

"Stroke" is defined by the World Health Organization as a rapidly developing clinical sign of focal or global disturbance of cerebral function with symptoms lasting at least 24 hours. Strokes are also implicated in deaths where there is no apparent cause other than an effect of vascular origin. Strokes are typically caused by blockages or occlusions of the blood vessels to the brain or within the brain.

With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

A subject having a stroke is so diagnosed by symptoms experienced and/or by a physical examination including interventional and non-interventional diagnostic tools such as CT and MR imaging. The methods of the invention are advantageous for the treatment of various clinical presentations of stroke subjects. A subject having a stroke may present with one or more of the following symptoms: paralysis, weakness, decreased sensation and/or vision, numbness, tingling, aphasia (e.g., inability to speak or slurred speech, difficulty reading or writing), agnosia (i.e., inability to recognize or identify sensory stimuli), loss of memory, co-ordination difficulties, lethargy, sleepiness or unconsciousness, lack of bladder or bowel control and cognitive decline (e.g., dementia, limited attention span, inability to concentrate). Using medical imaging techniques, it may be possible to identify a subject having a stroke as one having an infarct or one having hemorrhage in the brain.

The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of stroke.

The treatment and/or prevention of infection after stroke can be for patients who have experienced a stroke or can be a prophylactic treatment. Short term prophylactic treatment is indicated for subjects having surgical or diagnostic procedures which risk release of emboli, lowering of blood pressure or decrease in blood flow to the brain, to reduce the injury due to any ischemic event that occurs as a consequence of the procedure. Longer term or chronic prophylactic treatment is indicated for subjects having cardiac conditions that may lead to decreased blood flow to the brain, or conditions directly affecting brain vasculature. If prophylactic, then the treatment is for subjects having an abnormally elevated risk of an ischemic stroke, as described above. If the subject has experienced a stroke, then the treatment can include acute treatment. Acute treatment for prevention of infection after stroke in a patient means administration of an agent of the invention at the onset of symptoms of the condition or within 48 hours of the onset, preferably within 24 hours, more preferably within 12 hours, more preferably within 6 hours, and even more preferably within 3 hours of the onset of symptoms of the condition.

An important embodiment of the invention is treatment of a subject with an abnormally elevated risk of an ischemic stroke. As used herein, subjects having an abnormally elevated risk of an ischemic stroke is a category determined according to conventional medical practice; such subjects may also be identified in conventional medical practice as having known risk factors for stroke or having increased risk of cerebrovascular events. Subjects having an abnormally elevated risk of an ischemic stroke includes, for example, individuals undergoing surgical or diagnostic procedures which risk release of emboli, lowering of blood pressure or decrease in blood flow to the brain, such as carotid endarterectomy, brain angiography, neurosurgical procedures in which blood vessels are compressed or occluded, cardiac catheterization, angioplasty, including balloon angioplasty, coronary by-pass surgery, or similar procedures.

CNS Injury

Conditions suitable for treatment according to this invention include, for example, seizure disorders, pain syndromes, neurodegenerative diseases (including motor-neuron diseases, myelopathies, radiculopathies, and disorders of the sympathetic nervous system), dementias, cerebrovascular conditions, movement disorders, brain trauma, cranial nerve disorders, neuropsychiatric disorders, and other disease neuropathies (including viral associated neuropathies, diabetes associated neuropathies, Guillian-Barre syndrome, dysproteinemias, transthyretin-induced neuropathies, and carpal tunnel syndrome). The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of CNS Injury.

As used herein, seizure disorders include complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, mesial temporal lobe epilepsy, nocturnal frontal lobe epilepsy, progressive epilepsy with mental retardation, and progressive myoclonic epilepsy, as well as seizures associated with CNS mass lesions.

Pain syndromes include, for example, headaches (e.g., migraine, tension, and cluster), acute pain, chronic pain, neuropathic pain, nociceptive pain, central pain and inflammatory pain, drug-induced neuropathic pain, causalgia, complex regional pain syndrome types I and II, and reflex sympathetic dystrophy (RSDS).

Neurodegenerative diseases include Alzheimer's disease, Parkinson's Disease, multiple sclerosis, Huntington's Disease, ALS, spinal muscular atrophy, muscular dystrophies prion-related diseases, cerebellar ataxia, Friedrich's ataxia, SCA, Wilson's disease, RP, Gullian Bane syndrome, Adrenoleukodystrophy, Menke's Sx, cerebral autosomal dominant arteriopathy with subcortical infarcts (CADASIL), Charcot Marie Tooth diseases, neurofibromatosis, von-Hippel Lindau, Fragile X, spastic paraplegia, tuberous sclerosis complex, Wardenburg syndrome, spinal motor atrophies, Tay-Sachs, Sandoff disease, familial spastic paraplegia, myelopathies, radiculopathies, encephalopathies associated with trauma, radiation, drugs and infection, and disorders of the sympathetic nervous system (e.g., Shy Drager (familial dysautonomia), diabetic neuropathy, drug-induced and alcoholic neuropathy).

Dementias include Alzheimer's disease, Parkinson's disease, Pick's disease, fronto-temporal dementia, vascular dementia, normal pressure hydrocephalus, Huntington's disease, and MCI. Cerebrovascular conditions amenable to treatment according to the present invention include cerebrovascular disease and strokes (e.g., thrombotic, embolic, thromboembolic, hemorrhagic [including AVM and berry aneurysms], venoconstrictive, and venous).

Included in movement disorders are Parkinson's disease, dystonias, benign essential tremor, tardive dystonia, tardive dyskinesia, and Tourette's syndrome.

Brain trauma as used herein includes traumatic brain and spinal cord injuries as well as brain injuries from radiation.

Cranial nerve disorders include trigeminal neuropathy, trigeminal neuralgia, Menier's syndrome, glossopharangela neuralgia, dysphagia, dysphonia, cranial nerve palsies and Bell's palsy. Neuropsychiatric disorders include panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence/addiction (e.g., alcohol, psychostimulants (e.g., crack, cocaine, speed, meth), opioids, and nicotine), and drug-induced psychiatric disorders.

Other disease neuropathies that may be treated with the compositions and methods described herein include Guillian-Barre, diabetes associated neuropathies, dysproteinemias, transthyretin-induced neuropathies, neuropathy associated with HIV, herpes viruses (including herpes zoster) or other viral infection, neuropathy associated with Lyme disease, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy, postmeningitis syndrome, post-polio syndrome, prion diseases, and radiation associated neuropathic syndromes. Other diseases amenable to treatment with the present invention include fatigue syndromes (e.g., chronic fatigue syndrome and fibromyalgia), ataxic syndromes, olivopontoicerebellar degeneration, striatonigral degeneration, and axonic brain damage.

The present invention is particularly useful in the treatment of neuropsychiatric disorders such as depression, agitation, anxiety, seizure disorders such as grand mal seizures, status epilepticus, migraine pain treatment and prophylaxis, Alzheimer's disease, Parkinson's disease, and traumatic brain and spinal cord injury.

Also, the higher doses enabled by the present invention are expected to be of particular importance for dementias including Alzheimer's disease, Parkinson's disease, and vascular dementia, pain syndromes, including headaches and migraines, seizure disorders, movement disorders, and brain trauma.

Furthermore, the ease of use and convenience of a dosage form provided developed to be delivered at once per day or less frequent administration at a therapeutically effective quantity from the onset of therapy is of value in the treatment of dementias including Alzheimer's disease and Parkinson's disease, seizure disorders, pain syndromes, and cerebrovascular conditions.

Formulations for Alternate Specific Routes of Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The GCR antagonist may also be delivered in an aerosol spray preparation from a pressurized pack, a nebulizer or from a dry powder inhaler. Suitable propellants that can be used in a nebulizer include, for example, dichlorodifluoromethane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

Regenerative Therapy

The activities of GR agonists and their alteration of cellular functions are variable, depending on complex intracellular molecular signaling that are cell and tissue specific. Amongst the cells that have glucocorticoid receptors are stem and progenitor cells of all tissues and organs of the body. Thus, binding of such molecules to normative, "intissue" stem cells and the progeny of these stem cells, so-called "transit amplifying" progenitor cells, results in variable, cell and tissue specific effects, inhibitory or enhancing of stem and progenitor cell functions, including activation, proliferation, migration and differentiation all of which are dependent on the tissue/organ in question.

The present invention relates to the use of a GCR antagonist or active agent, such as for example, ORG34517, PT150, PT155, PT156, PT157, PT158, TCY1, combinations thereof, and pharmaceutically acceptable salts thereof, for the prevention or treatment of, will thus block the effects of GR-agonists in tissue specific fashion, enhancing stem/progenitor cell functioning in some, inhibiting it in others. GR-antagonists will have beneficial effects in specific clinical settings where regenerative medicine approaches to disease and wound healing may be of use, including: enhanced post-transplant functioning of autologous stem cell transplants (dependent on tissue of origin and/or target tissue). Attenuation of the peri-surgical effects of catabolic stress hormones related to surgical or other physical traumas (e.g. combat wounds).

Systemic GR blockade will be inappropriate, but direct application of The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of to site of injury/wounding, either topically (for example, to prevent wound dehiscence) or by direct injection or intravascular infusion (for visceral organ injuries) will be beneficial.

The present invention relates to the use of cortisol blockers (glucocorticoid receptor [GR] antagonists) to treat stem cells for regenerative therapy.

Stem Cells

The term "stem cell" generally refers to a cell that on division faces two developmental options: the daughter cells can be identical to the original cell (self-renewal) or they may be the progenitors of more specialized cell types (differentiation). The stem cell is therefore capable of adopting one or other pathway (a further pathway exists in which one of each cell type can be formed). Stem cells are therefore cells which are not terminally differentiated and are able to produce cells of other types.

Embryonic Stem (ESCs) cells may be isolated from the inner cell mass (ICM) of the blastocyst, which is the stage of embryonic development when implantation occurs.

Pluripotent stem cells are true stem cells, with the potential to make any differentiated cell in the body. However, they cannot contribute to making the extraembryonic membranes which are derived from the trophoblast.

Several types of pluripotent stem cells have been found.

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body contains them where they can replace dead or damaged cells. Methods of characterizing stem cells are known in the art, and include the use of standard assay methods such as clonal assay, flow cytometry, long-term culture and molecular biological techniques e.g. PCR, RT-PCR and Southern blotting.

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen.

Induced pluripotent stem cells, commonly abbreviated as iPS cells or iPSCs, are a type of pluripotent stem cell artificially derived from a non-pluripotent cell, typically an adult somatic cell, by inserting certain genes. iPS cells are reviewed and discussed in Takahashi, K. & Yamanaka (2006), Yamanaka S, et. al. (2007), Wernig M, et. al. (2007), Maherali N, et. al. (2007), Yu J, et al. (2007) and Takahashi et al., (2007), all of which are incorporated herein by reference.

iPS cells are typically derived by transfection of certain stem cell-associated genes into non-pluripotent cells, such as adult fibroblasts. Transfection is typically achieved through viral vectors, for example through retroviral reprogramming. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection. IPSCs may be induced from somatic cells such as fibroblasts by transfection with one or more transcription factors. In some cases, cells are transformed with Oct3/4, Sox2, c-Myc and Klf4. The cells may be additionally transfected with other genes, including transcription factors and/or marker genes. The genes may be introduced using a transposon system such as the Cre/loxP recombination system, or using non-integrating vectors in order to produce iPSCs free of exogenous reprogramming genes. Transfection may be achieved using viral vectors, such as a retrovirus. The virus may be an amphotropic virus. Once the cells have been transfected, they may be grown on feeder cells before transfer to an ESC culture medium.

iPS cells may be derived from any suitable cell type, including lung, foreskin fibroblasts, skin fibroblasts, keratinocytes, blood progenitor cells, bone marrow cells, hepatocytes, gastric epithelial cells, pancreatic cells, neural stem cells, B lymphocytes, ES derived somatic cells and embryonic fibroblasts. In some cases, the cells are not human dermal fibroblasts. The IPSCs may exhibit similar patterns of gene expression and phenotype to ESCs.

Sources of Induced Pluripotent Stem Cells

Several methods have now been provided for the isolation of pluripotent stem cells that do not lead to the destruction of an embryo, e.g. by transforming (inducing) adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell. 2. Reprogramming by fusion with embryonic stem cells. This technique involves the fusion of a somatic cell with an embryonic stem cell. This technique may also lead to the creation of animal-human hybrid cells, as in 1 above. 3. Spontaneous re-programming by culture.

This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004). 4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1~4 are described and discussed by Shinya Yamanaka in Strategies and New Developments in the Generation of Patient-Specific Pluripotent Stem Cells (Cell Stem Cell 1, July 2007 Elsevier Inc), incorporated herein by reference. 5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444: 512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko Ilic et al (Derivation of human tri embryonic stem cell lines from biopsied blastomeres on human feeders with a minimal exposure to xeno-materials. Stem Cells And Development—paper in pre-publication), all incorporated herein by reference. 6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference. 7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2): 152-61 who employed the chemical activation of nonfertilized metaphase II oocytes to produce stem cells. 8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by .beta.-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599) Kim et al (Ex vivo characteristics of human amniotic membrane-derived stem cells. Cloning Stem Cells 2007 Winter; 9(4):581-94, incorporated herein by reference) succeeded in isolating human amniotic membrane-derived mesenchymal cells from human amniotic membranes. Cimbilical cord is a tissue that is normally discarded and stem cells derived from this tissue have tended not to attract moral or ethical objection.

Induced pluripotent stem cells have the advantage that they can be obtained by a method that does not cause the destruction of an embryo, more particularly by a method that does not cause the destruction of a human or mammalian embryo. As such, aspects of the invention may be performed or put into practice by using cells that have not been prepared exclusively by a method which necessarily involves the destruction of human or animal embryos from which those cells may be derived. This optional limitation is specifically intended to take account of Decision G0002/06 of 25 Nov. 2008 of the Enlarged Board of Appeal of the European Patent Office.

Mesenchymal Stem Cells

Mesenchymal stem cells are known as being multipotent and exhibit the potential for differentiation into different cells/tissue lineages, including cartilage, bone, adipose tissue, tendon, and ligament. These multipotent mesenchymal progenitor cells are denoted as stromal or mesenchymal stem cells. Bone marrow contains two main cell types: hematopoietic cells and stromal cells. The stem cells for non hematopoietic tissues are referred as mesenchymal cells because of their ability to differentiate as mesenchymal or stromal cells.

Accordingly, in this specification mesenchymal stem cells (MSCs) refers to multipotent stem cells capable of differentiation into osteoblasts, chondrocytes, myocytes, adipocytes and endothelium. In this specification MSCs particularly refers to multipotent stem cells capable of differentiation into osteoblasts as part of the process of formation of bone.

Mesenchymal cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Suitable MSCs may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES British Journal of Haematology 121(2):368-374, April 2003) or Wharton's Jelly of the umbilical cord (e.g. Ta et al. Long-term Expansion and Pluripotent Marker Array Analysis of Wharton's Jelly-Derived Mesenchymal Stem Cells. Stem Cells Dev. 2009 Jul. 20 (Epub)).

Differentiation of MSCs to the osteogenic lineage may be achieved by culture in osteogenic medium. For example, MSCs are seeded at 3,000/cm.sup.2 in maintenance medium (DMEM, 1 g/l glucose, 10% FCS, 2 mM L-glutamine, 50 U/ml penicillin and 50 U/ml streptomycin) in 6-well, 12-well and chamber slides for 24 h before changing to osteogenic media (maintenance medium, 10 nM dexamethasone, 25 .mu.g/ml ascorbic acid and 10 mM beta-glycerophosphate). Cells are then maintained for up to 28 days with a media change every 3-4 days. After 14 days cells in the chamber slides may be fixed in 4% PFA and stored at 4. degree. C. in PBS for immunohistochemistry. After 14 and 28 days the cells are stained with alizarin red S for calcium, and von Kossa for calcium phosphate. RNA may also be extracted for analysis using the Nucleospin RNA extraction kit according to the manufacturer's instructions (Macherey Nagel) and protein samples may be extracted for analysis.

Differentiation of MSCs to the adipogenic lineage may be achieved by culture in adipogenic medium. For example, MSCs are seeded at 18,000/cm.sup.2 in maintenance medium and incubated as above for 2 days.

Media is removed and cells are washed once in PBS before the addition of adipogenic maintenance media (DMEM, 4.5 g/l glucose, 10% FCS, L-glutamine and penicillin and streptomycin) or adipogenic media (adipogenic maintenance media with 10 .mu.g/ml insulin, 115 microg/ml methyl-isobutylxanthine, 1 .mu.M dexamethasone and 20 .mu.M indomethazine). Cells are then maintained for up to 28 days with a media change every 3-4 days. After 14 and 28 days the cells may be stained with oil-red-O to stain the lipid droplets. RNA and protein may also be extracted for analysis.

Differentiation of MSCs to the chondrogenic lineage may be achieved by culture in chondrogenic medium. For example, MSCs are counted and resuspended at 5.times.10.sup.5 cells/ml in chondrogenic media (DMEM with Cambrex chondrogenic single aliquots) with or without 10 ng/ml TGF.quadrature.3 (Cambrex) and then 500 ml aliquots were put into 15 ml tubes before centrifugation at 150.times.g at room temperature for 10 min and incubated at 37° C. for 2 days. After two days the tubes will contain loose round pellets. Pellets are maintained for 21 days with a media change every 3-4 days before RNA is isolated using Trizol (Invitrogen) or cell pellets are fixed in 4% PFA and embedded for cryosectioning Serial sections are made before slides are stored at −80° C. for immunohistochemistry.

When osteogenic and adipogenic differentiation are investigated under confluent conditions, cells may be seeded at 30,000/cm$^2$ and allowed to reach confluence before switching to the relevant differentiation media and cultured as above.

Culture of Stem Cells

Any suitable method of culturing stem cells may be used, and any suitable container may be used to propagate stem cells. Suitable containers include those described in US Patent Publication US2007/0264713 (Terstegge).

Containers may include bioreactors and spinners, for example. A "bioreactor" is a container suitable for the cultivation of eukaryotic cells, for example animal cells or mammalian cells, such as in a large scale. A typical cultivation volume of a regulated bioreactor is between 20 ml and 500 ml. The bioreactor may comprise a regulated bioreactor, in which one or more conditions may be controlled or monitored, for example, oxygen partial pressure. Devices for measuring and regulating these conditions are known in the art. For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)).

Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 cm.sup.2. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture, aggregates of cells may be allowed to form. Whilst some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed.

Propagation with Passage. Methods of cell culture may comprise passaging, or splitting during culture. The methods may involve continuous or continual passage. Cells in culture may be dissociated from the substrate or flask, and "split", subcultured or passaged, by dilution into tissue culture medium and replating/re-culturing. The term "passage" may generally refer to the process of taking an aliquot of a cell culture, dissociating the cells completely or partially, diluting and inoculating into medium. The passaging may be repeated one or more times. The aliquot may comprise the whole or a portion of the cell culture. The cells of the aliquot may be completely, partially or not confluent. The passaging may comprise at least some of the following sequence of steps: aspiration, rinsing, trypsinization, incubation, dislodging, quenching, re-seeding and aliquoting. The protocol published by the Hedrick Lab, UC San Diego may be used.

The cells may be dissociated by any suitable means, such as mechanical or enzymatic means known in the art. The cells may be broken up by mechanical dissociation, for example using a cell scraper or pipette. The cells may be dissociated by sieving through a suitable sieve size, such as through 100 micron or 500 micron sieves. The cells may be split by enzymatic dissociation, for example by treatment with collagenase or trypLE harvested. The dissociation may be complete or partial. The dilution may be of any suitable dilution. The cells in the cell culture may be split at any suitable ratio. For example, the cells may be split at a ratio of 1:2 or more, 1:3 or more, 1:4 or more or 1:5 or more. Thus, stem cells may be passaged for 1 passage or more. For example, stem cells may be passaged for 2, 3, 4, 5, 6, 7, 8, 9, 10, 11, 12, 13, 14, 15, 16, 17, 18, 19, 20, 21, 22, 23, 24, 25 passages or more. Passages may be expressed as generations of cell growth. Stem cells may be propagated for 1, 2, 3, 4, 5, 6, 7, 8, 9, 10, 11, 12, 13, 14, 15, 16, 17, 18, 19, 20, 21, 22, 23, 24, 25 generations or more. Stem cells may be propagated for 1, 2, 3, 4, 5, 6, 7, 8, 9, 10, 11, 12, 13, 14, 15, 16, 17, 18, 19, 20, 21, 22, 23, 24, 25 cell doublings or more Co-Culture and Feeders Methods may comprise culturing stem cells in the presence or absence of co-culture. The term "co-culture" refers to a mixture of two or more different kinds of cells that are grown together. The two or more different kinds of cells may be grown on the same surfaces, such as particles or cell container surfaces, or on different surfaces. The different kinds of cells may be grown on different particles. Feeder cells may mean cells which are used for or required for cultivation of cells of a different type. In the context of stem cell culture, feeder cells have the function of securing the survival, proliferation, and maintenance of cell pluripotency or multipotency. Cell pluripotency/multipotency may be ensured by directly co-cultivating the feeder cells. For example, the inner surface of the container such as a culture dish may be coated with a feeder cell layer. The feeder cells release nutrients into the culture medium. Alternatively, or in addition, the feeder cells may be cultured in a medium to condition it. The conditioned medium may be used to culture the stem cells. Thus, arrangements in which feeder cells are absent or not required are also possible.

The invention provides the treatment of stem cells with GR antagonist to yield GR antagonist treated stem cells.

Osteoporosis and Bone Related Injuries

Glucocorticoids (GCs) are central to the treatment of inflammatory and immune disorders. These steroids, however, profoundly impact the skeleton, particularly when administered for prolonged periods. In fact, high-dose GC therapy is almost universally associated with bone loss, causing one of the most crippling forms of osteoporosis. Despite the frequency and severity of GC-induced osteoporosis, its treatment is less than satisfactory, suggesting that its pathogenesis is incompletely understood. The present invention provides a method and treatment for these disorders as well as the rapid site-specific bone growth by a combination cortisol blockers i.e. The present invention relates to the use of a GCR antagonist, such as for example, ORG34517, PT150, PT155, PT156, PT157, PT158, TCY1, combinations thereof, and pharmaceutically acceptable salts thereof, for the prevention or treatment of and the optional use of bone marrow irrigation, bone compatible cement and PTH therapy.

The present invention relates to the use of GR antagonists or GR antagonist treated stem cells for the prevention or treatment of stress induced osteoporosis and the rapid healing of bone related injuries The present invention is concerned with the therapeutic use (human and veterinary) of GR antagonists or GR antagonist treated stem cells to treat bone fracture. GR antagonists and GR antagonist treated stem cells are reported here to augment wound healing in bone. GR antagonists stimulate bone regeneration following injury and contribute to improved wound healing in bone. GR antagonists and GR antagonist treated stem cells provide improvements in the speed of bone fracture repair enabling a reduction in the recovery time from injury.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures. In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using GR antagonists include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella). Bone fracture also includes pathological porosity, such as that exhibited by subjects with osteoporosis. GR antagonists and GR antagonist treated stem cells and pharmaceutical compositions and medicaments comprising GR antagonists and GR antagonist treated stem cells are provided for use in a method of treatment of bone fracture in a mammalian subject.

Treatment may comprise wound healing in bone. The treatment may involve repair, regeneration and growth of bone. GR antagonists and GR antagonist treated stem cells facilitate fracture repair by facilitating new bone growth. GR antagonists act to improve the speed of fracture repair enabling bone healing to occur faster leading to improved recovery time from injury.

Treatment may lead to improved bone strength. Treatment may also include treatment of osteoporosis or osteoarthritis. Administration of GR antagonists and GR antagonist treated stem cells may for example be to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. GR antagonists and GR antagonist treated stem cells may be formulated in fluid or liquid form for injection, or as part of a gel suitable for application to bone or other tissue surrounding the fracture.

Administration is preferably in a "therapeutically effective amount", this being sufficient to improve healing of the bone fracture compared to a corresponding untreated fracture or to a fracture treated with GR antagonist treated stem cells obtained from culture in control conditions. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of GR antagonists or GR antagonist treated stem cell doses may be administered in accordance with the guidance of the prescribing medical practitioner. Examples of the techniques and protocols mentioned above can be found in Remington's Pharmaceutical Sciences, 20th Edition, 2000, pub. Lippincott, Williams & Wilkins.

GR antagonists or GR antagonist treated stem cells may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required GR antagonists or GR antagonist treated stem cells may be administered directly to (e.g. applied to) the fracture during the surgical procedure.

Pharmaceutical compositions and medicaments of the invention may take the form of a biomaterial that is coated and/or impregnated with GR antagonists or GR antagonist treated stem cells. An implant or prosthesis may be formed from the biomaterial. Such implants or prostheses may be surgically implanted to assist in bone growth, regeneration, restructuring and/or remodelling.

GR antagonists or GR antagonist treated stem cells may be applied to implants or prostheses to accelerate new bone formation at a desired location. The biomaterial may be coated or impregnated with GR antagonists or GR antagonist treated stem cells. Impregnation may comprise contacting the GR antagonists with the biomaterial such that they are allowed to be adsorbed and/or absorbed onto and/or into the biomaterial. Coating may comprise adsorbing the GR antagonists or GR antagonist treated stem cells onto the surface of the biomaterial. Coating or impregnation of the biomaterial may involve seeding GR antagonists or GR antagonist treated stem cells onto or into the biomaterial.

The biomaterial should allow the coated or impregnated GR antagonists or GR antagonist treated stem cells to be released from the biomaterial when administered to or implanted in the subject. Biomaterial release kinetics may be altered by altering the structure, e.g. porosity, of the biomaterial.

In addition to coating or impregnating a biomaterial with GR antagonists or GR antagonist treated stem cells, one or more biologically active molecules may be impregnated or coated on the biomaterial. For example, at least one chosen from the group consisting of: BMP-2, BMP-4, OP-1, FGF-1, FGF-2, TGF-beta1, TGF-beta2, TGF-beta3; VEGF; collagen; laminin: fibronectin; vitronectin. In addition or alternatively to the above bioactive molecules, one or more bisphosphonates may be impregnated or coated onto the biomaterial along with GR antagonists. Examples of useful bisphosphonates may include at least one chosen from the group consisting of: etidronate; clodronate; alendronate; pamidronate; risedronate; zoledronate. Optionally, GR antagonists or GR antagonist treated stem cells is excluded from being impregnated or coated on the biomaterial.

Biomaterials coated or impregnated with GR antagonists or GR antagonist treated stem cells may be useful in both medical and veterinary purposes. It will be appreciated that the present invention may improve the quality of life of a patient or potentially extend the life of an animal, for example a valuable race horse for use in breeding.

The biomaterial provides a scaffold or matrix support. The biomaterial may be suitable for implantation in tissue, or may be suitable for administration (e.g. as microcapsules in solution). The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium. The biomaterial may have a porous matrix structure which may be provided by a crosslinked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube Polymer Engineering & Science 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. Expert Reviews in Medical Devices. 2006; 3(1): 29-47; Wong C, Inman E, Spaethe R, Helgerson S. Thromb. Haemost. 2003 89(3): 573-582; Pandit A S, Wilson D J, Feldman D S. Fibrin scaffold as an effective vehicle for the delivery of acidic growth factor (FGF-1). J. Biomaterials Applications. 2000; 14(3); 229-242; DeBlois Cote M F. Doillon C J. Heparin-fibroblast growth factor fibrin complex: in vitro and in vivo applications to collagen based materials. Biomaterials. 1994; 15(9): 665-672).

Luong-Van et al (In vitro biocompatibility and bioactivity of microencapsulated heparan sulphate Biomaterials 28 (2007) 2127-2136), incorporated herein by reference, describes prolonged localised delivery of HS from polycaprolactone microcapsules. A further example of a biomaterial is a polymer that incorporates hydroxyapatite or hyaluronic acid.

The biomaterial can be supplemented with additional cells. For example, one can "seed" the biomaterial (or cosynthesise it) with fibroblast derived feeder cells, which may be useful for supporting growth and maintenance of the GR antagonists.

The subject to be treated may be any animal or human. The subject is preferably mammalian. In some embodiments the subject is a human. In other embodiments the subject is an animal, more preferably a nonhuman mammal. The non-human mammal may be a domestic pet, or animal kept for commercial purposes, e.g. a race horse, or farming livestock such as pigs, sheep or cattle. As such the invention may have veterinary applications. Non-human mammals include rabbits, guinea pigs, rats, mice or other rodents (including any animal in the order Rodentia), cats, dogs, pigs, sheep, goats, cattle (including cows or any animal in the order Bos), horse (including any animal in the order Equidae), donkey, and non-human primates. The subject may be male or female. The subject may be a patient.

Wound Healing and Transplants

While elevated cortisol plays important roles in physiologic homeostasis in the face of extreme physical and emotional stress, it can have negative effects on wound healing, by inhibiting cells important to wound repair (including stem cells) through binding to their glucocorticoid receptors (GR).

Application of a GR antagonist or active agent such as ORG 34517, PT150, PT155, PT156, PT157, PT158, TCY1, combinations thereof, and pharmaceutically acceptable salts thereof can improve wound healing in such circumstances. However, blockade of systemic cortisol binding to GR must be avoided. Thus, the present inventions provides for the local application of PT155, PT156, or PT157 to wounds (by topical application in cutaneous wounds or by direct injection or local vascular infusion) will help in wound repair in the face of acute physical trauma (e.g. war wounds) while at the same time preserving the systemic homeostasis to which cortisol contributes. Application of the same to stem cell therapies is also provided by pre-treatment of transplantable stem cells with ORG 34517, PT150, PT155, PT156, PT157, PT158, TCY1, combinations thereof, and pharmaceutically acceptable salts thereof. In addition, the invention provides for pre-treatment of an implantable organ prior to implantation in the recipient. The invention provides for treatment of an implantable organ during implantation in the recipient.

Perfusion Systems

A perfusion system for cells may be used to expose a tissue or organ to a GR antagonist in the form of a liquid or a semi-solid. Perfusion refers to continuous flow of a solution through or over a population of cells. It implies the retention of the cells within the culture unit as opposed to continuous-flow culture, which washes the cells out with the withdrawn media (e.g., chemostat). Perfusion allows for better control of the culture environment (pH, pO2, nutrient levels, GR antagonist levels, etc.) and is a means of significantly increasing the utilization of the surface area within a culture for cell attachment.

The technique of perfusion was developed to mimic the cells milieu in vivo where cells are continuously supplied with blood, lymph, or other body fluids. Without perfusion of a physiological nutrient solution, cells in culture go through alternating phases of being fed and starved, thus limiting full expression of their growth and metabolic potential. In the context of the present invention, a perfusion system may also be used to perfuse cells with an GR antagonist to induce stasis.

Those of skill in the art are familiar with perfusion systems, and there are a number of perfusion systems available commercially. Any of these perfusion systems may be employed in the present invention. One example of a perfusion system is a perfused packed-bed reactor using a bed matrix of a non-woven fabric (CelliGen®, New Brunswick Scientific, Edison, N.J.; Wang et al., 1992; Wang et al., 1993; Wang et al., 1994). Briefly described, this reactor comprises an improved reactor for culturing of both anchorage- and nonanchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 micrometer to 100 micrometer, providing for a high internal volume with pore volumes corresponding to 1 to 20 times the volumes of individual cells.

The perfused packed-bed reactor offers several advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium, which facilitates subsequent purification steps. This technology is explained in detail in WO 94/17178 (Aug. 4, 1994, Freedman et al.), which is hereby incorporated by reference in its entirety.

The Cellcube® (Corning-Costar) module provides a large styrenic surface area for the immobilization and growth of substrate attached cells. It is an integrally encapsulated sterile single-use device that has a series of parallel culture plates joined to create thin sealed laminar flow spaces between adjacent plates.

The Cellcube® module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Other commercially available perfusion systems include, for example, CellPerf® (Laboratories MABIO International, Tourcoing, France) and the Stovall Flow Cell (Stovall Life Science, Inc., Greensboro, N.C.). The timing and parameters of the production phase of cultures depends on the type and use of a particular cell line. Many cultures require a different media for production than is required for the growth phase of the culture. The transition from one phase to the other will likely require multiple washing steps in traditional cultures. However, one of the benefits of a perfusion system is the ability to provide a gentle transition between various operating phases. The perfusion system can also facilitate the transition from a growth phase to a static phase induced by an GR antagonist. Likewise, the perfusion system can facilitate the transition from a static phase to a growth phase by replacing the solution comprising an GR antagonist with, for example, a physiological nutrient media.

Formulations

The compounds of the invention may be administered enterally or parenterally. Mixed with pharmaceutically suitable auxiliaries, e.g., as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a smart capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage.

These forms are well known in the art and are packaged appropriately. The compositions can be formulated for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Dosage forms of the compositions of the present invention can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present invention, the combination of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), antioxidants (ascorbic acid of sodium bisulfite) or the like.

The invention provides a smart pill or smart capsule, which is, in an exemplary embodiment, an ingestible drug delivery device configured for wireless communication with other ingestible drug delivery devices, said drug delivery device comprising: a capsule body comprising: a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body; an electronics module, coupled to said sensor and said bioactive substance module, said electronics module comprising a processor, a transponder and a memory (e.g., flash, OTP, etc.), said memory comprising data selected from the group consisting of: (a) data related to the patient who is permitted to ingest said ingestible drug medical device; (b) data related to said bioactive substance; (c) data related to a healthcare provider that enabled said electronics module; (d) data related to said sensor; (e) data related to the provenance of said ingested drug medical device; (f) combinations thereof, a power source coupled to said sensor, said bioactive substance module and said electronics module; and wherein said processor controls said transponder to transmit at least one wireless signal and to receive at least one wireless signal from at least one other ingestible medical device, and wherein said processor receives said first signal and analyzes said first signal with all of said data along with said received at least one wireless signal for controlling said microactuator for dispensing said bioactive substance.

In exemplary embodiments, ORG 34517, PT150, PT155, PT156, PT157, PT158, TCY1, combinations thereof, and pharmaceutically acceptable salts thereof, is variable in capsule/tablets/smart pills, resulting in intermittent, rather than constant dosing, the pills could be coded (e.g. by color or shape) to indicate which pills would be taken in which order (per part of a day, or per day or week or month of pill taking protocol) to achieve the correct balance or GCR blockade (e.g. like daily birth control pills with variable hormonal contents over the course of a month). In other words, some capsule/tablets/smart pills would have just the opiate, some would have opiate plus one or several different doses of PT150 in the same capsule/tablet/smart pill, etc. In exemplary embodiments, the patient would not be aware of the contents of any given capsule/tablet/smart pill, but would know when in the course of their dosing regimen they should take a particular coded version.

In exemplary embodiments, the smart capsules could identify both quantity of pills taken as well as the kind of pill taken (with or without the ORG 34517, PT150, PT155, PT156, PT157, PT158, TCY1, combinations thereof, and pharmaceutically acceptable salts thereof) so as to provide a record for treating personnel as to what has been taken, but also to prevent opening of the smart pill if the wrong pill has been taken out of its intended sequence.

The dose administered must be carefully adjusted according to age, weight and condition of the patient, as well as the route of administration, dosage form and regimen and the desired result. The pharmaceutical compositions of the invention may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice.

These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above. In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

One embodiment of this invention includes methods of treating, preventing, or diagnosing a particular disease or condition by administering the disclosed nanoparticles, composite nanoparticles, nanosuspension, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

"Nanoparticles" are solid particles of an average particle diameter of, for example, less than about 1 micron (micrometer). One micron is 1,000 nanometers (nm). "Stabilized" nanoparticles are nanoparticles coated with a stabilizing material and having a reduced tendency for aggregation and loss of dispersion with respect to nanoparticles of the compound of the invention without a stabilizing coating. A nano-spray is a spray containing nanoparticles or a spray that produces nanoparticles. A nanodispersion is a dispersion containing nanoparticles. A nanosuspension is a suspension containing nanoparticles. The liquid formulations useful herein may comprise a solvent, solution, suspension, microsuspension, nanosuspension, emulsion, microemulsion, gel or even a melt containing the active component or components.

In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid.

Pharmaceutical compositions of the present invention can include nanoparticles, composite nanoparticles, nanosuspension, or nanocapsules of the present invention. In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Packaging/Treatment Kits

The present invention relates to a kit for conveniently and effectively carrying out the methods in accordance with the present invention. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists two or more separate compartments: Am dosage of this invention, and PM dosage of this invention, or mid-day dosage of this invention. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside.

In one aspect, blister packaging comprises at least two components (e.g., is a multi-ingredient combination of drugs of the invention): a thermoformed "blister" which houses the product (e.g., a pharmaceutical combination of the invention), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, 111) using regular heat seal tooling. This alternative aspect, using heat seal tooling, can seal common types of thermoformed packaging.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

In one aspect, laminated aluminum foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminum (e.g., alufoil) lidding material. In one aspect, hermetically-sealed high barrier aluminum (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

Topical Formulations

The term "topical" as employed herein relates to the use of a compound, derivative or analogue as described herein, incorporated in a suitable pharmaceutical carrier, and applied at the site for exertion of local action. Accordingly, such topical compositions including those forms in which the compound is applied externally by direct contact with the skin surface to be treated. Conventional forms for this purpose include ointments, liniments, creams, shampoos, lotions, pastes, jellies, sprays, aerosols, soaps, and the like, and may be applied in patches or impregnated dressings depending on the part of the body to be treated. The term "ointment" embraces formulations (including creams) having oleaginous, absorption, water-soluble and emulsion-type bases, e.g., petrolatum, lanolin, polyethylene glycols, as well as mixtures of these.

For topical use, the agent of the invention can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied is in the range of about 0.1 ng to about 100 mg per day, or about 1 ng to about 10 mg per day, or about 10 ng to about 1 mg per day depending on the formulation. Non-limiting examples of topical products can include, without limitation, application stick, mascara, eyebrow coloring products, eye shadow or other eye lid coloring products, eyeliner, make-up removal products, antiaging products, facial or body powder, nail polish, mousse, sprays, styling gels, nail conditioner, bath and shower gels, shampoos, conditioners, cream rinses, hair dyes and coloring products, hair conditioners, sun tanning lotions and creams and sprays, sunscreens and sunblocks, skin conditioners, cold creams, moisturizers, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, and rinses.

Furthermore, the topical product can be applied topically through the use of a patch or other delivery device. Delivery devices can include, but are not limited to, those that can be heated or cooled, as well as those that utilize iontophoresis or ultrasound.

For instance, the topical product can be applied, for example, by applying a composition in the form of a skin lotion, clear lotion, milky lotion, cream, gel, foam, ointment, paste, emulsion, spray, conditioner, tonic, cosmetic, application stick, pencil, foundation, nail polish, after-shave, or the like which is intended to be left on the skin or other keratinous tissue (i.e., a "leave-on" composition). After applying the composition to the keratinous tissue (e.g., skin), it in one embodiment, it is left on for a period of at least about 15 minutes, or at least about 30 minutes, or at least about 1 hour, or for at least several hours, e.g., up to about 12 hours. In one embodiment, the topical product is left on overnight. In another embodiment, the topical product is left on all day. Any part of the external portion of the face, hair, and/or nails can be treated, (e.g., face, lips, under-eye area, eyelids, scalp, neck, torso, arms, legs, chest, hands, legs, feet, fingernails, toenails, scalp hair, eyelashes, eyebrows, etc.)

Any suitable method can be used to apply the topical product, including but not limited to for example using the palms of the hands and/or fingers or a device or implement (e.g., a cotton ball, swab, pad, applicator pen, spray applicator, eyebrow brush, eyebrow brush pencil, pencil, mascara brush, etc.) Another approach to ensure a continuous exposure of the keratinous tissue to at least a minimum level of the topical product is to apply the compound by use of a patch applied, e.g., to the face. The patch can be occlusive, semi-occlusive or nonocclusive, and can be adhesive or non-adhesive. The topical product can be contained within the patch or be applied to the skin prior to application of the patch. The patch can also include additional actives such as chemical initiators for exothermic reactions such as those described in PCT application WO 9701313, and in U.S. Pat. Nos. 5,821,250, 5,981,547, and 5,972,957 to Wu, et al. The patch can be left on the for any suitable period of time. For example, a period of at least about 5 minutes, or at least about 15 minutes, or at least about 30 minutes, or at least about 1 hour, or at night as a form of night therapy, or in another embodiment all day.

Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The pharmaceutical compositions may also be delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

Typically, the composition may be applied repeatedly for a sustained period of time topically on the part of the body to be treated, for example, the eyelids, eyebrows, skin or scalp. The dosage regimen will generally involve regular, such as daily, administration for a period of treatment of at least one month, or at least three months, or at least six months.

Alternatively, the composition may be applied intermittently, or in a pulsed manner. Accordingly, an alternative embodiment of the invention is to apply the composition on an intermittent or pulsed dosage schedule. For example, the composition of the invention may be used for two or more days, stopped, then restarted again at a time from between 2 weeks to 3 months later, and at even more long-spaced intervals in the case of the scalp.

The routes of administration of a compound of the present invention will vary, naturally, with the location and nature of the condition to be treated, and include, e.g., inhalation, intradermal, transdemial, parenteral, intravenous, intramuscular, intranasal, subcutaneous, percutaneous, intratracheal, intraperitoneal, intratumoral, perfusion, lavage, direct injection, and oral administration and formulation. As detailed below, GR antagonists may be administered as medical gases by inhalation or intubation, as injectable liquids by intravascular, intravenous, intra-arterial, intracerobroventicular, intraperitoneal, subcutaneous administration, as topical liquids or gels, or in solid oral dosage forms.

Moreover, the amounts may vary depending on the type of biological matter (cell type, tissue type, organism genus and species, etc.) and/or its size (weight, surface area, etc.). It will generally be the case that the larger the organism, the larger the dose. Therefore, an effective amount for a mouse will generally be lower than an effective amount for a rat, which will generally be lower than an effective amount for a dog, which will generally be lower than an effective amount for a human. The effective concentration of a compound of the present invention to achieve stasis, for example, in a human depends on the dosage form and route of administration. For inhalation, in some embodiments effective concentrations are in the range of 50 ppm to 500 ppm, delivered continuously. For intravenous administration, in some embodiments effective concentrations are in the range of 0.5 to 50 milligrams per kilogram of body weight delivered continuously.

Similarly, the length of time of administration may vary depending on the type of biological matter (cell type, tissue type, organism genus and species, etc.) and/or its size (weight, surface area, etc.) and will depend in part upon dosage form and route of administration. In particular embodiments, a compound of the present invention may be provided for about or at least 30 seconds, 1 minute, 2 minutes, 3 minutes, 5 minutes, 10 minutes, 15 minutes, 30 minutes, 1 hour, 2 hours, 3 hours, four hours five hours, six hours, eight hours, twelve hours, twenty-four hours, or greater than twenty-four hours. A compound of the present invention may be administered in a single dos or multiple doses, with varying amounts of time between administered doses.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Alternatively, the amount specified may be the amount administered as the average daily, average weekly, or average monthly dose.

In the case of transplant, the present invention may be used pre- and or post-operatively to render host or graft materials quiescent. In a specific embodiment, a 30 surgical site may be injected or perfused with a formulation comprising an GR antagonist. The perfusion may be continued post-surgery, for example, by leaving a catheter implanted at the site of the surgery.

Further Delivery Devices or Apparatuses

In some embodiments it is contemplated that methods or compositions will involve a specific delivery device or apparatus. Any method discussed herein can be implemented with any device for delivery or administration including, but not limited, to those discussed herein.

For topical administration of GR antagonists of the invention may be formulated as solutions, gels, ointments, creams, suspensions, etc. as are well-known in the art. Systemic formulations may include those designed for administration by injection or infusion, e.g., subcutaneous, intravenous, intramuscular, intrathecal or intraperitoneal injection, as well as those designed for transdermal, transmucosal, oral or pulmonary administration.

The invention provides a topical pharmaceutical formulation for use in treatment of a subject, comprising the composition of the invention, and at least one pharmaceutically acceptable excipient.

The invention provides a method for treating a patient in need of such treatment comprising administration of the topical pharmaceutical composition of the invention.

The invention provides a topical pharmaceutical formulation for use in treatment of a subject, comprising a composition of the invention, and at least one pharmaceutically acceptable excipient. The invention further provides a topical formulation of the invention wherein said formulation is in a form selected from the group consisting of: cream, lotion, gel, oil, ointment, suppository, spray, foam, liniment, aerosol, buccal and sublingual tablet or a transdermal device or patch for absorption through the skin or mucous membranes. The invention further provides a topical formulation of the invention wherein said pharmaceutical formulation is a transdermal patch. The invention further provides a topical formulation of the invention wherein said pharmaceutical formulation is a buccal formulation.

For oral administration, the GR antagonists of the invention to be formulated as tablets, pills, dragees, capsules, liquids, gels, syrups, slurries, suspensions and the like, for oral ingestion by a patient to be treated or oral liquid preparations such as, for example, suspensions, elixirs and solutions.

For buccal administration, the compositions may take the form of tablets, lozenges, etc. formulated in conventional manner. Other intramucosal delivery might be by suppository or intranasally.

For administration directly to the lung by inhalation the compound of invention may be conveniently delivered to the lung by a number of different devices.

Another drug delivery system comprises one or more ball semiconductor aggregations and facilitating release of a drug stored in a reservoir. The first aggregate is used for sensing and memory, and a second aggregation for control aspects, such as for pumping and dispensing of the drug. The system may communicate with a remote control system, or operate independently on local power over a long period for delivery of the drug based upon a request of the patient, timed-release under control by the system, or delivery in accordance with measured markers. PUMPS and Infusion Devices: An infusion pump or perfusor infuses fluids, medication or nutrients into a patient's circulatory system. Infusion pumps can administer fluids in very reliable and inexpensive ways. For example, they can administer as little as 0.1 mL per hour injections (too small for a drip), injections every minute, injections with repeated boluses requested by the patient, up to maximum number per hour (e.g. in patient-controlled analgesia), or fluids whose volumes vary by the time of day.

Implantable Drug Delivery System: Another drug delivery system comprises one or more ball semiconductor aggregations and facilitating release of a drug stored in a reservoir. The first aggregate is used for sensing and memory, and a second aggregation for control aspects, such as for pumping and dispensing of the drug. The system may communicate with a remote control system, or operate independently on local power over a long period for delivery of the drug based upon a request of the patient, timed-release under control by the system, or delivery in accordance with measured markers.

Diagnostic Systems and Kits

A diagnostic kit may comprise some or all of the following components: 1) one or more standards comprised of one or more of the biomarker(s) of the invention, such as cortisol; 2) a ligand, such as an antibody or a plurality of antibodies, that are specific for the biomarker(s) that are to be assayed for using the kit; 3) written instructions; 4) diluents for samples and the standards; 5) a wash buffer; 6) color reagents; 7) stop solution; and 8) a ligand carrier, such as an antibody carrier, for example, a lateral flow device, or a microplate with bound antibody, or polystyrene beads. An example of such a kit is set forth in U.S. Patent Application Publication No. 20120201747 (Altschul et al.), incorporated herein in its entirety.

While the invention has been described in detail and with reference to specific examples thereof, it will be apparent to one skilled in the art that various changes and modifications can be made therein without departing from the spirit and scope thereof.

The invention will be illustrated in more detail with reference to the following Examples, but it should be understood that the present invention is not deemed to be limited thereto.

EXAMPLES

Example 1

Antiretroviral Activities of ORG34517 and PT155: Gain of Activity and Drop in Toxicity with PT155 in Comparison to ORG34517

Preliminary results revealed that the thiosemicarbazone modification of ORG34517 in form of PT155 is beneficial to overall antiretroviral activity and host cellular toxicity:

TABLE 12

Cytotoxicity and antiviral activity of ORG34517 and PT155 versus human immunodeficiency type 1 strain LAI (HIV-1LAI) in mammalian cells.

| Drug | Cytotoxicity $CC_{50}$ (µM) and cellular growth at fixed 100 µM concentration (%, in parentheses) | | | Anti-HIV-$1_{LAI}$ activity $EC_{50}$ (µM)/$EC_{90}$ (µM) in PBM cells | | | |
|---|---|---|---|---|---|---|---|
| | PBM cells | CCRF-CEM | Vero | $EC_{50}$ | $EC_{90}$ | $SI_{50}$ | $r^2$ |
| ORG34517 | 20.6 | 15.4 | 44.3 | 8.9 | 21.6 | 2.3 | 0.96 |
| PT155 | 82.6 | 7.1 | >100 (96.1) | 5.5 | 16.2 | 15.0 | 0.93 |
| AZT* | >100 | 14.3 | 56.0 | 0.0044 ± 0.0039 | 0.0299 ± 0.0245 | >22,696 | 0.98 |

Method of Determination: HIV-1 Replication Reverse Transcriptase (RT) Assay

HIV-1$_{LAI}$ (=HIV-1BRU=LAV-1) was assayed in primary [freshly donated from healthy (tested HIV-1-negative, HBV-negative, and HCV-negative) blood donors, and isolated by single-step Ficoll-Hypaque centrifugation method] human peripheral blood mononuclear (PBM) cells in the presence of a drug being evaluated. The parameter for antiviral activity was reduction of RT activity in the cell supernatant after Triton X-100-mediated lysis of released virions, as measured by [5fÑ-3H]dTTP (5fÑ-tritiated thymidine 5'-triphosphate) incorporation into poly(rA)•poly(dT) directed by the primed RNA template poly(rA)•oligo(dT). It should be noted that the assay did not detect RT inhibition by potential RT inhibitors per se, but indirectly quantified the amount of released HIV-1 in the supernatant. The detailed assay methodology was reported by Schinazi et al., as based on an older assay system of Spira et al. (ref. 38). The experiments were conducted in triplicate and treated statistically by regression curve analysis (r2 coefficient of determination). The RT inhibitor AZT (zidovudine, 3'-azido-3'-deoxythymidine; RETROVIR™) served as a positive control. Cytotoxicity on PBL cells exerted by the test compounds was determined as described by Stuyver et al., by application of the CellTiter 96® AQ$_{ueous}$ One Solution Cell Proliferation Assay (Promega Corp., Madison, WI). Briefly, the phenazine ethosulfate (PES)-coupled reduction of the tetrazolium salt 3-(4,5-dimethylthiazol-2-yl)-5-(3-carboxymethoxyphenyl)-2-(4-sulfophenyl)-2H-tetrazolium (MTS) to a purple, water-soluble formazan by living, undamaged cells was measured.

Example 2

(11β,17β)-17-Hydroxy-11-[3,4-(methylenedioxy)phenyl]-17-(1-propyn-1-yl)estra-4,9-dien-3-one (ORG34517)×(2EZ)-2-{(11β,17β)-17-hydroxy-11-[3,4-(methylenedioxy)phenyl]-17-(1-propyn-1-yl)estra-4,9-dien-3-ylidene}hydrazinecarbothioamide [71.8% (E), 28.2% (Z)] hemihydrate×¾ acetone× .ethanol (PT155)

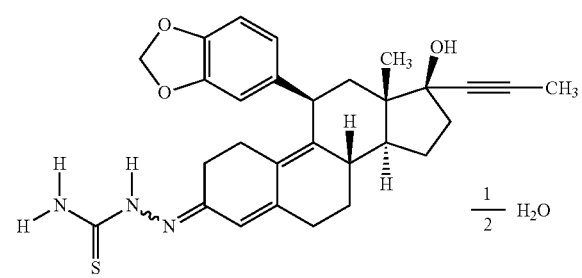

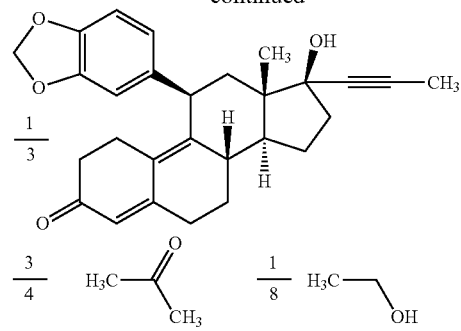

Materials:

„h ORG34517 [Pop Test Oncology LLC, Cliffside Park, NJ, USA; manufactured by Sai Life Sciences Ltd., Pune, India, Lot: SPO-MA1401-07; w (n/n)=99.72% (HPLC, UV detection at 210 nm)]

„h Thiosemicarbazide puriss. p.a. [Sigma-Aldrich Corp., St. Louis, MO, USA, Lot: 1167177V (Fluka); w (m/m)=100.1% (iodometric titration), mp 181° C. (dec.), residue on ignition <0.05%, metal trace analysis (inductively coupled plasma mass spectrometry)=50-5 mg/kg]

„h Glacial acetic acid (acetic acid 100% p.a.) [AppliChem GmbH, Darmstadt, Germany; Lot: 8Y002937; w (m/m) =100.0% (titration), water 0.0% (Karl Fischer titration), acetic anhydride=0.05%, formic acid=0.01%, non-volatile matter=0.001%]

Instruction:

ORG34517 (M=430.54 g/mol, 2.000 g, 4.6453 mmol) and thiosemicarbazide puriss. p.a. (M=91.14 g/mol, 435 mg, 4.7729 mmol) were suspended in in 90% (v/v) aqueous ethanol (100 ml). Glacial acetic acid (1000 µl, 17.4854 mmol) was added. The suspension was refluxed gently for 1 h. All solids went into solution which turned light yellow during reflux.

Afterwards, the yellow solution was left standing at room temperature (RT, f°=18.0° C.) for 12 min. Then the still warm yellow solution was filtered through one layer of filter paper. Residues were transferred and rinsed with 90% (v/v) aqueous ethanol (40 ml), and, successively, with water (40 ml). The yellow filtrate was cooled at +O-2° C. for 30 min. After addition of water (40 ml), the precipitating suspension was frozen at −25° C. for 2 h. The evolved first yield of the cream yellow, crude PT155 was filtered and dried over CaCl2 in vacuo. The filtrate was mixed with water (40 ml), and was frozen at −25° C. for 4 h. The evolved second yield of the cream yellow, crude PT155 was filtered and dried over CaCl2 in vacuo. Both yields were combined.

The crude product was dissolved in acetone (80 ml). Afterwards, water (2×40 ml) was added in portions under stirring to yield a yellowish emulsion. The precipitating emulsion with sticky yellow material pieces was frozen at −25° C. for 4 h. The evolved first yield (1.677 g) of the yellow PT155 was filtered and dried over CaCl$_2$) in vacuo. The filtrate was mixed with water (20 ml) and was frozen at −25° C. for 1 h. Afterwards, water (20 ml) was added and the precipitating suspension was frozen at −25° C. for 1 h. The evolved second yield (139 mg) of the yellow PT155 was filtered and dried over CaCl$_2$) in vacuo. Both yields were combined (1.816 g).

| | |
|---|---|
| Compound: | PT155 |
| Molecular formula: | ⅓ C$_{28}$H$_{30}$O$_4$ × C$_{29}$H$_{33}$N$_3$O$_3$S × ¾ C$_3$H$_6$O × ⅛ C$_2$H$_5$OH × ½ H$_2$O |
| Molecular weight: | 705.49 g/mol |
| Yield: | 1.816 g (74%) |
| Elemental analysis: | calculated: C 69.52% H 7.04% N 5.96% S 4.55% O 12.95% |
| | found: C 69.81% H 7.17% N 5.82% S 4.25% O 12.90% |
| | C 69.40% H 7.13% N 5.91% S 4.48% O 12.70% |
| $^1$H-NMR: | 0.41 (3 H, s; 18-CH$_3$, (E)-TSC*), 0.42 (1.18 H, s; 18-CH$_3$, (Z)-TSC**), |
| (DMSO-d$_6$, ppm) | 0.44 (1.393 H, s; 18-CH$_3$, ORG34517), 1.06 (0.523 H, t; $^3$J (H, H) = 7.1 Hz; ethanol CH$_3$), 1.23-2.77 (m; steroid CH and CH$_2$), 1.83 (5.58 H, br s; R—C≡C—CH$_3$ methyl, all three species), 2.09 (6.27 H, s; acetone CH$_3$), 3.44 (0.348 H, m; ethanol CH$_2$), 4.28 (0.393 H, m; 11α-CH, (Z)-TSC), 4.30 (1 H, d; $^3$J (H, H) = 7.7 Hz; 11α-CH, (E)-TSC), 4.35 (0.174 H, t; $^3$J (H, H) = 5.1 Hz; ethanol OH), 4.38 (0.464 H, d; $^3$J (H, H) = 7.1 Hz; 11α-CH, ORG34517), 5.11 (1 H, s; 17β-OH, (E)-TSC), 5.12 (0.393 H, s; 17β-OH, (Z)-TSC), 5.14 (0.464 H, s; 17β-OH, ORG34517), 5.66 (0.464 H, s; 4-CH, ORG34517), 5.86 (1 H, s; 4-CH, (E)-TSC), 5.97 (3.716 H, br s; O—CH$_2$—O benzodioxole, all three species), 5.97 (0.393 H, s; 4-CH, (Z)-TSC), 6.60 (1.858 H, d; $^3$J (H, H) = 8.3 Hz; 5'-CH benzodioxole, all three species), 6.67 (0.393 H, s; 2'-CH benzodioxole, (Z)-TSC), 6.77 (1.464 H, s; 2'-CH benzodioxole, (E)-TSC and ORG34517), 6.78 (0.393 H, d; $^3$J (H, H) = 8.0 Hz; 6'-CH benzodioxole, (Z)-TSC), 6.79 (1.464 H, d; $^3$J (H, H) = 8.0 Hz; 6'-CH benzodioxole, (E)-TSC and ORG34517), 7.51 (0.393 H, br s; NH$_2$, H$_A$, (Z)-TSC), 7.57 (1 H, br s; NH$_2$, H$_A$, (E)-TSC), 7.97 (0.393 H, br s; NH$_2$, H$_B$, (Z)-TSC), 8.08 (1 H, br s; NH$_2$, H$_B$, (E)-TSC), 10.05 (1 H, br s; N—H, (E)-TSC), 10.42 (0.393 H, br s; N—H, (Z)-TSC). |

*, **(E or Z)-TSC = (E or Z)-thiosemicarbazone.

Example 3

1/17(11β,17β)-17-Hydroxy-11-[3,4-(methylenedioxy)phenyl]-17-(1-propyn-1-yl)estra-4,9-dien-3-one (ORG34517)×(2EZ)-2-{(11β,17β)-17-hydroxy-11-[3,4-(methylenedioxy)phenyl]-17-(1-propyn-1-yl)estra-4,9-dien-3-ylidene}-N-phenylhydrazinecarbothioamide [74.1% (E), 25.9% (Z)]$^{11}$/$_{17}$ hydrate (PT156)

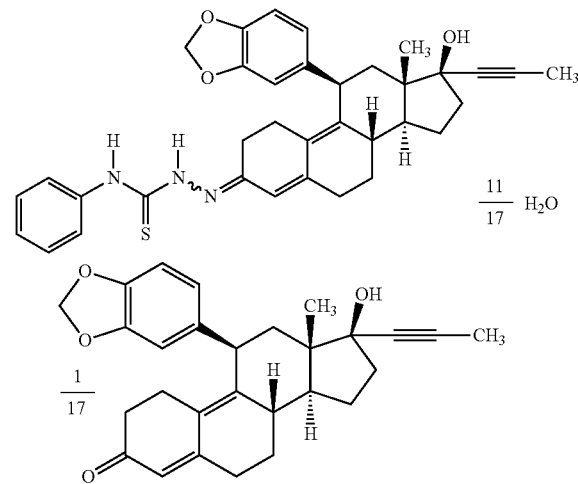

Materials:

ORG34517

4-Phenylthiosemicarbazide 99% [Sigma-Aldrich Corp., St. Louis, MO, USA, Lot: BCBL2527V (Aldrich); w (m/m)=99.7% (HClO$_4$ acidimetric titration), w (n/n)=99.3% (HPLC, area %), mp 138-140° C.]

Glacial acetic acid (acetic acid 100% p.a.) [AppliChem GmbH, Darmstadt, Germany; Lot: 8Y002937; w (m/m)=100.0% (titration), water 0.0% (Karl Fischer titration), acetic anhydride≤0.05%, formic acid≤0.01%, non-volatile matter≤0.001%]

Instruction:

ORG34517 (M=430.54 g/mol, 4.000 g, 9.2907 mmol) and 4-phenylthiosemicarbazide 99% (M=167.23 g/mol, 1.600 g, 9.5677 mmol) were suspended in in 90% (v/v) aqueous ethanol (100 ml). Glacial acetic acid (1000 µl, 17.4854 mmol) was added. The suspension was refluxed gently for 1 h. All solids went into solution which turned deep yellow during reflux.

Afterwards, the yellow solution was left standing at room temperature (RT, ϑ=15.6° C.) for 4 min. Then the still hot, cloudy, dirty yellow solution was filtered through one layer of filter paper. Residues were transferred and rinsed with 90% (v/v) aqueous ethanol (35 ml). The clear yellow filtrate was cooled at +0-2° C. for 4 h. The precipitating suspension was then frozen at −25° C. for 3 h. The evolved yield of the bright yellow, crude PT156 was filtered and dried over CaCl$_2$) in vacuo. The filtrate contained large amounts of impure ORG34517 and was discarded.

The crude product (3.463 g) was dissolved in acetone (30 ml). Afterwards, water (10 ml) was added in portions under stirring to yield an oily yellow emulsion. The sticky emulsion was re-dissolved by addition of acetone (15 ml). The mixture was then frozen at −25° C. for 2 h. Afterwards, water (5 ml) was added which resulted in precipitation of sticky material pieces. The mixture was shaken vigorously for 30 s, and was frozen at −25° C. for 70 min. Finally, water (20 ml) was added, the mixture was shaken vigorously for 30 s, and the precipitating emulsion was frozen at −25° C. for 75 min. The evolved first yield (3.285 g) of the bright yellow, crystalline PT156 was filtered and dried over CaCl$_2$) in vacuo. The filtrate was frozen at −25° C. for 12 h. The evolved second yield (29 mg) of the bright yellow, crystalline PT156 was filtered and dried over CaCl$_2$) in vacuo. The filtrate contained small amounts of pure ORG34517 and was discarded. Both yields were combined.

| | |
|---|---|
| Compound: | PT156 |
| Molecular formula: | 1/17 C$_{28}$H$_{30}$O$_4$ × C$_{35}$H$_{37}$N$_3$O$_3$S × 11/17 H$_2$O |
| Molecular weight: | 616.73 g/mol |
| Yield: | 3.314 g (61%) |
| Elemental analysis: | calculated: C 71.37% H 6.55% N 6.81% S 5.20% O 10.07%<br>found: C 71.47% H 6.83% N 6.83% S 5.58% O 10.05%<br>C 71.18% H 6.88% N 6.87% S 5.45% O 10.07% |
| $^1$H-NMR:<br>(DMSO-d$_6$, ppm) | 0.42 (3 H, s; 18-CH$_3$, (E)-PTSC*), 0.43 (1.05 H, s; 18-CH$_3$, (Z)-PTSC**), 0.44 (0.238 H, s; 18-CH$_3$, ORG34517), 1.24-2.80 (m; steroid CH and CH$_2$), 1.83 (4.288 H, br s; R—C≡C—CH$_3$ methyl, all three species), 2.09 (6 H, s; acetone CH$_3$), 4.31 (0.35 H, m; 11α-CH, (Z)-PTSC), 4.33 (1 H, d; $^3$J (H, H) = 7.6 Hz; 11α-CH, (E)-PTSC), 4.37 (0.079 H, d; $^3$J (H, H) = 7.2 Hz; 11α-CH, ORG34517), 5.12 (1 H, s; 17β-OH, (E)-PTSC), 5.13 (0.35 H, s; 17β-OH, (Z)-PTSC), 5.14 (0.079 H, s; 17β-OH, ORG34517), 5.66 (0.079 H, s; 4-CH, ORG34517), 5.97 (2.859 H, br s; O—CH$_2$—O benzodioxole, all three species), 6.00 (1.35 H, s; 4-CH, (E)-PTSC and (Z)-PTSC), 6.62 (1.429 H, d; $^3$J (H, H) = 8.0 Hz; 5'-CH benzodioxole, all three species), 6.73 (0.35 H, s; 2'-CH benzodioxole, (Z)-PTSC), 6.78 (1.079 H, s; 2'-CH benzodioxole, (E)-PTSC and ORG34517), 6.80 (0.35 H, d; $^3$J (H, H) = 8.0 Hz; 6'-CH benzodioxole, (Z)-PTSC), 6.80 (1.079 H, d; $^3$J (H, H) = 8.0 Hz; 6'-CH benzodioxole, (E)-PTSC and ORG34517), 7.14 (0.35 H, m; 4''-H phenyl, (Z)-PTSC), 7.15 (1 H, t; $^3$J (H, H) = 7.4 Hz; 4''-H phenyl, (E)-PTSC), 7.31 (0.7 H, m; 3'',5''-H phenyl, (Z)-PTSC), 7.33 (2 H, t; $^3$J (H, H) = 8.0 Hz; 3'',5''-H phenyl, (E)-PTSC), 7.60 (0.7 H, d; $^3$J (H, H) = 8.0 Hz; 2'',6''-H phenyl, (Z)-PTSC), 7.62 (2 H, d; $^3$J (H, H) = 7.6 Hz; 2'',6''-H phenyl, (E)-PTSC), 9.83 (0.35 H, br s; C$_6$H$_5$—N—H, (Z)-PTSC), 9.89 (1 H, br s; C$_6$H$_5$—N—H, (E)-PTSC), 10.48 (1 H, br s; =N—N—H, (E)-PTSC), 10.83 (0.35 H, br s; =N—N—H, (Z)-PTSC). |

*, **(E or Z)-PTSC = (E or Z)-4-phenylthiosemicarbazone.

PT150
Purification of Crude ORG34517 (PT150): (11β,17β)-17-hydroxy-11-[3,4-(methylenedioxy)phenyl]-17-(1-propyn-1-yl)estra-4,9-dien-3-one

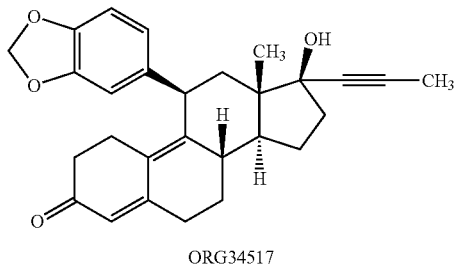

ORG34517

Materials: ORG34517 [Palisades Therapeutics, a division of Pop Test Oncology LLC, Cliffside Park, NJ, USA; manufactured by Wilmington PharmaTech Company LLC, Newark, DE, USA; delivered by TD2 Translational Drug Development, Scottsdale, AZ, USA, Lot: 1930-120-23], CAS Registry Number: [189035-07-2] Doubly-distilled water, purified and sterile, Ethyl acetate pro analysi [PanReac AppliChem GmbH, Lot: 0000518022; w (n/n)=99.9% (gas chromatography), w (H2O) (m/m)=0.01% (Karl Fischer titration), ethanol<0.1%, methanol<0.02%, methyl acetate<0.02%, trace elements (Cr, Fe, Ni, Pb, Zn, P, S, K, Mg)<0.00001%, Si<0.00002%, Na<0.0002%, non-volatile matter<0.001%, acidity/alkalinity<0.0005 meq/g] Instruction: ORG34517 (M=430.54 g/mol, 4.000 g, 9.2907 mmol) was suspended in distilled water (200 ml) in a 1000 ml round-bottomed flask. Then ethyl acetatepro analysi (EtOAc, 100 ml) was
added as a supernatant. The flask was stoppered carefully, and the mixture was shaken vigorously for exactly 1 min. After standing at room temperature (RT, 16.4° C.) for 1 min, the biphasic mixture was shaken vigorously for exactly 1 min. The initially yellow EtOAc phase lightened in color through the shaking procedures. After standing at RT for 1 min, the mixture was transferred into a 500 ml separation funnel and the phases were separated (ca. 10 min). The EtOAc phase was isolated. The isolated aqueous phase was re-extracted with EtOAc (100 ml) by shaking for exactly 10 s. The phases were separated (ca. 10 min). The first and the second EtOAc phase were combined. The isolated residual aqueous phase was re-extracted with EtOAc (50 ml) by shaking for exactly 5 s. The phases were separated (ca. 20 min). All EtOAc phases were combined [the residual aqueous phase was cooled at +0-2° C. for 1 h, the evolved EtOAc phase was separated (ca. 20 min) and combined with the frozen EtOAc phase], and were frozen at −25° C. for 1.5 h. The ice-cold, ice-containing EtOAc phase was decanted from the frozen aqueous residues sticking at the glass surface into a 500 ml round-bottomed flask. The volume of the EtOAc solution was reduced at low temperature (30-40° C.) in vacuo to a volume of ca. 20 ml when crystalline masses appeared (the evaporation was stopped before evaporating to dryness!). The crystalline material sticking at the glass surface was rinsed with 90% (v/v) aqueous ethanol (10 ml). Then the mixture was frozen at −25° C. for 80 min. Afterwards, water (30 ml) was added and the crystallizing suspension was frozen at −25° C. for 15 min. The evolved first yield (2.076 g) of beautiful crystalline ORG34517 (nearly white crystalline chucks) was filtered and dried over CaCl2 in vacuo. The sticky residues in the flask. The volume of the EtOAc solution was reduced at low temperature (30-40° C.) in vacuo to a volume of ca. 20 ml when crystalline masses appeared (the evaporation was stopped before evaporating to dryness!). The crystalline material sticking at the glass surface was rinsed with 90% (v/v) aqueous ethanol (10 ml). Then the mixture was frozen at −25° C. for 80 min. Afterwards, water (30 ml) was added and the crystallizing suspension was frozen at −25° C. for 15 min. The evolved first yield (2.076 g) of beautiful crystalline ORG34517 (nearly white crystalline chucks) was filtered and dried over CaCl2 in vacuo. The sticky residues in the flask were rinsed with 90% (v/v) aqueous ethanol (5 ml) and combined with the first filtrate. A phase separation occurred. The separated EtOAc phase was evaporated in the complete filtrate at the lowest possible temperature in vacuo (ca. 30 min). The crystallizing suspension was frozen at −25° C. for 15 min. The evolved second yield (1.573 g) of ORG34517 was filtered and dried over CaCl2 in vacuo. Residues in the flask (and the vacuum flask) were rinsed with 90% (v/v) aqueous ethanol (4 ml), and were combined with the second filtrate. The crystallizing suspension was frozen at −25° C. for 1.5 h. The evolved third yield (210 mg) of ORG34517 was filtered and dried over CaCl2 in vacuo. From the third filtrate few substance (difference to 100%: 141 mg) could be additionally recovered, if desired, by freezing for 1 h and treatment as before.

| Compound: | ORG34517 (PT150) |
|---|---|
| Molecular formula: | $C_{28}H_{30}O_4$ |
| Molecular weight: | 430.54 g/mol |
| Yield: | 3.859 g (96%) |
| Elemental analysis: | calculated: C 78.11% H 7.02% O 14.86% |
| | found: C 78.26% H 7.04% O 14.71% |
| | C 78.44% H 7.04% O 14.71% |
| $^1$H-NMR: (DMSO-d$_6$, ppm) | 0.44 (3 H, s; 18-CH$_3$), 1.24-2.76 (m; steroid CH and CH$_2$), 1.82 (3 H, s; R—C≡C—CH$_3$ methyl), 4.37 (1 H, d; $^3$J (H, H) = 7.7 Hz; 11□-CH), 5.14 (1 H, s; 17□-OH), 5.66 (1 H, s; 4-CH), 5.97 (2 H, s; O—CH$_2$—O benzodioxole), 6.60 (1 H, d; $^3$J (H, H) = 7.7 Hz; 5'-CH benzodioxole), 6.78 (1 H, s; 2'-CH benzodioxole), 6.79 (1 H, d; $^3$J (H, H) = 8.3 Hz; 6'-CH benzodioxole) |

Second Step (11β,17β)-17-Hydroperoxy-11-[3,4-(methylenedioxy)phenyl]-17-(1-propyn-1-yl)estra-4,9-dien-3-one-(11β,17β)-17-hydroxy-11-[3,4-(methylenedioxy)phenyl]-17-(1-propyn-1-yl)estra-4,9-dien-3-one (1:1) (PT157)

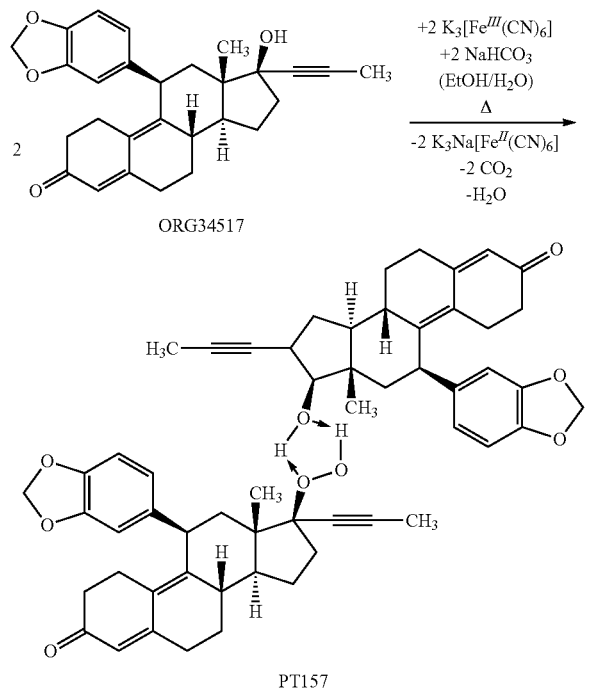

PT157

Materials:
Crystalline ORG34517, purified as before (also capsule- or tablet-extracted amorphous material can be used), CAS Registry Number: [189035-07-2]
Potassium ferricyanide K$_3$[Fe$^{III}$(CN)$_6$] [red prussiate of potash, potassium hexacyanoferrate(III)] BioChemica≥99% [AppliChem GmbH, Lot: 6Y000987; w (m/m)=99.9% (titration), pH (1 M in H$_2$O) 6.1, chloride≤0.05%, sulfate≤0.005%, Pb≤0.002%]
Sodium hydrogen carbonate (sodium bicarbonate) pro analysi NaHCO$_3$[AppliChem GmbH, Lot: 4W000829; w (m/m)=100.42% (titration), pH (5% in H$_2$O) 8.04 (20° C.), chloride≤0.001%, sulfate≤0.005%, phosphate≤0.005%, cations (K, Mg, Ca)≤0.005%, As≤0.0001%, heavy metals (Cu, Fe, Pb)≤0.0005%]
Instruction:
Crystalline (also amorphous material can be used) ORG34517 (M=430.54 g/mol, 3.136 g, 7.2839 mmol) was suspended in 90% (v/v) aqueous ethanol (110 ml) in a 500 ml round-bottomed flask. The suspension was heated and, finally, refluxed until all solid had dissolved (ca. 10 min). Independently, a solution of potassium ferricyanide K$_3$[Fe$^{III}$(CN)$_6$] (M=329.26 g/mol, 5.795 g, 17.6001 mmol=2.42×the molar amount of ORG34517) in water (65 ml) was prepared. The latter solution was poured in one portion into the hot ORG34517 solution. Residues were transferred and rinsed with water (15 ml). The dark yellow solution was mixed with 90% (v/v) aqueous ethanol (60 ml), and was refluxed for 8 min. Afterwards, a solution of sodium hydrogen carbonate (sodium bicarbonate) pro analysi NaHCO$_3$ (M=84.01 g/mol, 1.497 g, 17.8193 mmol) in water (15 ml) was added through the reflux condensor. Residues were transferred and rinsed with water (8 ml). The solution initially lightened in color, then darkened, and was refluxed for additional 12 min. Then the dark yellow solution was cooled at room temperature (RT, ϑ=17.1° C.) for 30 min. Crystals of K$_3$Na[Fe$^{II}$(CN)$_6$]×(H$_2$O)$_n$ appeared. The crystallizing suspension was cooled at +0-2° C. for 2.5 h. Afterwards, the suspension was filtered through two layers of filter paper. Residues were transferred and rinsed with 90% (v/v) aqueous ethanol (50 ml). Finally, the wet K$_3$Na[Fe$^{II}$(CN)$_6$]×(H$_2$O)$_n$ cake was pressed out with a spoon into the dark yellow filtrate (V≈320 ml). This filtrate was precipitated by addition of water (65 ml). The precipitating suspension was frozen at −25° C. for 1 h. Then additional water (35 ml) was added. The precipitating suspension was frozen at −25° C. for 4.5 h. The evolved first yield (2.464 g) of beige (off-white) PT157 was filtered on a sintered glass filter. The material was filtered dry on the filter by suction for 30 min. Successively, the material was washed on the filter with water (200 ml) free of yellow iron compounds, and was dried over CaCl$_2$) in vacuo. The filtrate was transferred and rinsed with water (100 ml), and was frozen at −25° C. for 3.5 h. The evolved second yield (304 mg) of beige (off-white) PT157 was filtered on a sintered glass filter. The material was filtered dry on the filter by suction for 30 min. Successively, the material was washed on the filter with water (200 ml) free of yellow iron compounds, and was dried over CaCl$_2$) in vacuo. Both yields were combined. The dark green filtrate was discarded.

| Compound: | PT157 |
|---|---|
| Molecular formula: | $C_{56}H_{60}O_9$ |
| Molecular weight: | 877.07 g/mol |

| | |
|---|---|
| Yield: | 2.768 g (87%) |
| Elemental analysis: | calculated: C 76.69% H 6.90% N 0.00% O 16.42% |
| | found: C 76.85% H 7.04% N 0.30% O 15.09% |
| | C 76.98% H 7.12% N 0.31% O 15.27% |
| Purity: | from the nitrogen content (0.30%), caused by admixture of $K_3Na[Fe^{II}CN)_6]$ (which has a nitrogen content of N 23.86%), it could be calculated that PT157 has a purity of 98.74% (m/m) [or 96.93% (n/n)] |
| $^1$H-NMR: (DMSO-$d_6$, ppm) | 0.44 (3 H, s; 18-$CH_3$), 1.24-2.76 (m; steroid CH and $CH_2$), 1.83 (3 H, s; R—C≡C—$CH_3$ methyl), 4.38 (1 H, d; $^3$J (H, H) = 7.1 Hz; 11☐-CH), 5.14 (1 H, s; 17☐-OH), 5.66 (1 H, s; 4-CH), 5.97 (2 H, s; O—$CH_2$—O benzodioxole), 6.61 (1 H, d; $^3$J (H, H) = 8.3 Hz; 5'-CH benzodioxole), 6.78 (1 H, s; 2'-CH benzodioxole), 6.79 (1 H, d; $^3$J (H, H) = 8.3 Hz; 6'-CH benzodioxole) |

Example 4

| | |
|---|---|
| Virus Screened: | Japanese encepahalitis virus |
| Virus Strain: | SA-14 |
| Cell Line: | Vero 76 |
| Vehicle: | DMSO |
| Drug Conc. Range: | 0.1-100 µg/ml |
| Control Conc. Range: | 0.00001-0.01 µg/ml |
| Experiment Number | JEV-043 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| Infergen | Primary | Visual (Cytopathic effect/Toxicity) | 0.000042 | | >0.01 | >238 | |
| Infergen | Primary | Neutral Red (Cytopathic effect/Toxicity) | 0.000038 | | >0.01 | >263 | |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$

Screening Results

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000163 | May 27, 2016 | PT155 | Secondary | Visual (Cytopathic effect/Toxicity) | | 10 | >100 | | >10 |
| 16-000163 | May 27, 2016 | PT155 | Secondary | Neutral Red (Cytopathic effect/Toxicity) | 2.9 | | >100 | >34 | |

Example 5

| | |
|---|---|
| Virus Screened: | West Nile virus |
| Virus Strain: | Kern 515, WN02 |
| Cell Line: | Vero 76 |
| Vehicle: | DMSO |
| Drug Conc. Range: | 0.1-100 µg/ml |
| Control Conc. Range: | 0.00001-0.01 µg/ml |
| Experiment Number: | WNV-0870 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| Infergen | Primary | Visual (Cytopathic effect/Toxicity) | 0.00001 | | >0.01 | >1000 | |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| Infergen | Primary | Neutral Red (Cytopathic effect/Toxicity) | 0.000056 | | >0.01 | >180 | |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$ Screening Results

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000163 | May 26, 2016 | PT155 | Primary | Visual (Cytopathic effect/Toxicity) | >22 | | 22 | 0 | |
| 16-000163 | May 26, 2016 | PT155 | Primary | Neutral Red (Cytopathic effect/Toxicity) | >15 | | 15 | 0 | |

Example 6

| | |
|---|---|
| Virus Screened: | Yellow fever virus |
| Virus Strain: | 17D |
| Cell Line: | Vero 76 |
| Vehicle: | DMSO |
| Drug Conc. Range: | 0.1-100 µg/ml |
| Control Conc. Range: | 0.1-100 µg/ml |
| Experiment Number: | YFV-1177 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 6-Azauridine | Primary | Visual (Cytopathic effect/Toxicity) | 0.28 | | >100 | >357 | |
| 6-Azauridine | Primary | Neutral Red (Cytopathic effect/Toxicity) | 0.67 | | 34 | 51 | |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$ Screening Results

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000163 | May 26, 2016 | PT155 | Primary | Visual (Cytopathic effect/Toxicity) | 32 | | 32 | 1 | |
| 16-000163 | May 26, 2016 | PT155 | Primary | Neutral Red (Cytopathic effect/Toxicity) | >14 | | 14 | 0 | |

Example 7

| Virus Screened: | Enterovirus 71 |
| --- | --- |
| Virus Strain: | Tainan/4643/98 |
| Cell Line: | Vero 76 |
| Vehicle: | DMSO |
| Drug Conc. Range: | 0.1-100 µg/ml |
| Control Conc. Range: | 0.01-10 µg/ml |
| Experiment Number: | ENTV-057 |

| Control Drug Name | Control Assay Order | Control Assay Name | $EC_{50}$ | $EC_{90}$ | $CC_{50}$ | $SI_{50}$ | $SI_{90}$ |
| --- | --- | --- | --- | --- | --- | --- | --- |
| Pirodavir | Secondary | Visual (Cytopathic effect/Toxicity) | | 0.23 | >10 | | >43 |
| Pirodavir | Secondary | Neutral Red (Cytopathic effect/Toxicity) | 0.081 | | >10 | >120 | |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$ Screening Results

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
| --- | --- | --- | --- | --- | --- | --- | --- | --- | --- |
| 16-000163 | May 27, 2016 | PT155 | Secondary | Visual (Virus yield reduction)/Neutral Red (Toxicity) | | >100 | >100 | | 0 |
| 16-000163 | May 27, 2016 | PT155 | Secondary | Neutral Red (Cytopathic effect/Toxicity) | 1.7 | | >100 | >59 | |

Example 8

| Virus Screened: | Poliovirus 3 |
| --- | --- |
| Virus Strain: | WM-3 |
| Cell Line: | Vero 76 |
| Vehicle: | DMSO |
| Drug Conc. Range: | 0.032-100 µg/ml |
| Control Conc. Range: | 0.0032-10 µg/ml |
| Experiment Number: | POV-0099 |

| Control Drug Name | Control Assay Order | Control Assay Name | $EC_{50}$ | $EC_{90}$ | $CC_{50}$ | $SI_{50}$ | $SI_{90}$ |
| --- | --- | --- | --- | --- | --- | --- | --- |
| Pirodavir | Secondary | Visual (Cytopathic effect/Toxicity) | | 0.14 | 7.8 | 56 | |
| Pirodavir | Secondary | Neutral Red (Cytopathic effect/Toxicity) | 0.058 | | 7.8 | 130 | |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$ Screening Results

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000163 | May 27, 2016 | PT155 | Secondary | Visual (Virus yield reduction)/Neutral Red (Toxicity) | | 10 | >100 | | >10 |
| 16-000163 | May 27, 2016 | PT155 | Secondary | Neutral Red (Cytopathic effect/Toxicity) | 2.9 | | >100 | >34 | |

Example 9

| | |
|---|---|
| Virus Screened: | Zika virus |
| Virus Strain: | MR766 |
| Cell Line: | HUH 7 |
| Vehicle: | DMSO |
| Drug Conc. Range: | 0.1-100 μg/ml |
| Control Conc. Range: | 0.1-100 μg/ml |
| Experiment Number: | Zika-073 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 6-Azauridine | Secondary | Visual (Virus yield reduction)/Neutral Red (Toxicity) | | 0.89 | >100 | | >112 |
| 6-Azauridine | Secondary | Neutral Red (Cytopathic effect/Toxicity) | 4.1 | | >100 | >24 | |

$EC_{50}$ - compound concentration that reduces viral replication by 50%

$EC_{90}$ - compound concentration that reduces viral replication by 90%

$CC_{50}$ - compound concentration that reduces cell viability by 50%

$SI_{50}$ - $CC_{50}/EC_{50}$ $SI_{90}$ - $CC_{50}/EC_{90}$

Example 10

| | |
|---|---|
| Virus Screened: | NV |
| Virus Strain: | GT1 |
| Cell Line: | HG23 |
| Vehicle: | DMSO |
| Drug Conc. Range: | 0.1-100 uM |
| Control Conc. Range: | 3.7-100 uM |
| Experiment Number: | 16-15 |

Screening Results

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000162 | May 18, 2016 | PT150 | Secondary | Visual (Virus yield reduction)/Neutral Red (Toxicity) | | 1.27 | 4.3 | | 3.4 |
| 16-000162 | May 18, 2016 | PT150 | Secondary | Neutral Red (Cytopathic effect/Toxicity) | 1.6 | | 4.3 | 2.7 | |
| 16-000163 | May 18, 2016 | PT155 | Secondary | Visual (Virus yield reduction)/Neutral Red (Toxicity) | | 0.82 | >100 | | >122 |
| 16-000163 | May 18, 2016 | PT155 | Secondary | Neutral Red (Cytopathic effect/Toxicity) | 0.056 | | >100 | >1800 | |

| Control Drug Name | Control Assay Order | Control Assay Name | EC$_{50}$ | EC$_{90}$ | CC$_{50}$ | SI$_{50}$ | SI$_{90}$ |
|---|---|---|---|---|---|---|---|
| 2' C-methyl cytidine | primary | RNA Hybridization (Replicon)/RNA Hybridization (Toxicity) | 6.4 | 19 | >300 | >47 | >16 |
| 16-000162 (Mar. 17, 2016) | primary | RNA Hybridization (Replicon)/RNA Hybridization (Toxicity) | 1.0 | 9.3 | >100 | >100 | >11 |
| 16-000163 (Mar. 17, 2016) | primary | RNA Hybridization (Replicon)/RNA Hybridization (Toxicity) | 42 | 115 | >100 | >2 | >1 |
| 16-000164 (Mar. 17, 2016) | primary | RNA Hybridization (Replicon)/RNA Hybridization (Toxicity) | >100 | >100 | >100 | 1 | 1 |

EC$_{50}$ - compound concentration that reduces viral replication by 50%
EC$_{90}$ - compound concentration that reduces viral replication by 90%
CC$_{50}$ - compound concentration that reduces cell viability by 50%
SI$_{50}$ - CC$_{50}$/EC$_{50}$
SI$_{90}$ - CC$_{50}$/EC$_{90}$ Screening Results

| ARB No. | Date Received m/dd/yy | Compound Name/ID | Drug Assay Order | Drug Assay Name | EC$_{50}$ | EC$_{90}$ | CC$_{50}$ | SI$_{50}$ | SI$_{90}$ |
|---|---|---|---|---|---|---|---|---|---|
| 16-000162 | May 9, 2016 | PT150 | primary | RNA Hybridization (Replicon)/RNA Hybridization (Toxicity) | 1.2 | 8.1 | >100 | >83 | >12 |
| 16-000163 | May 9, 2016 | PT155 | primary | RNA Hybridization (Replicon)/RNA Hybridization (Toxicity) | 37 | 141.0 | >100 | >3 | >1 |
| 16-000164 | May 9, 2016 | PT156 | primary | RNA Hybridization (Replicon)/RNA Hybridization (Toxicity) | >100 | >100 | >100 | 1 | 1 |

Example 11

| | |
|---|---|
| Virus Screened: | MNV |
| Virus Strain: | MNV-1 |
| Cell Line: | RAW267.4 |
| Vehicle: | DMSO |
| Drug Conc. Range: | 0.03-100 uM |
| Control Conc. Range: | 1.0-30 uM |
| Experiment Number: | 16-14 |

| Control Drug Name | Control Assay Order | Control Assay Name | EC$_{50}$ | EC$_{90}$ | CC$_{50}$ | SI$_{50}$ | SI$_{90}$ |
|---|---|---|---|---|---|---|---|
| 2' C-methyl cytidine | primary | Neutral Red (Cytopathology)/Neutral Red (Toxicity) | 1.0 | 3.1 | >30 | >30 | >10 |
| 16-000162 (Mar. 17, 2016) | primary | Neutral Red (Cytopathology)/Neutral Red (Toxicity) | 0.086 | 0.273 | 33 | 384 | 121 |
| 16-000163 (Mar. 17, 2016) | primary | Neutral Red (Cytopathology)/Neutral Red (Toxicity) | 0.082 | 0.267 | 35 | 427 | 131 |

-continued

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 16-000164 (Mar. 17, 2016) | primary | Neutral Red (Cytopathology)/ Neutral Red (Toxicity) | 0.091 | 0.29 | 33 | 363 | 114 |

$EC_{50}$ - compound concentration that reduces viral replication by 50%
$EC_{90}$ - compound concentration that reduces viral replication by 90%
$CC_{50}$ - compound concentration that reduces cell viability by 50%
$SI_{50}$ - $CC_{50}/EC_{50}$
$SI_{90}$ - $CC_{50}/EC_{90}$ Screening Results

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000162 | May 9, 2016 | PT150 | primary | Neutral Red (Cytopathology)/ Neutral Red (Toxicity) | 0.097 | 0.309 | 34 | 351 | 110 |
| 16-000163 | May 9, 2016 | PT155 | primary | Neutral Red (Cytopathology)/ Neutral Red (Toxicity) | 0.087 | 0.291 | 34 | 391 | 117 |
| 16-000164 | May 9, 2016 | PT156 | primary | Neutral Red (Cytopathology)/ Neutral Red (Toxicity) | 0.096 | 0.304 | 33 | 344 | 109 |

While the invention has been described in detail and with reference to specific examples thereof, it will be apparent to one skilled in the art that various changes and modifications can be made therein without departing from the spirit and scope thereof.

What is claimed is:

1. A pharmaceutical composition comprising:
at least one active agent selected from the group consisting of PT155, PT156, PT157, PT158, TCY1, combinations thereof, and pharmaceutically acceptable salts thereof;
optionally, at least one auxiliary agent selected from the group consisting of oxycodone, hydrocodone, hydromorphone and methadone.

2. The pharmaceutical composition of claim 1, wherein the composition is in a dosage form selected from the group consisting of a capsule, a tablet, a smart pill delivery device, and a smart capsule delivery device.

3. A method of treatment, comprising:
selecting a patient in need of treating a condition selected from the group consisting of nicotine, opioids, methamphetamine, and/or alcohol addiction; nicotine, opioids, methamphetamine, and/or alcohol addiction induced anxiety; and nicotine, opioids, methamphetamine, and/or alcohol withdrawal symptoms; and
administering to the patient in need of treating the condition an effective amount of at least one active agent selected from the group consisting of PT150, PT155, PT156, PT157, PT158, TCY1, combinations thereof, and pharmaceutically acceptable salts thereof.

4. A method of treatment, comprising:
selecting a patient in need of treating a condition selected from the group consisting of nicotine, opioids, methamphetamine, and/or alcohol addiction; nicotine, opioids, methamphetamine, and/or alcohol addiction induced anxiety; and nicotine, opioids, methamphetamine, and/or alcohol withdrawal symptoms;
administering a composition comprising:
i) a therapeutic selected from the group consisting of PT155, PT156, PT157, PT158, TCY1, combinations thereof, and pharmaceutically acceptable salts thereof;
ii) at least one additional therapeutic agent selected from the group consisting of:
(a) at least one anxiolytic selected from the group consisting of alprazolam, bromazepam, diazepam, lorazepam, clonazepam, temazepam, oxazepam, fluni-trazepam, triazolam, chlordiazepoxide, flurazepam, esta-zolam, nitrazepam, and pharmaceutically acceptable salts, isomers, and mixtures thereof,
(b) at least one antidepressant selected from the group consisting of citalopram, escitalopram oxalate, fluoxetine, fluvoxamine, paroxetine, sertraline, dapoxetine; venlafaxine and duloxetine; harma-line, iproniazid, isocarboxazid, nialamide, paigyline, phenelzine, selegiline, toloxatone, tranylcypromine, brofar-omine, moclobemide; amitriptyline, amoxapine, butrip-tyline, clomipramine, desipramine, dibenzepin, dothiepin, doxepin, imipramine, iprindole, lofepramine, melitracen, nortriptyline, opipramol, protriptyline, trimipramine; mapro-tiline, mianserin, nefazodone, trazodone, and pharmaceutically acceptable salts, isomers, and combinations thereof,
(c) at least one neuroleptic selected from the group consisting of Haloperidol, Droperidol, Benperidol, Triperi-dol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Que-tiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof, and (d) combinations thereof; and iii) at least one pharmaceutically acceptable carrier, wherein the therapeutic and the at least one additional therapeutic agent are each present in an amount which, in combination, is a therapeutically effective amount for treating the condition.

5. A method of treating nicotine, opioids, methamphetamine, and/or alcohol addiction, nicotine, opioids, methamphetamine, and/or alcohol addiction induced anxiety, and/or nicotine, opioids, methamphetamine, and/or alcohol withdrawal symptoms in a patient, comprising the steps of:

a) obtaining a test sample from the patient using a test sample collection unit;

b) combining said test sample with a buffering system to form a mixture in a reaction unit;

c) measuring a parameter of the mixture to determine a blank measurement;

d) combining said test sample and buffer mixture with a labeled ligand which binds cortisol in the reaction unit to produce an assay solution; or combining said test sample and buffer mixture and delivering it to a carrier containing a labeled ligand which binds cortisol in the reaction unit to produce an assay immobilized complex;

e) measuring a parameter of said assay solution or complex;

f) comparing the measurement of the assay solution relative to the blank measurement;

g) determining the patient's circulating cortisol levels based on the change of the measurement;

h) comparing the measured cortisol levels to a predetermined reference range cortisol levels, wherein when the level of cortisol is elevated relative to the predetermined reference range, then the patient has elevated cortisol, and thus is suitable for GCR (glucocorticoid receptor) antagonist therapy; and i) when the patient is suitable, administering a composition comprising a therapeutic is selected from the group consisting of PT155, PT156, PT157, PT158, TCY1, combinations thereof, and pharmaceutically acceptable salts thereof;

thereby treating nicotine, opioids, methamphetamine, and/or alcohol addiction, nicotine, opioids, methamphetamine, and/or alcohol addiction induced anxiety, and/or nicotine, opioids, methamphetamine, and/or alcohol withdrawal symptoms in the patient.

6. The method of claim 5, wherein the patient's test sample is selected from the group consisting of saliva, blood, plasma, serum, urine, other bodily fluids, and combinations thereof.

7. The method of claim 5, wherein the sample is obtained from the patient one time, selected from the group consisting of morning, noon, and evening.

8. The method of claim 5, wherein the sample is obtained from the patient over more than one time, and the predetermined time is selected to determine the nature of the cortisol circadian rhythm, including its possible disruption or elimination, from the group consisting of morning, noon, and evening.

9. The method of claim 5, wherein the sample is obtained from the patient over consecutive days.

10. The method of claim 5, wherein the method is to determine the circadian cycle of the cortisol levels in the patient, and the predetermined time is selected from the group consisting of hourly, every 4 hours, every 6 hours, every 8 hours, and every 12 hours.

11. The method of claim 5, wherein the predetermined reference range is a medically standard reference range.

12. The method of claim 5, wherein the predetermined reference range is the patient's previously measured level.

13. The method of claim 5, wherein the ligand is detectably labeled with a moiety selected from the group consisting of a radioisotope, a fluorophore, a quencher of fluorescence, an enzyme, an affinity tag, and an epitope tag.

14. The method of claim 5, wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means.

* * * * *